US010081648B2

(12) United States Patent
Sengupta et al.

(10) Patent No.: US 10,081,648 B2
(45) Date of Patent: Sep. 25, 2018

(54) LIPID-BASED PLATINUM COMPOUNDS AND NANOPARTICLES

(71) Applicant: AKAMARA THERAPEUTICS, INC., Philadelphia, PA (US)

(72) Inventors: Shiladitya Sengupta, Waltham, MA (US); Monideepa Roy, Allston, MA (US); Arindam Sarkar, New Delhi (IN); SK Samad Hossain, New Delhi (IN); Aniruddha Sengupta, New Delhi (IN); Pradip Kumar Dutta, New Delhi (IN); Aasif Ansari, New Delhi (IN); Swadhin K. Mandal, Mohanpur (IN)

(73) Assignee: Ankara Therapeutics, Inc., Philadelphia, PA (US)

( * ) Notice: Subject to any disclaimer, the term of this patent is extended or adjusted under 35 U.S.C. 154(b) by 0 days.

(21) Appl. No.: 14/898,355

(22) PCT Filed: Jun. 13, 2014

(86) PCT No.: PCT/US2014/042339
§ 371 (c)(1),
(2) Date: Dec. 14, 2015

(87) PCT Pub. No.: WO2014/201376
PCT Pub. Date: Dec. 18, 2014

(65) Prior Publication Data
US 2016/0145284 A1 May 26, 2016

(30) Foreign Application Priority Data
Jun. 14, 2013 (IN) .......................... 1781/DEL/2013

(51) Int. Cl.
C07F 15/00 (2006.01)
C07H 23/00 (2006.01)
C07J 41/00 (2006.01)

(52) U.S. Cl.
CPC ...... *C07F 15/0093* (2013.01); *C07F 15/0086* (2013.01); *C07H 23/00* (2013.01); *C07J 41/0055* (2013.01)

(58) Field of Classification Search
CPC ....... C07F 15/00; C07H 23/00; C07J 45/0055
USPC ....................................................... 556/136
See application file for complete search history.

(56) References Cited

U.S. PATENT DOCUMENTS

| 4,946,954 | A | 8/1990 | Talebian et al. |
| 4,952,676 | A | 8/1990 | Heffernan et al. |
| 2004/0235712 | A1 | 11/2004 | Lippard et al. |
| 2012/0189571 | A1* | 7/2012 | Sengupta ......... A61K 47/48176 424/78.27 |

FOREIGN PATENT DOCUMENTS

| JP | 2012-516898 A | 7/2012 |
| RU | 2074861 C1 | 3/1997 |
| WO | 99/31063 A1 | 6/1999 |
| WO | 2012/013652 A1 | 2/2012 |
| WO | 2013/072295 A1 | 5/2013 |
| WO | 2013/103707 A1 | 7/2013 |
| WO | 2013/188763 A1 | 12/2013 |
| WO | 2014/002958 A1 | 1/2014 |

OTHER PUBLICATIONS

Dhar et al., "Targeted delivery of cisplatin to prostate cancer cells by aptamer functionalized Pt(IV) prodrug-PLGA-PEG nanoparticles", PNAS 105(45):17356-17361 (2008).
Ferrari, "Cancer Nanotechnology: Opportunities and Challenges", Nature Reviews Cancer 5(3):161-171 (2005).
Haxton et al., "Polymeric Drug Delivery of Platinum-Based Anticancer Agents", Journal of Parmaceutical Sciences 98(7)1299-2316 (2009).
Lin et al., "Improved targeting of platinum chemotherapeutics. the antitumour activity of the HPMA copolymer platinum agent AP5280 in murine tumour models", European Journal of Cancer 40:291-297 (2004).
Rademaker-Lakhai et al., "A Phase I and Pharmacological Study of the Platinum Polymer AP5280 Given as an Intravenous Infusion Once Every 3 Weeks in Patients with Solid Tumors", Clinical Cancer Research 10:3386-3395 (2004).
Sengupta, Poulomi,et al. Cholesterol-tethered platinum II-based supramolecular nanoparticle increases antitumor efficacy and reduces nephrotoxicity, PNAS, 2012, 109 (28), pp. 11294-11299.
Aronov, Olga et al., Folate-Targeted PEG as a Potential Carrier for Carboplatin Analogs, Synthesis and in Vitro Studies, Bioconjugate Chemistry, vol. 14, No. 3, 2003, pp. 563-574.
Gandolfi, Ottavio, et al., Syntheses of cis-dichlorodiammineplatinum analogs having steroidal hormones bound to the metal atom via malonato bridges, Inorganica Chimica Acta, 1989, 161, pp. 113-123.
Database CA [Online} Chemical Abstracts Service Columbus, Ohio, US; Hendrickson, James et al.: "Seeking the ideal dehydrating reagent", retrieved from STN, Database accession No. 1987:515662.
Database CA [Online] Chemical Service, Columbus, Ohio, US; Sarioz, Ozlem et al.: "Aminophosphines derived from N-phenylpiperazine and N-ethylpiperazine: Synthesis, oxidation reactions, and molybdenum complexes", retrieved from STN Database accession No. 2011:692226.

(Continued)

*Primary Examiner* — Clinton Brooks
*Assistant Examiner* — Kofi Adzamli
(74) *Attorney, Agent, or Firm* — Baker & Hostetler LLP

(57) ABSTRACT

The present disclosure is in relation to the field of nanotechnology and cancer therapeutics. In particular, the present disclosure relates to platinum based compounds comprising platinum moiety, linker moiety and lipid moiety and corresponding nanoparticles thereof. The disclosure further relates to synthesis of said platinum based compounds, nanoparticles and compositions comprising said platinum based compounds/nanoparticles. The disclosure also relates to methods of managing cancer by employing aforesaid carbene compounds, platinum based compounds, nanoparticles and compositions thereof.

12 Claims, 21 Drawing Sheets

(56) References Cited

OTHER PUBLICATIONS

Database CA [Online] Chemical Abstracts Service, Columbus, Ohio, US; Nguyen Thanh Thuong et al.: "New phosphorylation reagent reacting by pseudoratation", retrieved from STN, Database accession No. 1978:509253.

Jayasuriya, A. Champa et al., Controlled release of cisplatin and cancer cell apoptosis with cisplatin encapsulated poly (lactic-co-glycolic acid) nanoparticles, Journal of Biomedical Science and Engineering, vol. 06, No. 05, May 2013, pp. 586-592.

\* cited by examiner

Dichloro (1,2-diammino-cyclohexane) platinum (II)

Reagents and conditions: (1) DCC, DMAP, CH2Cl2, r.t, 12h (2) TFA, CH2Cl2, 0°C to r.t, 6h (3) Ethyl bromo acetate, NaH, THF, r.t, 6h (4) LiOH, THF-H2O, r.t, 3h (5) DMF, DACHPt(H2O)2, r.t, 24h Reagents and conditions: (1) NaH, ethyl bromo acetate, THF, 0°C to r.t, 3h (2) LiAlH4, THF, 0°C to r.t, 3h (3) pTsCl, pyridine, CH2Cl2, 0°C to r.t, 6h (4) NaN3, DMF, r.t, 12h (5) TPP, THF-H2O, 6h, r.t, (6) NaH, ethyl bromo acetate, THF, 0°C to r.t, 3h (7) LiOH, THF-H2O, r.t, 3h (8) aq DACH(H2O)2Pt, DMF, r.t, 12h

LIPID-BASED PLATINUM COMPOUNDS AND NANOPARTICLES

CROSS REFERENCE TO RELATED APPLICATIONS

This application is a 371 National Phase Entry of International Patent Application No. PCT/US2014/042339 filed on Jun. 14, 2013 which claims benefit under 35 U.S.C. § 119(a)-119(d) of Indian Patent Application No. 1781/DEL/2013 filed Jun. 14, 2013, the contents of which are incorporated herein by reference in their entirety.

TECHNICAL FIELD

The present disclosure is in relation to the field of nanotechnology and cancer therapeutics. In particular, the present disclosure relates to platinum based compounds comprising platinum moiety, linker moiety and lipid moiety and corresponding nanoparticles thereof. The disclosure further relates to synthesis of said platinum based compounds, nanoparticles and compositions comprising said platinum based compounds/nanoparticles. The disclosure also relates to methods of managing cancer by employing aforesaid platinum based compounds, nanoparticles and compositions.

BACKGROUND

The use of nanotechnology in cancer is emerging globally. Although there are few reports on nanoparticles in cancer therapy but all have various drawbacks such as toxicity, low release kinetics of drug, low circulation stability and so on.

Lipidic nanoparticles (e.g. Doxil, a pegylated liposomal formulation of doxorubicin hydrochloride) and albumin-complexes (e.g. Abraxane, a paclitaxel-albumin complex) nanoparticles are used in humans and have been demonstrated as having improved systemic toxicity profile and have helped resolve certain formulation challenges (Ferrari M, Nature Rev. Cancer, 2005, 5:161). Platinum-based chemotherapeutic agents are used as first line of therapy in over 70% of all cancers. Cisplatin undergoes rapid formation of cis-[Pt(NH$_3$)$_2$Cl(OH$_2$)]$^+$ and cis-[Pt(NH$_3$)$_2$(OH$_2$)]$^{2+}$ resulting in nephrotoxicity. Further, aquation of both carboplatin and oxaliplatin are significantly slower, resulting in decreased potency. In the recent past, considerable progress has been made wherein, Dhar et al (PNAS, 2008, 105, 17356) generated a platinum (IV) complex (c,t,c-[Pt(NH$_3$)$_2$(O$_2$CCH$_2$CH$_2$CH$_2$CH$_3$)$_2$Cl$_2$] that is hydrophobic enough for encapsulation into PLGA-b-PEG nanoparticles. However, the prodrug in this case has to be intracellularly processed into cisplatin. Furthermore, alternative strategies based on conjugation of platinum to polymers (eg a polyamidoamine dendrimer-platinum complex) resulted in a 200-550 fold reduction in cytotoxicity than free cisplatin. This was a result of strong bonds formed between the polymer and platinum (J Pharm Sci, 2009, 98, 2299). Another example is AP5280, a N-(2-hydroxypropyl) methacrylamide copolymer-bound platinum that is less potent than carboplatin. Here, the platinum is held by an aminomalonic acid chelating agent coupled to the COOH-terminal glycine of a tetrapeptide spacer (Clin Can Res, 2004, 10, 3386; Eur J Can, 2004, 40, 291).

Further, WO 2010/091192 A2 (Sengupta et al) discloses biocompatible conjugated polymer nanoparticles including a copolymer backbone, a plurality of sidechains covalently linked to said backbone, and a plurality of platinum compounds dissociably linked to said backbone. The disclosure is further directed to dicarbonyl-lipid compounds wherein a platinum compound is dissociably linked to the dicarbonyl compound.

However, various drawbacks are associated with the presently employed nanoparticles. The present disclosure aims at overcoming the drawbacks of the prior art and providing for stable, potent and safer nano-platinates in cancer chemotherapy.

SUMMARY

In one aspect, the disclosure provides a compound comprising: (a) a platinum moiety; and (b) a lipid connected to said platinum moiety. In some embodiments, the compound is of formula (VIII):

wherein:
Q is a platinum containing moiety and the linker has at least one linkage to the platinum atom.

The disclosure also provides a method of obtaining Pt-lipid molecules disclosed herein. Accordingly, in one aspect the disclosure provides a method of obtaining a compound comprising: (a) a platinum moiety, and a lipid connected to said platinum moiety a method of obtaining a compound comprising, said method comprising conjugating the lipid with the platinum moiety to obtain said compound.

The disclosure also provides particles, such as nanoparticles comprising one or more of the Pt-lipid molecules disclosed herein. Thus, in one aspect, the disclosure provides a particle, for example, but not limited, a nanoparticle comprising a platinum based compound, wherein the platinum based compound comprises: (a) a platinum moiety; and (b) a lipid connected to said platinum moiety.

The disclosure also provides a pharmaceutical composition comprising the compound as disclosed above or the nanoparticle as disclosed above or a combination thereof, along with pharmaceutically acceptable excipient; and a method of managing or treating cancer, said method comprising step of administering the compound as disclosed above or the nanoparticle as disclosed above or the composition as disclosed above, to a subject in need thereof.

BRIEF DESCRIPTION OF THE DRAWINGS

In order that the invention may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure.

FIG. 3A represents the synthesis of Compound 32 (wherein, R=Cholesterol or other lipid). FIG. 3B represents the synthesis of Compound 33 (wherein, R=Cholesterol or other lipid). FIG. 3C represents the synthesis of Compound 34 (wherein, R=Cholesterol or other lipid). FIG. 3D represents the synthesis of Compound 35 (wherein, R=Cholesterol or other lipid). FIG. 3E represents the synthesis of Compound 36 (wherein, R=Cholesterol or other lipid);

FIG. 4A represents the synthesis of Compound 38. FIG. 4B represents the synthesis of Compound 39. FIG. 4C represents the synthesis of Compound 40. FIG. 4D represents the synthesis of Compound 41. FIG. 4E represents the synthesis of Compound 42.

DETAILED DESCRIPTION

Figure 1A:
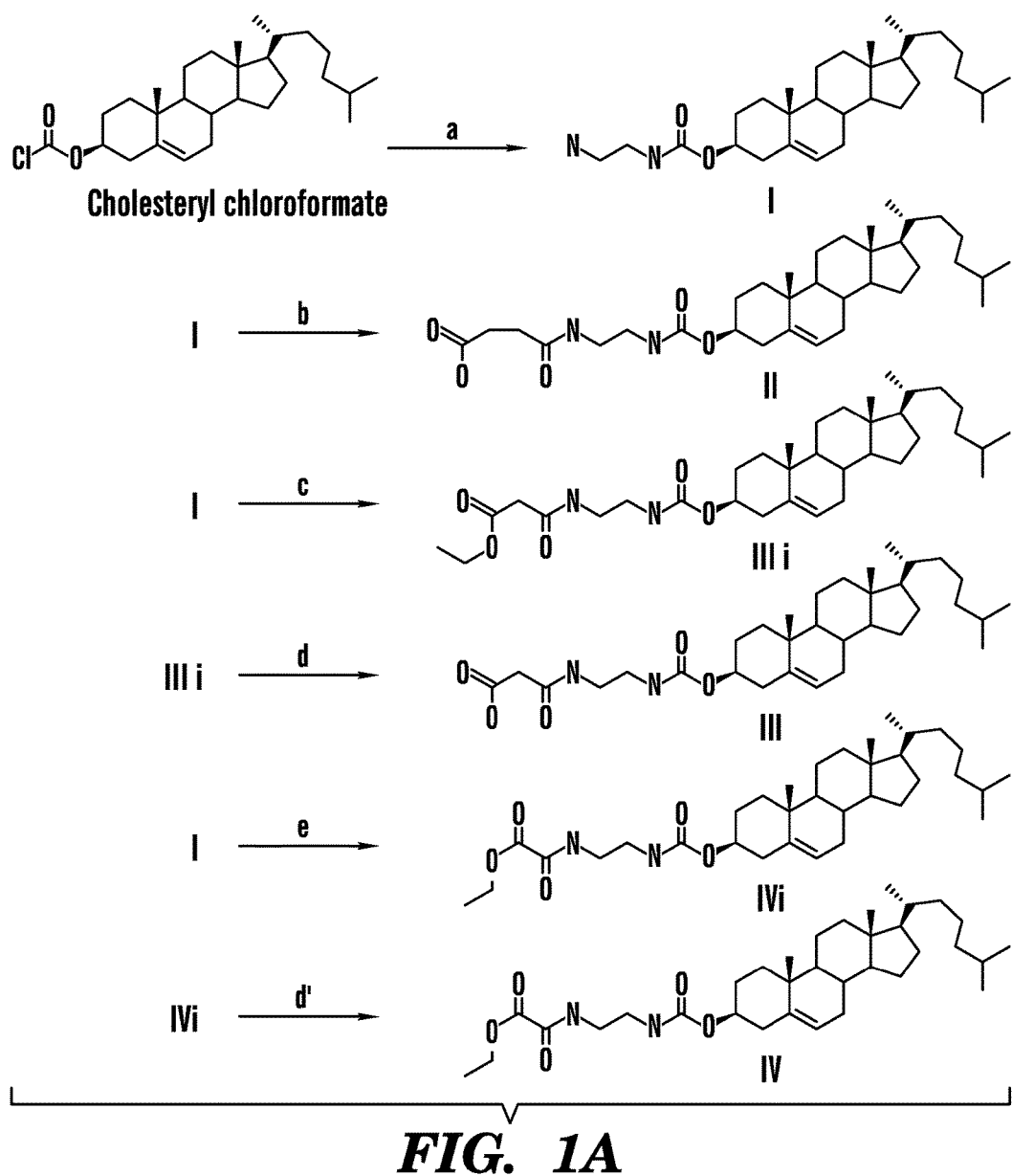
FIGS. 1A-1C depict the synthesis procedure of Cholesterol-Oxaliplatin compounds (Formula I) with carbamate linkage (Compounds 1, 2 and 3). Reagents and Conditions: a), Ethylenediammine (20 eq), Dry DCM, 0° C.-room temperature (RT), 24 hours; b) succinic anhydride, DCM, pyridine, RT, 24 hours; c) malonic acid monoethyl ester, DCM, EDCl, HOBt, RT, 24 hours; d, d') LiOH, THF, H$_2$O, 3 hours, RT; e) oxalic acid monoethyl ester, DCM, EDCl, HOBt, RT, 24 hours; f) AgNO$_3$, H$_2$O, RT, 24 hours; g, g', g") DMF, H$_2$O, RT, 24 hours.

In some embodiments, platinum based compounds are disclosed which comprises: (a) a Platinum moiety; (b) at least one linker connected to said Platinum moiety; and (c) a lipid connected to said linker.

In the compounds disclosed herein, the platinum moiety is linked to the lipid molecule either directly or via a linker molecule. In some embodiments, the platinum moiety is linked to the lipid molecule via a linker molecule. For example, the presence of a linker can provide for a carbamate and/or ether linkage connecting a dicarbonyl molecule (for linking with the platinum moiety) and the lipid molecule. In some other embodiments of the present disclosure, the platinum moiety is directly connected to the lipid molecule. All possible linker molecules providing a carbamate and/or ether linkage form a part of the instant disclosure.

In some embodiments, the platinum based compound disclosed herein is a compound of Formula (VIII):

Q-linker-lipid  (VII), wherein:
Q is a platinum containing moiety and the linker has at least one linkage to the platinum atom.

In some embodiments of the various aspects described herein, Q is

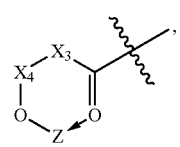

wherein: $X_3$ is selected from a group comprising $(CH_2)_n$, $CH_2$—NH and $C_4H_8$; $X_4$ is CO or —CH—CH$_3$; Z is a platinum containing compound, wherein the platinum forms a part of the ring; and n is 0, 1, or 2.

In some embodiments of the various aspects described herein, Q is

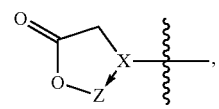

wherein: X is NH or N(CH$_2$COO$^-$); and Z is a platinum containing compound, wherein the platinum forms a part of the ring.

In some embodiments of the various aspects described herein, Q is

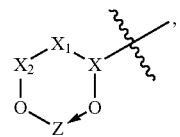

wherein: X is selected from a group comprising S$^+$, C, S$^+$=O, N$^+$H and P=O; $X_1$ is selected from a group comprising —CH, —CH$_2$ and —CH$_2$O; $X_2$ is C=O; and Z is a platinum containing compound, wherein the platinum forms a part of the ring.

In some embodiments of the various aspects described herein, Q is

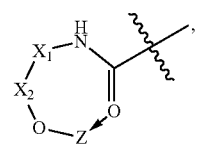

wherein $X_1$ is $(CH_2)_n$; $X_2$ is C=O; Z is a platinum containing compound, wherein the platinum forms a part of the ring; and n is 0, 1, or 2.

In some embodiments of the various aspects disclosed herein, the platinum is co-ordinated to a leaving group via a unique O—Pt monocarboxylato covalent bond and a=O→Pt coordinate bond. Further, the present disclosure also discloses platinum based compounds wherein the platinum is co-ordinated to a leaving group via O—Pt monocarboxylato or dicarboxylato covalent bond(s).

In some embodiments of the various aspects disclosed herein, the platinum moiety is a platinum (II) or platinum (IV) compound. In some embodiments, the platinum (II) compound is selected from the group comprising of DACH-platinum, cisplatin, oxaliplatin, carboplatin, paraplatin, sartraplatin, and various combinations thereof. In some embodiments, the platinum containing compound is Pt(II) compound, Pt(IV) compound or halide containing platinum compound. In a preferred embodiment, the platinum compounds are oxaliplatin.

In some embodiments, Z is

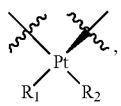

wherein $R_1$ and $R_2$ are independently halogen, alkyl, amino, alkylamino, dialkylamino, hydroxyl, alkoxy, thiol, thioalkyl, O-acyl, or any combinations thereof. In some embodiments, $R_1$ and $R_2$, together with the Pt atom form an optionally substituted cyclyl or heterocyclyl. In some embodiments, Z is

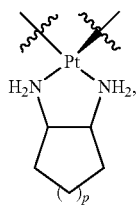

wherein p is 0, 1, 2, or 3. In one embodiment, p is 2.

In some embodiments, Z is

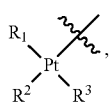

wherein $R^1$, $R^2$ and $R^3$ are independently halogen, alkyl, amino, alkylamino, dialkylamino, hydroxyl, alkoxy, thiol, thioalkyl, O-acyl,-linker-lipid, or any combinations thereof. In some embodiments, $R_1$ and $R_2$ together with the Pt atom or $R_2$ and $R_3$ together with the Pt atom form an optionally substituted cyclyl or heterocyclyl. In one embodiment, $R_1$ and $R_2$ together with the Pt atom and $R_2$ and $R_3$ together with the Pt atom form an optionally substituted cyclyl or heterocyclyl.

In some embodiments, Z is

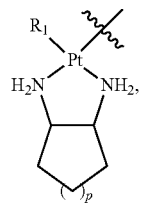

$R_1$ is halogen, alkyl, amino, alkylamino, dialkylamino, hydroxyl, alkoxy, thiol, thioalkyl, O-acyl, or any combinations thereof and p is 0, 1, 2, or 3. In some further embodiments of this, $R_1$ is halogen —Cl, —NCS, —O=S(CH$_3$)$_2$, —SCH$_3$, or -linker-lipid. In one embodiment, p is 2.

In some embodiments, Z is

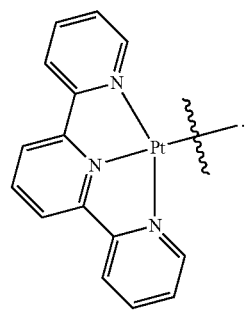

In some embodiments, Z is

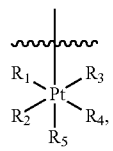

wherein $R_1$, $R_2$, $R_3$, $R_4$ and $R_5$ are independently halogen, alkyl, amino, alkylamino, dialkylamino, hydroxyl, alkoxy, thiol, thioalkyl, O-acyl, -linker-lipid, or any combinations thereof. In some embodiments, $R_1$ and $R_2$ together with the Pt atom form an optionally substituted cyclyl or heterocyclyl. In some embodiments, $R_1$ and $R_2$ together with the Pt atom form an optionally substituted cyclyl or heterocyclyl. In one embodiment, $R_1$ and $R_2$ together with the Pt atom form an optionally substituted cyclyl or heterocyclyl and $R_3$ and $R_4$ together with the Pt atom form an optionally substituted cyclyl or heterocyclyl. In some embodiments, $R_5$ is OH, OC(O)CH$_3$, or OC(O)-phenyl.

In some embodiments, Z is

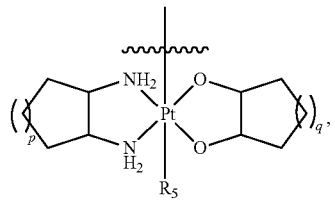

wherein p and q are independently 0, 1, 2, or 3. In some embodiments, p is 2. In some embodiments, q is 2. In one embodiment, p and q are both 2.

In one embodiment, Z is

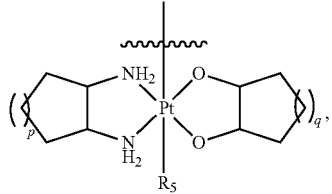

wherein p and q are both 2; and $R_5$ is OH, OC(O)CH$_3$, or OC(O)-phenyl.

In some embodiments, the platinum (II) compound comprises at least two nitrogen atoms, where said nitrogen atoms are directly linked to platinum. In a further embodiment, the two nitrogen atoms are linked to each other via an optionally substituted linker, e.g. acyclic or cyclic linker. A cyclic linker means a linking moiety that comprises at least one ring structure. Cyclic linkers can be aryl, heteroaryl, cyclyl or heterocyclyl.

In some embodiments, Q is

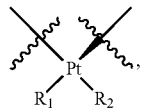

wherein $R_1$ and $R_2$ are independently halogen, alkyl, amino, alkylamino, dialkylamino, hydroxyl, alkoxy, thiol, thioalkyl, O-acyl, or any combinations thereof. In some embodiments, $R_1$ and $R_2$, together with the Pt atom form an optionally substituted cyclyl or heterocyclyl. In some embodiments, Q is

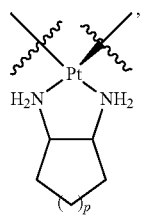

wherein p is 0, 1, 2, or 3. In one embodiment, p is 2.

In some embodiments, Q is

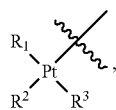

wherein $R^1$, $R^2$ and $R^3$ are independently halogen, alkyl, amino, alkylamino, dialkylamino, hydroxyl, alkoxy, thiol, thioalkyl, O-acyl, or any combinations thereof. In some embodiments, $R_1$ and $R_2$ together with the Pt atom or $R_2$ and $R_3$ together with the Pt atom form an optionally substituted cyclyl or heterocyclyl. In one embodiment, $R_1$ and $R_2$ together with the Pt atom and $R_2$ and $R_3$ together with the Pt atom form an optionally substituted cyclyl or heterocyclyl.

In some embodiments, Q is

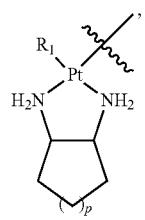

$R_1$ is halogen, alkyl, amino, alkylamino, dialkylamino, hydroxyl, alkoxy, thiol, thioalkyl, O-acyl, or any combinations thereof and p is 0, 1, 2, or 3. In some further embodiments of this, $R_1$ is halogen —Cl, —NCS, —O═S(CH$_3$)$_2$, —SCH$_3$, or -linker-lipid. In one embodiment, p is 2.

In some embodiments, Q is

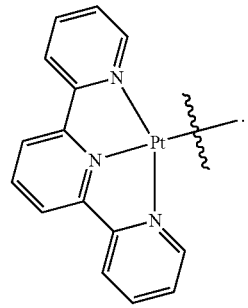

In some embodiments, Q is

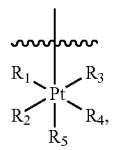

wherein $R_1$, $R_2$, $R_3$, $R_4$ and $R_5$ are independently halogen, alkyl, amino, alkylamino, dialkylamino, hydroxyl, alkoxy, thiol, thioalkyl, O-acyl, or any combinations thereof. In some embodiments, $R_1$ and $R_2$ together with the Pt atom form an optionally substituted cyclyl or heterocyclyl. In some embodiments, $R_1$ and $R_2$ together with the Pt atom form an optionally substituted cyclyl or heterocyclyl. In one embodiment, $R_1$ and $R_2$ together with the Pt atom form an optionally substituted cyclyl or heterocyclyl and $R_3$ and $R_4$ together with the Pt atom form an optionally substituted cyclyl or heterocyclyl. In some embodiments, $R_5$ is OH, OC(O)CH$_3$, or OC(O)-phenyl.

In some embodiments, Q is

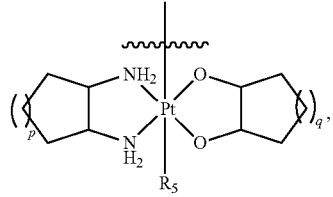

wherein p and q are independently 0, 1, 2, or 3. In some embodiments, p is 2. In some embodiments, q is 2. In one embodiment, p and q are both 2.

In one embodiment, Q is

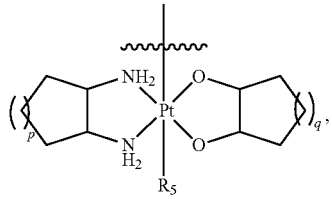

wherein p and q are both 2; and $R_5$ is OH, OC(O)CH$_3$, or OC(O)-phenyl.

The term "lipid" is used in the conventional sense and includes compounds of varying chain length, from as short as about 2 carbon atoms to as long as about 28 carbon atoms. Additionally, the compounds may be saturated or unsaturated and in the form of straight- or branched-chains or in the form of unfused or fused ring structures. Exemplary lipids include, but are not limited to, fats, waxes, sterols, steroids, bile acids, fat-soluble vitamins (such as A, D, E, and K), monoglycerides, diglycerides, phospholipids, glycolipids, sulpholipids, aminolipids, chromolipids (lipochromes), glycerophospholipids, sphingolipids, prenollipids, saccharolipids, polyketides, and fatty acids.

Without limitations the lipid can be selected from the group consisting of sterol lipids, fatty acids, fatty alcohols, glycerolipids (e.g., monoglycerides, diglycerides, and triglycerides), phospholipids, glycerophospholipids, sphingolipids, prenol lipids, saccharolipids, polyketides, and any combination thereof. The lipid can be a polyunsaturated fatty acid or alcohol. The term "polyunsaturated fatty acid" or "polyunsaturated fatty alcohol" as used herein means a fatty acid or alcohol with two or more carbon-carbon double bonds in its hydrocarbon chain. The lipid can also be a highly unsaturated fatty acid or alcohol. The term "highly polyunsaturated fatty acid" or "highly polyunsaturated fatty alcohol" as used herein means a fatty acid or alcohol having at least 18 carbon atoms and at least 3 double bonds. The lipid can be an omega-3 fatty acid. The term "omega-3 fatty acid" as used herein means a polyunsaturated fatty acid whose first double bond occurs at the third carbon-carbon bond from the end opposite the acid group.

In some embodiments, the lipid can be selected from the group consisting of 1,3-Propanediol Dicaprylate/Dicaprate; 10-undecenoic acid; 1-dotriacontanol; 1-heptacosanol; 1-nonacosanol; 2-ethyl hexanol; Androstanes; Arachidic Acid; Arachidonic Acid; arachidyl alcohol; Behenic acid; behenyl alcohol; Capmul MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/Capric Triglyceride; Ceramide phosphorylcholine (Sphingomyelin, SPH); Ceramide phosphorylethanolamine (Sphingomyelin, Cer-PE); Ceramide phosphorylglycerol; Ceroplastic acid; Cerotic acid; Cerotic acid; ceryl alcohol; Cetearyl alcohol; Ceteth-10; cetyl alcohol; Cholanes; Cholestanes; cholesterol; cis-11-eicosenoic acid; cis-11-octadecenoic acid; cis-13-docosenoic acid; cluytyl alcohol; coenzyme Q10 (CoQ10); Dihomo-γ-linolenic; Docosahexaenoic acid; egg lecithin; Eicosapentaenoic acid; Eicosenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glycerol Tricaprylate/Caprate (CAPTEX® 355 EP/NF); glyceryl monocaprylate (Capmul MCM C8 EP); Glyceryl Triacetate; Glyceryl Tricaprylate; Glyceryl Tricaprylate/Caprate/Laurate; Glyceryl Tricaprylate/Tricaprate; glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Lauric acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; γ-Linolenic acid; a fatty acid salt of 10-undecenoic acid, adapalene, arachidic acid, arachidonic acid, behenic acid, butyric acid, capric acid, caprylic acid, cerotic acid, cis-11-eicosenoic acid, cis-11-octadecenoic acid, cis-13-docosenoic acid, docosahexaenoic acid, eicosapentaenoic acid, elaidic acid, erucic acid, heneicosylic acid, heptacosylic acid, heptadecanoic acid, isostearic acid, lauric acid, lignoceric acid, linoelaidic acid, linoleic acid, montanic acid, myristic acid, myristoleic acid, neodecanoic acid, neoheptanoic acid, neononanoic acid, nonadecylic acid, oleic acid, palmitic acid, palmitoleic acid, pelargonic acid, pentacosylic acid, pentadecylic acid, recinoleaic acid (e.g. zinc recinoleate), sapienic acid, stearic acid, tricosylic acid, tridecylic acid, undecylenic acid, undecylic acid, vaccenic acid, valeric acid, α-linolenic acid, γ-linolenic acid; and any combinations thereof.

In some embodiments, the lipid is cholesterol or alpha tocopherol.

As used herein, the term "linker" means an organic moiety that connects two parts of a compound. Linkers typically comprise a direct bond or an atom such as oxygen or sulfur, a unit such as NR$^1$, C(O), C(O)NH, C(O)O, NHC(O)O, OC(O)O, SO, SO$_2$, SO$_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $NR^1$, C(O), C(O)NH, C(O)O, NHC(O)O, OC(O)O, $SO_2NH$, cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis. Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S— and —C(R)$_2$—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e g, linking groups that are cleaved by enzymes such as peptidases and proteases in cells, e.g., —NHCHR$^A$C(O)NHCHR$^B$C(O)—, where $R^A$ and $R^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.5, 6.0, 5.5, 5.0, or lower), or by agents such as enzymes that can act as a general acid.

Linkers according to the present invention include moieties comprising two or more carbon molecules such as, for example, ethylenediamine, ethyleneglycol, glycine, beta-alanine and polyethylene glycol (PEG) of molecular weight about 44 to about 200 kD. Further, it is to be understood from the present disclosure that the platinum moiety and/or the lipid may be modified to comprise functional groups for linking to the linker molecule.

In some embodiments of the various aspects disclosed herein, the linker is —X—$CH_2$—$X_2$—$X_1$—, wherein X is NH; $X_1$ is C(O)O, C(O)NH, O($CH_2$)—O, NH, or O; $X_2$ is ($CH_2$)$_n$ or C(O); and n is 0, 1, 2, 3, 4, or 5.

In some other embodiments, the linker is —($CH_2$)$_n$O—, —($CH_2$)$_n$NHC(O)O—, —($CH_2$)$_n$OC(O)NH—, —($CH_2$)$_n$C(O)NH($CH_2$)$_m$O—, —($CH_2$)$_n$O($CH_2$)$_m$O—, —($CH_2$)$_n$O(O)—, —($CH_2$)$_n$NHC(O)($CH_2$)$_m$O—, or —($CH_2$)$_n$C(O)O—; and n and m are independently 0, 1, 2, 3, 4, or 5.

In still some other embodiments, the linker is —$X_3$—$X_4X_5$—$X_6$—, wherein $X_3$ is CH, $CH_2$, or O; and $X_4$, $X_5$ and $X_6$ are independently same or different and are —$CH_2$O— or O.

In yet some other embodiments, the linker is —$CH_2$O—.

In some embodiments, the linker is selected from the group consisting of a bond, —O—, $NHCH_2CH_2NHC(O)$—, —$NHCH_2CH_2NHC(O)O$—, —$NHCH_2CH_2$—, —$NHCH_2CH_2O$—, —$NHCH_2C(O)$—, —$NHCH_2C(O)O$—, —$NHCH_2C(O)OCH_2CH_2CH_2$—, —$NHCH_2C(O)OCH_2CH_2CH_2O$—, —$NHCH_2C(O)NH$—, —$CH_2CH_2$—, —$CH_2CH_2O$—, —$CH_2CH_2NHC(O)$—, —$CH_2CH_2NHC$ (O)O—, —CH$_2$CH$_2$O—, —CH$_2$C(O)NHCH$_2$CH$_2$—, —CH$_2$C(O)NHCH$_2$CH$_2$O—, —CH$_2$CH$_2$OCH$_2$CH$_2$—, —CH$_2$CH$_2$OCH$_2$CH$_2$O—, —CH$_2$C(O)—, —CH$_2$C(O))—, —CH$_2$CH$_2$CH$_2$—, —CH$_2$CH$_2$CH$_2$O—, =CH—CH=CH$_2$—, =CH—CH=CHCH$_2$O—, —CH=CHCH$_2$—, —CH=CHCH$_2$O—, —OCH$_2$CH$_2$O—, —CH$_2$—, —CH$_2$O—, —NHC(O)CH$_2$—, —NHC(O)CH$_2$O—, —C(O)CH$_2$—, —C(O)CH$_2$O—, —OC(O)CH$_2$—, —OC(O)CH$_2$O—, —C(O)CH$_2$CH$_2$C(O)NHCH$_2$CH$_2$—, —OC(O)CH$_2$CH$_2$C(O)NHCH$_2$CH$_2$—, —C(O)CH$_2$CH$_2$C(O)NHCH$_2$CH$_2$O—, —OC(O)CH$_2$CH$_2$C(O)NHCH$_2$CH$_2$O—, —C(O)CH$_2$CH$_2$C(O)NHCH$_2$CH$_2$NHC(O)—, —OC(O)CH$_2$CH$_2$C(O)NHCH$_2$CH$_2$NHC(O)—, —C(O)CH$_2$CH$_2$C(O)NHCH$_2$CH$_2$NHC(O)O—, —OC(O)CH$_2$CH$_2$C(O)NHCH$_2$CH$_2$NHC(O)O—, and any combinations thereof.

In some embodiments, the platinum based compounds disclosed herein are represented by Formula (I):

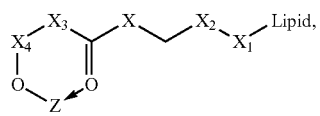

(I)

wherein,
X is NH;
X$_1$ is selected from a group comprising COOH, CONH$_2$, O—(CH$_2$)$_n$—OH, NH$_2$ and OH; X$_2$ is (CH$_2$)$_n$ or CO;
X$_3$ is selected from a group comprising (CH$_2$)$_n$, CH$_2$—NH and C$_4$H$_8$;
X$_4$ is CO or —CH—CH$_3$;
Z is a platinum containing compound, wherein the platinum forms a part of Formula I ring; and
N is 0, 1, or 2.

In some other embodiments, the platinum based compounds disclosed herein are represented by Formula (II):

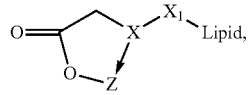

(II)

wherein,
X is NH or N—CH$_2$COO$^-$;
X$_1$ is selected from a group comprising —(CH$_2$)$_n$OH, —(CH$_2$)$_n$NHCOOH, —(CH$_2$)$_n$CONH(CH$_2$)$_n$OH, (CH$_2$)$_n$O(CH$_2$)$_n$OH, (CH$_2$)$_n$C=O, —(CH$_2$)$_n$NHCO(CH$_2$)$_n$OH and (CH$_2$)$_n$—COOH;
Z is platinum containing compound, wherein the platinum forms a part of Formula II ring; and
N is 0, 1, or 2.

In some embodiments, the platinum based compounds disclosed herein are represented by Formula (III):

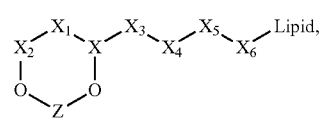

(III)

wherein,
X is selected from a group comprising S$^+$, C, S$^+$=O, N$^+$H and P=O;
X$_1$ is selected from a group comprising —CH, —CH$_2$ and —CH$_2$O;
X$_2$ is C=O;
X$_3$ is selected from CH, CH$_2$ or O;
X$_4$, X$_5$, X$_6$ is selected from —CH$_2$O or O
Z is platinum containing compound, wherein the platinum forms a part of Formula III ring.

In some embodiments, the platinum based compounds disclosed herein are represented by Formula (IV):

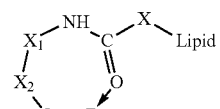

(IV)

wherein,
X is CH$_2$OH;
X$_1$ is (CH$_2$)$_n$;
X$_2$ is C=O;
Z is platinum containing compound, wherein the platinum forms a part of Formula IV ring; and
N is 0, 1, or 2.

Exemplary compounds of Formula (I) include, but are not limited to, the following compounds:

Compound 1

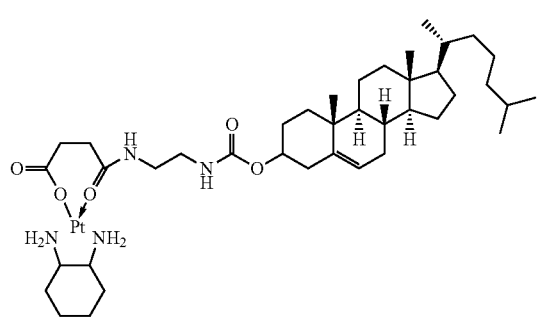

C$_{40}$H$_{69}$N$_4$O$_5$Pt
Mol. Wt.: 881.08

Compound 2

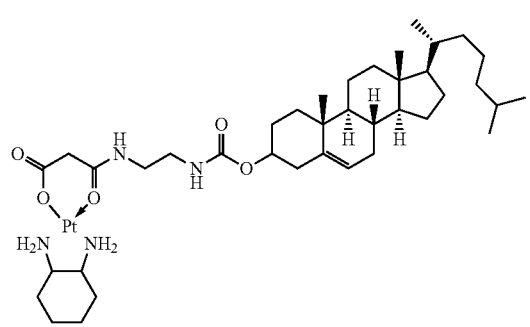

C$_{39}$H$_{67}$N$_4$O$_5$Pt
Mol. Wt.: 867.05

-continued
Compound 3
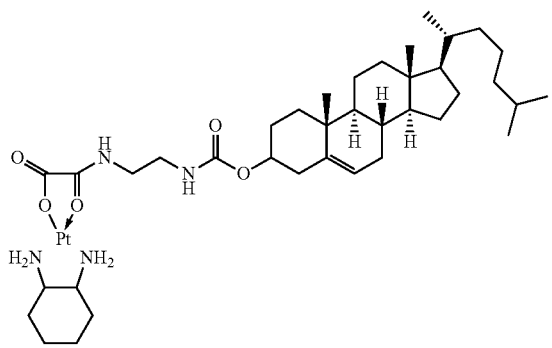
C38H65N4O5Pt
Mol. Wt.: 853.02
Compound 4
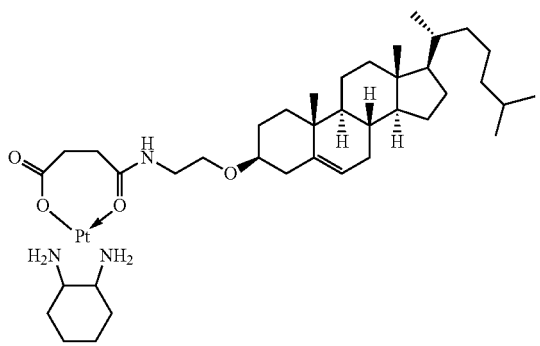
C39H68N3O4Pt
Mol. Wt.: 838.05
Compound 5
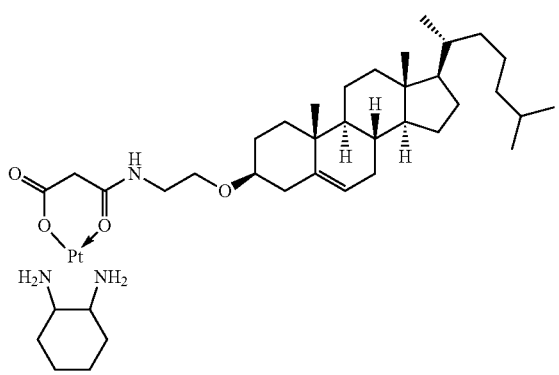
C38H66N3O4Pt
Mol. Wt.: 824.03
Compound 6
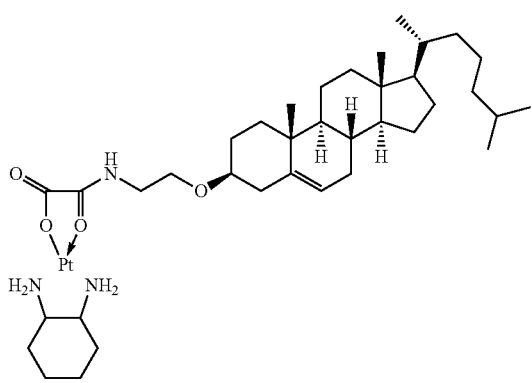
C37H64N3O4Pt
Mol. Wt.: 810.00
Compound 7
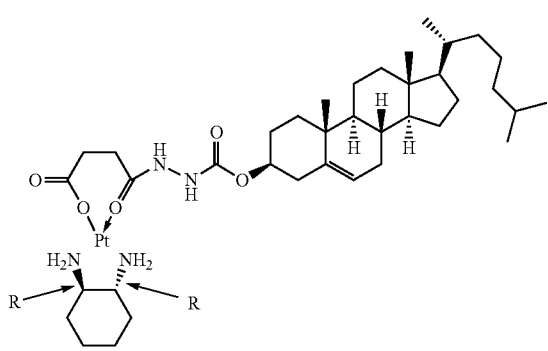
C40H69N4O5Pt
Mol. Wt.: 881.08
Compound 8
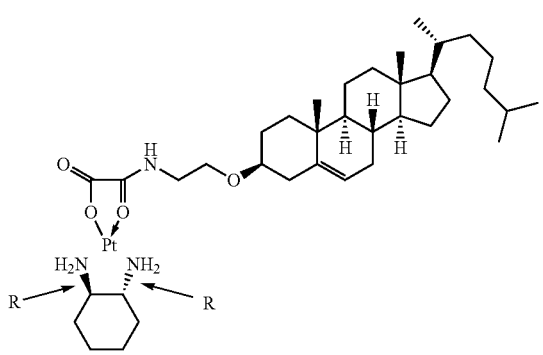
C37H64N3O4Pt
Mol. Wt.: 810.00

-continued
Compound 9
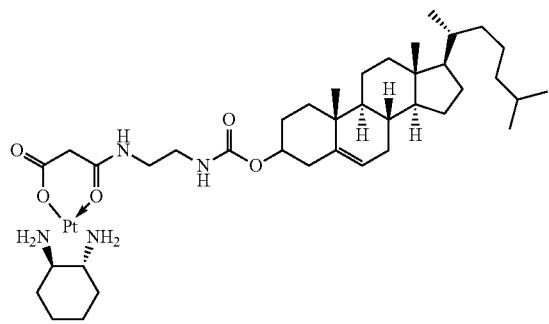
C<sub>39</sub>H<sub>67</sub>N<sub>4</sub>O<sub>5</sub>Pt
Mol. Wt.: 867.05
Compound 10
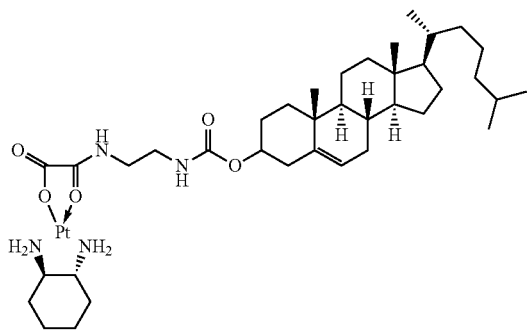
C<sub>38</sub>H<sub>65</sub>N<sub>4</sub>O<sub>5</sub>Pt
Mol. Wt.: 853.02
Compound 11
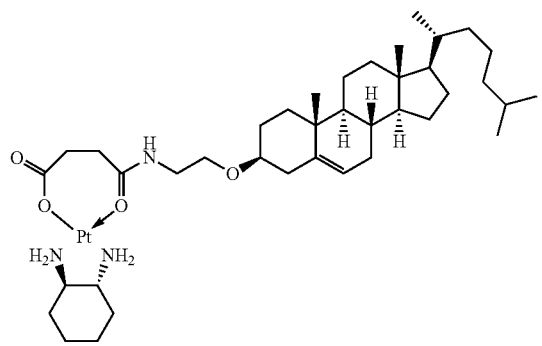
C<sub>39</sub>H<sub>68</sub>N<sub>3</sub>O<sub>4</sub>Pt
Mol. Wt.: 838.05
Compound 12
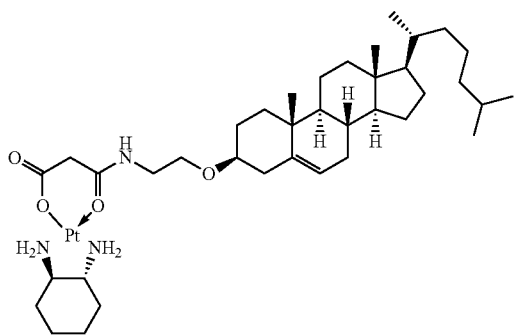
C<sub>38</sub>H<sub>66</sub>N<sub>3</sub>O<sub>4</sub>Pt
Mol. Wt.: 824.03
Compound 13
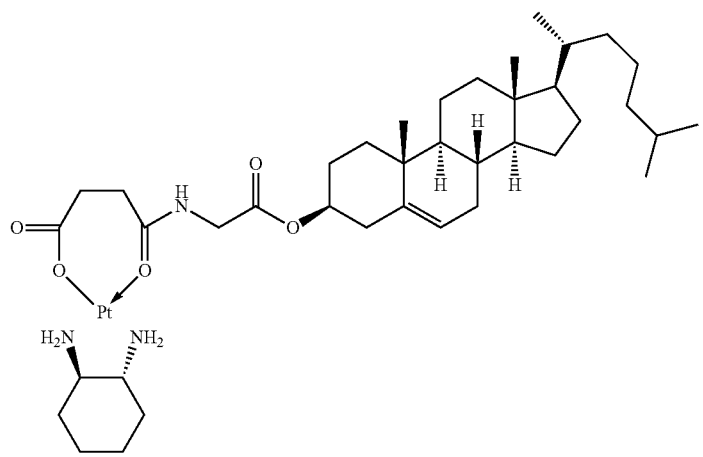
C<sub>39</sub>H<sub>66</sub>N<sub>3</sub>O<sub>5</sub>Pt
MW: 852.04

-continued
Compound 14
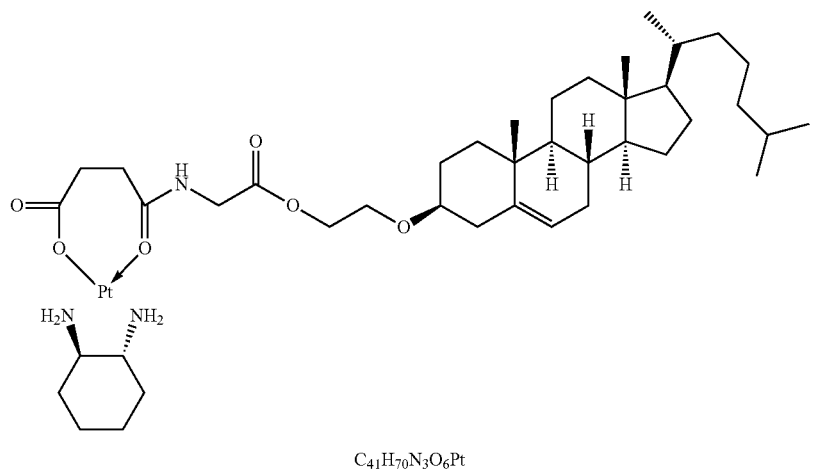
C$_{41}$H$_{70}$N$_3$O$_6$Pt
MW: 896.09
Compound 15
Compound 16
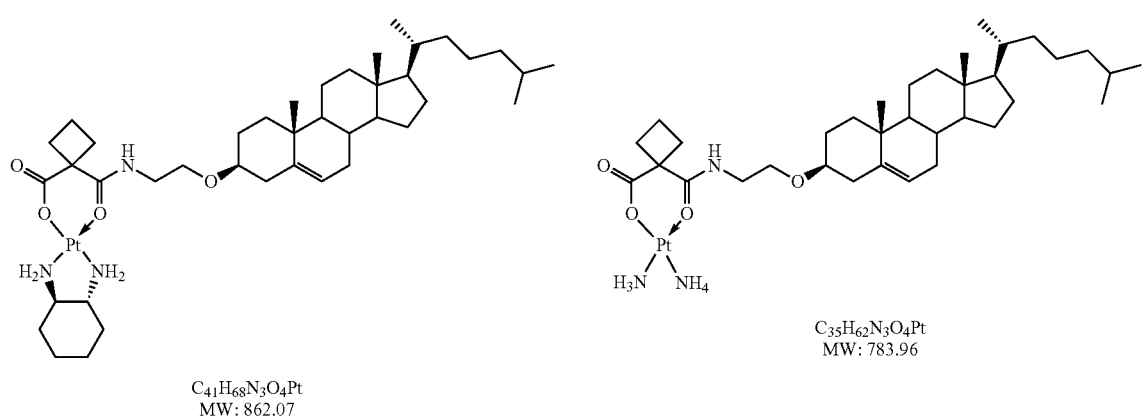
C$_{41}$H$_{68}$N$_3$O$_4$Pt
MW: 862.07
C$_{35}$H$_{62}$N$_3$O$_4$Pt
MW: 783.96
Compound 17
Compound 18
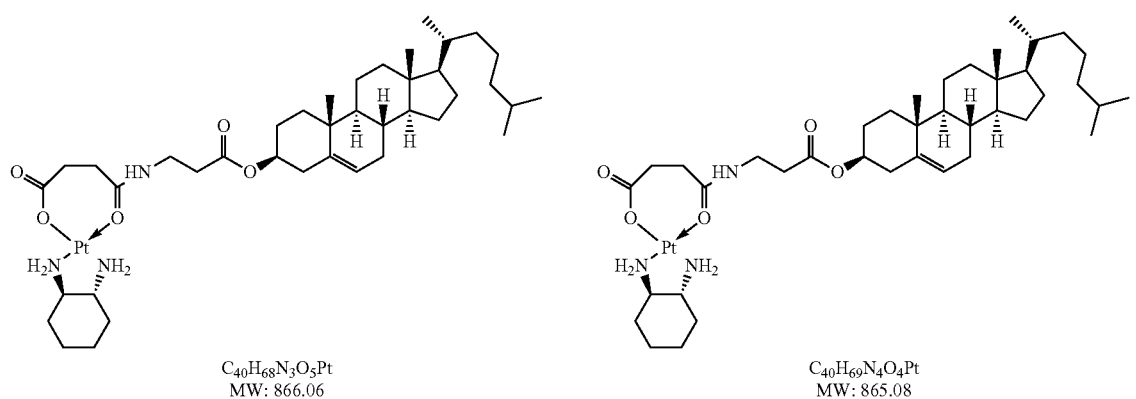
C$_{40}$H$_{68}$N$_3$O$_5$Pt
MW: 866.06
C$_{40}$H$_{69}$N$_4$O$_4$Pt
MW: 865.08

-continued
Compound 19
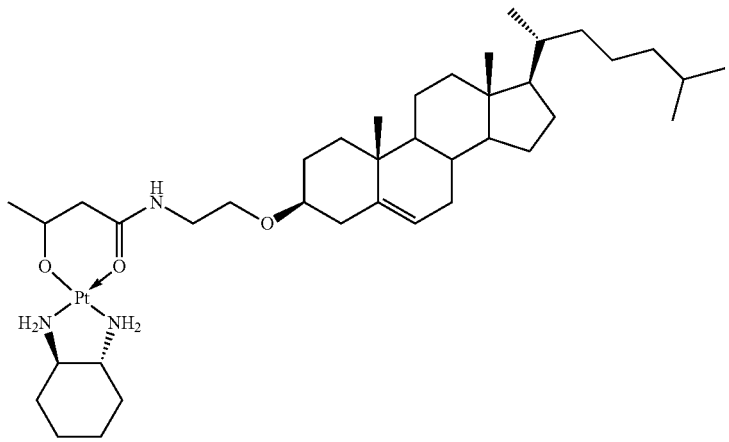
C$_{39}$H$_{68}$N$_3$O$_3$Pt
MW: 822.05
Compound 20
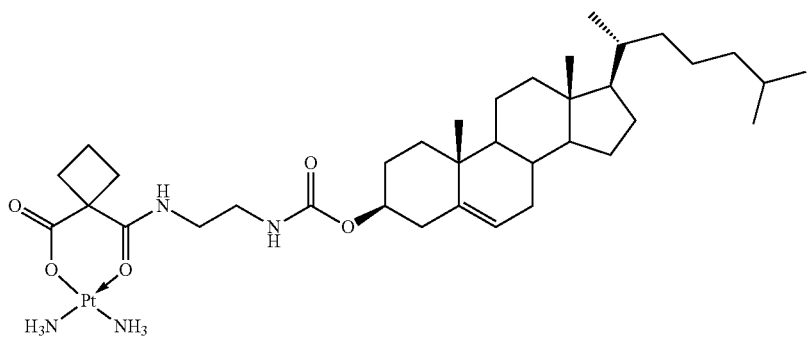
C$_{36}$H$_{63}$N$_4$O$_5$Pt
MW: 826.99
Compound 21
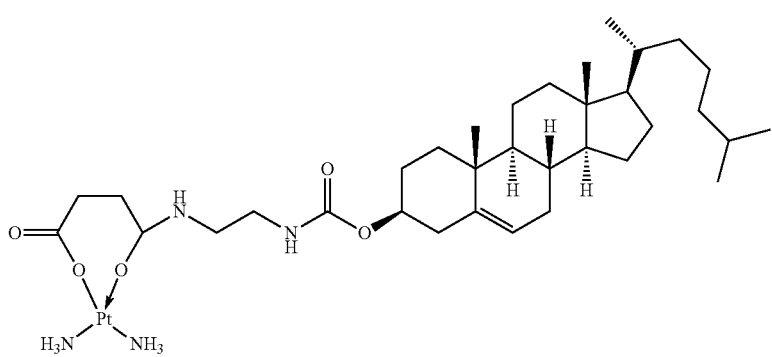
C$_{34}$H$_{61}$N$_4$O$_5$Pt
Mol. Wt.: 800.43

Exemplary compounds of Formula (II) include, but are not limited to, the following compounds:
Compound 25
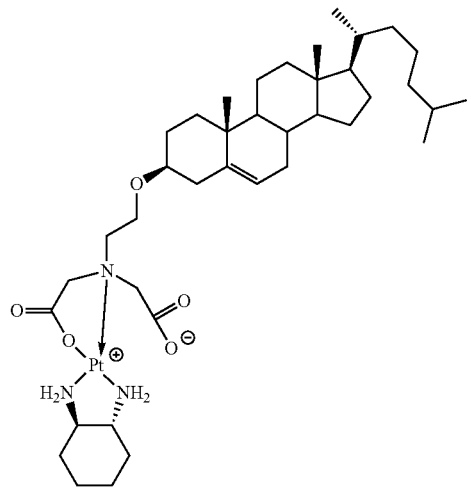
Compound 26
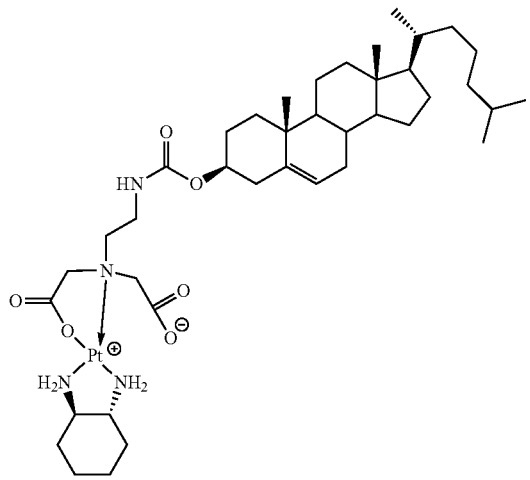
Compound 27
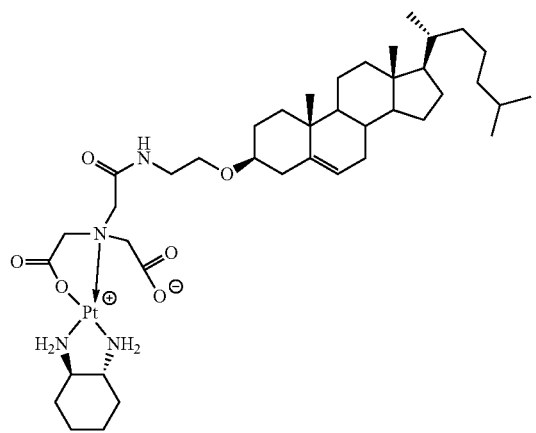
Compound 28
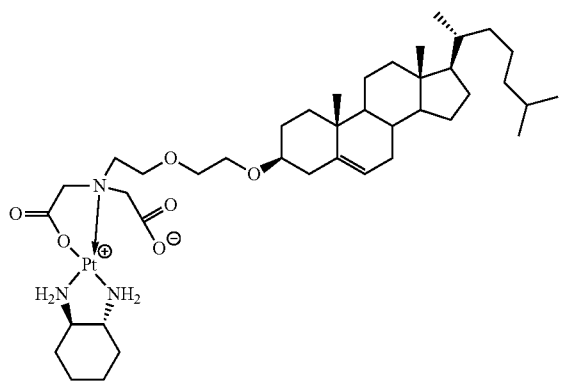
Compound 29
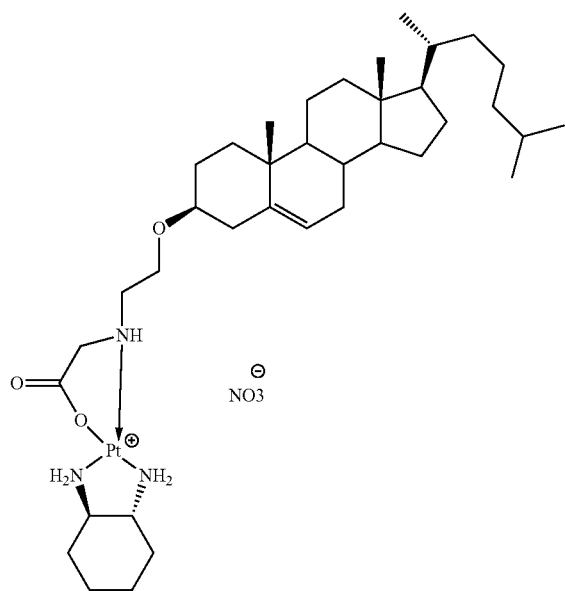

-continued
Compound 38
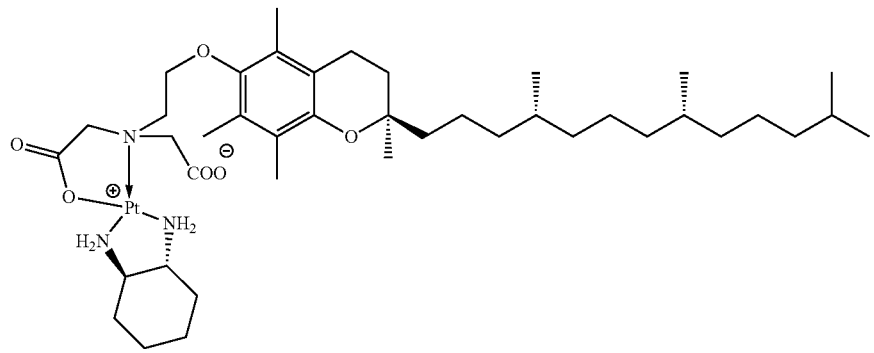
Lipid = alpha tocopherol
Compound 39
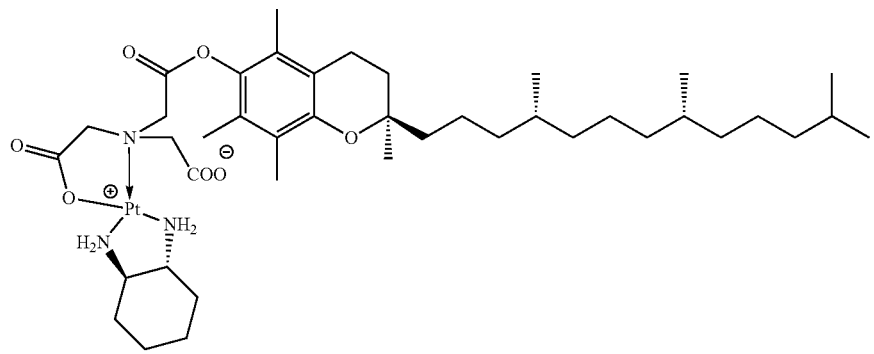
Lipid = alpha tocopherol
Compound 40
Compound 41
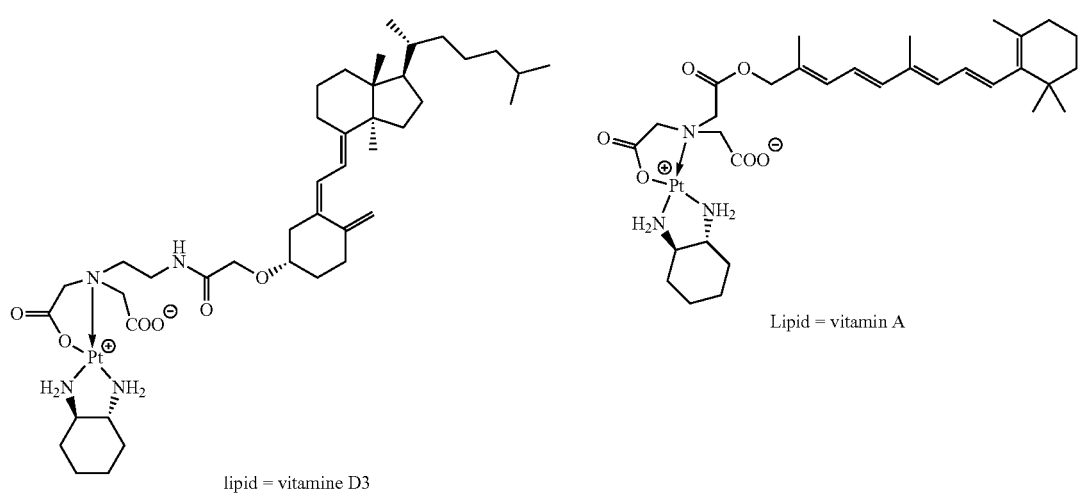
lipid = vitamine D3
Lipid = vitamin A Compound 42
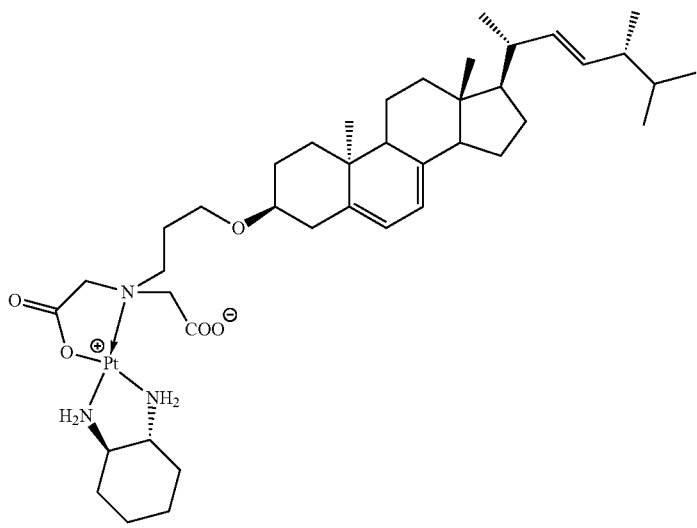
Lipid = Lumisterol
Exemplary compounds of Formula (III) include, but are not limited to, the following compounds:
Compound 66
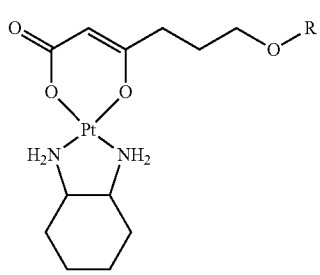
R = Lipid, Aromatic
Compound 67
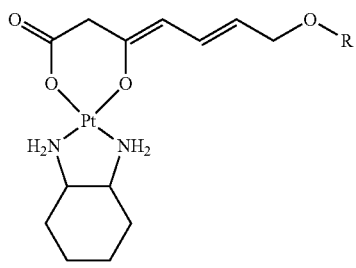
R = Lipid, Aromatic
Compound 68
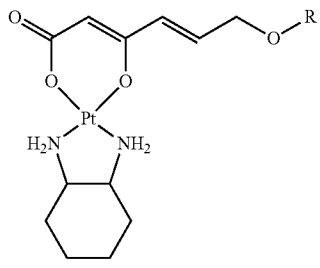
R = Lipid, Aromatic
Compound 69
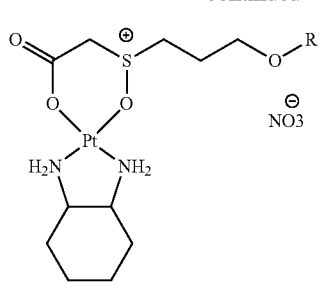
R = Lipid, Aromatic
Compound 70
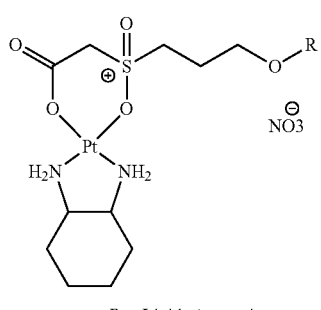
R = Lipid, Aromatic
Compound 72
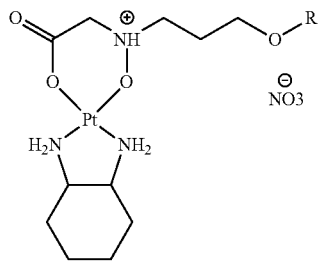
R = Lipid, Aromatic Compound 71

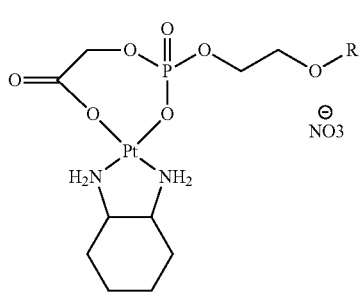

R = Lipid, Aromatic

Exemplary compounds of Formula (IV) include, but are not limited to, the following compounds:

The disclosure also provides the following compounds:

Compound 23

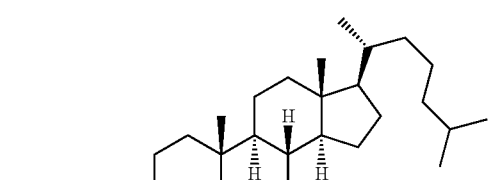

$C_{39}H_{65}N_3O_6Pt$
MW = 867.03

Compound 22

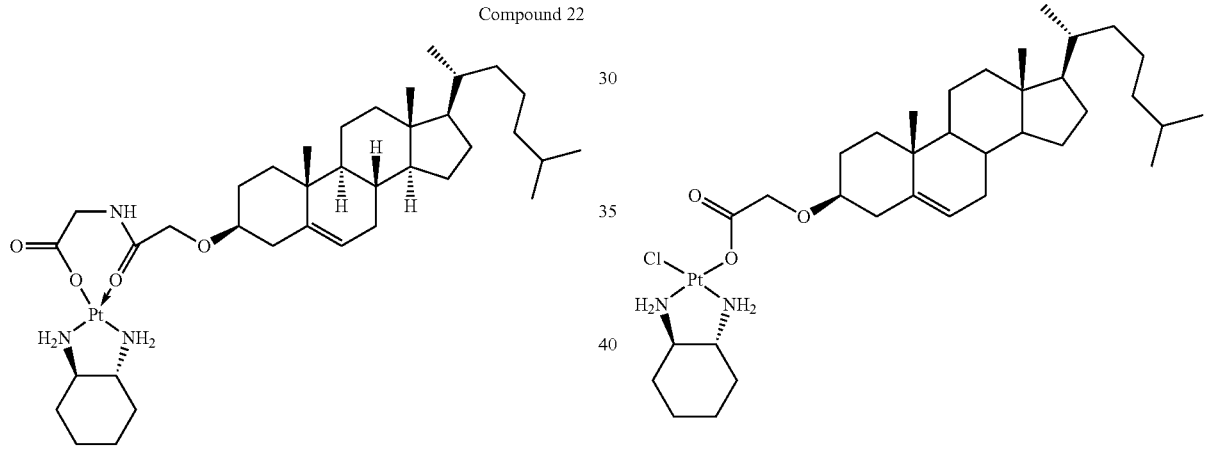

$C_{38}H_{66}N_3O_3Pt$
Mol. Wt.: 810.00

Compound 30

In some embodiments, the platinum moiety of the platinum based complexes of the present disclosure is a Platinum (IV) compound. Said complexes having Platinum (IV) compounds are represented as follows:

Compound 96

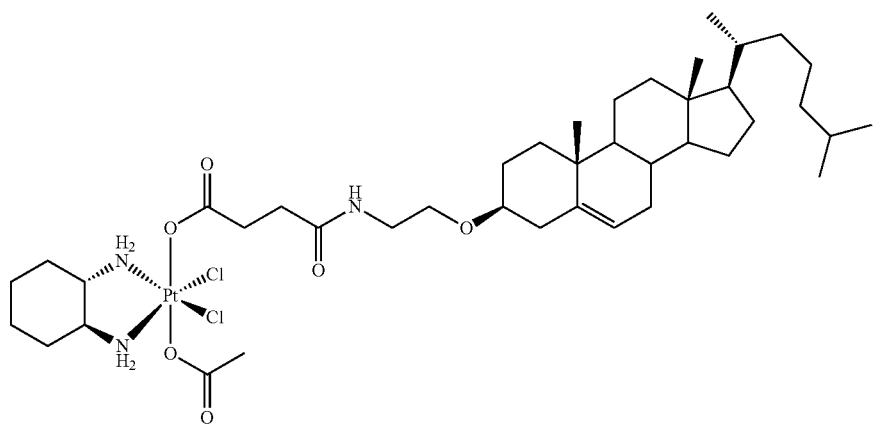

-continued
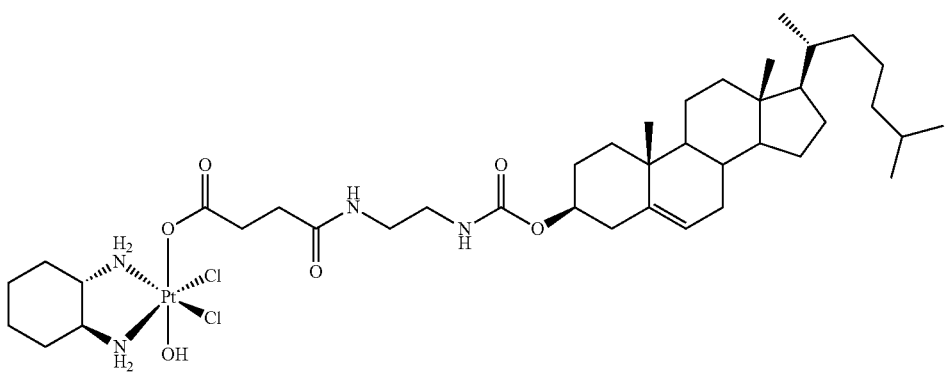
Compound 97
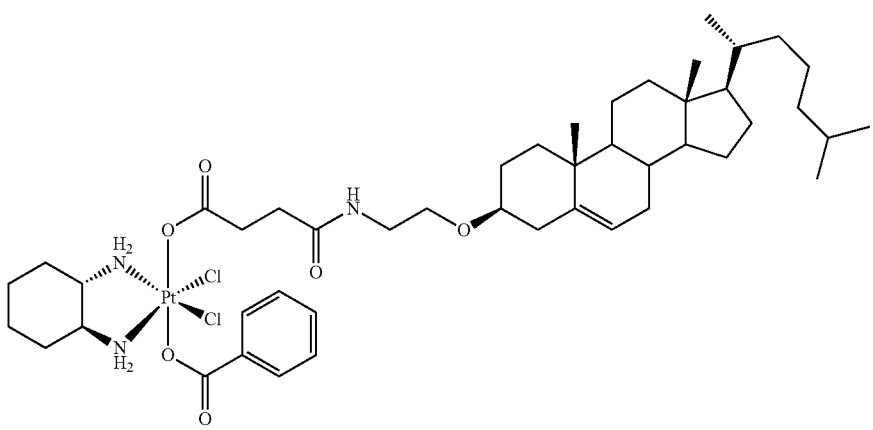
Compound 98
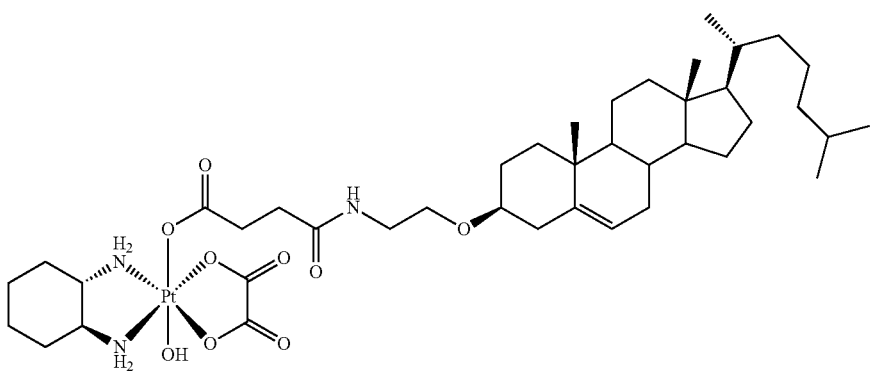
Compound 99
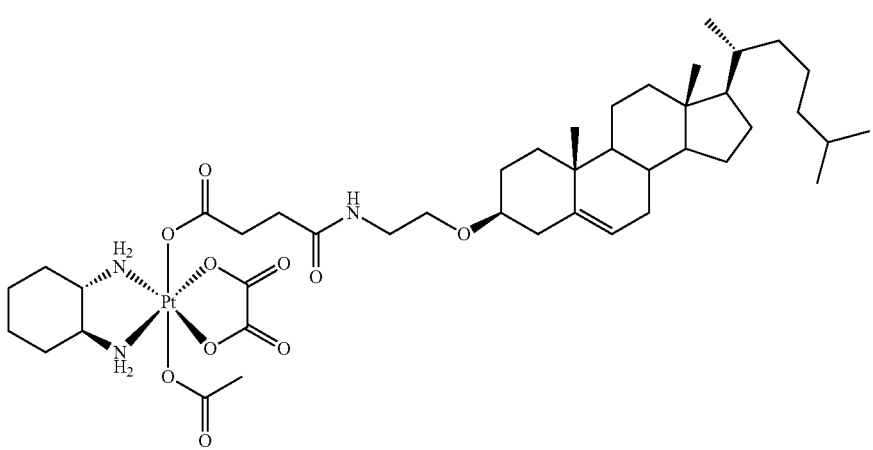
Compound 100

In some embodiments of the various aspects disclosed herein, the disclosure provides a platinum (II) compound of Formula (V):

(V)

wherein $X_1$, $X_2$, $X_3$ and $X_4$ are selected independently from the group consisting of O, P, S, Se, Cl, N, C, O-A, O—B, DACH, halides and chelated or non-chelated dicarboxylato linkage group, and any combinations thereof;

wherein A and B are selected independently from the group consisting of C, P, S, N, and any combinations thereof; and wherein $X_4$, is optional.

In some embodiments of the various aspects disclosed herein, the platinum (II) compound of Formula (V) is selected from a group comprising Compounds 43-65 and 73-85 and Compound 95. In a preferred embodiment, the Pt(II) compound is DACH-Pt.

Compound 43

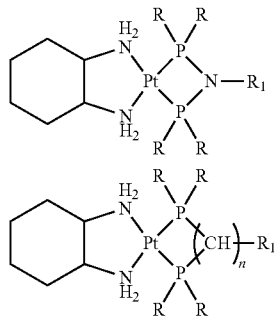

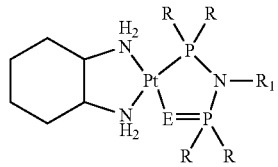

n = 1, 2
Compound 44 (n = 1) and
Compound 45 (n = 2)

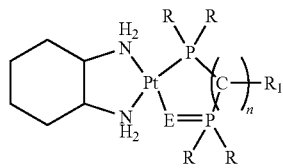

R = Alkyl or Aryl
Compounds 46 (E = O),
47 (E = S) and 48 (E = Se)

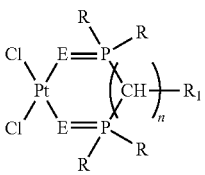

R = Alkyl or Aryl
Compounds 49 (E = O),
50 ( E = S) and
51 (E = Se)

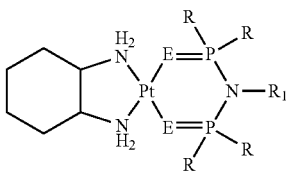

R = Alkyl or Aryl
Compounds 52 (E = O),
53 (E = S) and
54 (E = Se)

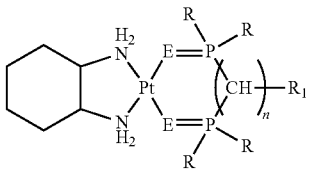

R = Alkyl or Aryl
Compounds 55 (E = O),
56 (E = S) and 57 (E = Se)

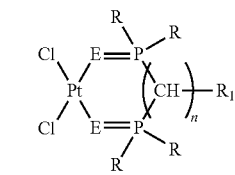

R = Alkyl or Aryl; n = 1, 2
Compounds 58 (E = O), 59 (E = S)
and 60 (E = Se)

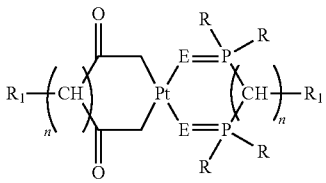

R = Alkyl or Aryl; n = 0, 1
Compounds 61 (E = S) and
62 (E = Se)

Compound 63

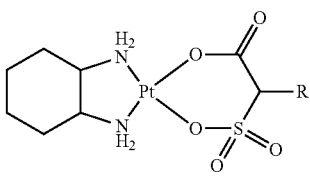

Compound 64

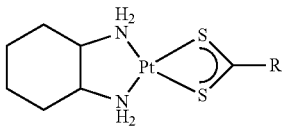

Compound 65

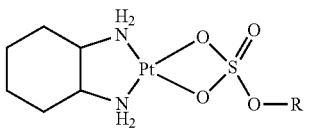

Compound 73
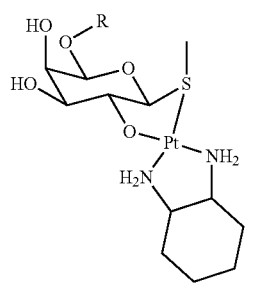
R = Aryl, Alkyl, Lipid
Compound 74
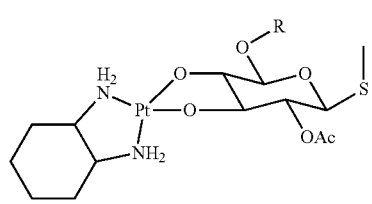
R = Aryl, Alkyl, Lipid
Compound 75
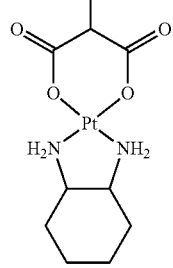
Compound 76
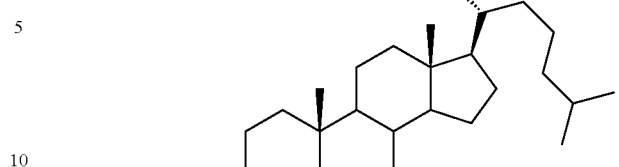
Compound 77
Compound 78
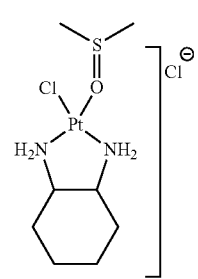

Compound 79
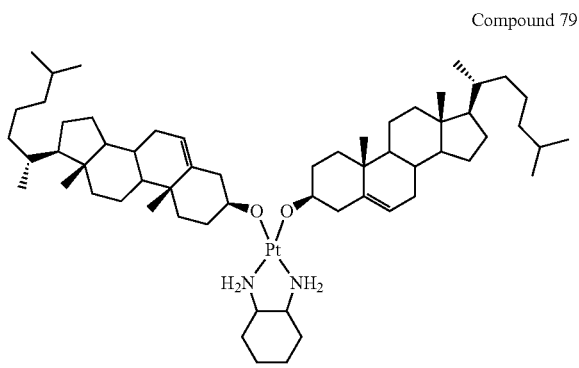

Compound 80
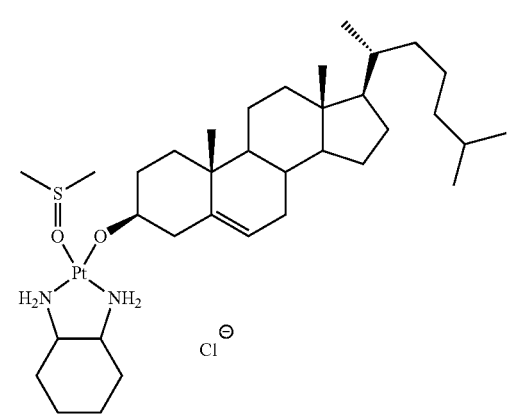

Compound 81
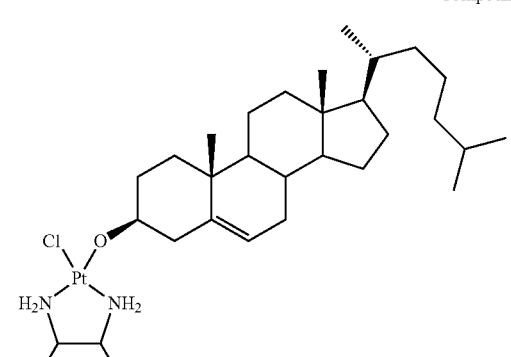

Compound 82
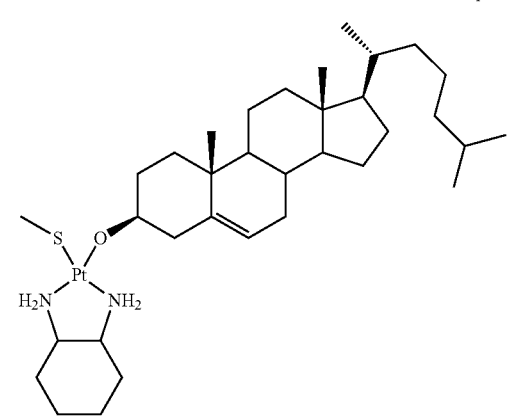

Compound 83
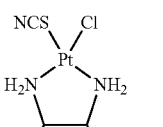

Compound 84
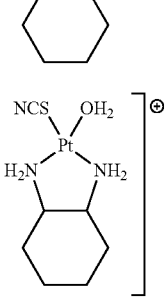

Compound 85
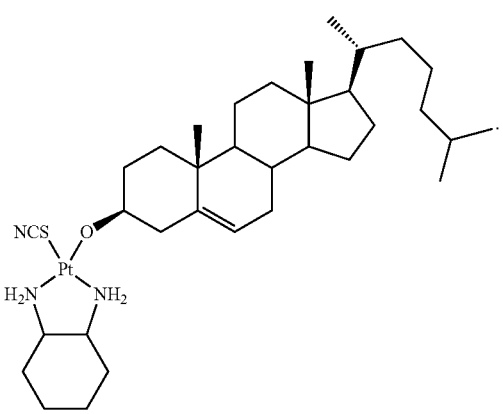

In the above compounds, $R^1$ is a -linker-lipid and n is 1 unless defined otherwise.

In still another embodiment, a Platinum (II) compound [Compound 95] is also provided by the present disclosure.

Compound 95
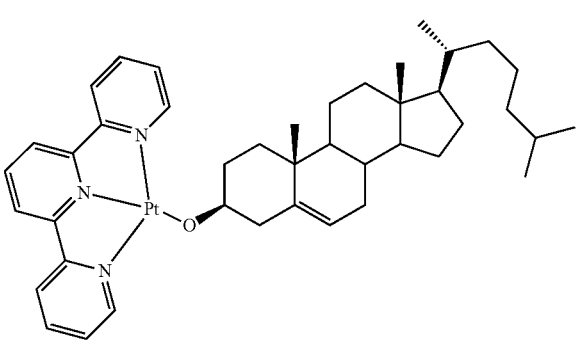

Synthesis of some exemplary compounds of Formula (V) is described at in the Examples section.

Figure 8:
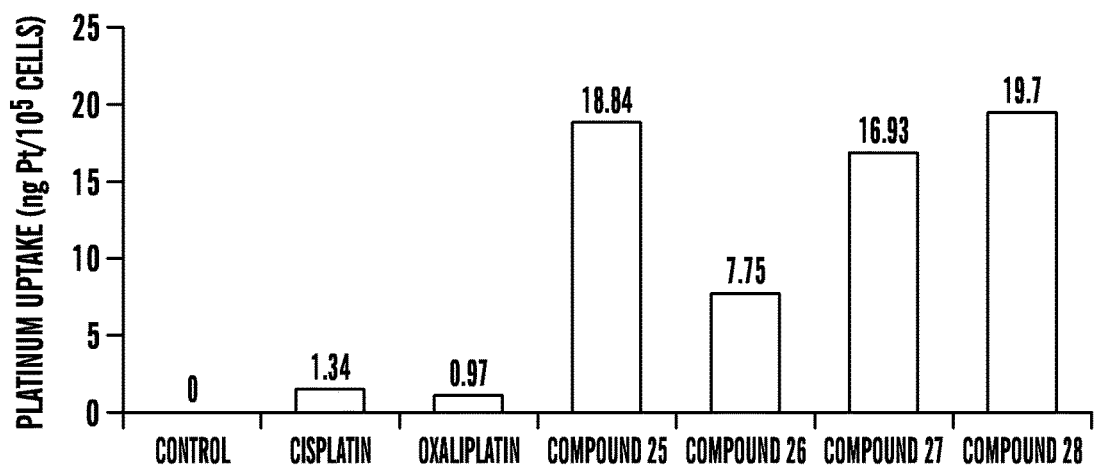
FIG. 8 shows cellular uptake of platinum compounds. Cells were incubated with 50 μM concentration of platinum compounds for 5 hours. The amount of platinum accumulated in cells was measured by AAS and expressed as ng of platinum accumulated per 10$^5$ cells.

Without wishing to be bound by a theory, compounds disclosed herein have higher uptake of platinum in cancer cells relative to cisplatin and oxaliplatin. As shown in FIG. 8, the uptake of cisplatin and oxaliplatin are similar in MDA-MB-231 cells. However, all the exemplary compounds tested showed higher uptake (~7-20 fold). These results indicate that when administered at platinum equivalent concentrations, the uptake of exemplary compounds is significantly higher in comparison to cisplatin or oxaliplatin in cancer cells. In some embodiements, the compounds disclosed herein have about 25%, about 50%, about 75%, about 1-fold, about 5-folds, about 10-folds, about 15-folds, about 20-folds, about 25-folds or higher platinum uptake in cancer cells relative to cisplatin or oxaliplatin at equivalent dosage.

In addition, the compounds disclosed herein also have higher accumulation of platinum in tissue, such as, but not limited to a tumor, relative to cisplatin and oxaliplatin when dosed at equivalent amount. For example, the compounds disclosed herein have about 25%, about 50%, about 75%, about 1-fold, about 5-folds, about 10-folds, about 15-folds, about 20-folds, about 25-folds or higher platinum accumulation tissue relative to cisplatin or oxaliplatin when dosed at equivalent amounts.

The present disclosure relates to the synthesis of a series of platinum based nanoparticles wherein, the diamminocyclohexyl-Pt (DACH-Pt) has a monocarboxylated covalent bond through a carboxylic acid and a co-ordination bond with amide oxygen. Dicarbonyl molecules (dicarboxylic acids) such as succinic acid, malonic acid and oxalic acid are used which eventually form seven, six and five member rings with platinum (II) respectively. The linker between the platinum ring and cholesterol helps in forming linkages selected from a group comprising carbamate linkage (compounds 1, 2, 3), ether linkage (compounds 6, 4, 5) or the likes or any combinations thereof. Therefore, some of the embodiments of the present disclosure relates to compounds represented by the general backbone: lipid-linker-dicarbonyl. These molecules are used to complex platinum compounds such as DACH-Pt, oxaliplatin, cisplatin, platinum containing carbenes or other platinates and platinum compounds, through covalent and/or coordination bonds.

In an embodiment of the present disclosure, several variants of platinum based compounds such as racemates, diastereomers and the likes are also provided (for example, Compounds 1-6).

In an embodiment of the present disclosure, any molecule that has two carbonyl groups may be used. In one embodiment, the dicarbonyl molecule is a dicarboxylic acid, such as, for example, succinic acid, malonic acid or oxalic acid.

The disclosure also provides particles comprising one or more of the platinum based compounds described herein. Generally, the particle disclosed herein can be of any shape or form, e.g., spherical, rod, elliptical, cylindrical, capsule, or disc; and these particles can be part of a network or an aggregate.

In some embodiments, the particle is a microparticle or a nanoparticle. As used herein, the term "microparticle" refers to a particle having a particle size of about 1 µm to about 1000 µm. As used herein, the term "nanoparticle" refers to particle having a particle size of about 0.1 nm to about 1000 nm. Generally, the particles have any size from nm to millimeters. In some embodiments, the particles can have a size ranging from about 5 nm to about 5000 nm. In some embodiments, the particles have an average diameter of from about 50 nm to about 2500 nm. In some embodiments, the particles have an average diameter of from about 100 nm to about 2000 nm. In some embodiments, the particles have an average diameter of from about 150 nm to about 1700 nm. In some embodiments, the particles have an average diameter of from about 200 nm to about 1500 nm. In some embodiment, the particles have an average diameter of about 260 nm. In one embodiment, the particles have an average diameter of about 30 nm to about 150 nm. In some embodiments, the particle have an average diameter of about 100 nm to about 1000 nm, from about 200 nm to about 800 nm, from about 200 nm to about 700 nm, or from about 300 nm to about 700 nm.

Figure 5:
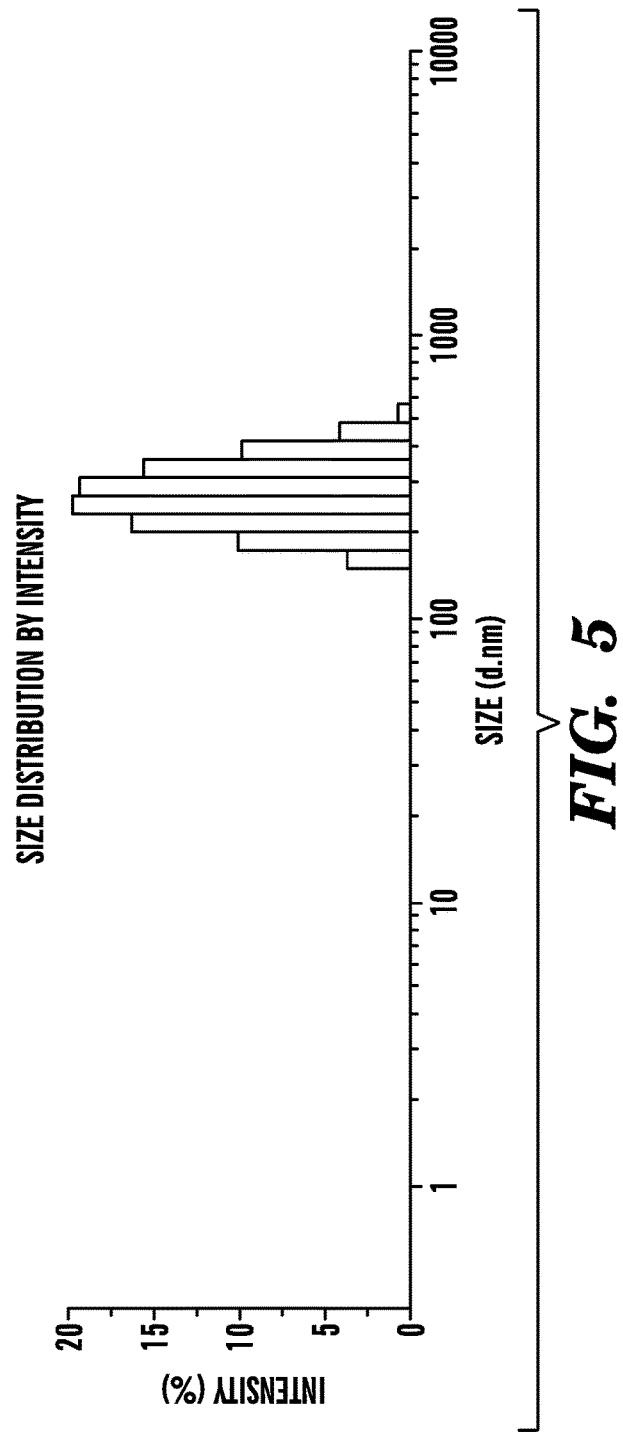
FIG. 5 depicts the physicochemical characterization of nanoparticles. DLS plot is represented which show the distribution of particle size.

In some embodiments, the particle has an average size of about 50 to about 1000 nm. In a further embodiment, the nanoparticles of the present invention are in the range of about 50 to about 500 nm. In another embodiment, the nanoparticles of the present invention are in the range of about 50 to about 500 nm (FIG. 5). In one embodiment, the particle has a sie of about 500 nm.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In addition to the platinum compounds disclosed herein, the particle can comprise co-lipids and/or stabilizers. Additional lipids can be included in the partilces for a variety of purposes, such as to prevent lipid oxidation, to stabilize the bilayer, to reduce aggregation during formation or to attach ligands onto the particle surface. Any of a number of additional lipids and/or other components can be present, including amphipathic, neutral, cationic, anionic lipids, and programmable fusion lipids. Such lipids and/or components can be used alone or in combination. One or more components of particle can comprise a ligand, e.g., a targeting ligand.

In some embodiments, the particle further compises a phospholipid. Without limitations, the phospholipids can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl cholines with defined acyl groups having 6 to 22 carbon atoms, phosphatidyl ethanolamines, phosphatidyl inositols, phosphatidic acids, phosphatidyl serines, sphingomyelin or phosphatidyl glycerols. Suitable phospholipids include, but are not limited to, phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, dioleyl-phosphatidylcholine, dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoylphosphatidylethanolamine 4-(N-maleimidomethyl)-cyclohexane-1-carboxylate (DOPE-mal), 1-stearoyl-2-oleoyl phosphatidylcholine (SOPC), 1,2-distearoyl-sn-glycem-3-phosphoethanolamine (DSPE), and any combinations thereof. Non-phosphorus containing lipids can also be used. These include, e.g., stearylamine, docecylamine, acetyl palmitate, fatty acid amides, and the like. Other phosphorus-lacking compounds, such as sphingolipids, glycosphingolipid families, diacylglycerols, and β-acyloxyacids, can also be used In some embodiments, the phospholipid in the particle is selected from the group consisting of 1,2-Didecanoyl-sn-glycero-3-phosphocholine; 1,2-Dierucoyl-sn-glycero-3-phosphate (Sodium Salt); 1,2-Dierucoyl-sn-glycero-3-phosphocholine; 1,2-Dierucoyl-sn-glycero-3-phosphoethanolamine; 1,2-Dierucoyl-sn-glycero-3[Phospho-rac-(1-glycerol) (Sodium Salt); 1,2-Dilinoleoyl-sn-glycero-3-phosphocholine; 1,2-Dilauroyl-sn-glycero-3-phosphate (Sodium Salt); 1,2-Dilauroyl-sn-glycero-3-phosphocholine; 1,2-Dilauroyl-sn-glycero-3-phosphoethanolamine; 1,2-Dilauroyl-sn-glycero-3[Phospho-rac-(1-glycerol) (Sodium Salt); 1,2-Dilauroyl-sn-glycero-3[Phospho-rac-(1-glycerol) (Ammonium Salt); 1,2-Dilauroyl-sn-glycero-3-phosphoserine (Sodium Salt); 1,2-Dimyristoyl-sn-glycero-3-phosphate (Sodium Salt); 1,2-Dimyristoyl-sn-glycero-3-phosphocholine; 1,2-Dimyristoyl-sn-glycero-3-phosphoethanolamine; 1,2-Dimyristoyl-sn-glycero-3[Phospho-rac-(1-glycerol) (Sodium Salt); 1,2-Dimyristoyl-sn-glycero-3[Phospho-rac-(1-glycerol) (Ammonium Salt); 1,2-Dimyristoyl-sn-glycero-3[Phospho-rac-(1-glycerol) (Sodium/Ammonium Salt); 1,2-Dimyristoyl-sn-glycero-3-phosphoserine (Sodium Salt); 1,2-Dioleoyl-sn-glycero-3-phosphate (Sodium Salt); 1,2-Dioleoyl-sn-glycero-3-phosphocholine; 1,2-Dioleoyl-sn-glycero-3-phosphoethanolamine; 1,2-Dioleoyl-sn-glycero-3[Phospho-rac-(1-glycerol) (Sodium Salt); 1,2-Dioleoyl-sn-glycero-3-phosphoserine (Sodium Salt); 1,2-Dipalmitoyl-sn-glycero-3-phosphate (Sodium Salt); 1,2-Dipalmitoyl-sn-glycero-3-phosphocholine; 1,2-Dipalmitoyl-sn-glycero-3-phosphoethanolamine; 1,2-Dipalmitoyl-sn-glycero-3[Phospho-rac-(1-glycerol) (Sodium Salt); 1,2-Dipalmitoyl-sn-glycero-3[Phospho-rac-(1-glycerol) (Ammonium Salt); 1,2-Dipalmitoyl-sn-glycero-3-phosphoserine (Sodium Salt); 1,2-Distearoyl-sn-glycero-3-phosphate (Sodium Salt); 1,2-Distearoyl-sn-glycero-3-phosphocholine; 1,2-Distearoyl-sn-glycero-3-phosphoethanolamine; 1,2-Distearoyl-sn-glycero-3[Phospho-rac-(1-glycerol) (Sodium Salt); 1,2-Distearoyl-sn-glycero-3[Phospho-rac-(1-glycerol) (Ammonium Salt); 1,2-Distearoyl-sn-glycero-3-phosphoserine (Sodium Salt); Egg-PC; Hydrogenated Egg PC; Hydrogenated Soy PC; 1-Myristoyl-sn-glycero-3-phosphocholine; 1-Palmitoyl-sn-glycero-3-phosphocholine; 1-Stearoyl-sn-glycero-3-phosphocholine; 1-Myristoyl-2-palmitoyl-sn-glycero 3-phosphocholine; 1-Myristoyl-2-stearoyl-sn-glycero-3-phosphocholine; 1-Palmitoyl-2-myristoyl-sn-glycero-3-phosphocholine; 1-Palmitoyl-2-oleoyl-sn-glycero-3-phosphocholine; 1-Palmitoyl-2-oleoyl-sn-glycero-3-phosphoethanolamine; 1-Palmitoyl-2-oleoyl-sn-glycero-3[Phospho-rac-(1-glycero 1)] (Sodium Salt); 1-Palmitoyl-2-stearoyl-sn-glycero-3-phosphocholine; 1-Stearoyl-2-myristoyl-sn-glycero-3-phosphocholine; 1-Stearoyl-2-oleoyl-sn-glycero-3-phosphocholine; and 1-Stearoyl-2-palmitoyl-sn-glycero-3-phosphocholine. In some embodiments, the phospholipid is SPOC, egg PC, or Hydrogenated Soy PC (HSPC). In one, the phospholipid in the composition is HSPC.

In some embodiments, the particle further comprises a polyethylene glycol (PEG). The PEG can be included in the particle by itself or conjugated with a component present in the particle. For example, the PEG can be conjugated with the platinum based compound or a co-lipid/stablaizer component of the particle. In some embodiments, the PEG is conjugated with a co-lipid component of the particle. Without limitations, the PEG can be conjugated with any co-lipid. For example, the PEG conjugated co-lipid can be selected from the group consisting of PEG conjugated diacylglycerols and dialkylglycerols, PEG-conjugated phosphatidylethanolamine, PEG conjugated to phosphatidic acid, PEG conjugated ceramides (see, U.S. Pat. No. 5,885,613), PEG conjugated dialkylamines, PEG conjugated 1,2-diacyloxypropan-3-amines, and PEG conjugated to 1,2-distearoyl-sn-glycem-3-phosphoethanolamine (DSPE), and any combinations thereof. In some embodiments, the PEG conjugated lipid is 1,2-distearoyl-sn-glycem-3-phosphoethanolamine-N-[amino(polyethylene glycol)-2000] (DSPE-PEG2000).

In some embodiments, the particle further comprises a surfactant. Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

In some embodiments, th particle can further comprise acationic lipid. Exemplary cationic lipids include, but are not limited to, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.C1), 1,2-Dilinoleoyl-3-trimethylaminopropane chloride salt (DLin-TAP.C1), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech Gi), or a mixture thereof.

In some embodiments, the particle further comprises a non-cationic lipid. The non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof.

The conjugated lipids that inhibits aggregation of particles can also be included in the particles disclosed herein. Such lipids include, but ar not limited to, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be from 0.01 mol % to about 20 mol % or about 2 mol % of the total lipid present in the particle.

In some embodiments, the particle is in the form of a liposome, vesicle, or emulsion. As used herein, the term "liposome" encompasses any compartment enclosed by a lipid layer. Liposomes can have one or more lipid membranes. Liposomes can be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

In order to form a liposome the lipid molecules comprise elongated non-polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae. The lamellae are composed of two mono layer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane.

A liposome composition can be prepared by a variety of methods that are known in the art. See e.g., U.S. Pat. No. 4,235,871, No. 4,897,355 and No. 5,171,678; published PCT applications WO 96/14057 and WO 96/37194; Feigner, P. L. et al., *Proc. Natl. Acad. Sci., USA* (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757, content of all of which is incorporated herein by reference in its entirety.

The liposomes can be prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323, content of which is incorporated herein by reference in its entirety.

The particles can also be in the form of an emulsion. Emulsions are typically heterogenous systems of one liquid dispersed in another in the form of droplets (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the conjugate disclosed herein can be present as a solution in either the aqueous phase or the oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers can broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials can also be included in emulsion formulations and contribute to the properties of emulsions. These include, but are not limited to, fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The applications of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199).

Exemplary surfactants for inclusion in the particles disclosed herein include but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and triglycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs. Microemulsions have also been effective in the transdermal delivery of active components in both cosmetic and pharmaceutical applications. It is expected that the microemulsion compositions and formulations of the present invention will facilitate the increased systemic absorption of the platinum based compounds from the gastrointestinal tract, as well as improve the local cellular uptake of platinum based compounds disclosed herein.

Without wishing to be bound by a theory, nanoparticles disclosed herein have higher uptake of platinum in cancer cells relative to cisplatin and oxaliplatin. In some embodiments, the nanoparticles disclosed herein have about 25%, about 50%, about 75%, about 1-fold, about 5-folds, about 10-folds, about 15-folds, about 20-folds, about 25-folds or higher platinum uptake in cancer cells relative to cisplatin or oxaliplatin at equivalent dosage.

In addition, the nanoparticles disclosed herein also have higher accumulation of platinum in tissue, such as, but not limited to a tumor, relative to cisplatin and oxaliplatin when dosed at equivalent amount. For example, the nanoparticles disclosed herein have about 25%, about 50%, about 75%, about 1-fold, about 5-folds, about 10-folds, about 15-folds, about 20-folds, about 25-folds or higher platinum accumulation tissue relative to cisplatin or oxaliplatin when dosed at equivalent amounts.

Figure 1B:
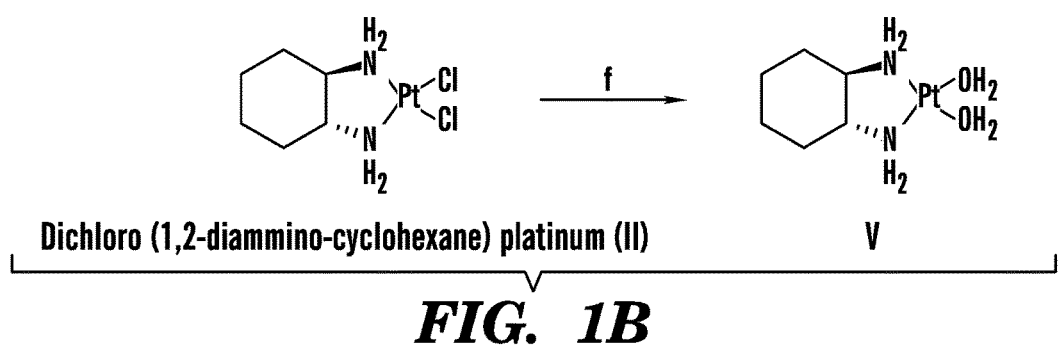
Figure 1C:
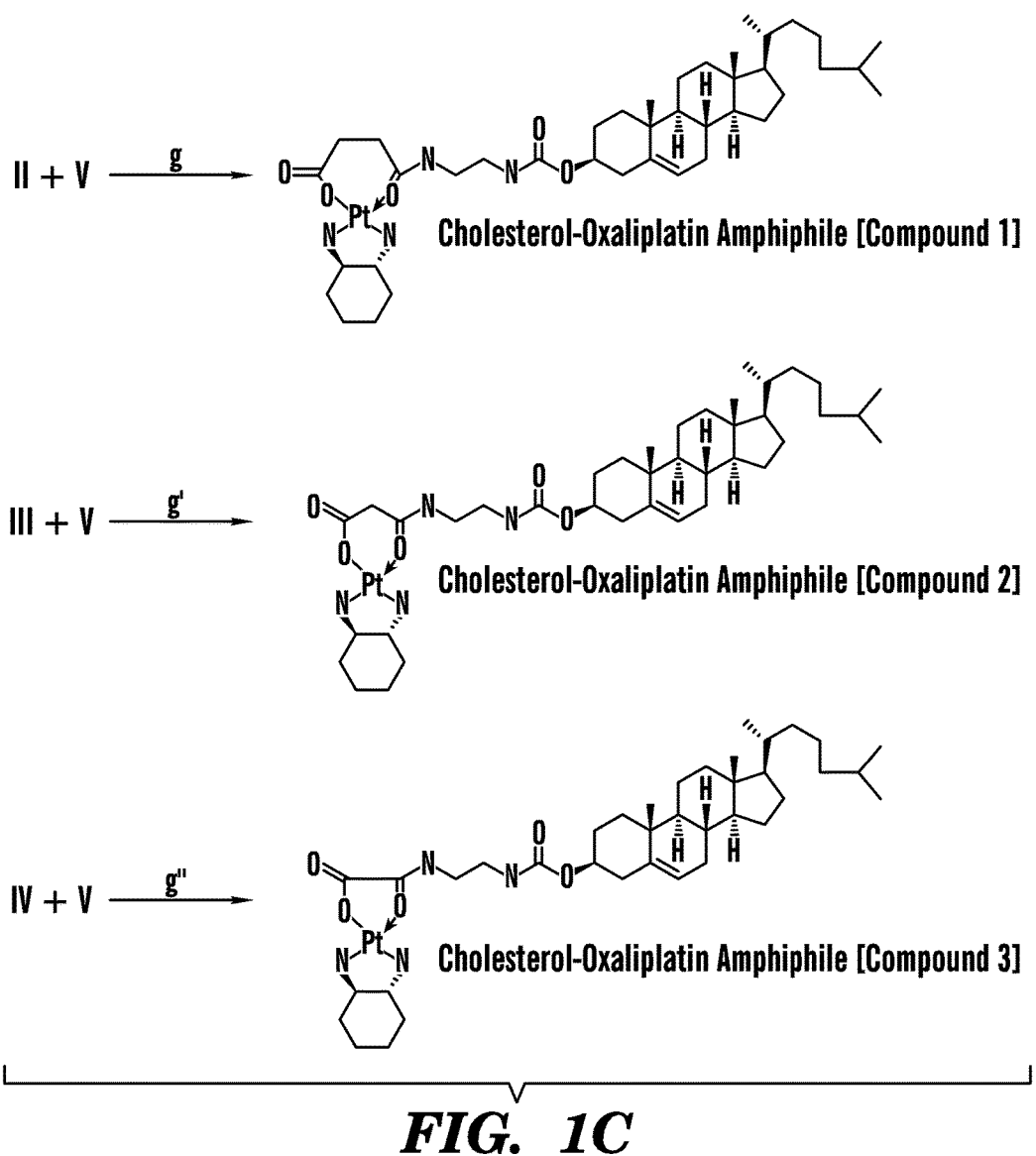

The design and synthesis of oxaliplatin nanoparticle is based on their structure-activity relationship. The present disclosure describes the synthesis of various platinum based amphiphiles by functional group interchange chemistry. In a specific embodiment, for obtaining a carbamate linkage, cholesteryl chloroformate is employed as a starting material to which ethylene diamine (a) (linker) is added to obtain an ethylene diamine conjugated cholesterol where one amine group of ethylene diamine forms a carbamate bond with cholesterol and the other amine is free (FIG. 1A). In the next step, the free amine reacts with one of the carboxyl groups of succinic anhydride (b) (a dicarbonyl derivative which is capable of forming seven membered ring molecules) to form an amide bond and the other free carboxylic acid group remains for platinum co-ordination (FIG. 1A). Dichlorodiammino-platinum (II) [RR isomer] is hydrated with silver nitrate overnight to obtain aquated oxaliplatin (FIG. 1B) which forms an adduct with intermediate II/III/IV (as depicted in FIG. 1A) via. the formation of a covalent monocarboxylato bond and another co-ordination bond of amide oxygen (FIG. 1C).

Figure 2A:
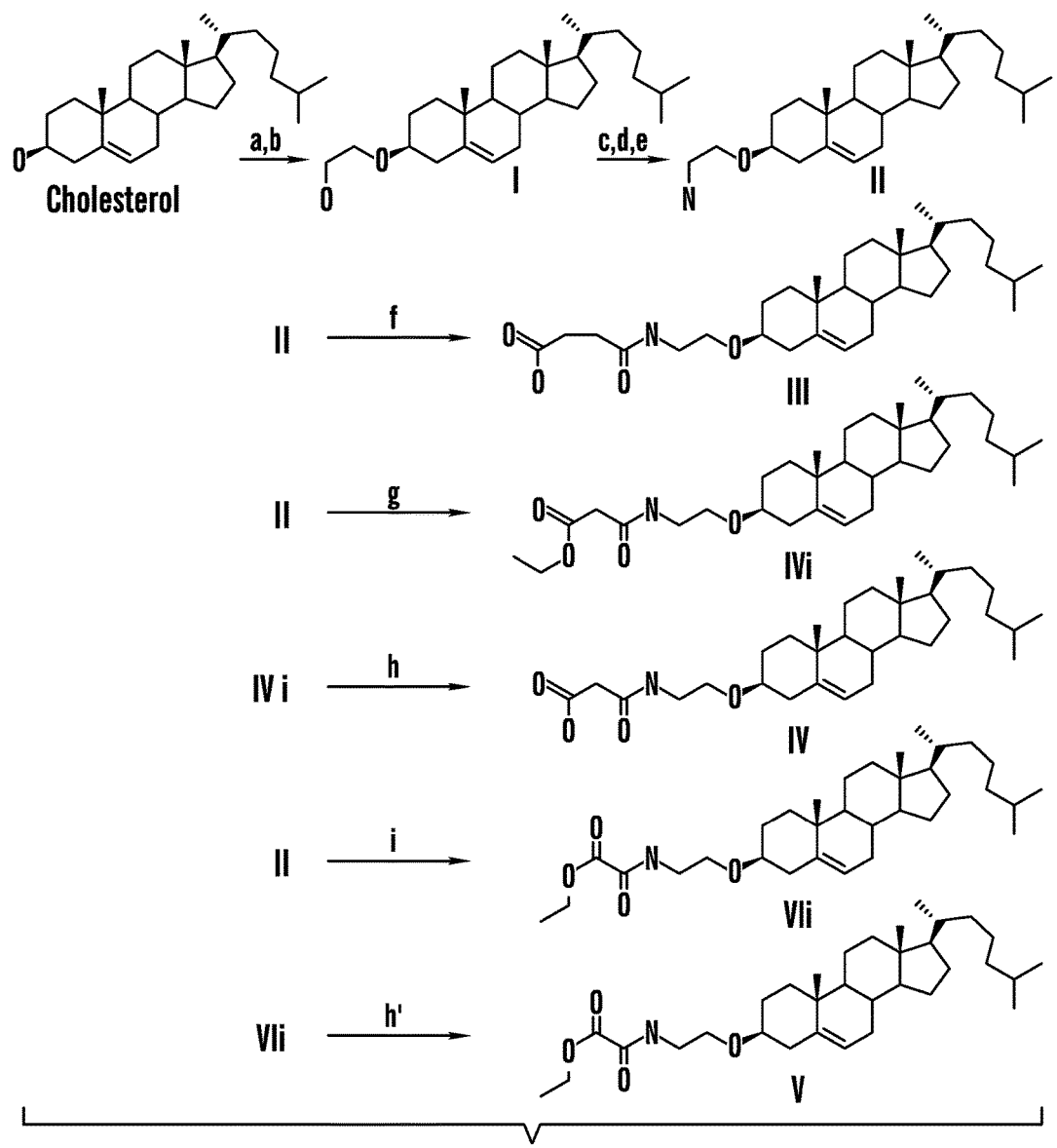
FIGS. 2A-2C depict the synthesis procedure of Cholesterol-Oxaliplatin compounds (Formula I) with ether linkage (Compounds 6, 4 and 5). Reagents and Conditions: a) TsCl, Dry DCM, Pyridine, RT, 6 hours; b) ethylene glycol, dioxane, reflux, 4 hours; c) TsCl, DCM, Pyridine, RT, 6 hours; d) NaN$_3$, DMF, 3 hours, RT; e) PPh$_3$, THF, H$_2$O, RT, 4 hours; f) succinic anhydride, DCM, pyridine, RT, 24 hours; g) malonic acid monoethyl ester, DCM, EDCl, HOBt, RT, 24 hours; h,h') LiOH, THF, H$_2$O, 3 hours, RT; i) oxalic acid monoethyl ester, DCM, EDCl, HOBt, RT, 24 hours; j) AgNO$_3$, H$_2$O, RT, 24 hours; k,k',k'') DMF, H$_2$O, RT, 24 hours.
Figure 2B:
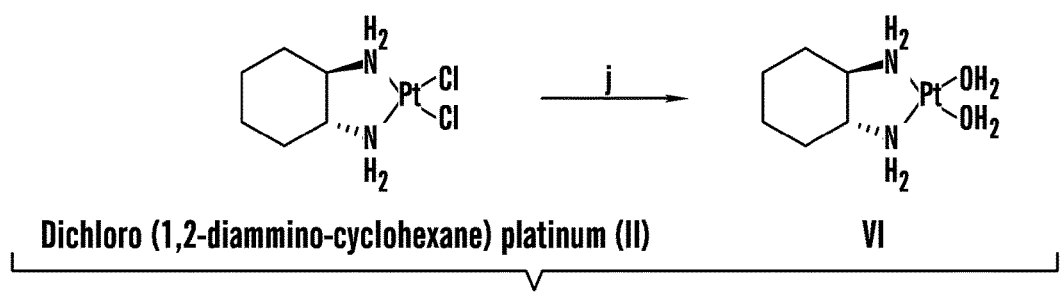
Figure 2C:
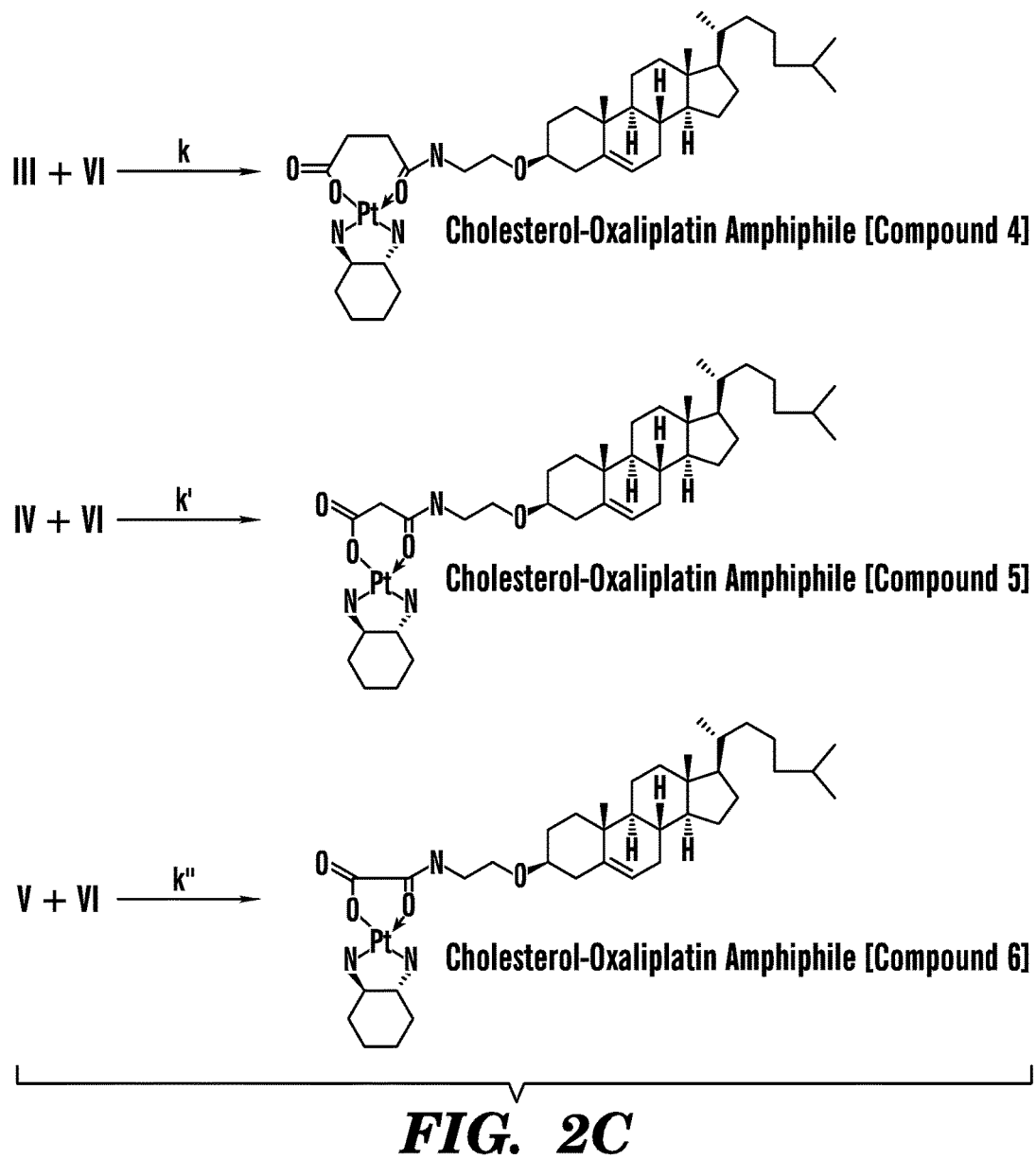
Figure 3A:
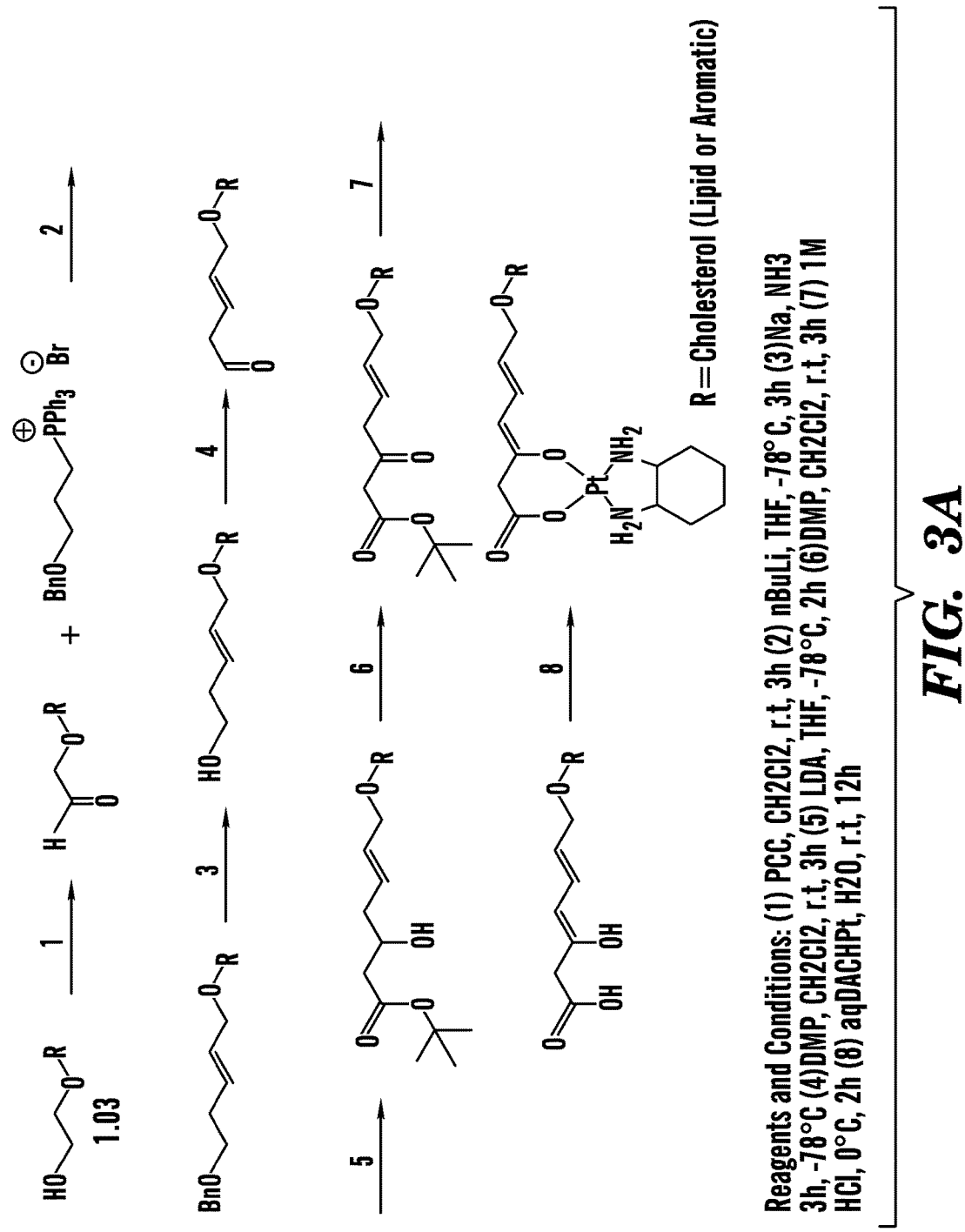
FIGS. 3A-3E depict the synthesis procedure of compounds of Formula III.
Figure 3B:
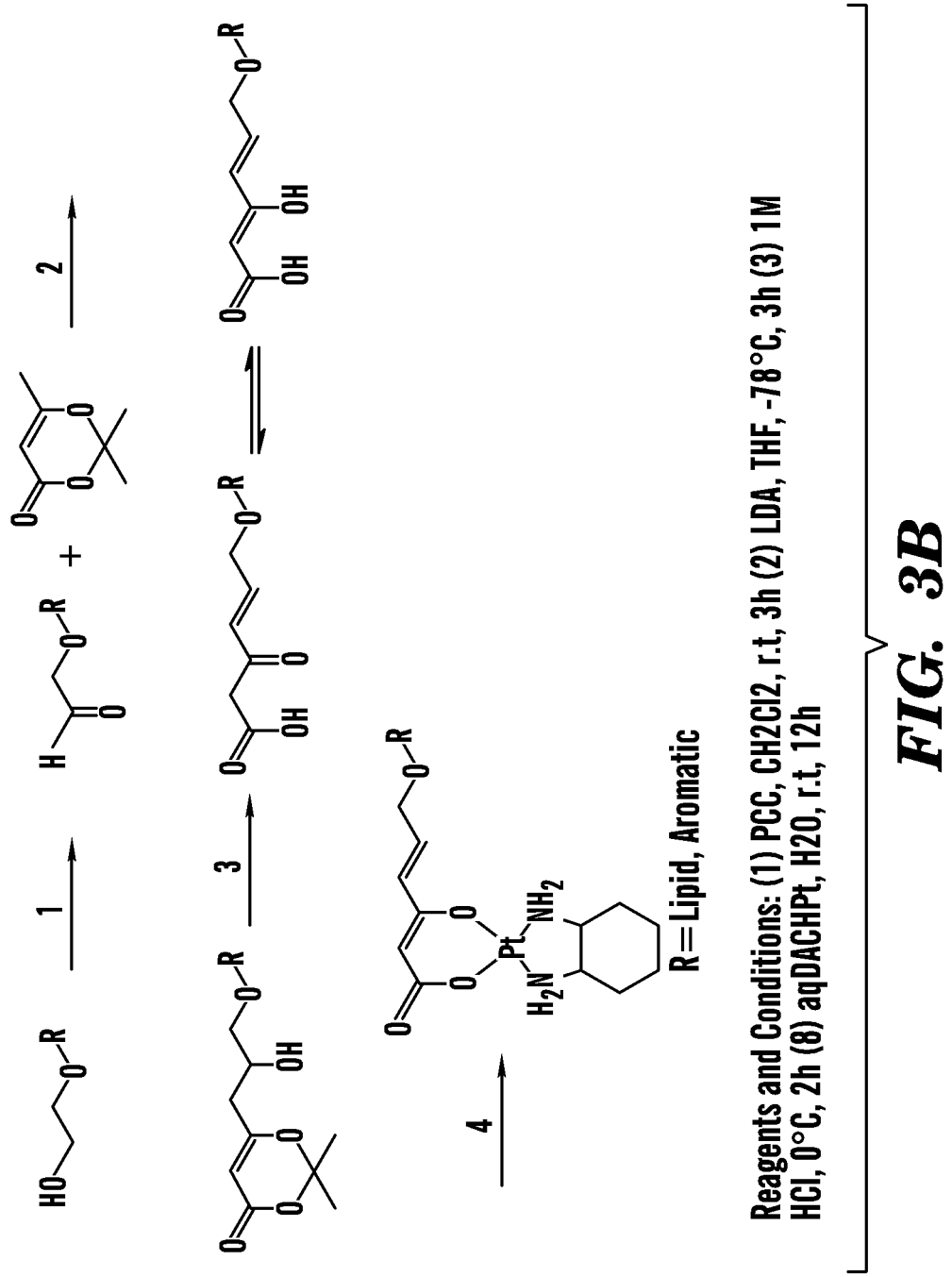
Figure 3C:
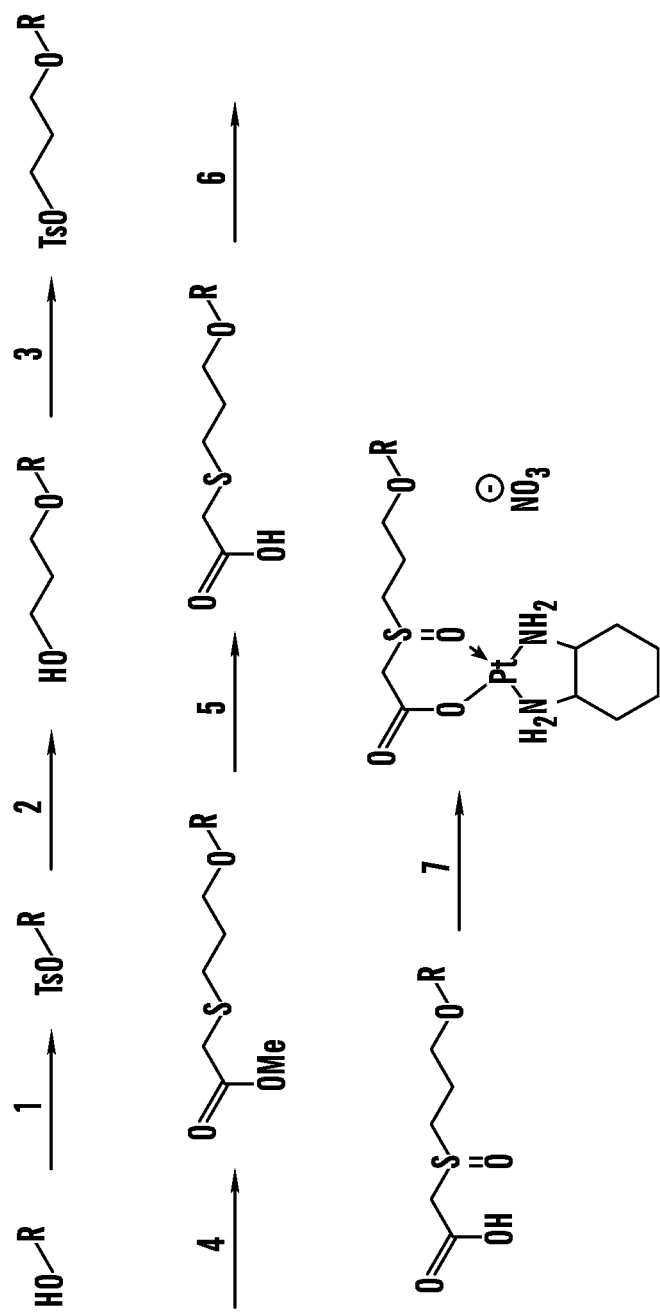
Figure 3D:
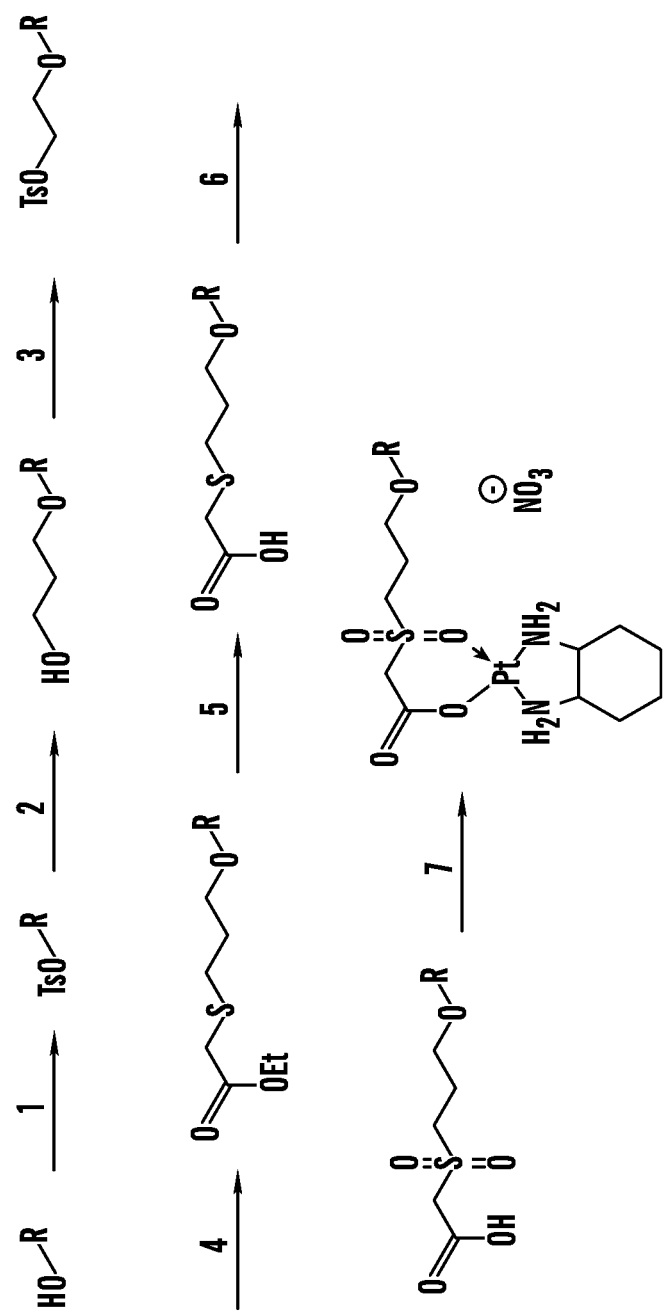
Figure 3E:
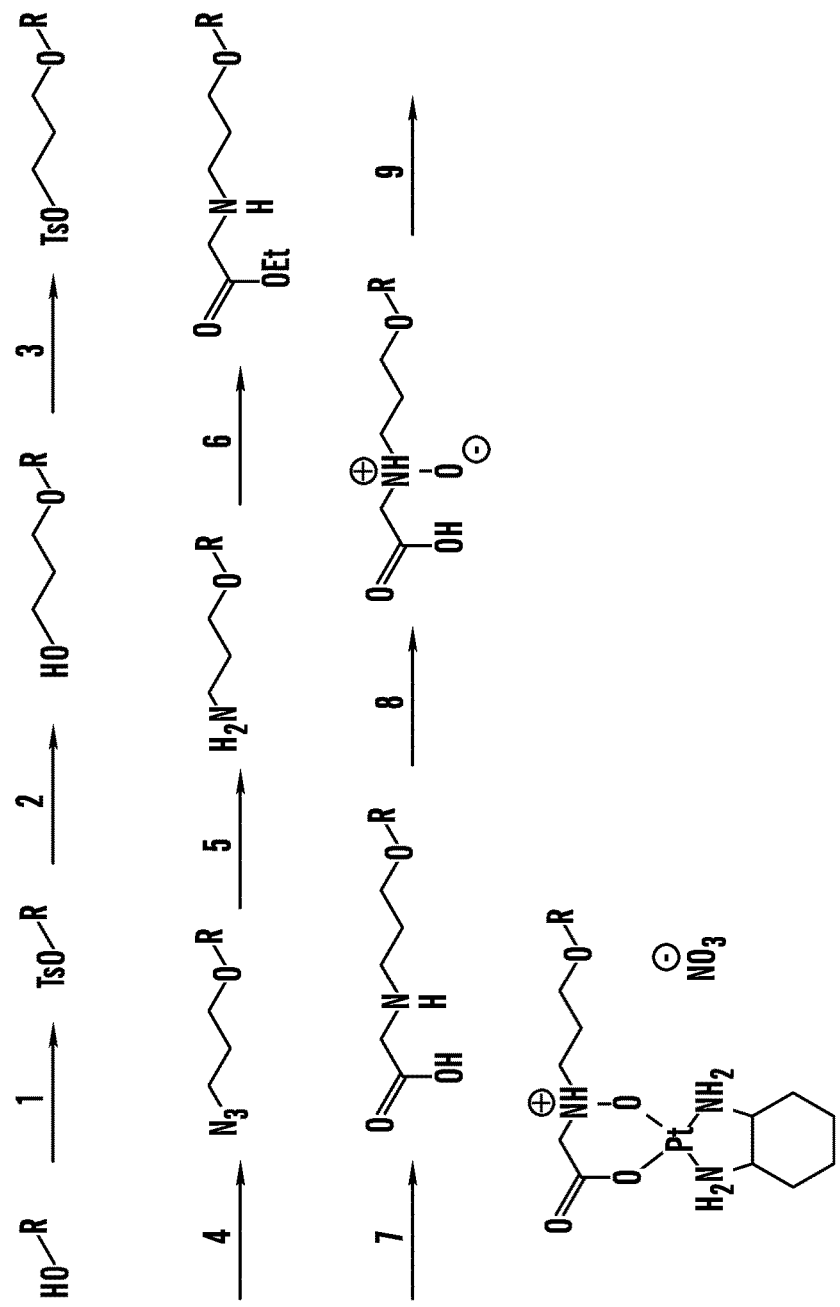
Figure 4A:
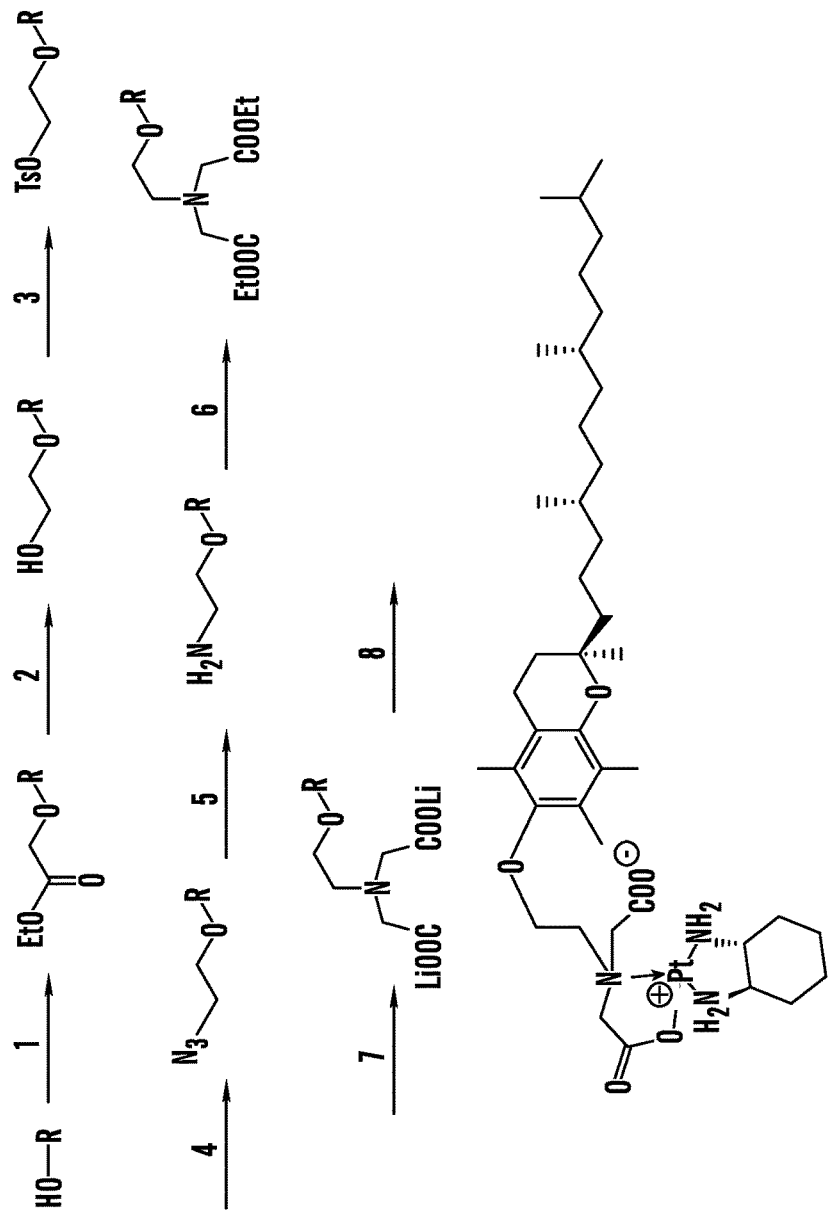
FIGS. 4A-4E depict the synthesis procedure of compounds of Formula II.
Figure 4B:
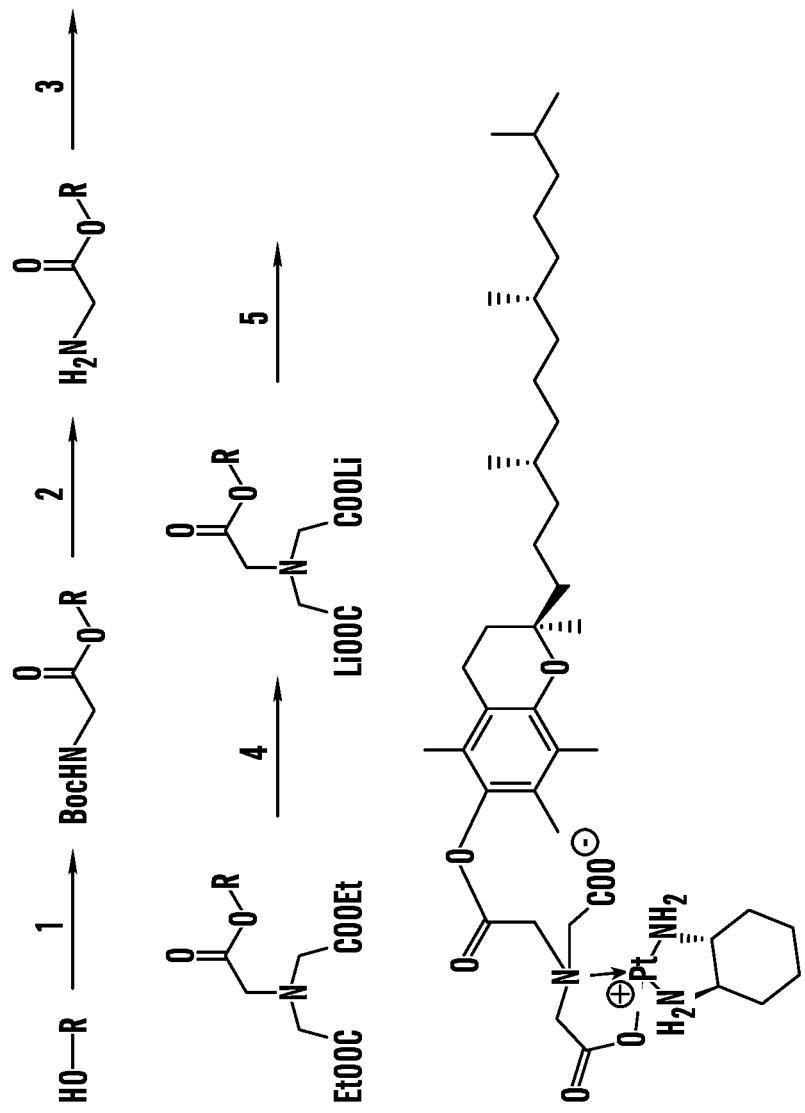
Figure 4C:
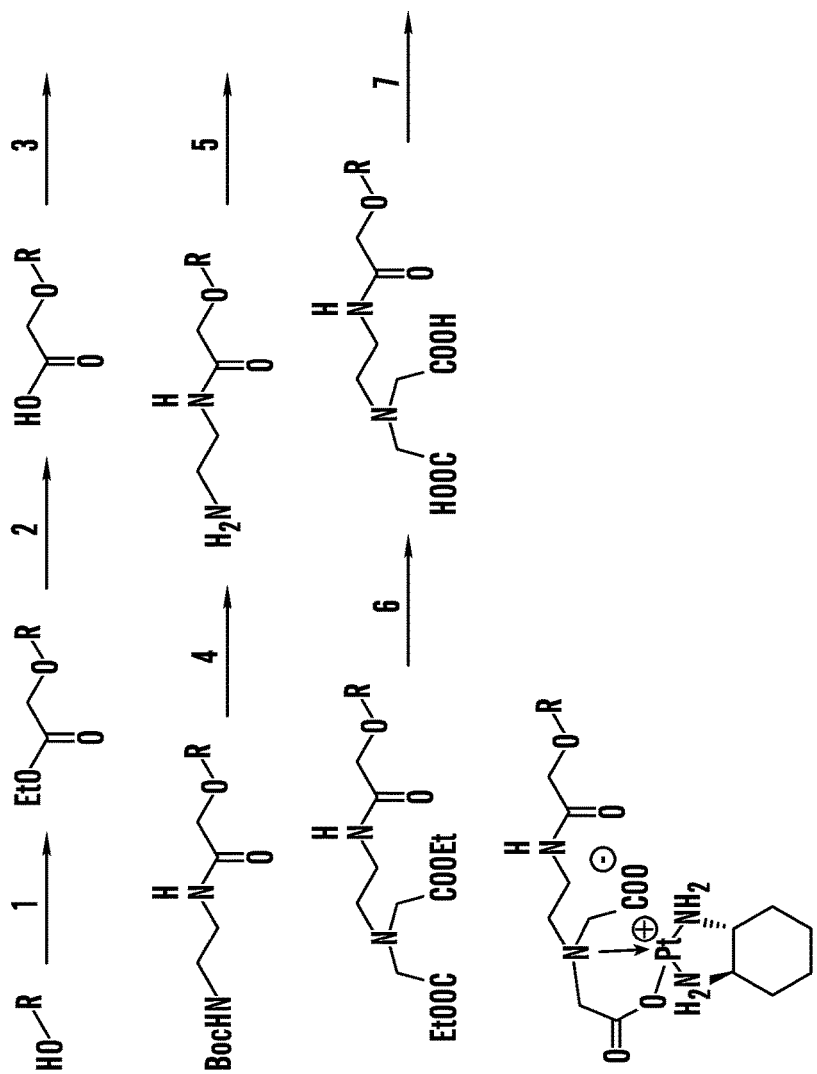
Figure 4D:
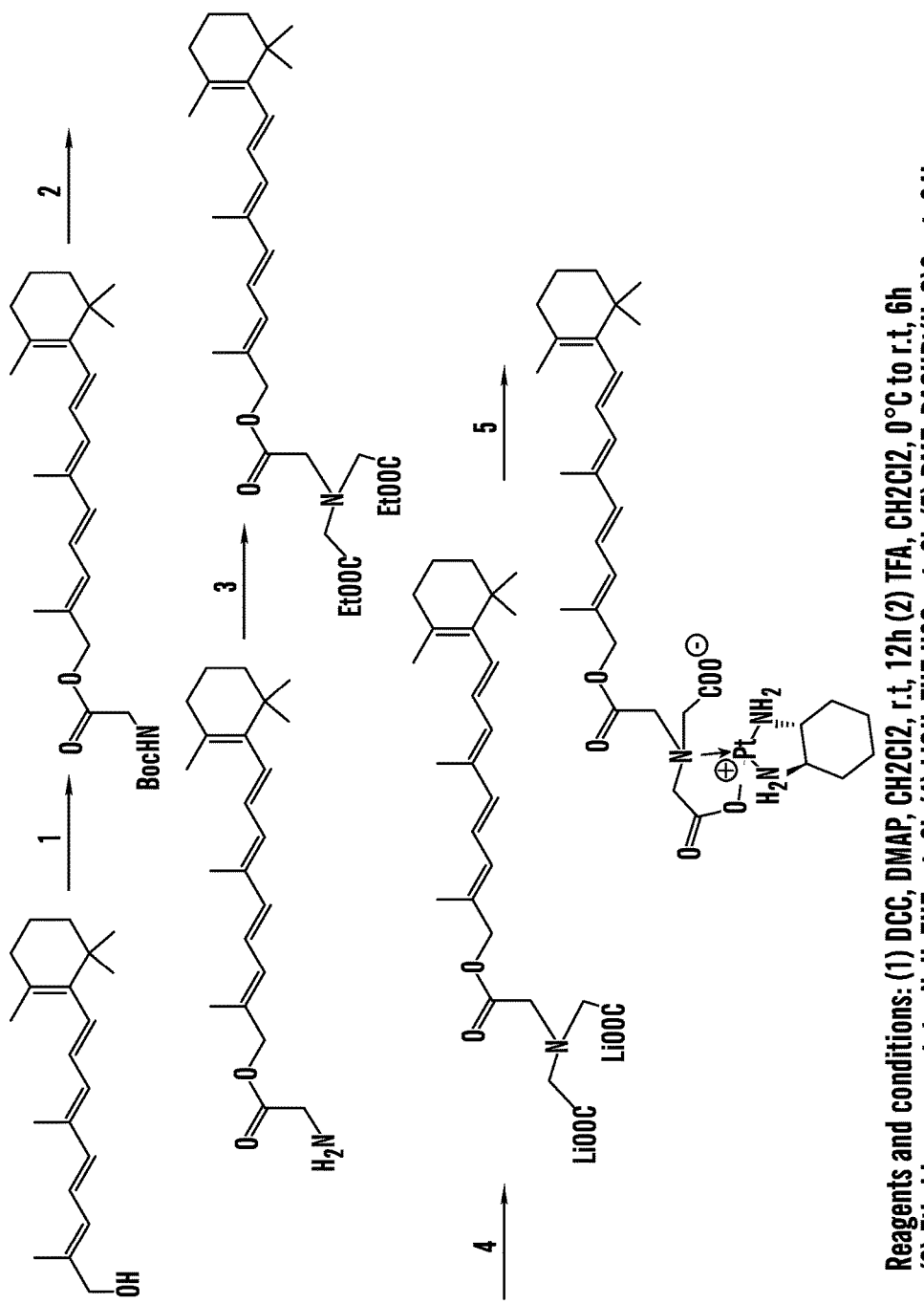
Figure 4E:
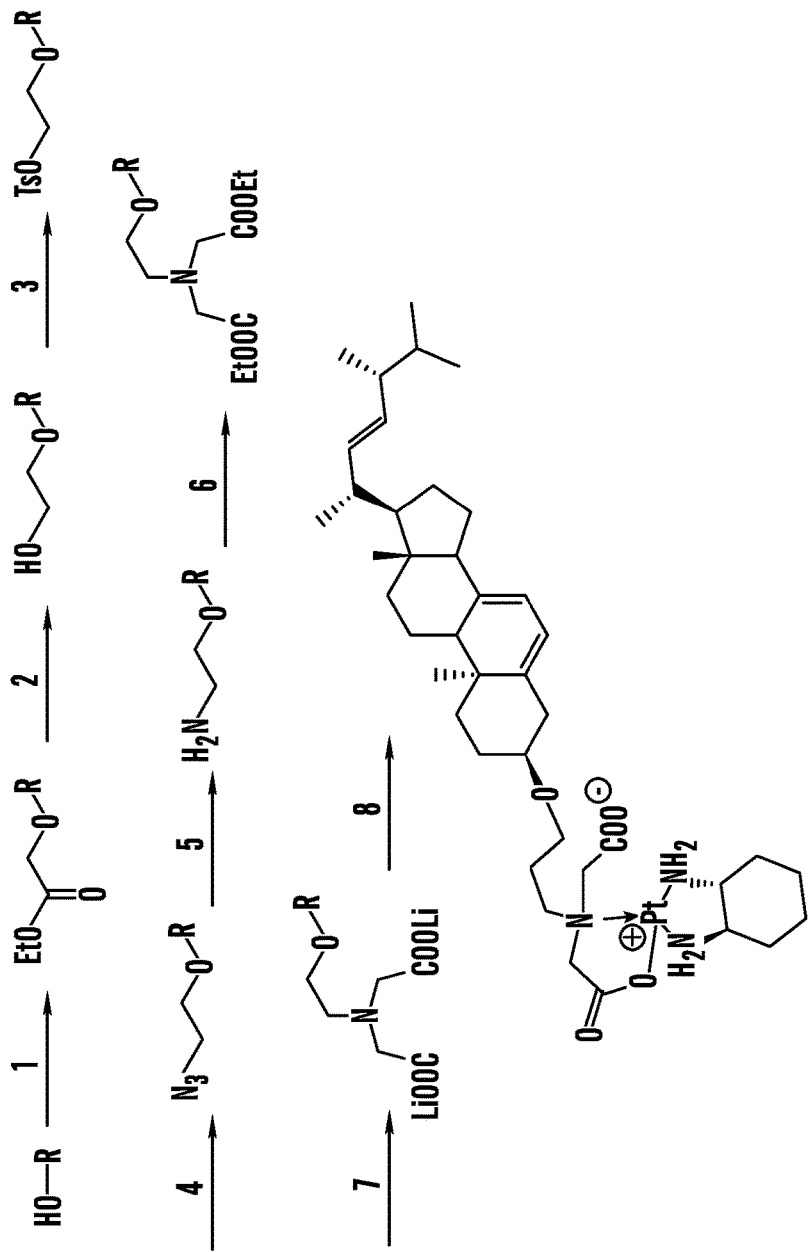

Similarly, in yet another embodiment, the synthesis of ether linked platinum amphiphiles have been summarized in FIG. 2 wherein, cholesterol molecule is initially transformed into intermediate I by functional group interchange (FIG. 2A). This intermediate I is transformed into intermediate II which in turn leads to final adduct by similar reaction steps as used for the synthesis of carbamate linkage as described above. Similarly, for synthesizing the six and five membered ring molecules as described above, monoethyl esters of malonic acid and oxalic acid have been used for the synthesis of both carbamate linked and ether linked platinum amphiphiles respectively (FIGS. 1A and 2A) followed by ethyl ester deprotection.

After the synthesis, the final platinum adducts are formulated into nanoparticles with different co-lipids selected from Soy-PC, DOPE, DOPC etc and stabilizers selected from DSPE-PEG-OMe etc. Further, the characterization of all intermediates are performed by $^1$HNMR and the characterization of the final oxaliplatin amphiphile molecule is carried out using $^1$HNMR and MALDI-TOF respectively.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred. As used herein, the term ED denotes effective dose and is used in connection with animal models. The term EC denotes effective concentration and is used in connection with in vitro models.

TABLE 1

Classification of Platinum (II) compounds (includes Formula III compounds) based upon coordination environment:

| Class-I Symmetric coordination with one side DACH | Class-II Asymmetric coordination with one side DACH | Class-III Symmetric coordination with one side DACH and other side O—O coordination, but the asymmetry is introduced by secondary atom/s which is not connected to Pt | Class-IV Symmetric coordination with no DACH | Class-V Asymmetric coordination with no DACH |
|---|---|---|---|---|
| [structure: DACH-Pt(X)(X)] X = O, P, S, Se | [structure: DACH-Pt(X)(Y)] X, Y = O, P, S, Se | [a sub class of Class-I (a)] [structure with O—X, O—Y] X, Y = C, P, S, N | [structure: Pt(X)(X)(O)(O)] X, Y = O, Cl, S, Se | [structure: Pt(X)(Y)(X)(Y)] |
| a) 'Pt' is connected to two 'O' Compounds 52, 55, 65, 74, 75, 76, 79 | a) 'Pt' is connected to 'P' and 'O' Compounds 46, 49, | a) One 'O' connected to 'S' other 'O' connected to 'CO' Compounds 63, 69, 70 | a) One side two 'O' other side two 'Cl' Compound 58 | |

Without wishing to be bound by a theory, the nanoparticle compositions of the present disclosure show significant cancer cell killing efficacy. Exemplary nanoparticles were tested in different cancer cell lines and it was observed that the compounds demonstrated significantly better cell killing efficacy than the control compounds such as conventionally known platinum drugs oxaliplatin, cisplatin, oxaliplatin, carboplatin, paraplatin and sartraplatin.

Accordingly, in another aspect, described herein is a method of treating cancer, Generally, the method comprises administering a therapeutically effective amount of a platinum based compounds disclosed herein to a subject in need thereof.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Determination of a therapeutically effective amount is well within the capability of those skilled in the art. Generally, a therapeutically effective amount can vary with the subject's history, age, condition, sex, as well as the severity and type of the medical condition in the subject, and administration of other agents alleviate the disease or disorder to be treated.

Usually the amount of active compounds is between 0.1-95% by weight of the preparation, preferably between 0.2-20% by weight in preparations for parenteral use and preferably between 1 and 50% by weight in preparations for oral administration.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized.

The therapeutically effective dose can be estimated initially from cell culture assays. A dose can be formulated in animal models to achieve a circulating plasma concentration range that includes the IC50 (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

The dosage can be determined by a physician and adjusted, as necessary, to suit observed effects of the treatment. Generally, the composittions are administered so that the agent is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that the agent has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, the platinum based compound can be administrated to a subject in combination with a pharmaceutically active agent, e.g., a second therapeutic agent. Exemplary pharmaceutically active compound include, but are not limited to, those found in *Harrison's Principles of Internal Medicine,* 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; and United States Pharmacopeia, The National Formulary, USP XII NF XVII, 1990, the complete contents of all of which are incorporated herein by reference. The platinum based compound and the the second therapeutic agent can be administrated to the subject in the same pharmaceutical composition or in different pharmaceutical compositions (at the same time or at different times).

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrastemal injection and infusion. In some embodiments, the compositions are administered by intravenous infusion or injection.

As used herein, the term "cancer" refers to an uncontrolled growth of cells that may interfere with the normal functioning of the bodily organs and systems. Cancers that migrate from their original location and seed vital organs can eventually lead to the death of the subject through the functional deterioration of the affected organs. Metastasis is a cancer cell or group of cancer cells, distinct from the primary tumor location resulting from the dissemination of cancer cells from the primary tumor to other parts of the body. At the time of diagnosis of the primary tumor mass, the subject may be monitored for the presence of in transit metastases, e.g., cancer cells in the process of dissemination. As used herein, the term cancer, includes, but is not limited to the following types of cancer, breast cancer, biliary tract cancer, bladder cancer, brain cancer including Glioblastomas and medulloblastomas; cervical cancer; choriocarcinoma; colon cancer; endometrial cancer; esophageal cancer, gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma, Wilms tumor. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, Glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. Other cancers will be known to the artisan.

As used herein, the term "cancer" includes, but is not limited to, solid tumors and blood born tumors. The term cancer refers to disease of skin, tissues, organs, bone, cartilage, blood and vessels. The term "cancer" further encompasses primary and metastatic cancers. Examples of cancers that can be treated with the compounds of the invention include, but are not limited to, carcinoma, including that of the bladder, breast, colon, kidney, lung, ovary, pancreas, stomach, cervix, thyroid, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma; hematopoietic tumors of myeloid lineage including, but not limited to, acute and chronic myelogenous leukemias and promyelocytic leukemia; tumors of mesenchymal origin including, but not limited to, fibrosarcoma, rhabdomyosarcoma, and osteosarcoma; other tumors including melanoma, seminoma, tetratocarcinoma, neuroblastoma, and glioma; tumors of the central and peripheral nervous system including, but not limited to, astrocytoma, neuroblastoma, glioma, and schwannomas; and other tumors including, but not limited to, xenoderma, pigmentosum, keratoactanthoma, thyroid follicular cancer, and teratocarcinoma. The methods disclosed herein are useful for treating patients who have been previously treated for cancer, as well as those who have not previously been treated for cancer. Indeed, the methods and compositions of this invention can be used in first-line and second-line cancer treatments.

As used herein, the term "precancerous condition" has its ordinary meaning, i.e., an unregulated growth without metastasis, and includes various forms of hyperplasia and benign hypertrophy. Accordingly, a "precancerous condition" is a disease, syndrome, or finding that, if left untreated, can lead to cancer. It is a generalized state associated with a significantly increased risk of cancer. Premalignant lesion is a morphologically altered tissue in which cancer is more likely to occur than its apparently normal counterpart. Examples of pre-malignant conditions include, but are not limited to, oral leukoplakia, actinic keratosis (solar keratosis), Barrett's esophagus, atrophic gastritis, benign hyperplasia of the prostate, precancerous polyps of the colon or rectum, gastric epithelial dysplasia, adenomatous dysplasia, hereditary nonpolyposis colon cancer syndrome (HNPCC), Barrett's esophagus, bladder dysplasia, precancerous cervical conditions, and cervical dysplasia.

In some embodiments, the cancer is selected from the group consisting of: breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.

In some embodiments, the methods described herein relate to treating a subject having or diagnosed as having cancer. Subjects having cancer can be identified by a physician using current methods of diagnosing cancer. Symptoms and/or complications of cancer which characterize these conditions and aid in diagnosis are well known in the art and include but are not limited to, growth of a tumor, impaired function of the organ or tissue harboring cancer cells, etc. Tests that may aid in a diagnosis of, e.g. cancer include, but are not limited to, tissue biopsies and histological examination. A family history of cancer, or exposure to risk factors for cancer (e.g. tobacco products, radiation, etc.) can also aid in determining if a subject is likely to have cancer or in making a diagnosis of cancer.

In some embodiments, the method further comprises co-administering one or more additional anti-cancer therapy to the patient. In some embodiments, the additional therapy is selected from the group consisting of surgery, chemotherapy, radiation therapy, thermotherapy, immunotherapy, hormone therapy, laser therapy, anti-angiogenic therapy, and any combinations thereof. In some embodiments, the additional therapy comprises administering an anti-cancer agent to the patient. In some embodiments, the method comprises co-administering the conjugate and an anti-cancer agent or chemotherapeutic agent to the subject. As used herein, the term "anti-cancer agent" is refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; platinate; carmustine; carmustine with Polifeprosan Implant; celecoxib; chlorambucil; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is herein incorporated by reference in its entirety.

The methods of the invention are especially useful in combination with anti-cancer treatments that involve administering a second drug that acts in a different phase of the cell cycle.

For administration to a subject, the platinum based compounds and/or particles comprising said platinum based compounds are provided in pharmaceutically acceptable compositions. Accordingly, the disclosure also provides pharmaceutical compositions comprising the platinum based compounds or particles as disclosed herein. These pharmaceutically acceptable compositions comprise a therapeutically-effective amount of one or more of the platinum based compounds or particles described herein, formulated together with one or more pharmaceutically acceptable carriers (additives) and/or diluents. The said pharmaceutical compositions of the present invention are specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, the compounds of the present disclosure can be implanted into a patient or injected using a drug delivery system.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zincstearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (S) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyllaurate; (13) agar; (14) buffering agents, such as magnesium hydroxide and aluminum hydroxide; (15) alginic acid; (16) pyrogen-free water; (17) isotonic saline; (IS) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the likes are used interchangeably herein.

In some embodiments, the pharmaceutical composition comprising a platinum based compound can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a composition as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, a composition as described herein can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

Embodiments of various aspects described herein can be defined in any of the following numbered paragraphs:
1. A compound comprising:
    (a) a platinum moiety; and
    (b) a lipid connected to said platinum moiety.
2. The compound of paragraph 1, wherein the compound comprises a carbonyl moiety.
3. The compound of paragraph 2, wherein the carbonyl moiety is a carboxylic acid selected from the group consisting of succinic acid, malonic acid, oxalic acid, keto acid, and any combination thereof
4. The compound of any of paragraphs 1-3, wherein the platinum atom or moiety is conjugated to said lipid via covalent bond, coordinate bond or a combination thereof
5. The compound of any of paragraphs 1-4, wherein the compound comprises at least one linker between the platinum moiety and the lipid.
6. The compound of any of paragraphs 1-5, wherein the compound is of Formula (VIII):

Q-linker-lipid (VIII), wherein:
Q is

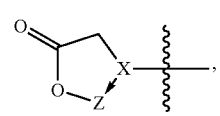     (i)

wherein: X is NH or $N(CH_2COO^-)$; and Z is a platinum containing compound, wherein the platinum forms a part of the ring;

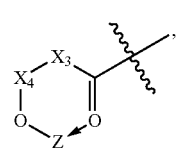     (ii)

wherein: $X_3$ is selected from a group comprising $(CH_2)_n$, $CH_2$—NH and $C_4H_8$; $X_4$ is CO or —CH—$CH_3$; Z is a platinum containing compound, wherein the platinum forms a part of the ring; and n is 0, 1, or 2;

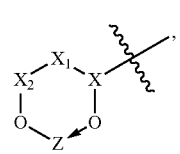     (iii)

wherein: X is selected from a group comprising $S^+$, C, $S^+$=O, $N^+H$ and P=O; $X_1$ is selected from a group comprising —CH, —$CH_2$ and —$CH_2O$; $X_2$ is C=O; and Z is a platinum containing compound, wherein the platinum forms a part of the ring;

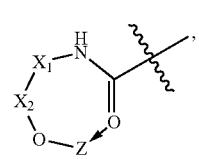     (iv)

wherein $X_1$ is $(CH_2)_n$; $X_2$ is C=O; Z is a platinum containing compound, wherein the platinum forms a part of the ring; and n is 0, 1, or 2;

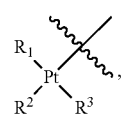     (v)

wherein $R^1$, $R^2$ and $R^3$ are independently halogen, alkyl, amino, alkylamino, dialkylamino, hydroxyl, alkoxy, thiol, thioalkyl, O-acyl, -linker-lipid, or any combinations thereof, or $R_1$ and $R_2$ together with the Pt atom or $R_2$ and $R_3$ together with the Pt atom form an optionally substituted cyclyl or heterocyclyl, or $R_1$ and $R_2$ together with the Pt atom and $R_2$ and $R_3$ together with the Pt atom form an optionally substituted cyclyl or heterocyclyl; or (vi)

wherein $R_1$, $R_2$, $R_3$, $R_4$ and $R_5$ are independently halogen, alkyl, amino, alkylamino, dialkylamino, hydroxyl, alkoxy, thiol, thioalkyl, O-acyl, -linker-lipid, or any combinations thereof, $R_1$ and $R_2$ together with the Pt atom form an optionally substituted cyclyl or heterocyclyl or. $R_3$ and $R_4$ together with the Pt atom form an optionally substituted cyclyl or heterocyclyl.

7. The compound of paragraph 6, wherein Z is wherein $R_1$ and $R_2$ are independently halogen, alkyl, amino, alkylamino, dialkylamino, hydroxyl, alkoxy, thiol, thioalkyl, O-acyl, or any combinations thereof or $R_1$ and $R_2$, together with the Pt atom form an optionally substituted cyclyl or heterocyclyl.

8. The compound of paragraph 7, wherein Z is wherein p is 0, 1, 2, or 3.

9. The compound of paragraph 8, wherein p is 2.
10. The compound of any of paragraphs 1-9, wherein the linker is selected from the group consisting of:
    (i) —X—CH$_2$—X$_2$—X$_1$—, wherein X is NH; X$_1$ is C(O)O, C(O)NH, O(CH$_2$)—O, NH, or O; X$_2$ is (CH$_2$)$_n$ or C(O); and n is 0, 1, 2, 3, 4, or 5;
    (ii) —(CH$_2$)$_n$O—, —(CH$_2$)$_n$NHC(O)O—, —(CH$_2$)$_n$OC(O)NH—, —(CH$_2$)$_n$C(O)NH(CH$_2$)$_m$O—, —(CH$_2$)$_n$O(CH$_2$)$_m$O—, —(CH$_2$)$_n$O(O)—, —(CH$_2$)$_n$ NHC(O)(CH$_2$)$_m$O—, or —(CH$_2$)$_n$C(O)O—; wherein n and m are independently 0, 1, 2, 3, 4, or 5;
    (iii) —X$_3$—X$_4$X$_5$—X$_6$—, wherein X$_3$ is CH, CH$_2$, or O; and X$_4$, X$_5$ and X$_6$ are independently same or different and are —CH$_2$O— or a; and
    (iv) any combinations of (i)-(iii).
11. The compound of any of paragraphs 1-10, wherein the linker is selected from the group consisting of: a bond, ethylene diamine, ethylene glycol, diethylene glycol, 1,3-propanediol, glycine, beta alanine, —O—, —CH$_2$O— NHCH$_2$CH$_2$NHC(O)—, —NHCH$_2$CH$_2$NHC(O)O—, —NHCH$_2$CH$_2$—, —NHCH$_2$CH$_2$O—, —NHCH$_2$C(O)—, —NHCH$_2$C(O)O—, —NHCH$_2$C(O)OCH$_2$CH$_2$CH$_2$—, —NHCH$_2$C(O)OCH$_2$CH$_2$CH$_2$O—, —NHCH$_2$C(O)NH—, —CH$_2$CH$_2$—, —CH$_2$CH$_2$O—, —CH$_2$CH$_2$NHC(O)—, —CH$_2$CH$_2$NHC(O)O—, —CH$_2$CH$_2$O—, —CH$_2$C(O)NHCH$_2$CH$_2$—, —CH$_2$C(O)NHCH$_2$CH$_2$O—, —CH$_2$CH$_2$OCH$_2$CH$_2$—, —CH$_2$CH$_2$OCH$_2$CH$_2$O—, —CH$_2$C(O)—, —CH$_2$C(O)O—, —CH$_2$CH$_2$CH$_2$—, —CH$_2$CH$_2$CH$_2$O—, =CH—CH=CH$_2$—, =CH—CH=CHCH$_2$O—, —CH=CHCH$_2$—, —CH=CHCH$_2$O—, —OCH$_2$CH$_2$O—, —CH$_2$—, —CH$_2$O—, —NHC(O)CH$_2$—, —NHC(O)CH$_2$O—, —C(O)CH$_2$—, —C(O)CH$_2$O—, —OC(O)CH$_2$—, —OC(O)CH$_2$O—, —C(O)CH$_2$CH$_2$C(O)NHCH$_2$CH$_2$—, —OC(O)CH$_2$CH$_2$C(O)NHCH$_2$CH$_2$—, —C(O)CH$_2$CH$_2$C(O)NHCH$_2$CH$_2$O—, —OC(O)CH$_2$CH$_2$C(O)NHCH$_2$CH$_2$O—, —C(O)CH$_2$CH$_2$C(O)NHCH$_2$CH$_2$NHC(O)—, —OC(O)CH$_2$CH$_2$C(O)NHCH$_2$CH$_2$NHC(O)—, —C(O)CH$_2$CH$_2$C(O)NHCH$_2$CH$_2$NHC(O)O—, —OC(O)CH$_2$CH$_2$C(O)NHCH$_2$CH$_2$NHC(O)O—, and any combinations thereof 12. The compound of any of paragraphs 1-11, wherein the lipid is selected from fats, waxes, sterols, steroids, bile acids, fat-soluble vitamins, monoglycerides, diglycerides, phospholipids, glycolipids, sulpholipids, aminolipids, chromolipids, glycerophospholipids, sphingolipids, prenol lipids, saccharolipids, polyketides and fatty acids or any combination thereof, preferably sterols selected from cholesterol, cholesterol chloroformate or derivatives thereof, and any combination thereof.
13. The compound of paragraph 12, wherein the lipid is cholesterol or alpha-tocopherol
14. The compound of any of paragraphs 1-13, wherein the compound is represented by:
    (i) Formula I:

(I)

wherein,
X is NH;
$X_1$ is selected from a group comprising COOH, CONH$_2$, O—(CH$_2$)$_n$—OH, NH$_2$ and OH;
$X_2$ is (CH$_2$)$_n$ or CO;
$X_3$ is selected from a group comprising (CH$_2$)$_n$, CH$_2$—NH and C$_4$H$_8$;
$X_4$ is CO or —CH—CH$_3$; and
Z is platinum containing compound, wherein the platinum forms a part of Formula I ring; and
n is 0, 1, or 2;

(ii) Formula II:

(II)

wherein,
X is NH or N—CH$_2$COO$^-$;
$X_1$ is selected from a group comprising —(CH$_2$)$_n$OH, —(CH$_2$)$_n$NHCOOH, —(CH$_2$)$_n$CONH(CH$_2$)$_n$OH, (CH$_2$)$_n$O(CH$_2$)$_n$OH, (CH$_2$)$_n$C=O, —(CH$_2$)$_n$NHCO(CH$_2$)$_n$OH and (CH$_2$)$_n$—COOH;

Z is platinum containing compound, wherein the platinum forms a part of Formula II ring; and
n is 0, 1, or 2;
(iii) Formula III:

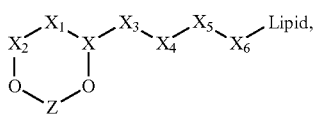

wherein,
X is selected from a group comprising $S^+$, C, $S^+$=O, $N^+H$ and P=O;
$X_1$ is selected from a group comprising —CH, —$CH_2$ and —$CH_2O$;
$X_2$ is C=O;
$X_3$ is selected from CH, $CH_2$ or O;
$X_4$, $X_5$, $X_6$ is selected from —$CH_2O$ or O; and
Z is platinum containing compound, wherein the platinum forms a part of Formula III ring;
(iv) Formula IV:

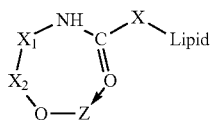

wherein,
X is $CH_2OH$;
$X_1$ is $(CH_2)_n$;
$X_2$ is C=O;
Z is platinum containing compound, wherein the platinum forms a part of Formula IV ring; and
n is 0, 1, or 2;
(v) Formula VI:

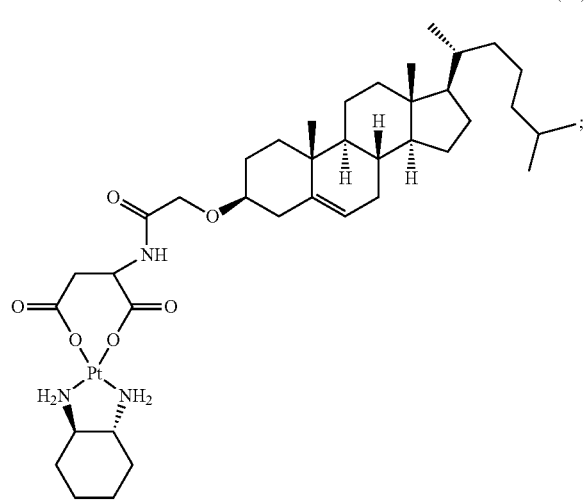

$C_{39}H_{65}N_3O_6Pt$
MW = 867.03

(vi) Formula VII:

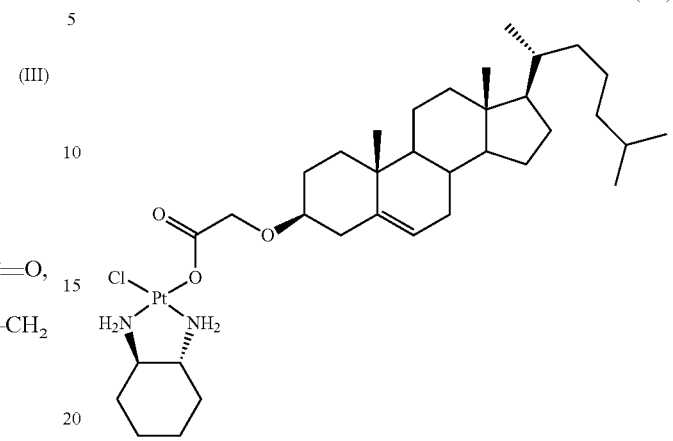

15. A compound of Formula (V):

wherein
$X_1$, $X_2$, $X_3$ and $X_4$ are selected independently from the group consisting of O, P, S, Se, Cl, N, C, O-A, O—B, DACH, halides and chelated or non-chelated dicarboxylato linkage group, and any combinations thereof;
wherein A and B are selected independently from the group consisting of C, P, S, N, and any combinations thereof; and
wherein $X_4$ is optional.

16. A method for preparing a compound comprising:
a platinum moiety; and
a lipid connected to said platinum,
said method comprising conjugating the lipid with the platinum moiety to obtain said compound.

17. The method of paragraph 16, wherein method further comprises:
(a) reacting the lipid with a linker to obtain a first compound;
(b) optionally reacting the first compound of step (a) with a carbonyl moiety to obtain a second compound; and
(c) conjugating the first compound of step (a) or the second compound of step (b) with the platinum moiety to obtain said compound.

18. The method of paragraph 16 or 17, wherein the compound is a compound of any of paragraphs 1-15.

19. A nanoparticle containing a compound comprising:
(a) a platinum moiety; and
(b) a lipid connected to said lipid.

20. The nanoparticle of paragraph 19, wherein the compound is a compound of any of paragraphs 1-15.

21. The nanoparticle of paragraph 19 or 20, wherein the nanoparticle further comprises a co-lipid and/or stabilizer.

22. The nanoparticle of paragraph 21, wherein ratio of the compound to co-lipid and/or stabilizer ranges from 99:1 to 1:99 (w/w), (mol/mol) or (vol/vol).

23. The nanoparticle of paragraph 21, wherein the nanoparticle comprises Soy-phosphatidyl choline and 1,2-Distearoyl-sn-Glycero-3-Phosphoethalonamine-N-[Methoxy (Polyethylene glycol)-2000] as co-lipids, and wherein the ratio of the compound and the co-lipids ranges from about 1:1:0.01 to about 1:4:3.

24. A pharmaceutical composition comprising a nanoparticle of any of paragraphs 19-23.

25. A pharmaceutical composition comprising a compound of any of paragraphs 1-15.

26. The pharmaceutical composition of paragraph 24 or 25, wherein the excipient is selected from a group comprising granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material, spheronization agents, and any combination thereof 27. The pharmaceutical composition of any of paragraphs 24-26, wherein the composition is formulated into a dosage form selected from the group consisting of injectable, tablet, lyophilized powder, liposomal suspension, and any combinations thereof 28. A method of treating or managing cancer in a subject, the method comprising administering a therapeutically effective amount of a compound of any of paragraphs 1-15 or a nanoparticle of any of paragraphs 19-23 to a subject in need thereof 29. The method of paragraph 28, wherein the cancer is selected from the group consisting of breast, head and neck, ovarian, testicular, pancreatic, oral-esophageal, gastrointestinal, liver, gall bladder, lung, melanoma, skin, sarcoma, blood, brain, glioblastoma, tumor of neuroectodermal origin and any combinations thereof.

30. The method of paragraph 28 or 29, wherein said administration is via intravenous administration, intra articular administration, pancreatic duodenal artery administration, intraperitoneal administration, hepatoportal administration, intramuscular administration, or any combinations thereof 31. The nanoparticle of any of paragraphs 19-23, wherein the nanoparticle has increased cellular uptake of platinum relative to cisplatin or oxaliplatin in cancer cells.

32. The nanoparticle of any of paragraphs 19-23, and 31, wherein the nanoparticle has a higher accumulation of platinum in a tumor relative to cisplatin or oxaliplatin at an equivalent dosage amount of amount of cisplatin or oxaliplatin.

33. The compound of any of paragraphs 1-15, wherein the compound has increased cellular uptake of platinum relative to cisplatin or oxaliplatin in cancer cells.

34. The compound of any of paragraphs 1-15, and 33, wherein the compound has a higher accumulation of platinum in a tumor relative to cisplatin or oxaliplatin at an equivalent dosage amount of amount of cisplatin or oxaliplatin.

35. A method for preparing a nanoparticle:
   a. providing a platinum compound, wherein the platinum compound comprises platinum moiety and a lipid connected to said platinum moiety; and
   b. reacting the compound with a co-lipid in presence of solvent to obtain the nanoparticle 36. The method of paragraph 35, wherein the platinum compound is prepared according to the method of any of paragraphs 16-18.

37. The method of paragraph 35 or 36, wherein the solvent is selected from the group comprising chloroform, methanol, dichloromethane, ethanol, and any combinations thereof.

38. The method of any of paragraphs 35-37, wherein the co-lipid is selected from the group consisting of sSoy-phosphatidyl choline (fully hydrogenated), 1,2-Distearoyl-sn-Glycero-3-Phosphoethalonamine-N-[Methoxy (Polyethylene glycol)-2000], dioleoyl phosphatidylcholine (DOPC), DSPE-PEG-OMe, dioleoyl phosphatidylethanolamine (DOPE), and any combination thereof 39. The method of paragraph 35-38, wherein step (b) further comprises steps of drying, incubation and optional addition of a stabilizer.

40. The method of paragraph 39, wherein the stabilizer is selected from the group consisting of DSPE-PEG-OMe, DSPE-PEG-NH2, PEG, inorganic salt, carbohydrate, and any combinations thereof 41. The method of paragraph 40, wherein the inorganic salt is selected from the group consisting of ammonium chloride, potassium chloride, sodium chloride, disodium hydrogen phosphate, sodium dihydrogen phosphate, and any combination thereof 42. The method of paragraph 40 or 41, wherein the carbohydrate is selected from the group consisting of glucose, dextrose, and any combinations thereof 43. The method of any of paragraphs 35-42, wherein the co-lipid is Soy-phosphatidyl choline and 1,2-Distearoyl-sn-Glycero-3-Phosphoethalonamine-N-[Methoxy(Polyethylene glycol)-2000].

44. The method of any of paragraphs 35-43, wherein the ratio of the platinum compound and the co-lipids is from about 1:1:0.01 to about 1:4:3.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2 SD) away from a reference level. The term refers to statistical evidence that there is a difference. It is defined as the probability of making a decision to reject the null hypothesis when the null hypothesis is actually true.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, "management" or "managing" refers to preventing a disease or disorder from occurring in a subject, decreasing the risk of death due to a disease or disorder, delaying the onset of a disease or disorder, inhibiting the progression of a disease or disorder, partial or complete cure of a disease or disorder and/or adverse effect attributable to the said disease or disorder, obtaining a desired pharmacologic and/or physiologic effect (the effect may be prophylactic in terms of completely or partially preventing a disorder or disease or condition, or a symptom thereof and/or may be therapeutic in terms of a partial or complete cure for a disease or disorder and/or adverse effect attributable to the disease or disorder), relieving a disease or disorder (i.e. causing regression of the disease or disorder). Further, the present disclosure also envisages treating the said disease by administering the therapeutic composition of the instant disclosure.

The terms "subject" and "individual" are used interchangeably herein, and mean a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of cancer. In addition, the methods described herein can be used to treat domesticated animals and/or pets. A subject can be male or female. A subject can be one who has been previously diagnosed with or identified as suffering from cancer, but need not have already undergone treatment.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

Synthesis of Cholesterol-Oxaliplatin Compounds [Formula I] with Carbamate Linkage Cholesterol-Oxaliplatin complexes comprising Carbamate linkage were synthesized as follows (FIG. 1):

Part A (FIG. 1A): (Step a): In a 250 mL round bottom flask, ethylenediamine (about 22.2 mL, 30 eq) was added to about 50 mL of dry DCM (dichloromethane). The reaction flask was cooled to about 0° C. under ice bath. Solid cholesteryl chloroformate (about 5.0 g, 11.14 mmol) dissolved in another 50 mL of dry DCM was added to the reaction flask dropwise with a dropping funnel for a period of about 30 to about 45 minutes with vigorous stirring. The resulting solution was stirred at room temperature (25° C.) for overnight (about 8 hours to 12 hours). The solution was thereafter taken in chloroform (about 100 mL) and washed sequentially for about one time to 3 times with water (3×50 mL) and brine (1×50 mL). The organic layer obtained was dried over anhydrous sodium sulfate, filtered and the solvent from the filtrate was removed by rotary evaporation. The residue upon column chromatographic purification with 60-120 mesh silica gel using 1% methanol-chloroform (v/v) as eluent gave 0.4.12 g (78%) of the pure intermediate I [FIG. 1, Part A]. ($R_f$=0.2 using 10% methanol-chloroform v/v, as the TLC developing solvent).

The characterization of intermediate (I) was carried out by proton NMR and the results are as follows: $^1$H NMR (500 MHz, CDCl$_3$) δ 5.30 (s, 1H, —C=CH), 5.05 (s, 1H, —O—CO—NH), 4.42 (s, 1H, —CH—O—), 3.18 (s, 2H, —HN—CH$_2$—CH$_2$—), 2.79 (s, 2H, —O—CO—NH—CH$_2$), 2.35-0.60 (m, 45H, cholesterol backbone).

(Step b): The intermediate I obtained in step (a) (about 1.0 g, 2.12 mmol) and succinic anhydride (about 1.04 g, 10.57 eq) together were dissolved in dry DCM (about 20 mL) and were stirred at room temperature (25° C.) for a time-period ranging from about 15 minutes to about 30 minutes. Pyridine (about 3.41 mL, 20 eq) was added dropwise and the reaction mixture was stirred for overnight (about 8 hours to 12 hours). The reaction mixture was then diluted with about 50 mL of chloroform and was washed for about three times with 0.1N HCl (3×100 mL) and brine (1×100 mL). The organic layer obtained was dried over anhydrous sodium sulfate, filtered and the solvent from the filtrate was removed by rotary evaporation and thereafter purified by silica gel chromatography to afford about 1.06 g (87%) of intermediate II. ($R_f$=0.2 using 20% Methanol-chloroform v/v, as the TLC developing solvent).

The characterization of intermediate II was carried out by proton NMR and the results are as follows: $^1$H NMR (500 MHz, CDCl$_3$) δ 6.72 (s, 1H, NH), 5.32 (s, 1H, —C=CH), 5.09 (s, 1H, NH), 4.42 (s, 1H, CH—O—), 3.35-3.18 (m, 4H, —CO—NH—CH$_2$, CO$_2$H—CH$_2$—), 2.65 (s, 2H, —O—CO—NH—CH$_2$—), 2.48 (s, 2H, —NH—CO—CH$_2$—), 2.25-0.62 (m, 43H, cholesterol backbone). ESIMS m/z=572 [M+1]$^+$ for C$_{34}$H$_{56}$N$_2$O$_5$ (Step c):In a 50 ml single neck round bottom flask about 0.15 ml (1.27 mmol) monoethylmalonate was taken along with about 185 mg (1.37 mmol) HOBt and about 263 mg (1.37 mmol) EDCl. About 7 ml dry DCM was added and the reaction mixture was continuously stirred for a time-period of about 20 minutes to 30 minutes under N$_2$ atmosphere. At 0° C., about 500 mg (1.06 mmol) of the intermediate I obtained in step (a) [Example 1] dissolved in about 5 ml dry DCM (20 mL) was added to the reaction mixture. DIPEA (N,N-Diisopropylethylamine) was added dropwise until the pH of reaction mixture reached alkaline. The reaction was continuously stirred at room temperature (of about 20° C. to 25° C.) for overnight (about 8 hours to 12 hours). The reaction mixture was thereafter washed for about three times with 0.1 N HCl (1×30 ml), saturated NaHCO$_3$ (1×50 ml) and brine (1×30 ml). The organic layer obtained was dried over anhydrous Na$_2$SO$_4$ and evaporation was carried out in rotary evaporator. Column chromatographic purification (1.5% chloroform-methanol) was performed which resulted in yield of about 530 mg (85%) of the intermediate IIIi product. ($R_f$=0.6 using 10% Methanol-chloroform v/v, as the TLC developing solvent).

The characterization of the intermediate product IIIi obtained above was carried out by proton NMR and the results are as follow: $^1$H NMR (500 MHz, CDCl$_3$) δ 7.34 (s, 1H, —CH2-NH—CO—), 5.30 (s, 1H, —CH2-CH=C—), 4.90 (s, 1H, —OCO—NH—CH2-), 4.42 (s, 1H, —CH—OCO—), 4.14 (m, 2H, —OCH2-CH3), 3.48-3.27 (m, 6H), 2.37-0.61 (m, 46H, cholesterol backbone).

(Step d): In a 50 ml single neck round bottom flask, about 1.03 g (1.75 mmol) of intermediate obtained in step (c) [Example 1] was taken in THF:H$_2$O (15 ml:5 ml) and the mixture was stirred for about 5 minutes at room temperature (about 20° C. to 25° C.). To this reaction mixture, about 146 mg (3.50 mmol) of LiOH (Lithium hydroxide) was added and the mixture was stirred for an additional time-period of about 2-3 hours at room temperature (about 25° C.). After completion of the reaction, the mixture was diluted with chloroform (about 100 ml) and acidified with about 50 ml diluted HCl (0.1N). The organic layer obtained was washed with NaHCO$_3$ solution (about 50 ml) and dried over anhydrous Na$_2$SO$_4$. Column chromatographic purification (4% methanol-chloroform) was performed which afforded about 631 mg (64%) of intermediate III. ($R_f$=0.4 using 20% Methanol-chloroform v/v, as the TLC developing solvent).

(Step e): In a 50 ml single neck round bottom flask, about 0.12 ml (1.27 mmol) monoethyloxalate was taken along with about 185 mg (1.37 mmol) HOBt and about 263 mg (1.37 mmol) EDCl. About 7 ml dry DCM was added and the reaction mixture was continuously stirred for a time-period of about 20 minutes to about 30 minutes under N$_2$ atmosphere. At 0° C., about 500 mg (1.06 mmol) of the intermediate I obtained in step (a) [Example 1] dissolved in about 5 ml dry DCM (about 20 mL) was added to the reaction mixture. DIPEA was added dropwise until the pH of reaction mixture reaches alkaline. The reaction mixture was continuously stirred at room temperature for overnight. The reaction mixture was washed with 0.1N HCl (1×30 ml), saturated NaHCO$_3$ (1×50 ml) and brine (1×30 ml). The organic layer obtained was dried over anhydrous Na$_2$SO$_4$ and evaporated in rotary evaporator. Column chromatographic purification (1.5% methanol-chloroform) was performed which yielded about 570 mg (94%) of intermediate product IVi. (R$_f$=0.6 using 10% Methanol-chloroform v/v, as the TLC developing solvent).

The characterization of the intermediate product IVi obtained above was carried out by proton NMR and the results are as follows: $^1$H NMR (500 MHz, CDCl$_3$) δ 7.40 (s, 1H, —CO—NH—CH2-), 5.28 (s, 1H, —CH═C—), 4.30 (q, J=7.1 Hz, 2H, —O—CH2-CH3), 3.52 (d, J=3.7 Hz, 2H, —O—CH2-CH2-), 3.46 (d, J=4.2 Hz, 2H, —NH—CH2-CH2-), 3.11 (t, J=11.0 Hz, 1H, —O—CH—CH2-), 2.33-0.55 (m, 47H, cholesterol back bone).

(Step d'): In a 50 ml single neck round bottom flask, about 500 mg (0.87 mmol) intermediate obtained in step (e) [Example 1] was taken in THF:H$_2$O (15 ml:5 ml) and stirred for about 5 minutes at room temperature. To this reaction mixture, about 75 mg (1.75 mmol) of LiOH was added and the mixture was stirred for an additional time-period of about 2 hours at room temperature. After completion of the reaction, the mixture was diluted with chloroform (about 50 ml) and acidified with about 50 ml diluted HCl (0.1N). The organic layer was washed with NaHCO$_3$ solution (50 ml) and dried over anhydrous Na$_2$SO$_4$. Column chromatographic purifation (4% methanol-chloroform) was performed which afforded about 180 mg (38%) of intermediate IV. (R$_f$=0.2 using 10% Methanol-chloroform v/v, as the TLC developing solvent).

Part B (FIG. 1B): (Step f): Dichloro (1,2-diammino-cyclohexane) platinum (II) (about 300 mg, 0.79 mmol) was partially dissolved in about 40.0 mL of H$_2$O. To the solution, silver nitrate (about 340 mg, 1.58 mmol) was added and the resulting reaction mixture was stirred at room temperature for a time-period of about 24 hours. When the mixture appeared milky white, silver chloride was removed by centrifuging at about 12000 rpm for about 30 minutes. Finally, the aquated oxaliplatin V was obtained by filtration through 0.2 μM filter.

Part C (FIG. 1C): (Step g): Synthesis of Compound 1: Intermediate II (about 407 mg, 0.71 mmol) obtained in step b (Example 1, PART A) was dissolved in about 1.5 mL DMF. To the solution, about 40.0 mL of aquated oxaliplatin V (0.09 mmol) obtained in step f (Example 1, PART B) was added and the reaction mixture was stirred for about 24 hours. Lyophilization of the reaction mixture yielded cholesterol-oxaliplatin compound Compound 1.

The characterization results (proton NMR and MALDI-TOF MS) of Compound 1 are as follow: $^1$H NMR (500 MHz, CDCl$_3$) δ 6.65 (s, 1H, NH), 5.30 (s, 1H, —C═CH), 5.01 (s, 1H, NH), 4.42 (s, 1H, CH—O—), 3.42 (s, 2H, Pt—NH$_2$—CH—), 3.38-3.18 (m, 4H, —CO—NH—CH$_2$, CO$_2$H—CH$_2$—), 2.65 (s, 2H, —O—CO—NH—CH$_2$—), 2.48 (s, 2H, —NH—CO—CH$_2$—), 2.30-0.58 (m, 55H, cholesterol backbone and amino cyclohexane). MALDI-TOF MS=880.4784 [M]$^+$ for C$_{40}$H$_{69}$N$_4$O$_5$Pt Step (g'): Synthesis of Compound 2: Intermediate III (about 58 mg, 0.11 mmol) obtained in step d (Example 1, PART A) was dissolved in about 1.5 mL DMF. To the solution, about 8.0 mL of aquated oxaliplatin V (0.11 mmol) obtained in step f (Example 1, PART B) was added and the reaction mixture was stirred for about 24 hours. Lyophilization of the reaction mixture afforded cholesterol-oxaliplatin compound Compound 2.

The characterization results (proton NMR and MALDI-TOF MS) of Compound 2 are as follows: $^1$H NMR (500 MHz, CDCl$_3$) δ 7.41 (s, H, —CO—NH—CH2-), 5.40 (s, 1H, —CH2-CH═C—), 5.07 (s, 1H, —OCO—NH—CH2-),-), 4.49 (m, 1H, —CH—OCO—), 3.48-3.27 (m, 6H), 2.88 (s, 1H, —CH—NH2), 2.81 (s, 1H, —CH—NH2), 2.30-0.51 (m, 46H, cholesterol backbone and amino cyclohexane). MALDI-TOF MS=886.5048 [M]$^+$ for C$_{39}$H$_{67}$N$_4$O$_5$Pt.

Step (g''): Synthesis of Compound 3: Intermediate IV (about 57 mg, 0.11 mmol) obtained in step d' (Example 1, PART A) was dissolved in about 1.5 mL DMF. To the solution, about 8.0 mL of aquated oxaliplatin V (0.11 mmol) obtained in step f (Example 1, PART B) was added and the reaction mixture was stirred for about 24 hours. Lyophilization of the reaction mixture afforded cholesterol-oxaliplatin compound Compound 3.

The characterization results (proton NMR and MALDI-TOF MS) of Compound 3 are as follows: $^1$H NMR (500 MHz, CDCl$_3$) δ 7.84 (s, 1H, —O—CO—NH—CH2-), 5.31 (s, 1H, —CH═C—), 4.89 (s, 1H, —CO—NH—CH2-), 4.44 (s, 1H, —O—CH—CH2-), 3.48-3.40 (m, 2H, —CO—NH—CH$_2$-), 3.37-3.28 (m, 2H, —O—CO—NH—CH$_2$-), 2.91 (s, 1H, NH2-CH—CH2-), 2.83 (s, 1H, NH2-CH—CH2-), 2.33-0.56 (m, 55H, cholesterol back bone, and cyclohexane ring protons). MALDI-TOF MS=853.4823 [M]$^+$ for C$_{38}$H$_{65}$N$_4$O$_5$Pt Example 2

Synthesis of Cholesterol-Oxaliplatin Compounds [Formula I] with Ether Linkage

Cholesterol-Oxaliplatin complexes comprising ether linkage were synthesized as follows (FIG. 2):

Part A (FIG. 2A): (Steps a-e): Synthesis of amine intermediate (II): Steps a to e was carried out as described in Example 3 (Steps 1 to 5; Synthesis of Compound 25).

(Step f): To a 100 mL single round bottom flask, intermediate II obtained after steps (a-e) [Example 2, PART A] (amine 500 mg, 1.164 mmol) was taken in DCM (about 10 mL) under N$_2$ atmosphere and stirred for a time-period ranging from about five minutes to about ten minutes at room temperature. The reaction mixture was cooled to about 0° C. and succinic anhydride (about 570 mg, 5.82 mmol) followed by pyridine (about 1.88 ml, 23.3 mmol) was added and the reaction mixture was again allowed to stir for about 24 hours at room temperature.

After completion of the stirring process (checked by TLC), the reaction mixture was diluted with CH$_2$Cl$_2$ (about 20 mL) and washed with 0.1N HCl (about 500 mL, to remove pyridine completely) followed by drying over anhydrous Na$_2$SO$_4$. The organic layer was concentrated under vacuo and purified by silica gel chromatography which afforded the required intermediate III in 95% yield (about 585 mg).

The characterization of intermediate III was carried out by proton NMR and the results are as follows: $^1$H NMR (500 MHz, CDCl$_3$) δ 6.18 (s, 1H, —CO—NH—CH2-), 5.28 (s, 1H, —CH═C—), 3.49 (d, J=4.4 Hz, 2H, —O—CH2-CH2-), 3.38 (d, J=4.4 Hz, 2H, —NH—CH2-CH2-), 3.11 (t, J=11.1 Hz, 1H, —O—CH—CH1-), 2.63 (t, J=6.4 Hz, 2H, —NH—CO—CH2-), 2.47 (t, J=6.4 Hz, 2H, HOOC—CH2-), 2.31-0.55 (m, 43H, cholesterol back bone).

(Step g): In a 50 ml single neck round bottom flask, about 0.07 ml (0.64 mmol) monoethylmalonate was taken with 74 mg (0.64 mmol) HOBt and about 134 mg (0.69 mmol) EDCl. About 7 ml dry DCM was added and reaction mixture was continuously stirred for a time-period of about 20 minutes to 30 minutes under N$_2$ atmosphere. At about 0°

C., about 250 mg (0.58 mmol) of the intermediate II obtained after steps (a-e) [Example 2, PART A] dissolved in about 5 ml dry DCM (20 mL) was added to the reaction mixture. DIPEA was added dropwise until the pH of reaction mixture turned alkaline. The reaction mixture was continuously stirred at about room temperature for overnight and washed for about 3-4 times with 0.1N HCl (1×30 ml), saturated NaHCO$_3$ (1×50 ml) and brine (1×30 ml) successively. The organic layer was dried over anhydrous Na$_2$SO$_4$ and evaporation was carried out in rotary evaporator. Column chromatographic purification (1.5% methanol-chloroform) was performed which yielded about 290 mg (92% pure) of intermediate IVi compound ($R_f$=0.5 using 5% Methanol-chloroform v/v, as the TLC developing solvent).

The characterization of the intermediate product IVi obtained above was carried out by proton NMR and the results are as follows: $^1$H NMR (500 MHz, CDCl$_3$) δ 7.27 (s, 1H, —CO—NH—CH2-), 5.28 (s, 1H, —CH=C—), 4.13 (q, J=7.1 Hz, 2H, —O—CH2-CH3), 3.49 (d, J=4.0 Hz, 2H, —O—CH2-CH2-), 3.40 (d, J=4.8 Hz, 2H, —NH—C H2-CH2-), 3.25 (s, 2H, —CO—CH2-CO—), 3.10 (t, J=10.9 Hz, 1H, —O—CH—CH2-), 2.34-0.55 (m, 46H, cholesterol back bone).

(Step h): In a 25 ml single neck round bottom flask, about 250 mg (0.46 mmol) intermediate IVi obtained in step (g) [Example 2] was taken in THF:H$_2$O (9 ml:3 ml) and the mixture was stirred for about 5 minutes at room temperature. To this reaction mixture, about 58 mg (1.38 mmol) LiOH was added and the mixture was stirred for an additional time-period of about 3 hours at room temperature (about 20° C. to 25° C.). After completion of the reaction, the mixture was diluted with chloroform (about 50 ml) and acidified with about 10 ml diluted HCl (0.1N). The organic layer was washed with NaHCO$_3$ solution (about 20 ml) and dried over anhydrous Na$_2$SO$_4$. Column chromatographic purification (4% methanol-chloroform) was performed which afforded about 228 mg (96%) of intermediate IV. ($R_f$=0.4 using 20% Methanol-chloroform v/v, as the TLC developing solvent).

(Step i): In a 50 ml single neck round bottom flask, about 0.06 ml (10.64 mmol) monoethyloxalate was taken along with about 74 mg (0.64 mmol) HOBt and about 145 mg (0.76 mmol) EDCl. About 7 ml dry DCM was added and the reaction mixture was continuously stirred for a time-period of about 20 minutes to about 30 minutes under N$_2$ atmosphere. At 0° C., about 250 mg (0.58 mmol) of the intermediate II obtained after steps (a-e) dissolved in about 5 ml dry DCM (20 mL) was added to the reaction mixture. DIPEA was added dropwise until the pH of the reaction mixture turned alkaline. The reaction mixture was continuously stirred at room temperature for overnight followed by washing with 0.1N HCl (1×30 ml), saturated NaHCO$_3$ (1×50 ml) and brine (1×30 ml) successively. The organic layer was dried over anhydrous Na$_2$SO$_4$ and evaporated in rotary evaporator. Column chromatographic purification (1.5% methanol-chloroform) was performed which yielded about 128 mg (41%) of intermediate VIi compound. ($R_f$=0.5 using 10% Methanol-chloroform v/v, as the TLC developing solvent).

The characterization of the intermediate product VIi obtained above was carried out by proton NMR and the results are as follows: $^1$H NMR (500 MHz, CDCl$_3$) δ 7.40 (s, 1H, —CO—NH—CH2-), 5.28 (s, 1H, —CH=C—), 4.30 (q, J=7.1 Hz, 2H, —O—CH2-CH3), 3.52 (d, J=3.7 Hz, 2H, —O—CH2-CH2-), 3.46 (d, J=4.2 Hz, 2H, —NH—C H2-CH2-), 3.11 (t, J=11.0 Hz, 1H, —O—CH—CH2-), 2.33-0.55 (m, 47H, cholesterol back bone).

Step (h'): In a 25 ml single neck round bottom flask, about 128 mg (0.22 mmol) intermediate as obtained in step (i) [Example 2] above was taken in THF:H$_2$O (3 ml:1 ml) and stirred for about 5 minutes at room temperature. To this reaction mixture, about 18 mg (0.45 mmol) LiOH was added and the reaction mixture was stirred for an additional time-period of about 2 hours at room temperature. After completion of the reaction, the reaction mixture was diluted with chloroform (about 15 ml) followed by acidification with about 10 ml diluted HCl (0.1N). The organic layer was washed with NaHCO$_3$ solution (about 20 ml) and dried over anhydrous Na$_2$SO$_4$. Column chromatographic purification (4% methanol-chloroform) was performed which afforded about 79 mg (66% pure) of intermediate V. ($R_f$=0.2 using 10% Methanol-chloroform v/v, as the TLC developing solvent).

Part B (FIG. 2B): Step (j): Dichloro (1,2-diaminocyclohexane) platinum (II) (about 300 mg, 0.79 mmol was partially dissolved in about 40.0 mL of H$_2$O. Silver nitrate (about 340 mg, 1.58 mmol) was added to the same and the resulting reaction mixture is stirred at room temperature for about 24 hours. After the appearance of milky white, silver chloride was removed by centrifuging at around 12000 rpm for about 30 minutes. Finally, the aquated oxaliplatin VI was obtained by filtration through 0.2 μM filter.

Part C (FIG. 2C): Step (k): Synthesis of Compound 4: Intermediate III (about 69 mg, 0.13 mmol) obtained in step (f) (Example 2, PART A) was dissolved in about 1.5 mL DMF. Thereafter, about 10 mL of aquated oxaliplatin VI (0.13 mmol) as obtained in step (j) (Example 2, PART B) was added and the reaction mixture was stirred for about 24 hours. Lyophilization of the reaction mixture affords cholesterol-oxaliplatin compound Compound 4.

The characterization results (proton NMR and MALDI-TOF MS) of Compound 4 are as follows: $^1$H NMR (500 MHz, CDCl3) δ 6.12 (s, 1H, —CO—NH—CH2-), 5.30 (d, J=4.9 Hz, 1H, —CH=C—), 3.50 (t, J=4.8 Hz, 2H, —O—CH2-CH2-), 3.43-3.35 (m, 2H, —NH—CH2-CH2-), 3.17-3.05 (m, 1H, —O—CH—CH2-), 2.91 (s, 1H, NH2-CH—), 2.84 (s, 1H, NH2-CH—), 2.65 (dd, J=7.6, 5.1 Hz, 2H, —O—CO—CH2-CH2), 2.56-2.46 (m, 2H, —NH—CO—CH2-), 2.30-0.56 (m, 55H, cholesterol back bone, and cyclohexane ring protons). MALDI-TOF MS=837.5227 [M]$^+$ for $C_{39}H_{68}N_3O_4Pt$ Step (k'): Synthesis of Compound 5: Intermediate IV (27 mg, 0.05 mmol) obtained in step h (Example 2, PART A) was dissolved in about 1.5 mL DMF. Thereafter, about 10 mL of aquated oxaliplatin VI (0.05 mmol) obtained in step j (Example 2, Part B) was added and the reaction mixture was stirred for about 24 hours. Lyophilization of the reaction mixture afforded cholesterol-oxaliplatin compound Compound 5.

The characterization results (proton NMR and MALDI-TOF MS) of Compound 5 are as follows: $^1$H NMR (500 MHz, CDCl3) δ 6.52 (s, 1H, —CO—NH—CH2-), 5.28 (d, J=5.0 Hz, 1H, —CH=C—), 3.51 (t, J=4.5 Hz, 2H, —O—CH2-CH2-), 3.41 (m, 2H, —NH—CH2-CH2-), 3.27 (s, 2H, —CO—CH2-CO—), 3.17-3.02 (m, 1H, —O—CH—CH2-), 2.89 (s, 1H, NH2-CH—), 2.82 (S, 1H, NH2-CH—), 2.30-0.56 (m, 55H, cholesterol back bone, and cyclohexane ring protons). MALDI-TOF MS=823.5242 [M]$^+$ for $C_{38}H_{66}N_3O_4Pt$ Step (k"): Synthesis of Compound 6: Intermediate V (26 mg, 0.05 mmol) obtained in step h' (Example 2, PART A) was dissolved in about 1.5 mL DMF. Thereafter, about 5 mL of aquated oxaliplatin VI (0.05 mmol) obtained in step e (Example 2, PART B) was added and the reaction mixture was stirred for about 24 hours. Lyophilization of the reaction mixture afforded cholesterol-oxaliplatin compound Compound 6.

The characterization results (proton NMR and MALDI-TOF MS) of Compound 6 are as follows: $^1$H NMR (500 MHz, CDCl$_3$) δ 7.96 (s, 1H, —CO—N$\underline{H}$—CH2-), 5.28 (s, 1H, —C$\underline{H}$=C—), 3.61-3.42 (m, 4H, —OC$\underline{H}$2-CH2-, —NH—C$\underline{H}$2-CH2), 3.18-3.02 (m, 1H, —OC$\underline{H}$—CH2-), 2.90 (s, 1H, NH2-C$\underline{H}$—), 2.82 (s, 1H, NH2-C$\underline{H}$—), 2.31-0.56 (m, 55H, cholesterol back bone, and cyclohexane ring protons). MALDI-TOF MS=809.5258 [M]$^+$ for C$_{37}$H$_{64}$N$_3$O$_4$Pt Similar to the synthetic procedures as described above, Compound 7-21 were prepared by employing necessary carboxylic acids, linker molecules, lipid and platinum moieties.

Example 3

Synthesis of Compounds of Formula II

Synthesis of Compound 25

Step 1: To an ice cooled solution of cholesterol 1.01 (about 10 g, 0.026 mol) in CH$_2$Cl$_2$ (about 45 mL), pyridine (about 15 mL) is added and stirred for about 15 minutes. To this solution, p-toluene sulphonyl chloride (about 9.8 g, 0.052 mol) is added and stirred for about 6 h at about 0° C. and thereafter, TLC is checked. After completion, the reaction mixture is diluted with CHCl$_3$ (about 20 mL) and washed with about 1N HCl (3×50 mL) and brine (about 20 mL) successively. The organic layer is dried over anhydrous Na$_2$SO$_4$ and concentrated under vacuum to afford intermediate 1.02 and the said intermediate is directly taken for the next reaction without further purification.

Step 2: To the solution of tosylated cholesterol 1.02 (about 10 g, 0.018 mol) in dioxane (about 45 mL), ethylene glycol (about 15 mL) is added and refluxed for about 4 h. The TLC is checked. After completion, the reaction mixture is extracted with ethyl acetate and washed with water (about 3×50 mL) and brine (about 20 mL) successively. The organic layer is dried over anhydrous Na$_2$SO$_4$ and concentrated under vacuum and column purified to afford intermediate 1.03.

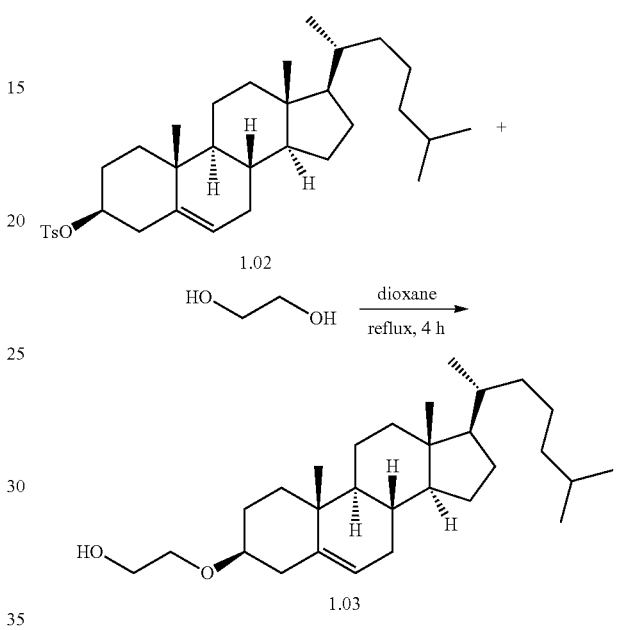

Step 3: To an ice cooled solution of cholesteryl ethylene glycol 1.03 (about 6.95 g, 16.13 mmol) in dichloro methane (about 15 ml) pyridine (about 13 mL) is added under nitrogen atmosphere and stirred for about 15 minutes. To this solution, p-toluene sulphonyl chloride (about 3.7 g, 19.35 mmol) is added and stirred for about 5 h at about 0° C. and TLC is checked. After completion, the reaction mixture is diluted with CHCl$_3$ (about 20 mL) and washed with about 1N HCl (3×50 mL) and brine (about 20 mL) successively. The organic layer is dried over anhydrous Na$_2$SO$_4$ and concentrated under vacuum and purified by silica gel chromatography to obtain intermediate 1.04.

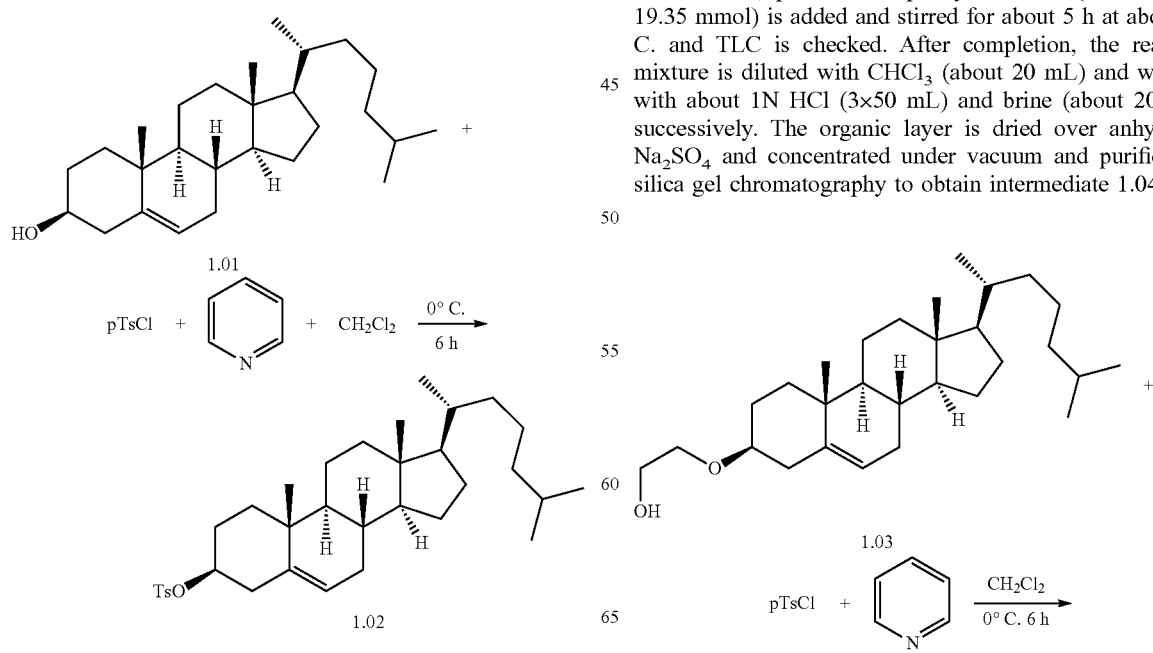

-continued

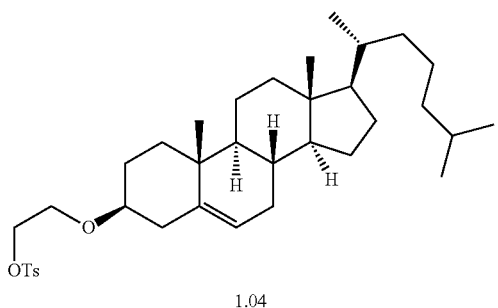
1.04

Step 4: To a 50 mL round bottomed flask, compound 1.04 (about 6 g, 10.26 mmol) is taken in DMF (about 20 ml) under nitrogen atmosphere and is stirred for about 30 minutes to get a clear solution (warm if necessary). To this solution, sodium azide (about 3.4 g, 51.33 mmol) is added and stirred for about 18 h at room temperature and TLC is checked. After completion, the reaction mixture is concentrated under vacuum to remove THF and is purified by flash chromatography to obtain intermediate 1.05.

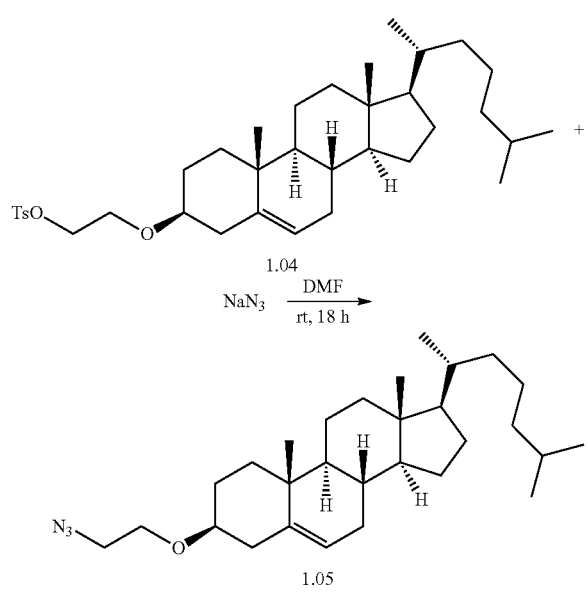

Step 5: To a solution of azide 1.05 (about 3 g, 7.6 mmol) in dry DMF (about 15 ml), TPP (about 1.5 g, 15.2 mmol) is added under nitrogen atmosphere. The reaction is stirred for about 6 h at room temperature and about 2 mL of water is added to the reaction mixture. The reaction mixture is stirred for additional time-period of about 6 h and TLC is checked. After completion, the reaction mixture is concentrated under reduced pressure and is purified by silica gel chromatography utilizing methanol/chloroform as eluent to achieve amine intermediate 1.06.

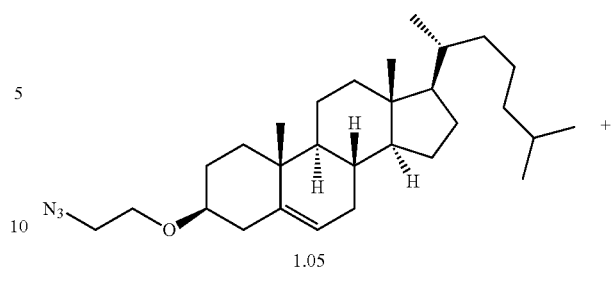

Step 6: To an ice cool solution of amine 1.06 (about 300 mg, 0.698 mmol) in THF (about 5 mL), NaH (about 120 mg, 2.094 mmol) is added by pinch over a period of about 10 minutes. The resulting solution is stirred for about 20 minutes and ethyl bromo acetate is added and stirred for a time-period of about 6 h at room temperature. After completion, the reaction mixture is cooled to about 0° C. and quenched with water and the compound is extracted with ethyl acetate (about 2×20 mL). The organic layer is dried over anhydrous Na2SO4, concentrated and purified by silica gel chromatography to obtain diester intermediate 1.07 in about 52% yield.

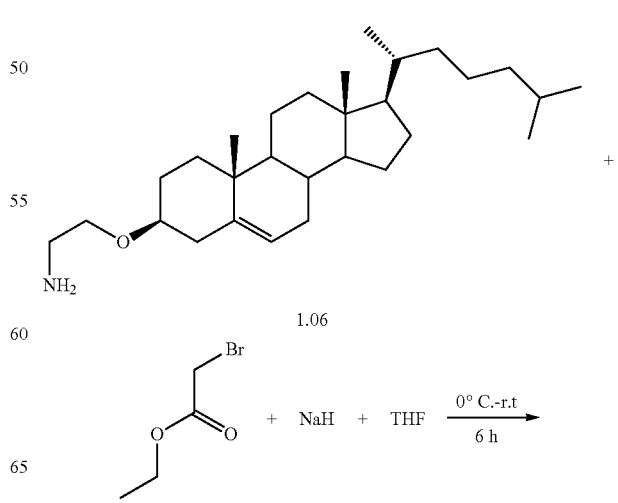

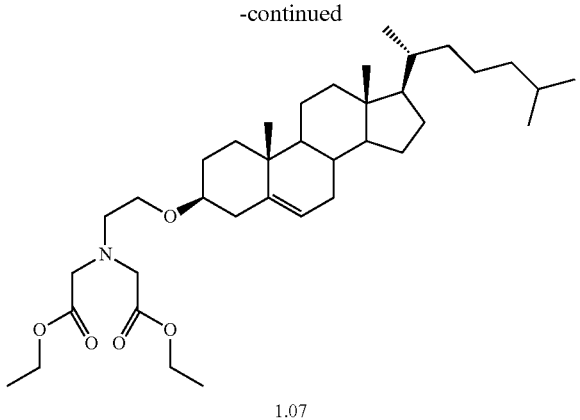

1.07

Step 7: To a 50 mL single neck round bottom flask, diester compound 1.07 (about 218 mg, 0.363 mmol) is taken in THF/water (about 4 mL, at a ratio of about 3:1) and cooled to about 0° C. To this cooled solution, LiOH (about 34 mg, 1.45 mmol) is added and stirred at room temperature for a time-period of another 6 h. After completion, the reaction mixture is concentrated under reduced pressure to remove THF and the aqueous layer is washed with ethyl acetate. The aqueous layer is lyophilized to get solid di-lithium salt of 1.08 with a quantitative yield.

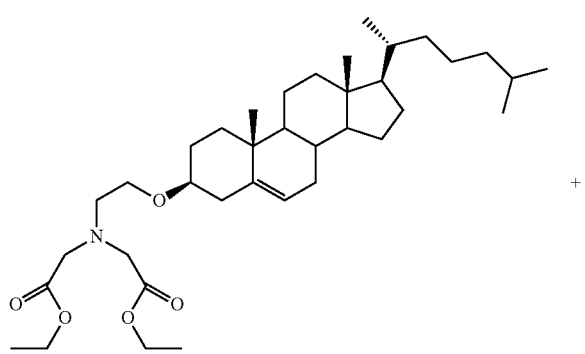

1.07

+ LiOH + THF/H$_2$O $\xrightarrow{r.t}$

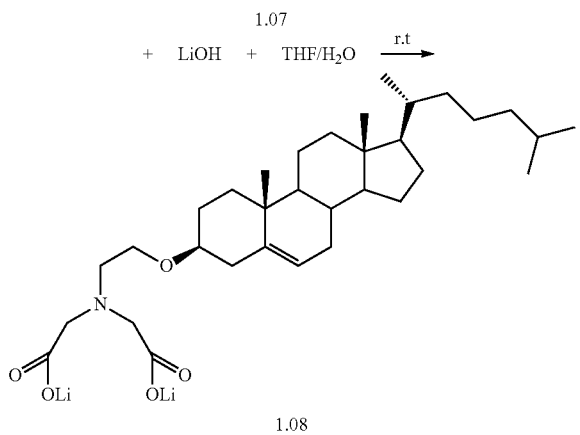

1.08

Step 8: Synthesis of DACH-Pt(H$_2$O)$_2$: To a 50 mL single neck round bottom flask dichloro (1,2-diammino-cyclohexane) platinum 1.09 (about 200 mg, 0.526 mmol) is taken in about 20.0 mL of H$_2$O. To this suspension, silver nitrate (about 178.7 mg, 1.052 mmol) is added and the reaction mixture is stirred at room temperature for about 24 h. The milky white solution is centrifuged and the solution is filtered through 0.22 μM syringe filter to obtain aquated DACH-Pt 1.10 in quantitative yield (about 10 mg/mL).

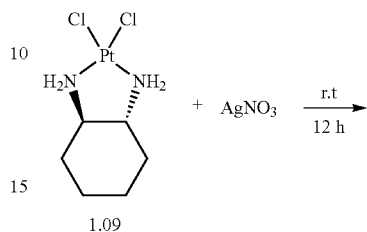

1.09

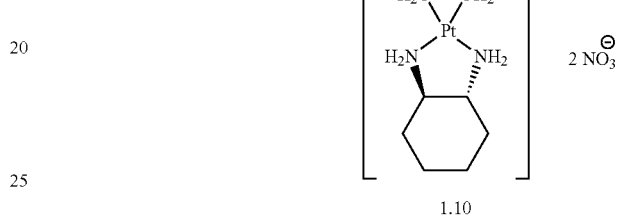

1.10

Step 9: To a 100 mL single neck round bottom flask intermediate 1.08 (about 202 mg, 0.363 mmol) is taken in about 1.0 mL water. To this solution, DACHPt(H$_2$O)$_2$ (about 13.8 mL) obtained in the previous step is added and stirred for another 12 h. The solid residue is filtered and washed with water (about 20 mL). The white solid residue is lyophilized and dissolved in excess methanol, filtered and concentrated under reduced pressure to afford cholesterol-oxaliplatin amphiphile Compound 25 in about 85% yield.

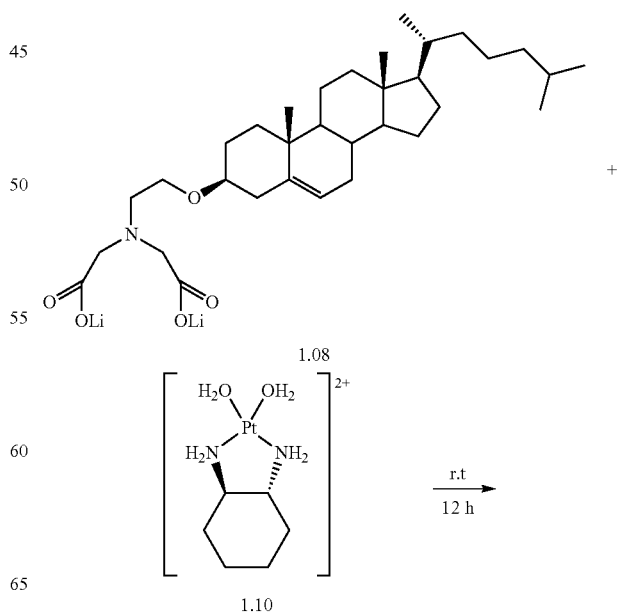

1.08

1.10

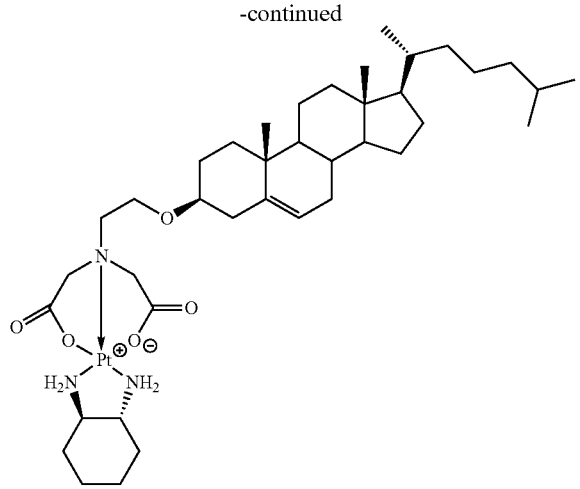

Synthesis of Compound 26

Step 1: To an ice cooled solution of ethylene diamine (about 22.2 mL) in CH$_2$Cl$_2$ (about 40 mL), a solution of compound 1.11 (about 5 g) in CH$_2$Cl$_2$ (about 50 mL) is added dropwise over a period of about 45 min and the reaction mixture is stirred at the same temperature for about 1 h and is further allowed to stir at room temperature for an additional time-period of about 20 h. After completion (checked by TLC), the reaction mixture is quenched with water and extracted with dichloro methane (about 4×50 mL), the combined organic layer is dried over anhydrous Na$_2$SO$_4$ and concentrated under vacuum. The residue is purified by column chromatography utilizing methanol-chloroform as eluent to obtain intermediate 1.12.

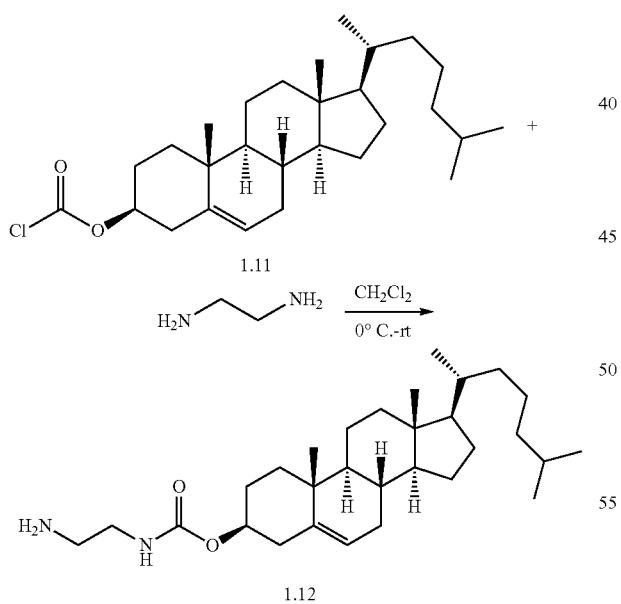

Step 2: To a 50 mL single neck round bottom flask amine 1.12 (about 300 mg 0.634 mmol) is taken in THF (about 5 mL) under nitrogen atmosphere. The reaction mixture is cooled to about 0° C. under ice bath and NaH (about 130 mg, 3.17 mmol) is added by pinch over a period of about 10 minutes. The resulting solution is stirred for about 20 minutes and ethyl bromo acetate is added. The reaction mixture is stirred for about 2 h at room temperature and TLC is checked. After completion, the reaction mixture is cooled to about 0° C. and quenched with cold water (about 5 mL), extracted with ethyl acetate (about 2×20 mL), dried over anhydrous Na$_2$SO$_4$ and thereafter concentrated. The residue is purified by column chromatography utilizing methanol-chloroform as eluent to obtain intermediate 1.13.

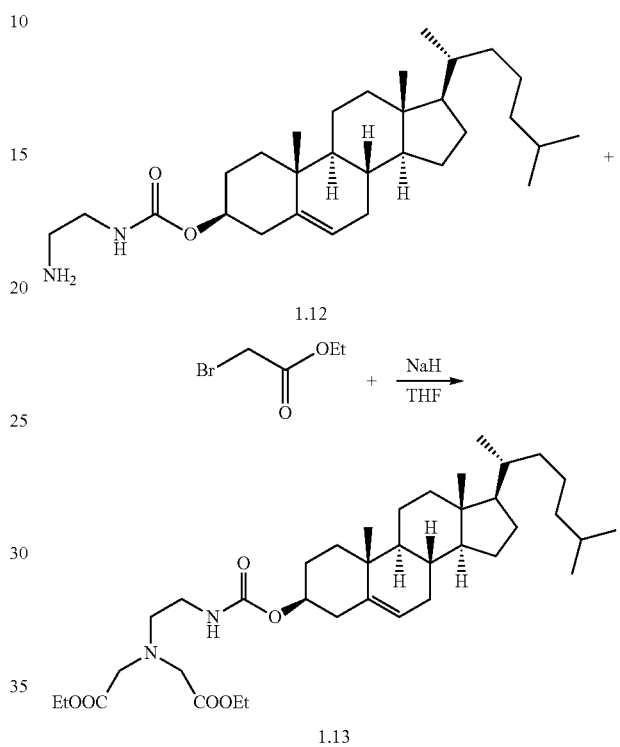

Step 3: To a 50 mL single neck round bottom flask, diester 1.13 (about 1.7 g, 2.63 mmol) is taken in THF/water (about 3:1) (about 16 mL). The reaction mixture is cooled to about 0° C. under ice bath and LiOH (about 130 mg, 5.27 mmol) is added to the reaction mixture. The resulting solution is stirred for about 6 h at room temperature and TLC is checked. After completion, the reaction mixture is concentrated under reduced pressure to remove THF and diluted with water (about 5 mL). The water layer is washed with ethyl acetate and CH$_2$Cl$_2$ successively and lyophilized to obtain intermediate 1.14 in quantitative yield.

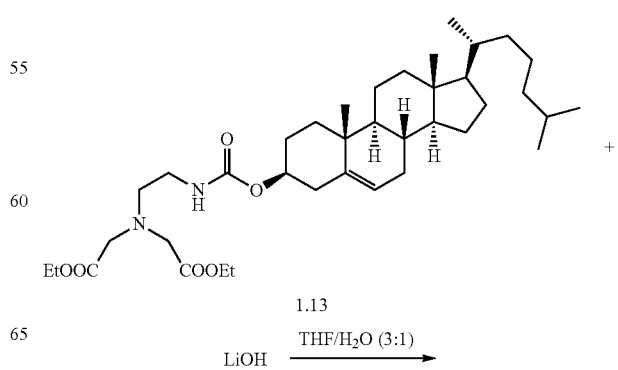

-continued

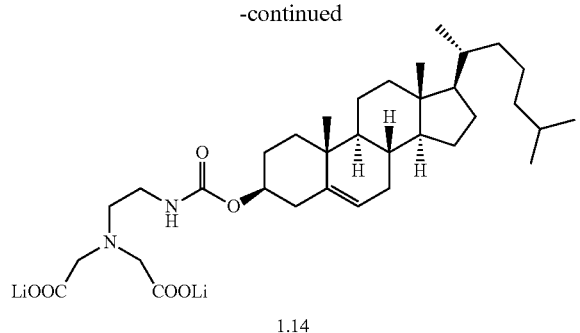

1.14

Step 4: To a 100 mL single neck round bottom flask, intermediate 1.14 is taken in about 1.0 mL water. To this solution, DACHPt(H$_2$O)$_2$ is added and stirred for a time-period of another 12 h. The solid residue obtained is filtered, washed with water and lyophilized. The residue is dissolved in excess methanol, filtered and concentrated under reduced pressure to afford cholesterol-oxaliplatin amphiphile Compound 26.

Synthesis of Compound 27

Step 1: To a 50 mL single neck round bottom flask, BocHNCH$_2$COOH (about 370 mg, 2.08 mmol) is taken in CH$_2$Cl$_2$ (about 10 mL) under nitrogen atmosphere. Solid EDCl (about 400 mg, 2.08 mmol) and HOBT (about 285 mg, 2.08 mmol) are added successively to the reaction mixture. DIPEA is added to make the solution alkaline and the reaction mixture is stirred for another 20 minutes. To this activated acid solution, amine 1.06 (about 450 mg, 1.04 mmol) is added and the mixture is stirred at room temperature for about 12 h and TLC is checked. After completion, the reaction mixture is quenched with water, extracted with chloroform, dried over anhydrous Na$_2$SO$_4$ and thereafter concentrated. The residue is purified by silica gel chromatography utilizing methanol-chloroform as eluent to obtain intermediate 1.15.

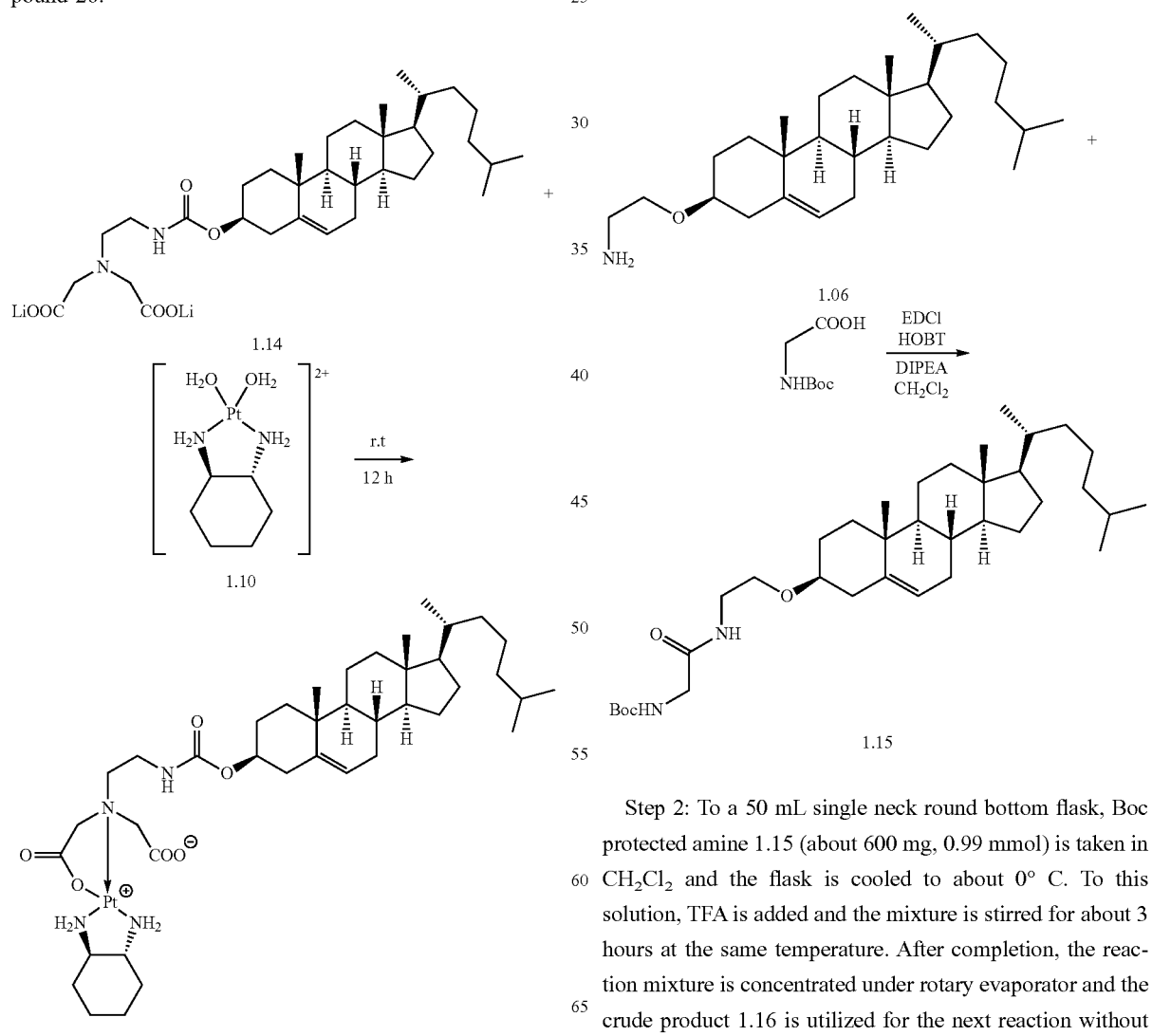

Step 2: To a 50 mL single neck round bottom flask, Boc protected amine 1.15 (about 600 mg, 0.99 mmol) is taken in CH$_2$Cl$_2$ and the flask is cooled to about 0° C. To this solution, TFA is added and the mixture is stirred for about 3 hours at the same temperature. After completion, the reaction mixture is concentrated under rotary evaporator and the crude product 1.16 is utilized for the next reaction without further purification.

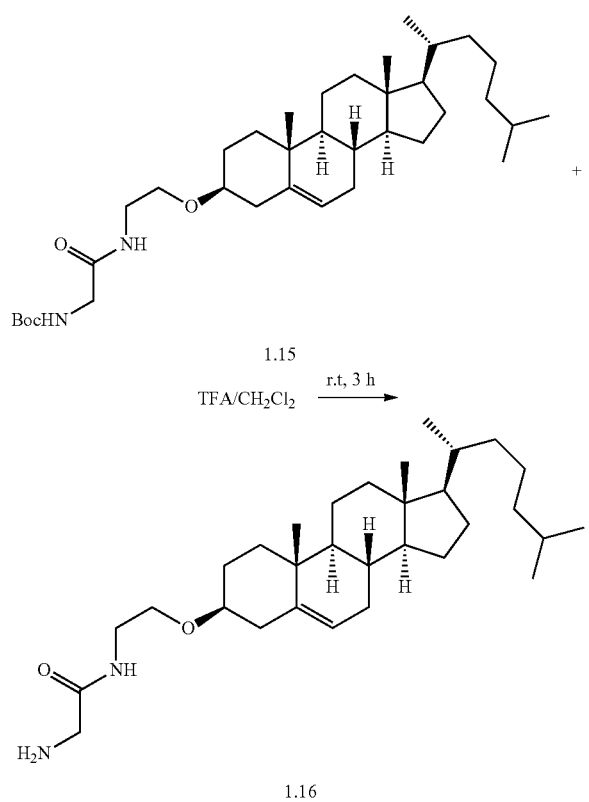

1.15

TFA/CH₂Cl₂, r.t, 3 h 1.16

Step 3: To a 50 mL single neck round bottom flask, crude amine 1.16 (about 400 mg, 0.821 mmol) is taken in THF (about 10 mL) under nitrogen atmosphere. The solution is cooled to about 0° C. under ice bath and solid NaH (about 160 mg, 4.10 mmol) is added pinch wise over a period of about 10 minutes. The resulting solution is stirred for an additional 20 minutes and ethyl bromo acetate is added. After completion, the reaction mixture is cooled to about 0° C. and quenched with water, extracted with ethyl acetate, dried over anhydrous Na₂SO₄ and thereafter concentrated under vacuum. The residue is purified by silica gel chromatography utilizing methanol-chloroform as eluent to obtain intermediate 1.17.

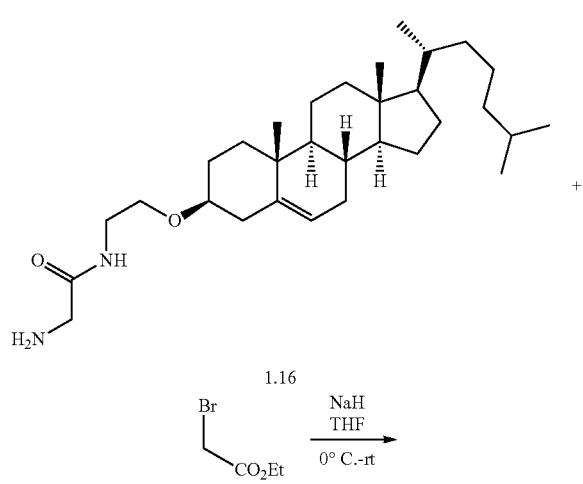

1.16

NaH
THF
0° C.-rt

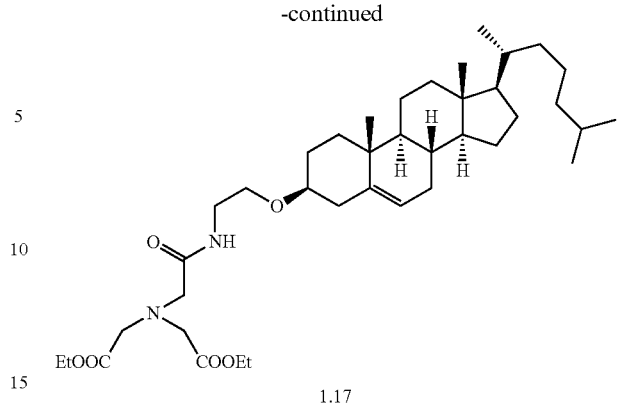

1.17

Step 4: To a 50 mL single neck round bottom flask, diester 1.17 (about 200 mg, 0.303 mmol) is taken in THF/water (about 3:1) (about 4 mL) at about 0° C. Solid LiOH (about 15 mg, 0.606 mmol) is added to the reaction mixture and stirred for about 6 hours at room temperature. After completion, the reaction mixture is concentrated and diluted with water (about 4 mL). The aqueous layer is washed with ethyl acetate and dichloro methane successively and is lyophilized to obtain solid powder of acid salt 1.18 in quantitative yield.

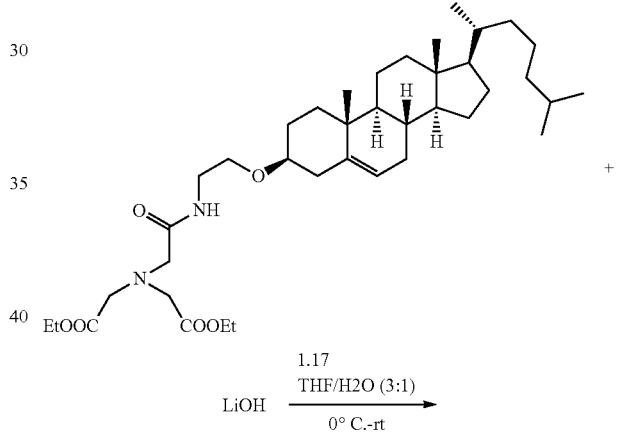

1.17

LiOH, THF/H2O (3:1), 0° C.-rt

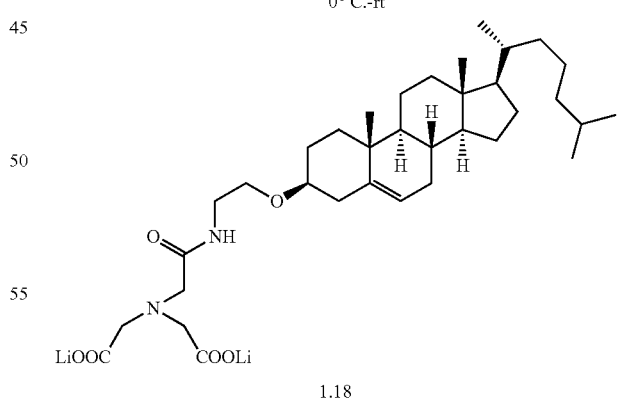

1.18

Step 5: To a 100 mL single neck round bottom flask, intermediate 1.18 is taken in about 1.0 mL water. To this solution, DACHPt(H₂O)₂ is added and stirred for another 12 hours. The solid residue is filtered and washed with water and thereafter lyophilized. The residue is dissolved in excess methanol, filtered and concentrated under reduced pressure to afford cholesterol-oxaliplatin amphiphile Compound 27.

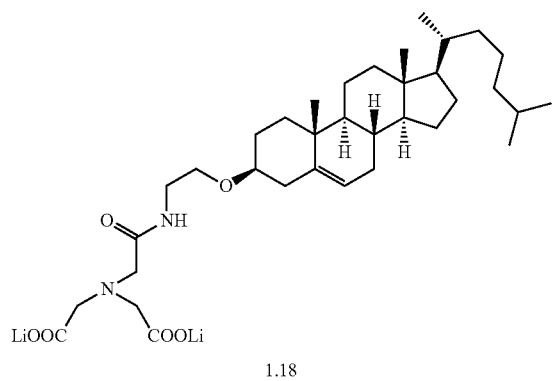

1.18

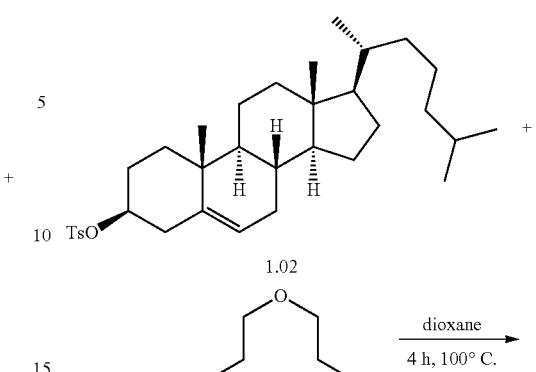

1.02

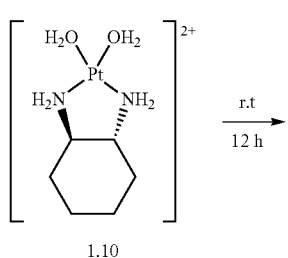

1.10

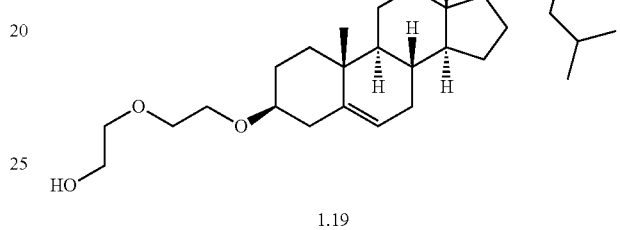

1.19

Step 2: To an ice cooled solution of cholesteryl alcohol 1.19 (about 5 g, 10.54 mmol) and p-toluene sulphonyl chloride (about 4 g, 21.09 mmol) in DCM (about 25 ml) under nitrogen atmosphere, pyridine (about 13 mL) is added. The solution is stirred for about 5 hours at about 0° C. and TLC is checked. After completion, the solution is diluted with $CHCl_3$ (about 20 mL) and washed with about 10% copper (II) sulphate solution (about 3×50 mL) and brine (about 20 mL) successively. The organic layer is dried over anhydrous $Na_2SO_4$ and concentrated under reduced pressure. The residue is purified by silica gel chromatography utilizing ethyl acetate/hexane as eluent to obtain intermediate 1.20.

Synthesis of Compound 28

Step 1: To the solution of intermediate 1.02 (about 6 g, 0.011 mol) in dioxane (about 30 mL) is added diethylene glycol (about 20 mL) and allowed to reflux for about 4 hours. After completion, the reaction mixture is quenched with water (about 20 mL) and extracted with ethyl acetate. The organic layer is washed with water (about 3×50 mL) and brine (about 20 mL) successively and dried over anhydrous $Na_2SO_4$. The combined organic layer is concentrated under reduced pressure and the residue is purified by silica gel chromatography utilizing methanol-chloroform as eluent to obtain intermediate 1.19.

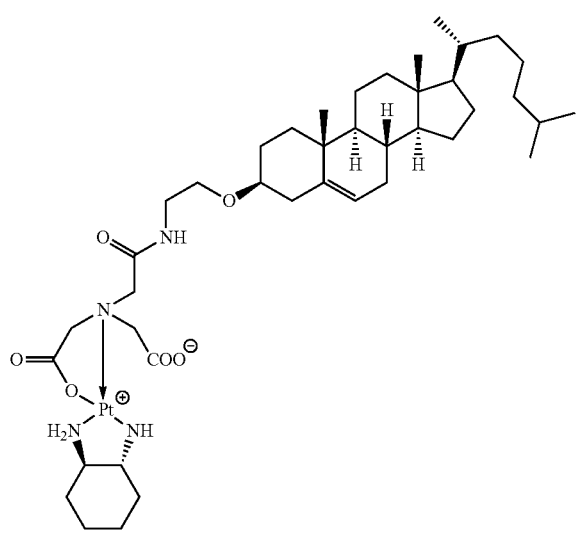

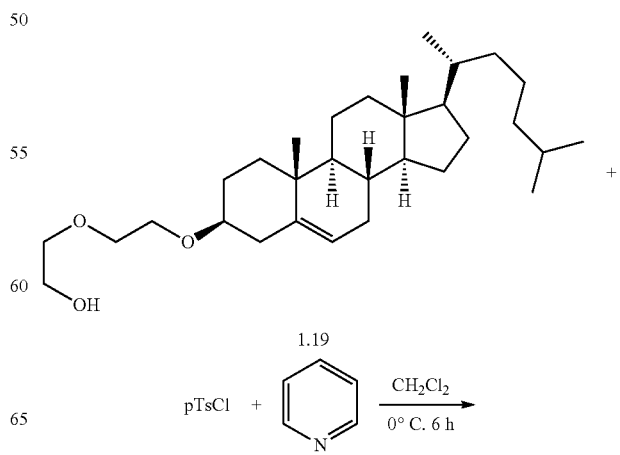

1.19

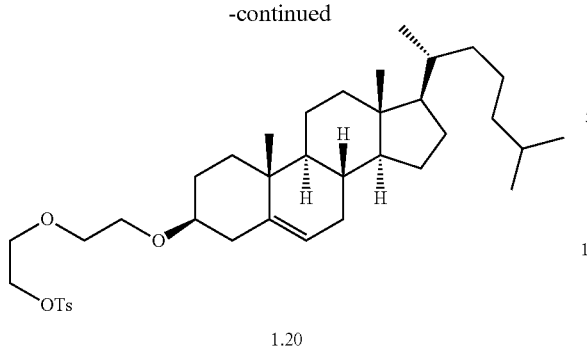

1.20

Step 3: To a 50 mL round bottom flask tosyl compound 1.20 (about 3 g, 4.76 mmol) is taken in DMF (about 15 ml) under nitrogen atmosphere and stirred for about 30 minutes to get a clear solution (warm if necessary). To this solution, solid sodium azide (about 1.55 g, 23.84 mmol) is added and stirred for about 18 h at room temperature and TLC is checked. After completion, the reaction mixture is diluted with water (about 50 mL), extracted with ethyl acetate (about 3×20 mL). The organic layer is washed with water (about 2×20 mL) and brine (about 20 mL) successively. The combined organic layer is dried over anhydrous Na2SO4, concentrated under reduced pressure and purified by flash chromatography to obtain intermediate 1.21.

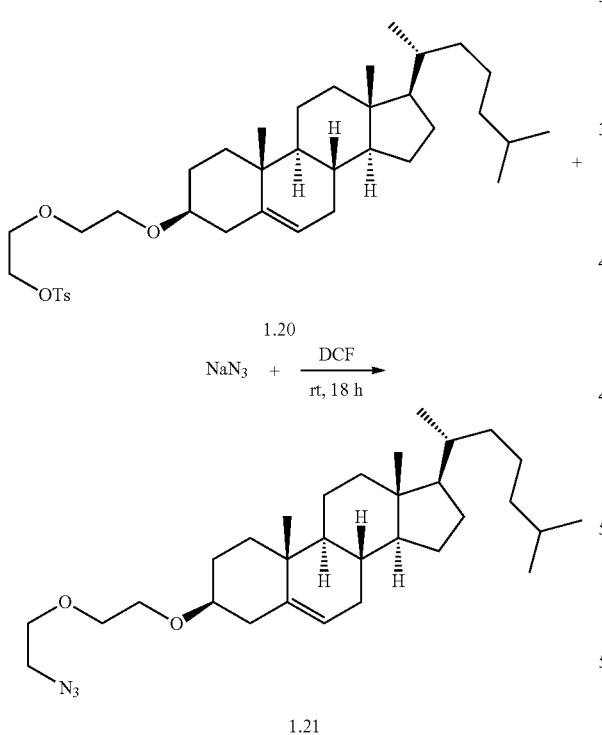

Step 4: To a solution of azide 1.21 (about 1 g, 2.01 mmol) in dry DMF (about 10 ml) triphenyl phosphene (TPP) (about 1.04 g, 4.02 mmol) is added under nitrogen atmosphere. The reaction mixture is stirred for about 6 hours at room temperature and water (about 1 mL) is added to it. The resulting solution is stirred for an additional 6 hours at the same temperature and TLC is checked. After completion, organic solvent is removed under vacuum and the residue is purified by silica gel chromatography utilizing methanol/chloroform as eluent to obtain amine intermediate 1.22.

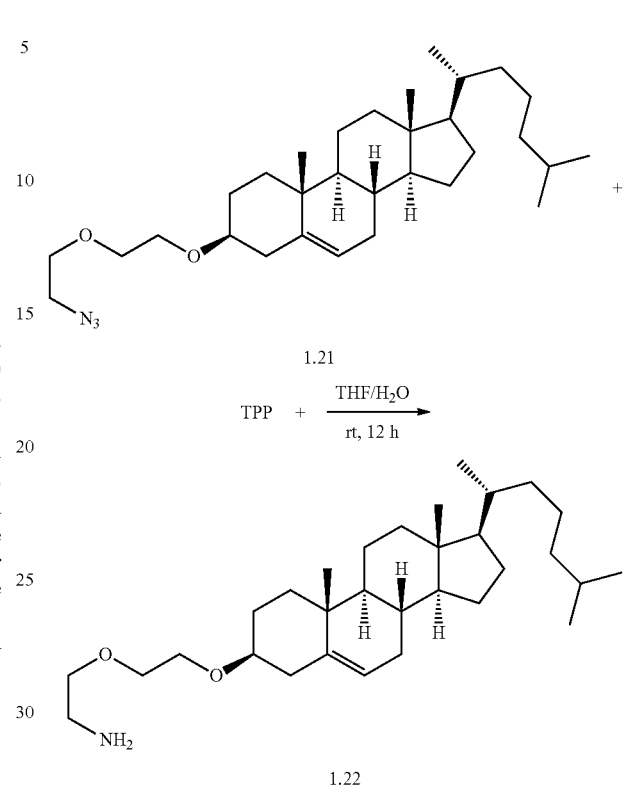

Step 5: To an ice cool solution of amine 1.22 (about 800 mg, 1.68 mmol) in THF (about 10 mL), NaH (about 200 mg, 5.02 mmol) is added under nitrogen atmosphere over a period of about 10 minutes. The resulting solution is stirred for about 20 minutes and ethyl bromo acetate (about 0.78 mL, 6.72 mmol) is added and stirred for another 6 hours at room temperature. After completion, the reaction mixture is cooled to about 0° C. and quenched with water and extracted with ethyl acetate (about 2×20 mL). The combined organic layer is dried over anhydrous Na$_2$SO$_4$, concentrated and purified by silica gel chromatography to obtain diester intermediate 1.23.

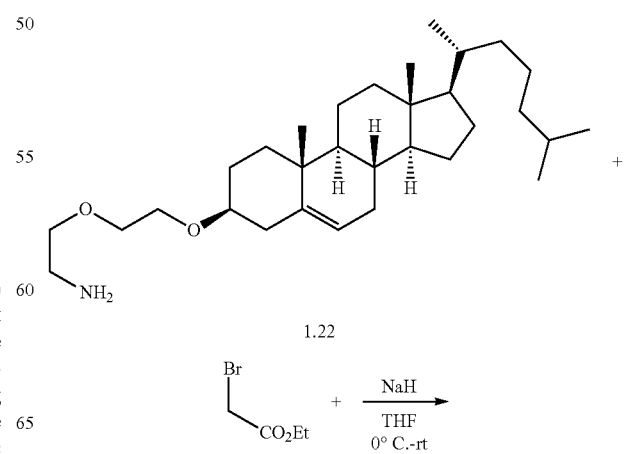

-continued

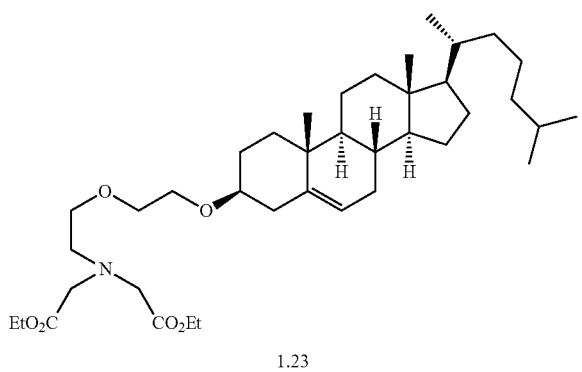

1.23

Step 6: To a 50 mL single neck round bottom flask diester 1.23 (about 220 mg, 0.340 mmol) is taken in THF/water (about 3:1) (about 4 mL) at about 0° C. Solid LiOH (about 20 mg, 0.640 mmol) is added to the reaction mixture and stirred for about 6 hours at room temperature. After completion, the reaction mixture is concentrated and diluted with water (about 4 mL). The aqueous layer is washed with ethyl acetate and dichloro methane successively and lyophilized to obtain solid powder of acid salt 1.24 in quantitative yield.

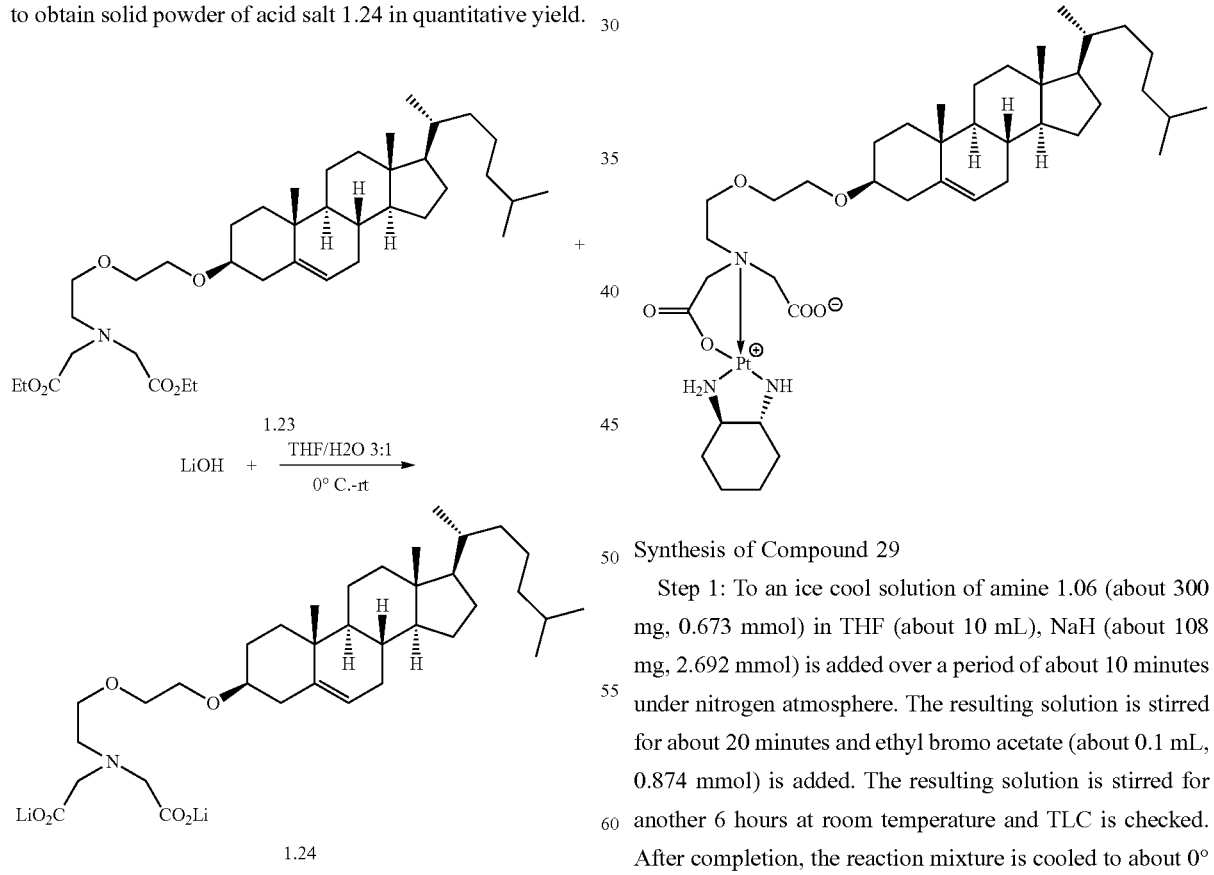

Step 7: To a 50 mL single neck round bottom flask, dilithium salt 1.24 is taken in water (about 1.0 mL). To this solution, DACHPt(H₂O)₂ is added and stirred for a time-period of another 12 hours and thereafter filtered. The solution is lyophilized to afford cholesterol-oxaliplatin amphiphile Compound 28.

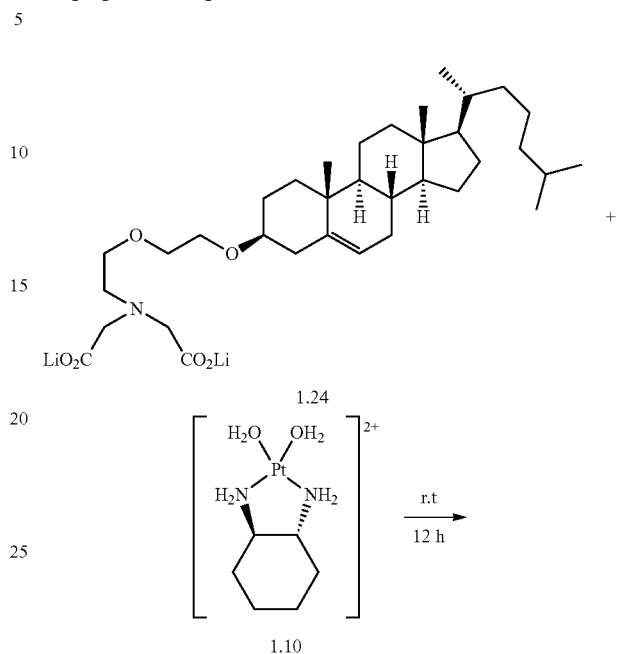

Synthesis of Compound 29

Step 1: To an ice cool solution of amine 1.06 (about 300 mg, 0.673 mmol) in THF (about 10 mL), NaH (about 108 mg, 2.692 mmol) is added over a period of about 10 minutes under nitrogen atmosphere. The resulting solution is stirred for about 20 minutes and ethyl bromo acetate (about 0.1 mL, 0.874 mmol) is added. The resulting solution is stirred for another 6 hours at room temperature and TLC is checked. After completion, the reaction mixture is cooled to about 0° C. and quenched with water and extracted with ethyl acetate (about 2×15 mL). The combined organic layer is dried over anhydrous Na₂SO₄, concentrated and purified by silica gel chromatography to obtain diester intermediate 1.25.

91

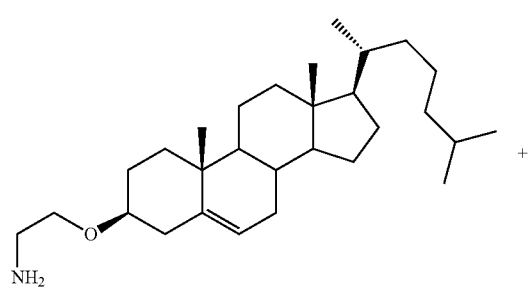

1.06

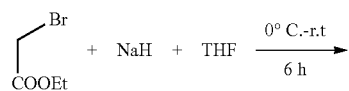

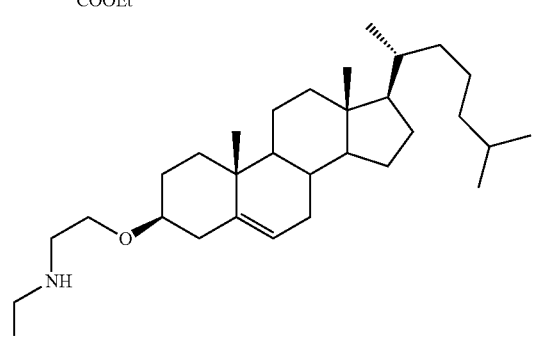

1.25

Step 2: To a 50 mL single neck round bottom flask, diester 1.25 (about 200 mg, 0.388 mmol) is taken in THF/water (about 3:1) (about 4 mL) at about 0° C. Solid LiOH (about 38 mg, 1.55 mmol) is added to the reaction mixture and stirred for about 6 hours at room temperature. After completion, the reaction mixture is concentrated and diluted with water (about 4 mL). The aqueous layer is acidified with NaHSO₄ solution, extracted with dichloro methane (about 3×10 mL) and further concentrated to obtain a solid powder of acid 1.26 in good yield.

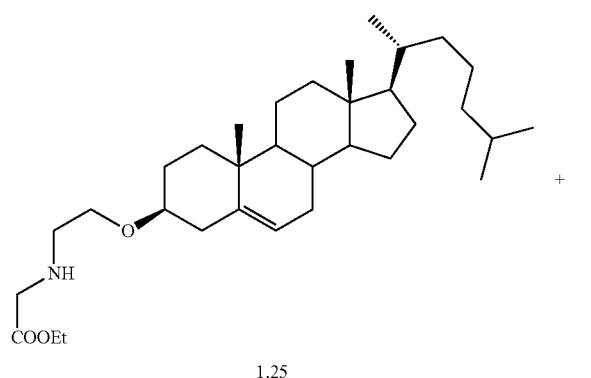

1.25

92

-continued

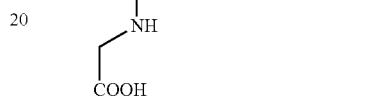

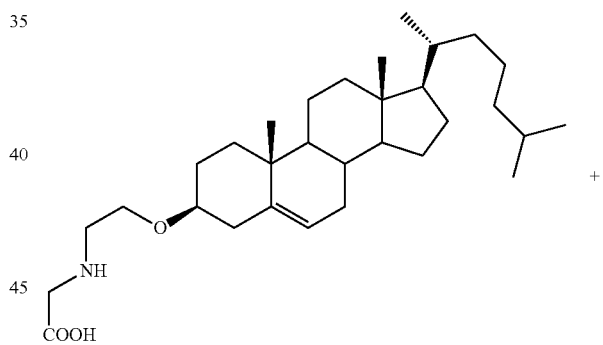

1.26

Step 3: To a 50 mL single neck round bottom flask acid 1.26 (about 70 mg, 0.143 mmol) is taken in about 1.0 mL DMF. To this solution, DACH-Pt(H₂O)₂ is added and stirred for a time-period of another 12 hours. The reaction mixture is lyophilized to afford cholesterol-oxaliplatin amphiphile Compound 29.

1.26

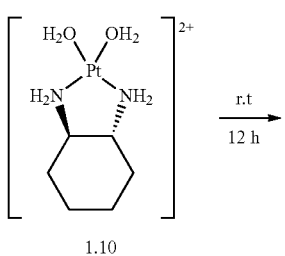

1.10

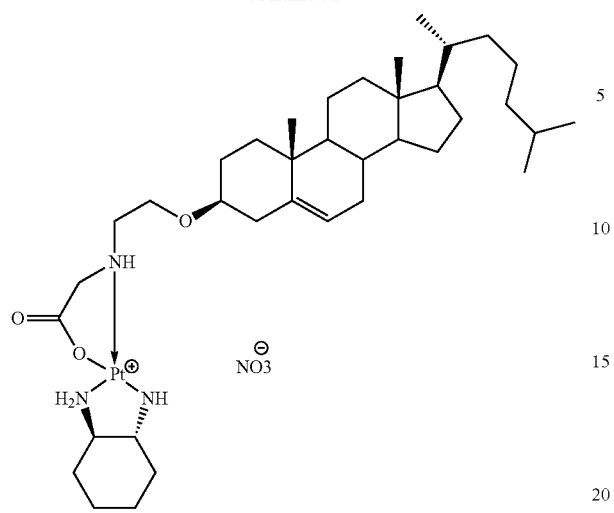

Synthesis of Compounds 38, 39, 40, 41 and 42

The synthetic methods for compounds 38, 39, 40, 41 and 42 are similar to the method of synthesis of compound 25. The lipid moiety varies in the said compounds. The different lipid moieties (R) present in compounds 38-42 are as follows:

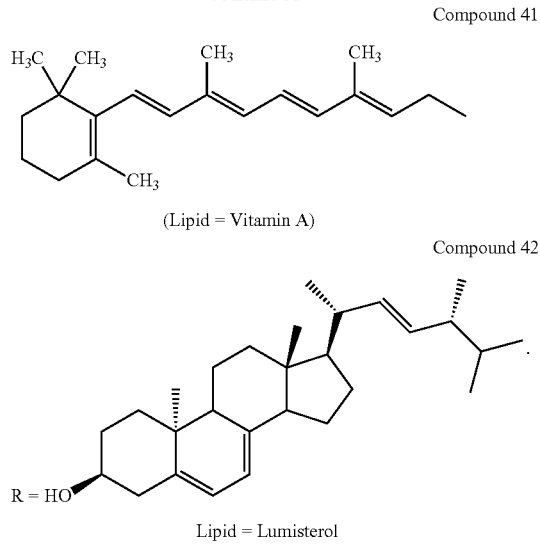

The synthetic routes of said compounds 38-42 are provided in FIG. 4.

Modified Synthesis of Compound 25

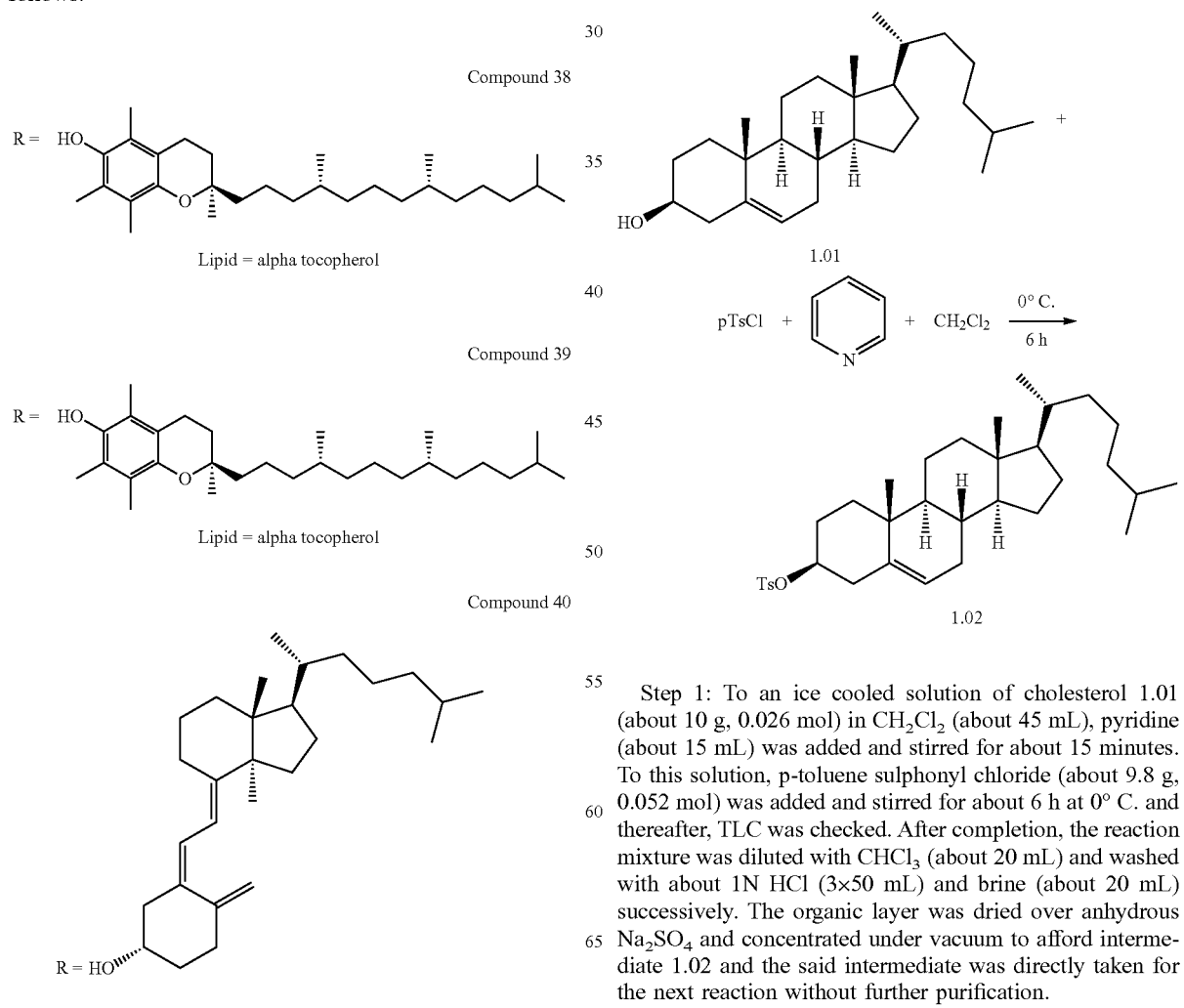

Step 1: To an ice cooled solution of cholesterol 1.01 (about 10 g, 0.026 mol) in $CH_2Cl_2$ (about 45 mL), pyridine (about 15 mL) was added and stirred for about 15 minutes. To this solution, p-toluene sulphonyl chloride (about 9.8 g, 0.052 mol) was added and stirred for about 6 h at 0° C. and thereafter, TLC was checked. After completion, the reaction mixture was diluted with $CHCl_3$ (about 20 mL) and washed with about 1N HCl (3×50 mL) and brine (about 20 mL) successively. The organic layer was dried over anhydrous $Na_2SO_4$ and concentrated under vacuum to afford intermediate 1.02 and the said intermediate was directly taken for the next reaction without further purification.

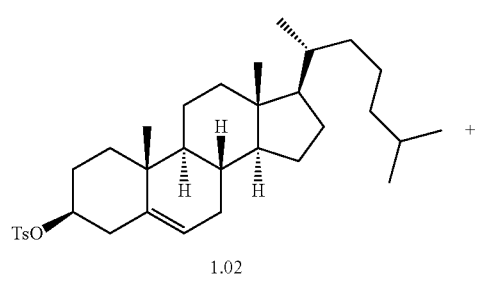

1.02

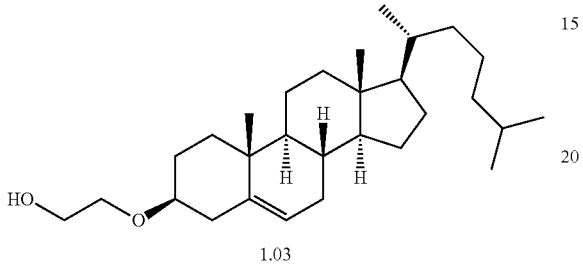

1.03

Step 2: To the solution of tosylated cholesterol 1.02 (about 10 g, 0.018 mol) in dioxane (about 45 mL), ethylene glycol (about 15 mL) was added and refluxed for about 4 h. The TLC was checked. After completion, the reaction mixture was extracted with ethyl acetate and washed with water (about 3×50 mL) and brine (about 20 mL) successively. The organic layer was dried over anhydrous Na₂SO₄ and concentrated under vacuum and column purified to afford intermediate 1.03.

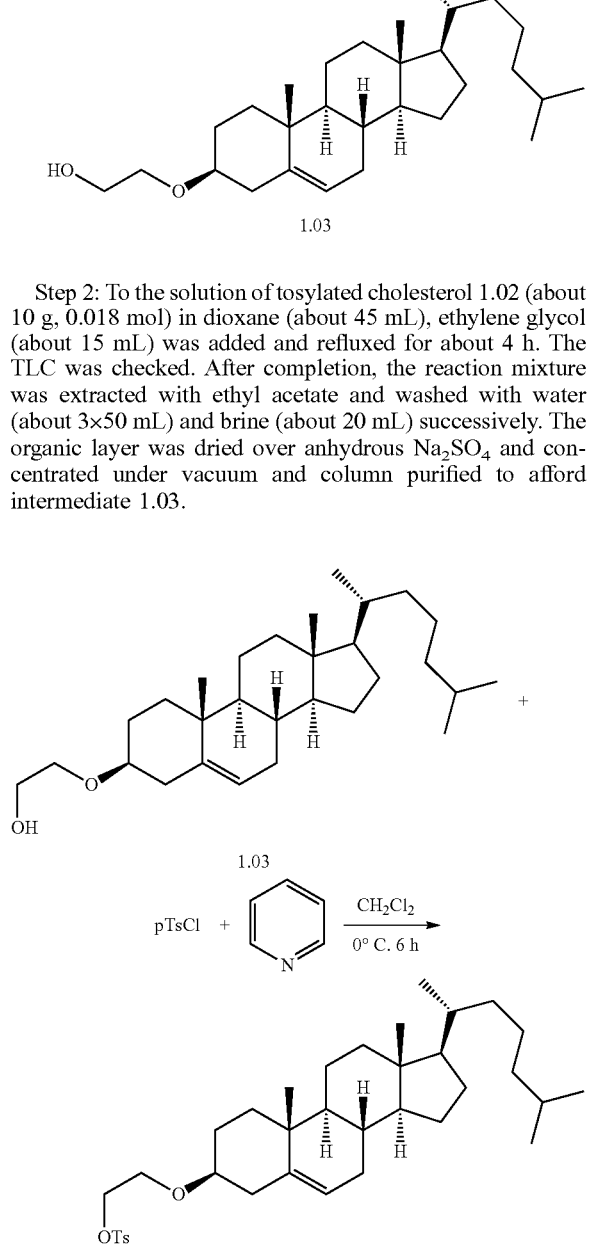

Step 3: To an ice cooled solution of cholesteryl ethylene glycol 1.03 (about 6.95 g, 16.13 mmol) in dichloro methane (about 15 ml) pyridine (about 13 mL) was added under nitrogen atmosphere and stirred for about 15 minutes. To this solution, p-toluene sulphonyl chloride (about 3.7 g, 19.35 mmol) was added and stirred for about 5 h at about 0° C. and TLC was checked. After completion, the reaction mixture was diluted with CHCl₃ (about 20 mL) and washed with about 1N HCl (3×50 mL) and brine (about 20 mL) successively. The organic layer was dried over anhydrous Na₂SO₄ and concentrated under vacuum and purified by silica gel chromatography to obtain intermediate 1.04.

Step 4: To a 50 mL round bottomed flask, compound 1.04 (about 6 g, 10.26 mmol) was taken in DMF (about 20 ml) under nitrogen atmosphere and was stirred for about 30 minutes to get a clear solution (warm if necessary). To this solution, sodium azide (about 3.4 g, 51.33 mmol) was added and stirred for about 18 h at room temperature and TLC was checked. After completion, the reaction mixture was concentrated under vacuum to remove THF and was purified by flash chromatography to obtain intermediate 1.05.

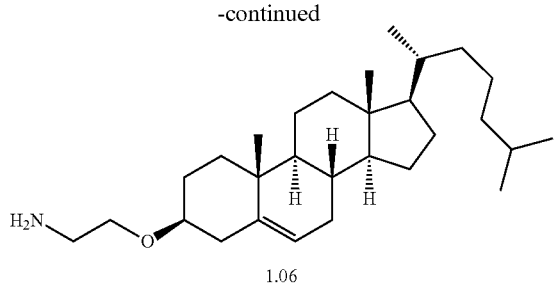

1.06

Step 5: To a solution of azide 1.05 (about 3 g, 7.6 mmol) in dry DMF (about 15 ml), TPP (about 1.5 g, 15.2 mmol) was added under nitrogen atmosphere. The reaction was stirred for about 6 h at room temperature and about 2 mL of water was added to the reaction mixture. The reaction mixture was stirred for additional time-period of about 6 h and TLC was checked. After completion, the reaction mixture was concentrated under reduced pressure and was purified by silica gel chromatography utilizing methanol/chloroform as mobile phase to achieve amine intermediate 1.06.

1.06

1.07

Step 6: To an ice cool solution of amine 1.06 (about 300 mg, 0.698 mmol) in THF (about 5 mL), NaH (about 120 mg, 2.094 mmol) was added by pinch over a period of about 10 minutes. The resulting solution was stirred for about 20 minutes and ethyl bromo acetate was added and stirred for a time-period of about 6 h at room temperature. After completion, the reaction mixture was cooled to about 0° C. and quenched with water and the compound was extracted with ethyl acetate (about 2×20 mL). The organic layer was dried over anhydrous Na2SO4, concentrated and purified by silica gel chromatography to obtain diester intermediate 1.07 in about 52% yield. $^1$H NMR (500 MHz, CDCl$_3$) δ: 5.34 (dd, J=8.1, 5.5 Hz, 1H), 4.19 (q, J=7.1 Hz, 4H), 3.73-3.61 (m, 6H), 3.14 (dt, J=15.5, 5.5 Hz, 1H), 3.02 (t, J=5.4 Hz, 2H), 2.28-0.64 (m, 49H, Cholesterol backbone).

1.07

1.08

Step 7: To a 50 mL single neck round bottom flask, diester compound 1.07 (about 218 mg, 0.363 mmol) was taken in THF/water (about 4 mL, at a ratio of about 3:1) and cooled to about 0° C. To this cooled solution, LiOH (about 34 mg, 1.45 mmol) was added and stirred at room temperature for a time-period of another 6 h. After completion, the reaction mixture was concentrated under reduced pressure to remove THF and the aqueous layer was washed with ethyl acetate. The aqueous layer was lyophilized to get solid di-lithium salt of 1.08 with a quantitative yield.

Step 8: Synthesis of DACH—Pt(H$_2$O)$_2$ 1.09

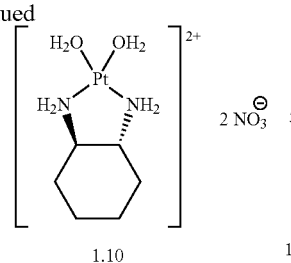

To a 50 mL single neck round bottom flask dichloro (1,2-diammino-cyclohexane) platinum 1.09 (about 200 mg, 0.526 mmol) was taken in about 20.0 mL of H$_2$O. To this suspension, silver nitrate (about 178.7 mg, 1.052 mmol) was added and the reaction mixture was stirred at room temperature for about 24 h. The milky white solution was centrifuged and the solution was filtered through 0.22 µM syringe filter to obtain aquated DACH—Pt 1.10 in quantitative yield (about 10 mg/mL).

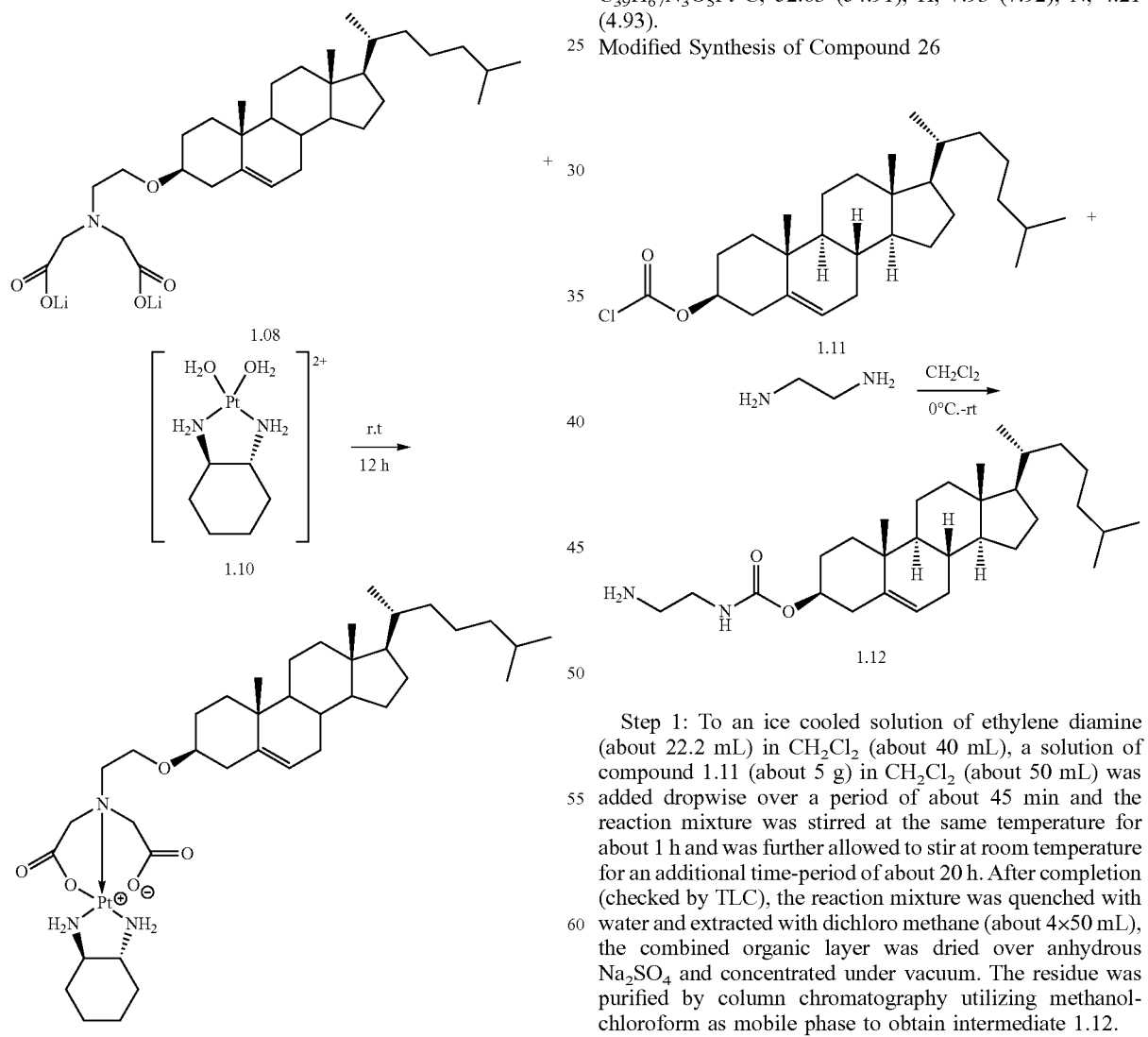

Step 9: To a 100 mL single neck round bottom flask intermediate 1.08 (about 202 mg, 0.363 mmol) was taken in about 1.0 mL water. To this solution, DACHPt(H$_2$O)$_2$ (about 13.8 mL) obtained in the previous step was added and stirred for another 12 h. The solid residue was filtered and washed with water (about 20 mL). The white solid residue was lyophilized and dissolved in excess methanol, filtered and concentrated under reduced pressure to afford cholesterol-oxaliplatin amphiphile Compound 25 in about 85% yield. $^1$H NMR of compound 25 (500 MHz, CDCl$_3$) δ: 5.36 (s, 1H), 3.71 (s, 4H), 3.64 (m, 2H), 3.16 (m, 1H), 2.86-2.78 (m, 2H), 2.36-0.62 (57H, cholesterol back bone). $^{13}$C NMR of IO-125_01 (125 MHz, CD$_2$Cl$_2$—CD3OD) δ:183.13, 182.80, 171.64, 171.35, 140.13, 122.08, 79.93, 56.73, 56.17, 50.19, 42.22, 39.75, 39.41, 38.87, 38.66, 37.00, 36.71, 36.11, 35.75, 32.16, 31.84, 29.54, 28.24, 28.13, 28.08, 27.90, 24.34, 24.19, 24.13, 23.72, 22.31, 22.06, 20.97, 18.97, 18.94, 18.32, 11.44; IR of compound 25 (KBr): 3416.28, 3162.69, 2933.20, 1654.62, 1599.66, 1455.99, 1377.89, 1317.14, 1174.44, 1091.51, 1061.62; MALDI-TOF MS of compound 25 C39H67N3O5Pt (m/z)=853.644 (M)$^+$; 195Pt of compound 25 (108 MHz, CD2Cl2-MeOD) −2316.5 and −2341.82; Analytical calculation found for C$_{39}$H$_{67}$N$_3$O$_5$Pt C, 52.63 (54.91), H, 7.93 (7.92), N, 4.21 (4.93).

Modified Synthesis of Compound 26

Step 1: To an ice cooled solution of ethylene diamine (about 22.2 mL) in CH$_2$Cl$_2$ (about 40 mL), a solution of compound 1.11 (about 5 g) in CH$_2$Cl$_2$ (about 50 mL) was added dropwise over a period of about 45 min and the reaction mixture was stirred at the same temperature for about 1 h and was further allowed to stir at room temperature for an additional time-period of about 20 h. After completion (checked by TLC), the reaction mixture was quenched with water and extracted with dichloro methane (about 4×50 mL), the combined organic layer was dried over anhydrous Na$_2$SO$_4$ and concentrated under vacuum. The residue was purified by column chromatography utilizing methanol-chloroform as mobile phase to obtain intermediate 1.12.

$^1$H NMR (500 MHz, CDCl$_3$) δ: 5.30 (s, 1H), 5.05 (s, 1H), 4.42 (s, 1H), 3.18 (s, 2H), 2.79 (s, 2H), 2.35-0.60 (m, 45H, cholesterol backbone).

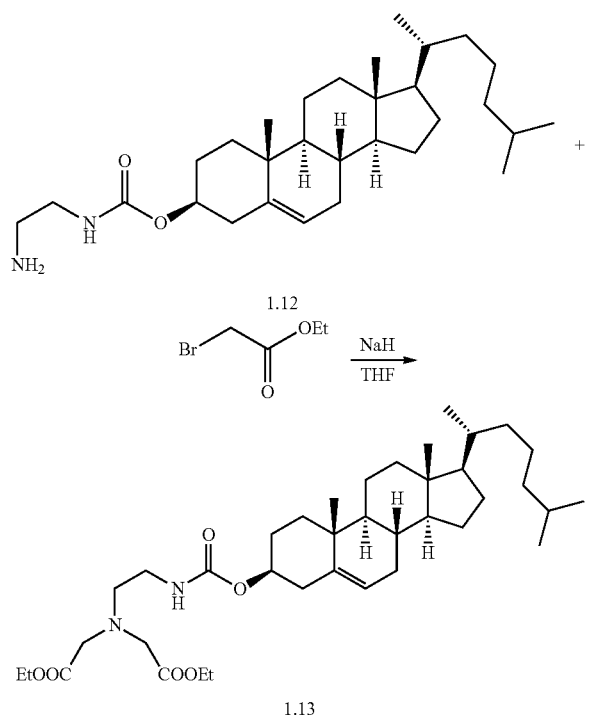

1.12

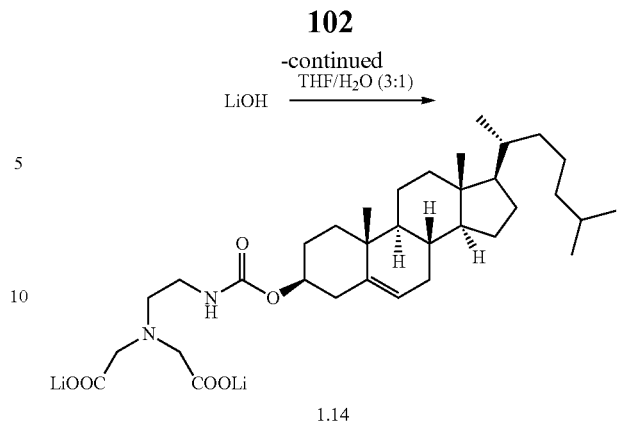

1.14

Step 3: To a 50 mL single neck round bottom flask, diester 1.13 (about 1.7 g, 2.63 mmol) was taken in THF/water (about 3:1) (about 16 mL). The reaction mixture was cooled to about 0° C. under ice bath and LiOH (about 130 mg, 5.27 mmol) was added to the reaction mixture. The resulting solution was stirred for about 6 h at room temperature and TLC was checked. After completion, the reaction mixture was concentrated under reduced pressure to remove THF and diluted with water (about 5 mL). The water layer was washed with ethyl acetate and CH$_2$Cl$_2$ successively and lyophilized to obtain intermediate 1.14 in quantitative yield.

Step 2: To a 50 mL single neck round bottom flask amine 1.12 (about 300 mg 0.634 mmol) was taken in THF (about 5 mL) under nitrogen atmosphere. The reaction mixture was cooled to about 0° C. under ice bath and NaH (about 130 mg, 3.17 mmol) was added by pinch over a period of about 10 minutes. The resulting solution was stirred for about 20 minutes and ethyl bromo acetate was added. The reaction mixture was stirred for about 2 h at room temperature and TLC was checked. After completion, the reaction mixture was cooled to about 0° C. and quenched with cold water (about 5 mL), extracted with ethyl acetate (about 2×20 mL), dried over anhydrous Na$_2$SO$_4$ and thereafter concentrated. The residue was purified by column chromatography utilizing methanol-chloroform as mobile phase to obtain intermediate 1.13.

$^1$H NMR (500 MHz, CDCl$_3$) δ: 5.85 (s, 1H), 5.39 (d, J=4.9 Hz, 1H), 4.50 (m, 1H), 4.25-4.15 (m, 4H), 3.63 (m, 4H), 3.30 (bs, 2H), 2.98 (bs, 2H), 2.44-0.71 (m, 49H, cholesterol backbone).

$^{13}$C NMR (500 MHz, CDCl$_3$) δ: 171.32, 156.37, 140.00, 122.28, 74.14, 60.79, 56.66, 56.09, 55.16, 53.36, 49.97, 42.28, 39.71, 39.49, 38.57, 37.00, 36.54, 36.15, 35.77, 31.88, 31.85, 28.21, 28.14, 27.99, 24.26, 23.79, 22.80, 22.55, 21.01, 19.32, 18.68, 14.19, 11.83;

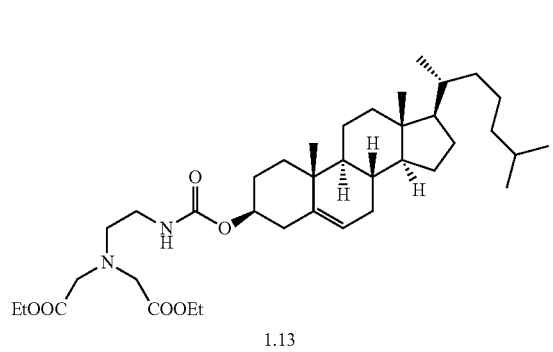

1.13

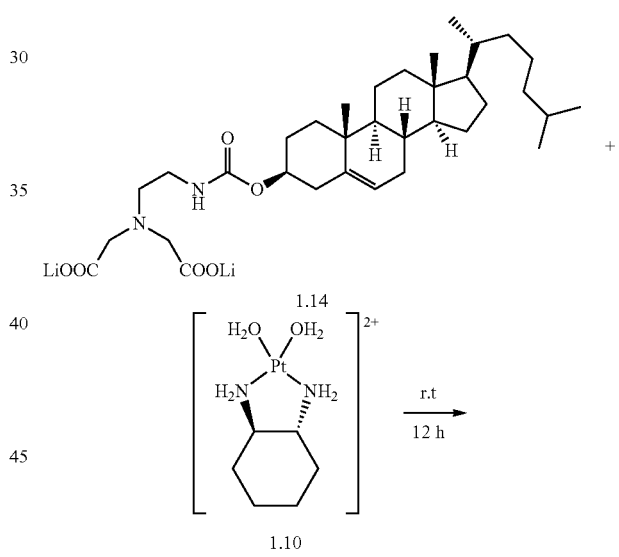

1.10

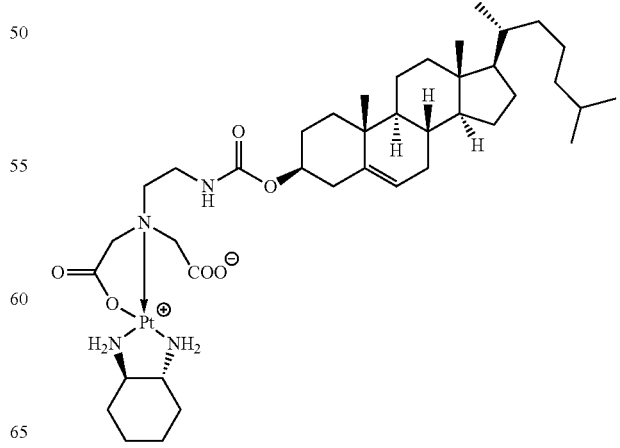

Step 4: To a 100 mL single neck round bottom flask, intermediate 1.14 was taken in about 1.0 mL water. To this solution, DACHPt(H$_2$O)$_2$ was added and stirred for a time-period of another 12 h. The solid residue obtained was filtered, washed with water and lyophilized. The residue was dissolved in excess methanol, filtered and concentrated under reduced pressure to afford cholesterol-oxaliplatin amphiphile Compound 26. $^1$H NMR of compound 26 (500 MHz, CDCl$_3$) δ: 5.40 (s, 1H), 4.89 (bS, 1H), 4.52 (m, 1H), 3.61 (s, 4H), 3.40-3.28 (m, 2H), 2.73-2.66 (m, 2H), 2.44-0.60 (57H, cholesterol back bone). $^{13}$C NMR of compound 26 (125 MHz, CD$_2$Cl$_2$—CD3OD) δ: 186.87, 186.49, 175.25, 174.91, 161.48, 161.24, 143.69, 126.49, 79.20, 60.62, 60.04, 53.92, 46.19, 43.62, 43.38, 42.4, 42.32, 40.86, 40.46, 40.05, 39.68, 36.13, 35.80, 35.73, 33.97, 32.10, 31.96, 31.87, 28.21, 28.14, 27.70, 26.58, 26.32, 23.09, 22.51, 15.66; IR of compound 26 (KBr): 3403.74, 2931.27, 1665.23, 1632.45, 1444.42, 1382.71, 1131.05; MALDI-TOF MS of compound 26 C40H68N4O6Pt (m/z)=896.5292 (M)$^+$; 195Pt of compound 26 (108 MHz, MeOD) −2280.34 and −2305.06; Analytical calculation found for C$_{40}$H$_{68}$N$_4$O$_6$Pt C, 51.96(53.62), H, 7.82(7.65), N, 5.39 (6.25).

Modified Synthesis of Compound 27

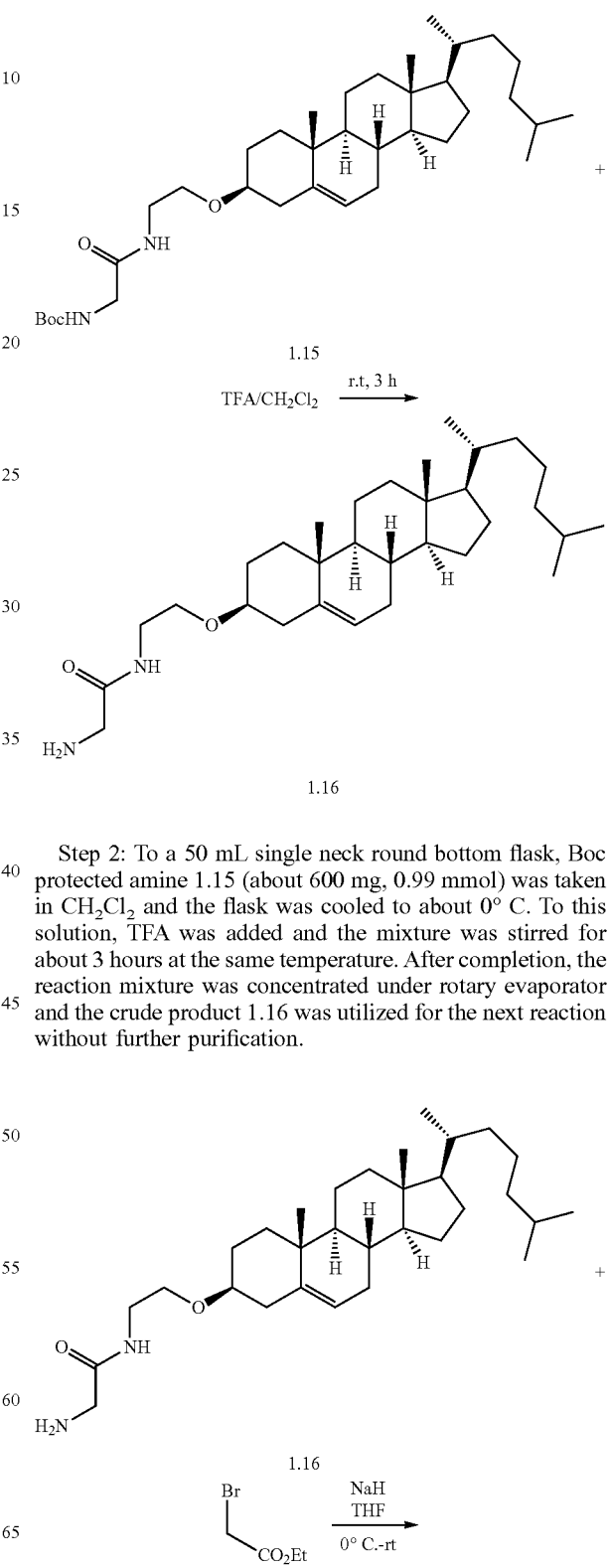

completion, the reaction mixture was quenched with water, extracted with chloroform, dried over anhydrous Na$_2$SO$_4$ and thereafter concentrated. The residue was purified by silica gel chromatography utilizing methanol-chloroform as mobile phase to obtain intermediate 1.15.

Step 2: To a 50 mL single neck round bottom flask, Boc protected amine 1.15 (about 600 mg, 0.99 mmol) was taken in CH$_2$Cl$_2$ and the flask was cooled to about 0° C. To this solution, TFA was added and the mixture was stirred for about 3 hours at the same temperature. After completion, the reaction mixture was concentrated under rotary evaporator and the crude product 1.16 was utilized for the next reaction without further purification.

Step 1: To a 50 mL single neck round bottom flask, BocHNCH$_2$COOH (about 370 mg, 2.08 mmol) was taken in CH$_2$Cl$_2$ (about 10 mL) under nitrogen atmosphere. Solid EDCl (about 400 mg, 2.08 mmol) and HOBT (about 285 mg, 2.08 mmol) are added successively to the reaction mixture. DIPEA was added to make the solution alkaline and the reaction mixture was stirred for another 20 minutes. To this activated acid solution, amine 1.06 (about 450 mg, 1.04 mmol) was added and the mixture was stirred at room temperature for about 12 h and TLC was checked. After

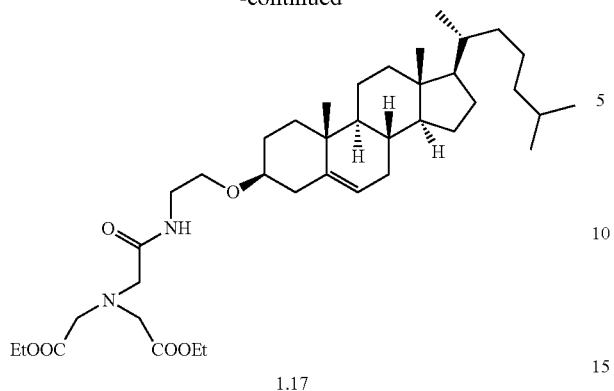

1.17

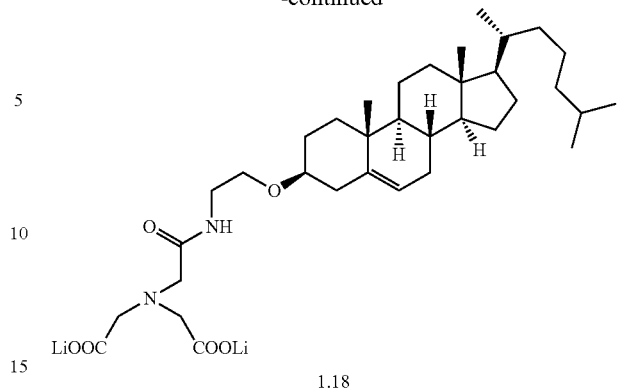

1.18

Step3: To a 50 mL single neck round bottom flask, crude amine 1.16 (about 400 mg, 0.821 mmol) was taken in THF (about 10 mL) under nitrogen atmosphere. The solution was cooled to about 0° C. under ice bath and solid NaH (about 160 mg, 4.10 mmol) was added pinch wise over a period of about 10 minutes. The resulting solution was stirred for an additional 20 minutes and ethyl bromo acetate was added. After completion, the reaction mixture was cooled to about 0° C. and quenched with water, extracted with ethyl acetate, dried over anhydrous $Na_2SO_4$ and thereafter concentrated under vacuum. The residue was purified by silica gel chromatography utilizing methanol-chloroform as mobile phase to obtain intermediate 1.17. $^1$H NMR (500 MHz, $CDCl_3$) δ: 5.33-5.29 (m, 1H), 4.19-4.12 (q, J=7.25 Hz, 4H), 3.56-3.49 (m, 6H), 3.43 (dd, J=11.6, 5.9 Hz, 2H), 3.39 (s, 2H), 3.14 (m, 1H), 2.44-0.71 (m, 50H, cholesterol backbone). $^{13}$C NMR (500 MHz, $CDCl_3$) δ: 170.90, 170.66, 140.77, 121.54, 79.15, 66.33, 60.85, 58.82, 56.70, 56.09, 55.57, 50.12, 42.25, 39.71, 39.45, 39.35, 38.95, 37.14, 36.79, 36.12, 35.71, 31.87, 31.83, 28.26, 28.16, 27.93, 24.22, 23.75, 22.74, 22.49, 21.00, 19.29, 18.65, 14.15, 11.79;

Step 4: To a 50 mL single neck round bottom flask, diester 1.17 (about 200 mg, 0.303 mmol) was taken in THF/water (about 3:1) (about 4 mL) at about 0° C. Solid LiOH (about 15 mg, 0.606 mmol) was added to the reaction mixture and stirred for about 6 hours at room temperature. After completion, the reaction mixture was concentrated and diluted with water (about 4 mL). The aqueous layer was washed with ethyl acetate and dichloro methane successively and was lyophilized to obtain solid powder of acid salt 1.18 in quantitative yield.

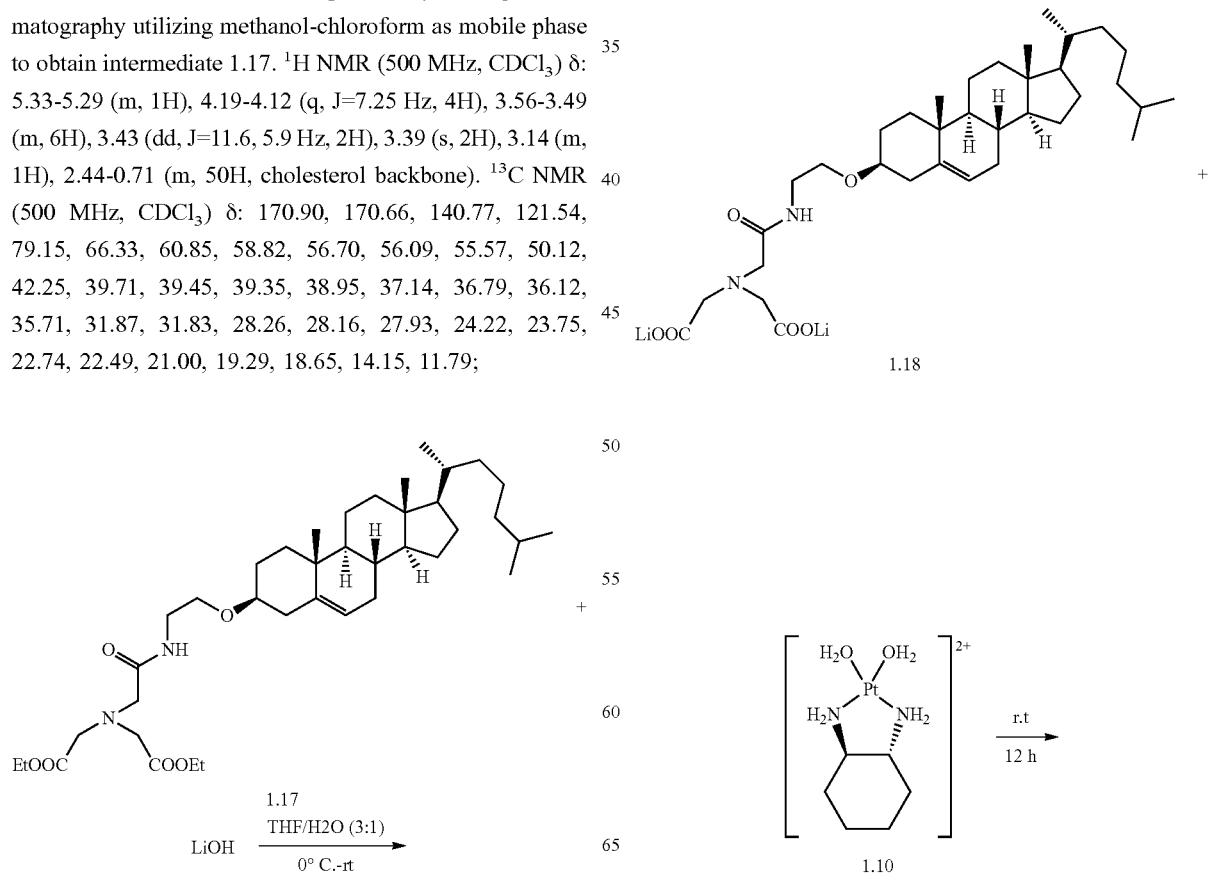

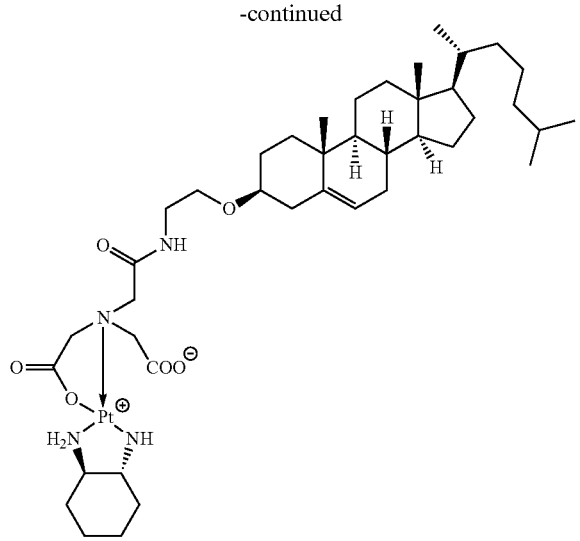

Step 5: To a 100 mL single neck round bottom flask, intermediate 1.18 was taken in 1 mL water. To this solution, DACHPt(H$_2$O)$_2$ was added and stirred for another 12 hours. The solid residue was filtered and washed with water and thereafter lyophilized. The residue was dissolved in excess methanol, filtered and concentrated under reduced pressure to afford cholesterol-oxaliplatin amphiphile Compound 27. $^1$H NMR of compound 27 (500 MHz, CDCl$_3$—CD3OD) δ: 5.28 (s, 1H), 4.11 (d, J=14.1 Hz, 1H), 3.65-3.25 (m, 8H), 3.17-3.05 (m, 1H), 2.44-0.60 (57 H, cholesterol back bone). $^{13}$C NMR of compound 27 (125 MHz, DMSOd6) δ: 180.1, 168.19, 166.47, 140.36, 121.06, 78.25, 65.47, 63.65, 61.23, 61.14, 60.31, 56.09, 55.48, 49.50, 41.76, 38.54, 36.57, 36.19, 35.56, 35.09, 31.32, 31.27, 28.88, 27.94, 27.68, 27.30, 23.77, 23.08, 22.58, 22.31, 20.51, 18.98, 18.46, 11.59; IR of compound 27 (KBr): 3447.72, 3245.64, 2935.69, 1617.40, 1392.53, 1096.25; MALDI-TOF MS of compound 27 C41H70N4O6Pt (m/z)=910.6240 (M)$^+$; 195Pt of compound 27 (108 MHz, MeOD) −2260.12 and −2271.67; Analytical calculation found for C$_{41}$H$_{70}$N$_4$O$_6$Pt C, 52.85(54.11), H, 7.77(7.75), N, 5.26 (6.16).

Example 4

Synthesis of Compounds of Formula III

Synthesis of Compound 31

Step 1: To a 50 mL single neck round bottom flask, acetonide protected keto-acid (about 121.5 mg, 0.854 mmol) is taken in about 2 mL anhydrous THF and the mixture is cooled to about −78° C. To this solution, LiHMDS (about 0.85 mL, 5 equiv, 1 mmolar solution in Toluene) is added and the mixture is stirred for about 15 minutes at the same temperature. To this solution, tosyl compound 1.04 (about 100 mg, 0.171 mmol) in THF (about 2 mL) is added and again the mixture is allowed to stir for about 2 hours at about −78° C. After completion, the reaction mixture is cooled to about 0° C. and quenched with water and extracted with ethyl acetate (about 2×15 mL). The organic layer is dried over anhydrous Na$_2$SO$_4$, concentrated and purified by silica gel chromatography to obtain diester intermediate 1.27.

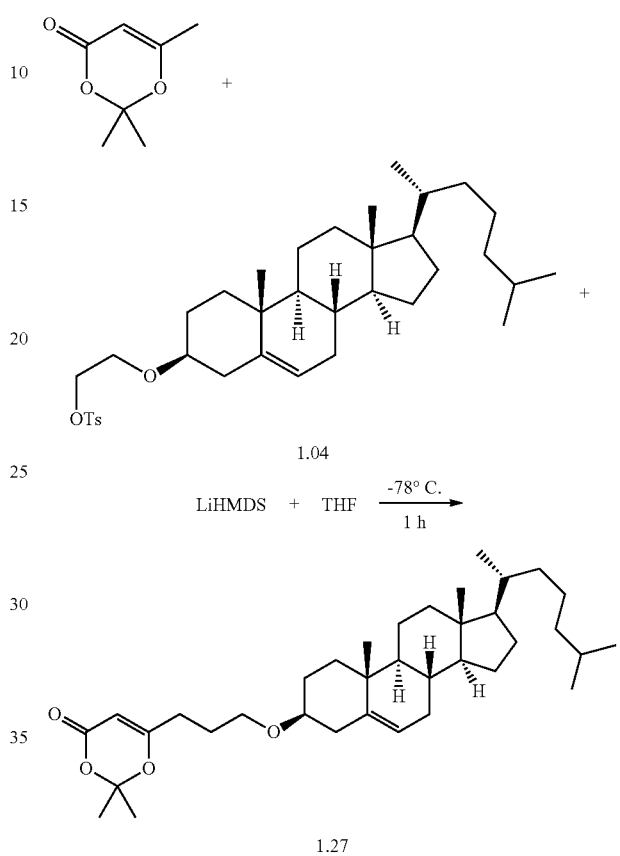

Step 2: Acetonide protected compound 1.27 in about 1 mL THF is taken in a 50 mL round bottom flask and HCl (about 1 M) at about 0° C. is added. The reaction mixture is stirred for about 3 hours at room temperature and TLC is carried out. After completion, the reaction mixture is diluted with water (about 5 mL) and extracted with ethyl acetate (about 20 mL). The organic layer is dried over anhydrous Na$_2$SO$_4$, concentrated and purified by silica gel chromatography to obtain intermediate 1.28.

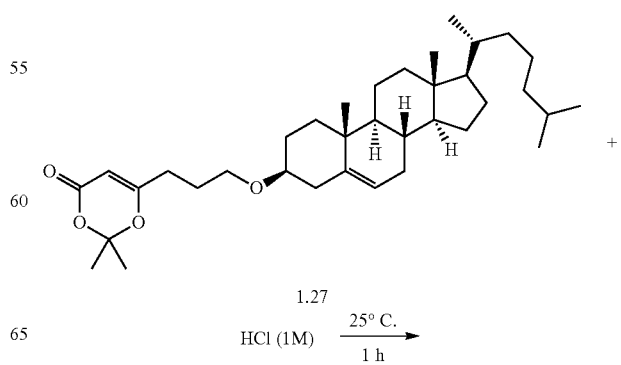

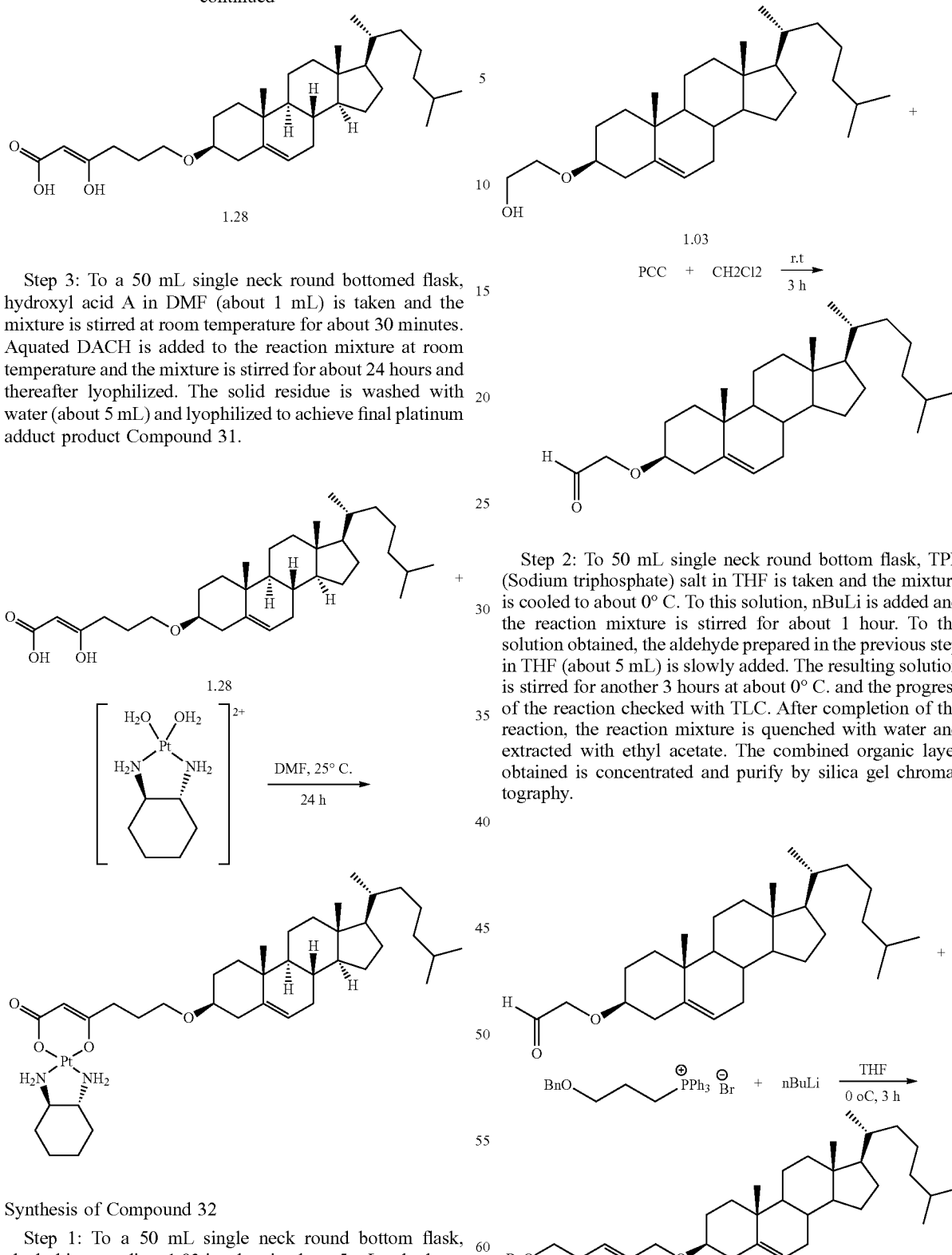

Step 3: To a 50 mL single neck round bottomed flask, hydroxyl acid A in DMF (about 1 mL) is taken and the mixture is stirred at room temperature for about 30 minutes. Aquated DACH is added to the reaction mixture at room temperature and the mixture is stirred for about 24 hours and thereafter lyophilized. The solid residue is washed with water (about 5 mL) and lyophilized to achieve final platinum adduct product Compound 31.

Synthesis of Compound 32

Step 1: To a 50 mL single neck round bottom flask, alcohol intermediate 1.03 is taken in about 5 mL anhydrous $CH_2Cl_2$ and cooled to about 0° C. To this solution, (Pyridinium Chlorochromate) PCC is added and the reaction mixture is stirred at room temperature for about 3 hours and thereafter, the reaction is checked with TLC. After completion, the reaction mixture is concentrated and purified by silica gel chromatography to obtain aldehyde intermediate.

Step 2: To 50 mL single neck round bottom flask, TPP (Sodium triphosphate) salt in THF is taken and the mixture is cooled to about 0° C. To this solution, nBuLi is added and the reaction mixture is stirred for about 1 hour. To the solution obtained, the aldehyde prepared in the previous step in THF (about 5 mL) is slowly added. The resulting solution is stirred for another 3 hours at about 0° C. and the progress of the reaction checked with TLC. After completion of the reaction, the reaction mixture is quenched with water and extracted with ethyl acetate. The combined organic layer obtained is concentrated and purify by silica gel chromatography.

Step 3: To a 50 mL single neck round bottom flask, liquid ammonia in THF is taken at about −78° C. To this solution, metallic sodium is added slowly over a period of about 20 minutes. To the obtained blue solution, benzyl protected compound in THF is added over a period of about 10 minutes. The resulting solution is stirred for about 3 hours at the same temperature and the progress of the reaction is checked by TLC. After completion of the reaction, the reaction mixture is left for about 12 hours at room temperature and thereafter, quenched with ammonium chloride solution, extracted with ethyl acetate and finally concentrated under reduced pressure. The residue is purified by silica gel chromatography.

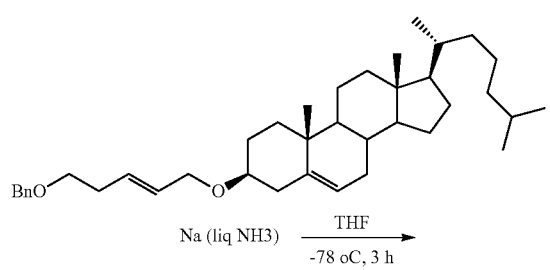

Step 4: To 50 mL single neck round bottom flask, hydroxyl compound in $CH_2Cl_2$ is taken at about 0° C. To this solution, solid Dess-Martin Periodinane (DMP) is added and the mixture is stirred for about 3 hours and the reaction is monitored by TLC. After completion of the reaction, the reaction mixture is quenched with water and extracted with $CH_2Cl_2$. The organic layer is thereafter concentrated and purified by silica gel chromatography.

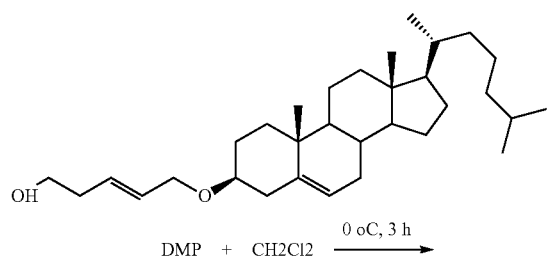

Step 5: To 50 mL single neck round bottom flask, lithium diisopropylamide (LDA) is added at about −78° C. To this, tertiary butyl acetate in THF is added and the mixture stirred for about 0.5 hours. To this solution, the aldehyde prepared in the previous step in THF (about 5 mL) is slowly added. The resulting solution is stirred for another 2 hours at about −78° C. and the reaction is monitored by TLC. After completion, the reaction mixture is quenched with water and extracted with ethyl acetate. The combined organic layer is concentrated and purified by silica gel chromatography.

Step 6: To 50 mL single neck round bottom flask, hydroxyl compound in $CH_2Cl_2$ is taken at about 0° C. To this solution, solid Dess-Martin Periodinane (DMP) is added and the mixture is stirred for about 3 hours and the progress of the reaction is checked by TLC. After completion, the reaction mixture is quenched with water and extracted with $CH_2Cl_2$. The organic layer obtained is concentrated and purified by silica gel chromatography.

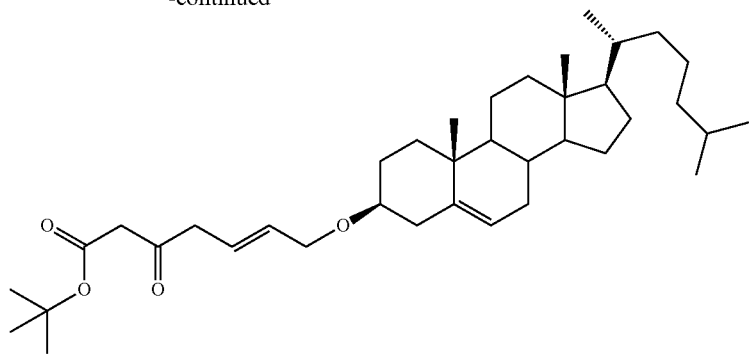

Step 7: To a 50 mL single neck round bottom flask, tertiary butyl ester in THF is taken and the solution is cooled to about 0° C. To the cooled solution, about 1 (M) HCl is added and the reaction mixture is stirred for about 2 hours at the same temperature. After completion of the reaction, the compound is extracted with ethyl acetate and concentrated under reduced pressure. The residue is purified by silica gel chromatography.

is taken and cooled to about 0° C. To this solution, PCC is added and the reaction mixture is stirred at room temperature for about 3 hours and the reaction progresses is checked by TLC. After completion, the reaction mixture is concentrated and thereafter, purification is carried out by silica gel chromatography to obtain aldehyde intermediate.

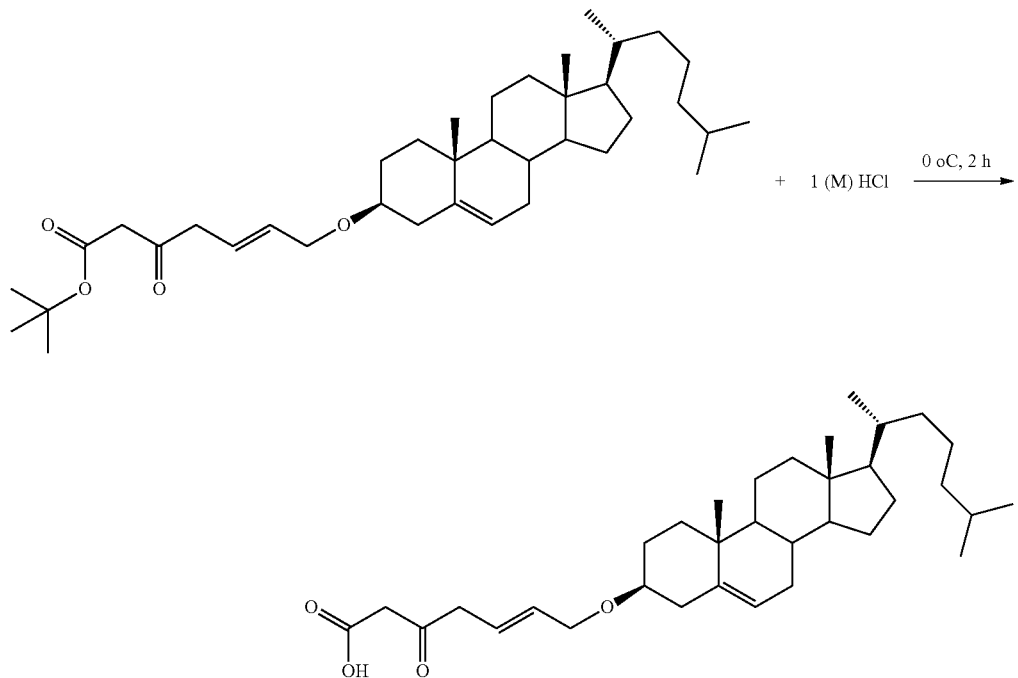

Step 8: To a 50 mL single neck round bottomed flask, hydroxyl acid in DMF (about 1 mL) is taken and the mixture is stirred at room temperature for about 30 minutes. Aquated DACH is added to the reaction mixture at room temperature and stirred for about 24 hours and thereafter lyophilized. The solid residue is washed with water (about 5 mL) and lyophilized to obtain the final platinum adduct product Compound 32.

Synthesis of Compound 33

Step 1: To a 50 mL single neck round bottom flask, alcohol intermediate 1.03 in about 5 mL anhydrous $CH_2Cl_2$

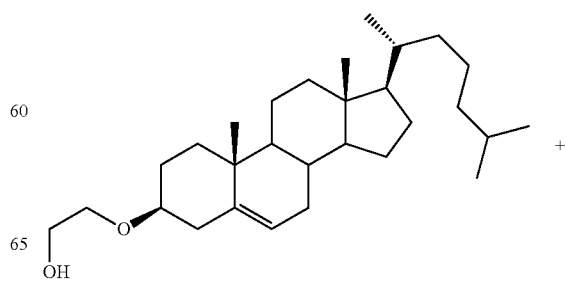

-continued

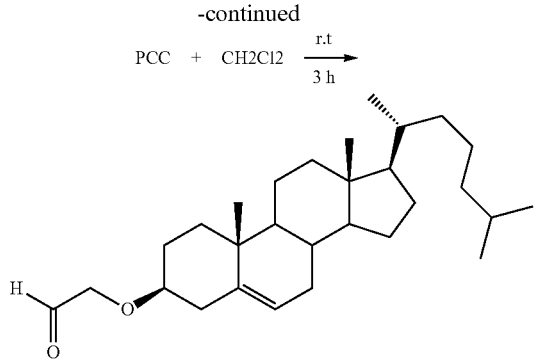

Step 2: In 50 mL single neck round bottom flask, LDA is generated at about −78° C. in THF. To this solution, 1,3-dioxinones is added in THF and the reaction mixture is -continued

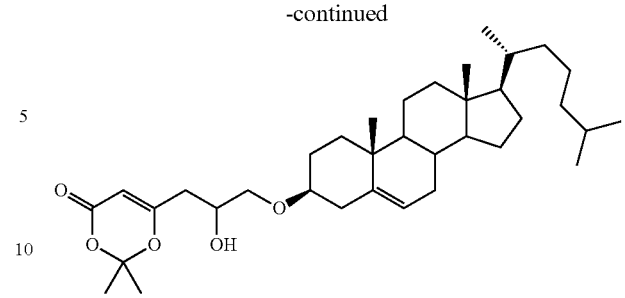

Step 3: To a 50 mL single neck round bottom flask, acetonide protected compound in THF is taken at about 0° C. To this solution, 1 (M) HCl is added and the reaction mixture is stirred for about 2 hours at same temperature. After completion of the reaction, the compound is extracted with ethyl acetate and concentrated under reduced pressure. The residue is purified by silica gel chromatography.

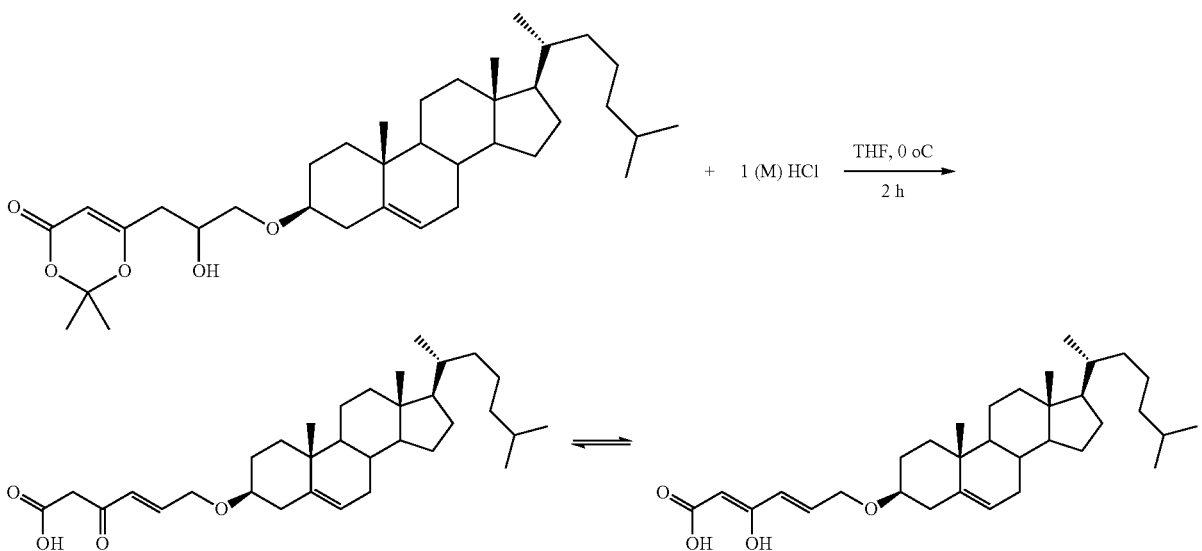

stirred for about 0.5 hours. To this solution, previously prepared aldehyde in THF (about 5 mL) is slowly added, and the resulting solution is stirred for another 2 hours at about −78° C. and the reaction is checked by TLC. After completion, the reaction mixture is quenched with water and extracted with ethyl acetate. The combined organic layer is concentrated and thereafter purification is carried out by silica gel chromatography.

Step 4: To a 50 mL single neck round bottomed flask, hydroxyl acid in DMF (about 1 mL) is taken and the solution is stirred at room temperature for about 30 minutes. Aquated DACH—Pt(H2O) is added to the reaction mixture at room temperature and the reaction mixture is stirred for another 24 hours and thereafter lyophilized. The solid residue is washed with water (about 5 mL) and thereafter lyophilized to obtain final platinum adduct product Compound 33.

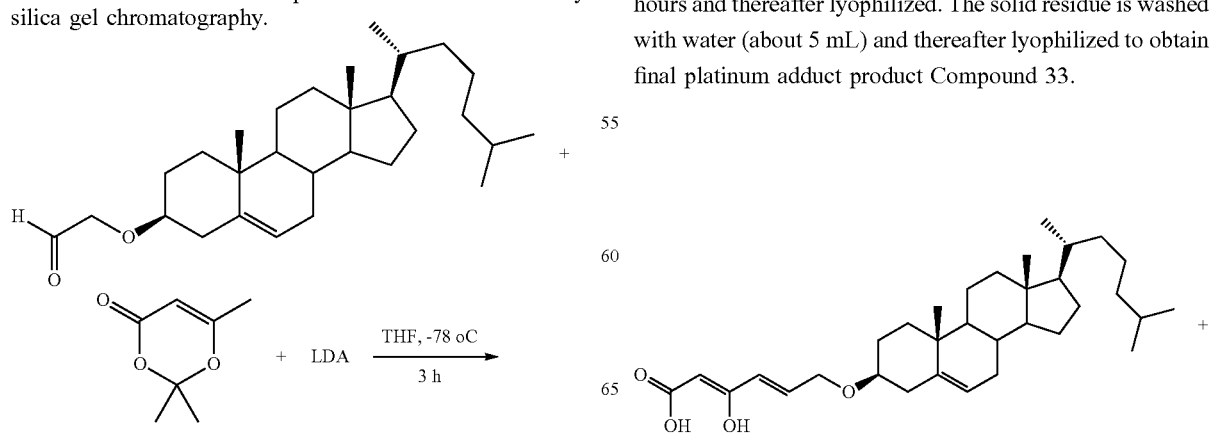

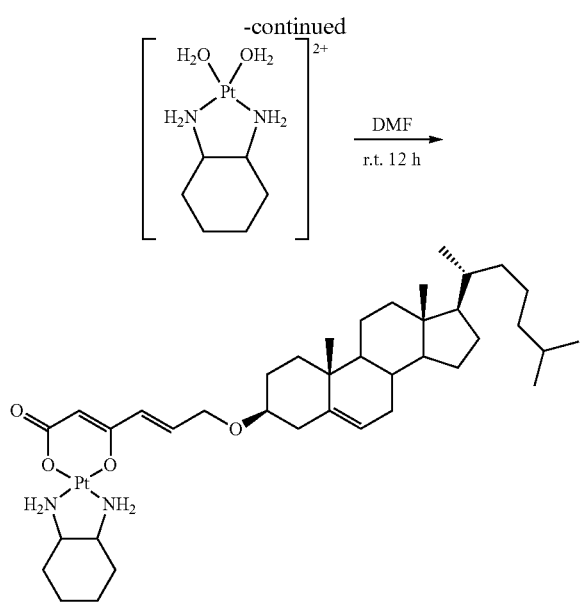

Synthesis of Compound 34 [wherein, R=Cholesterol or other Lipid]

Step 1: To an ice cooled solution of cholesterol 1.01 in CH$_2$Cl$_2$, pyridine is added and stirred for about 15 minutes. To this solution, p-toluene sulphonyl chloride is added and stirred for another 6 h at about 0° C. After completion, the reaction mixture is diluted with CHCl$_3$ and washed with about 1N HCl and brine successively. The organic layer is dried over anhydrous Na$_2$SO$_4$ and concentrated under vacuum to afford intermediate 1.02 and the intermediate is employed for the next reaction without further purification.

water and brine successively. The organic layer is removed over anhydrous Na$_2$SO$_4$ and concentrated under vacuum and finally the residue is purified on silica gel column to afford alcohol intermediate.

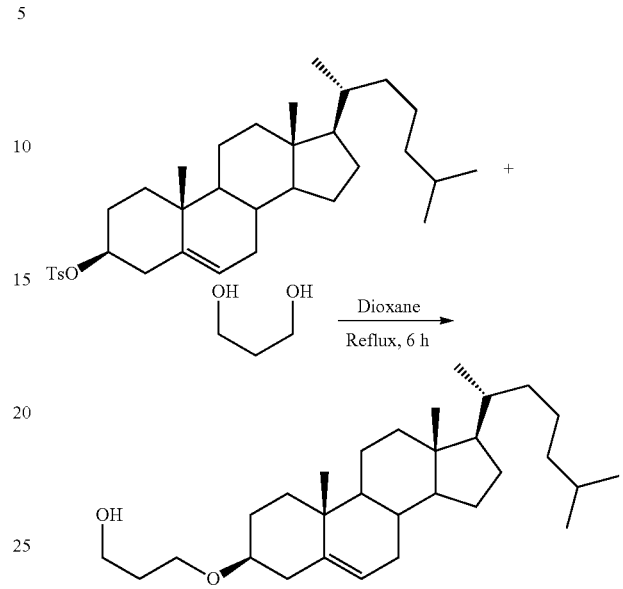

Step 3: To an ice cooled solution of alcohol in CH$_2$Cl$_2$, pyridine is added and stirred for about 15 minutes. To this solution, p-toluene sulphonyl chloride is added and the reaction mixture is stirred for another 6 h at about 0° C. After completion, the reaction mixture is diluted with CHCl$_3$ and washed with about 1N HCl and brine successively. The organic layer is dried over anhydrous Na$_2$SO$_4$ and thereafter concentrated under vacuum. The residue is purified on silica gel column to afford tosyl intermediate.

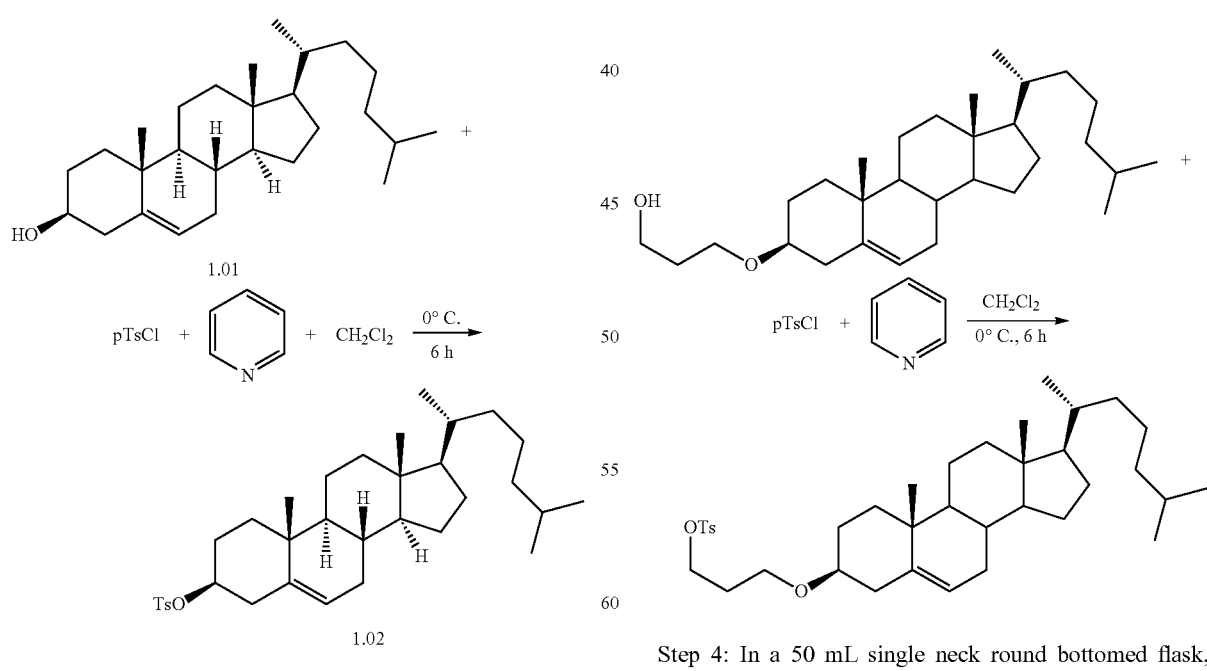

Step 2: To the solution of crude tosyl cholesterol 1.02 in dioxane, 1,3-propanediol is added and the reaction mixture is refluxed for about 4 hours. After completion, the reaction mixture is extracted with ethyl acetate and washed with Step 4: In a 50 mL single neck round bottomed flask, methyl-3-mercapto propionate in DMF (about 10 mL) is taken at about 0° C. under nitrogen atmosphere. Potassium carbonate is added to the reaction mixture followed by the addition of tosyl compound. The mixture is stirred at room temperature for another 24 hours. After completion, the reaction mixture is quenched with water and thereafter extracted with ethyl acetate. The organic layer is dried over anhydrous Na₂SO₄ and concentrated under reduced pressure. The residue is finally purified by silica gel chromatography to yield sulfide intermediate.

Step 6: In a 50 mL single neck round bottom flask, the acid intermediate obtained in the previous step in CH₂Cl₂ is taken and the mixture is cooled to about 0° C. To this solution, m-chloroperoxybenzoic acid (mCPBA) (about 0.9 equivalents) is added and the reaction mixture is stir at the same temperature (i.e. 0° C.) for about 1 hour and the progress of the reaction is checked by TLC. After completion of the reaction, the reaction mixture is quenched with water and further extracted with CH₂Cl₂. The organic layer is dried over anhydrous Na₂SO₄, concentrated and purified by silica gel chromatography to obtain partially oxidized intermediate.

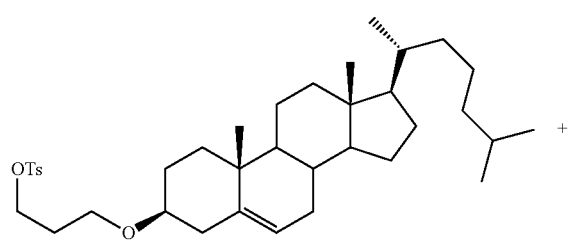

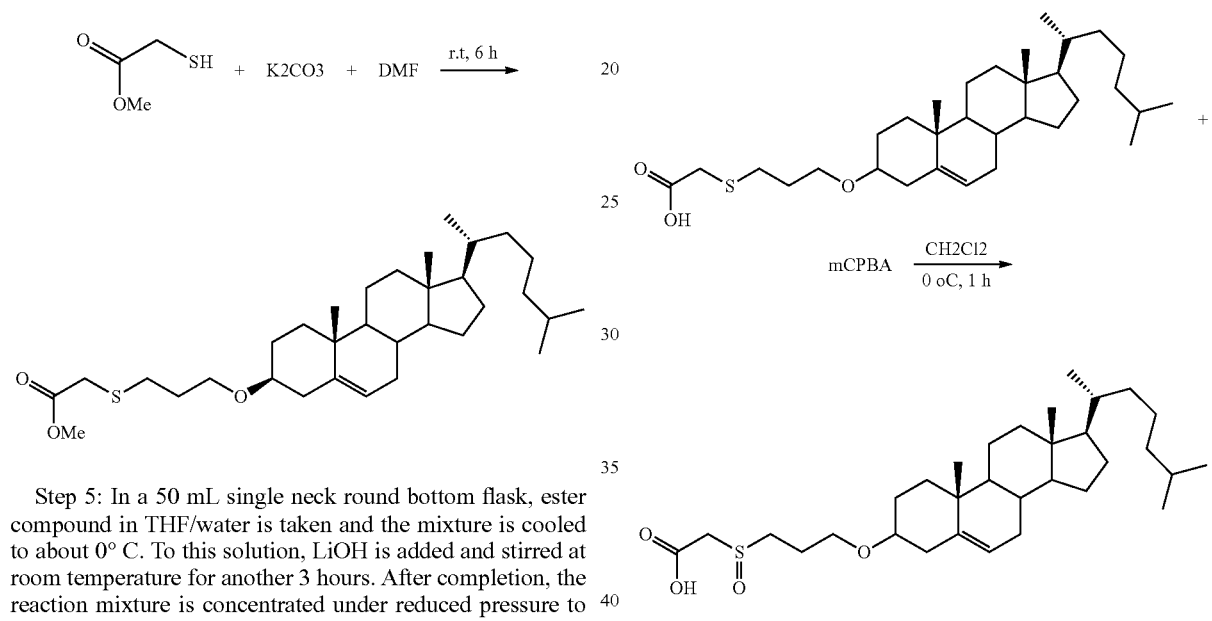

Step 5: In a 50 mL single neck round bottom flask, ester compound in THF/water is taken and the mixture is cooled to about 0° C. To this solution, LiOH is added and stirred at room temperature for another 3 hours. After completion, the reaction mixture is concentrated under reduced pressure to remove THF and further extracted with ethyl acetate. The organic layer is dried over anhydrous Na₂SO₄, concentrated and finally purified by silica gel chromatography to obtain acid intermediate.

Step 7: In a 50 mL single neck round bottom flask, acid intermediate in DMF is taken and the mixture is stirred at room temperature for about 15 minutes. To this solution, DACHPt(H₂O)₂ is added and the reaction mixture is stirred for another 24 hours. The solution is lyophilized to afford amphiphile Compound 34 in good yield.

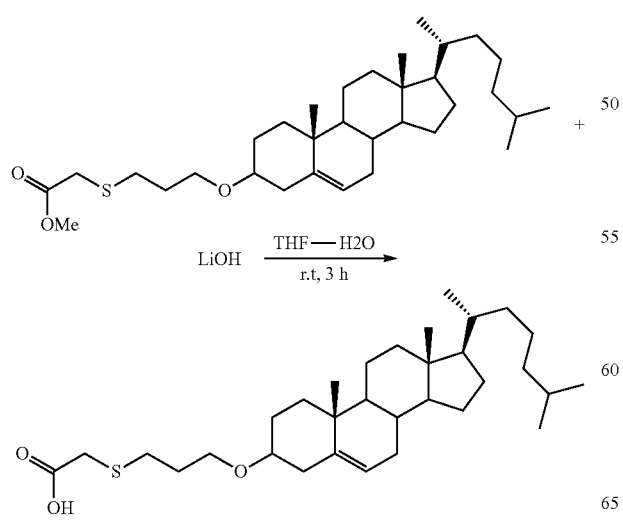

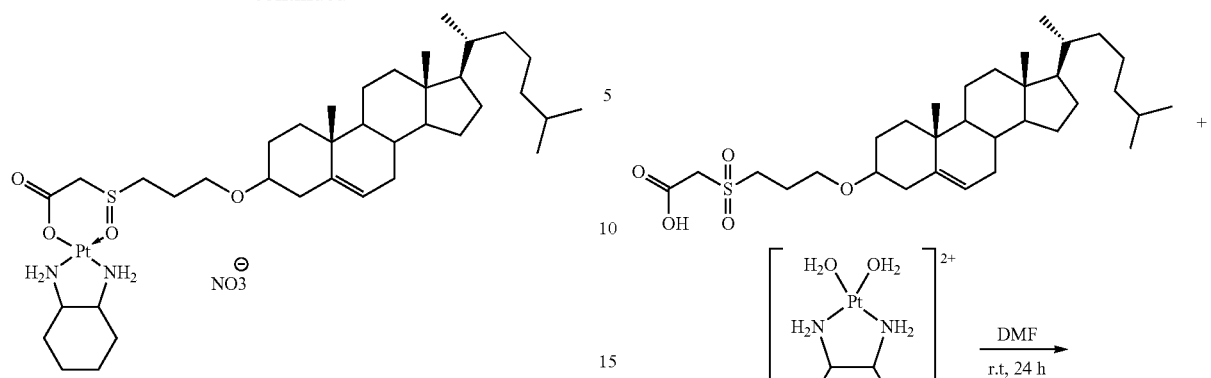

Synthesis of Compound 35 [wherein, R=Cholesterol or other Lipid]

Steps 1-5: The sulphide intermediate obtained during the synthesis of compound 34 (Steps 4 and 5) is taken as the starting reactant.

Step 6: In a 50 mL single neck round bottom flask, the aforesaid sulphide intermediate in CH₂Cl₂ is taken and the mixture is cooled to about 0° C. To this solution, mCPBA (about 1.8 equivalent) is added and the reaction mixture is stirred at same temperature for about 1 hour and the reaction progress is checked by TLC. After completion, the reaction mixture is quenched with water and thereafter extracted with CH₂Cl₂. The organic layer is dried over anhydrous Na₂SO₄, concentrated and purified by silica gel chromatography to obtain fully oxidized intermediate.

Step 7: In a 50 mL single neck round bottom flask, acid intermediate in DMF is taken and stirred at room temperature for about 15 minutes. To this solution, DACHPt(H₂O)₂ is added and the reaction mixture is stirred for another 24 hours. The solution is lyophilized to afford amphiphile Compound 35 in good yield.

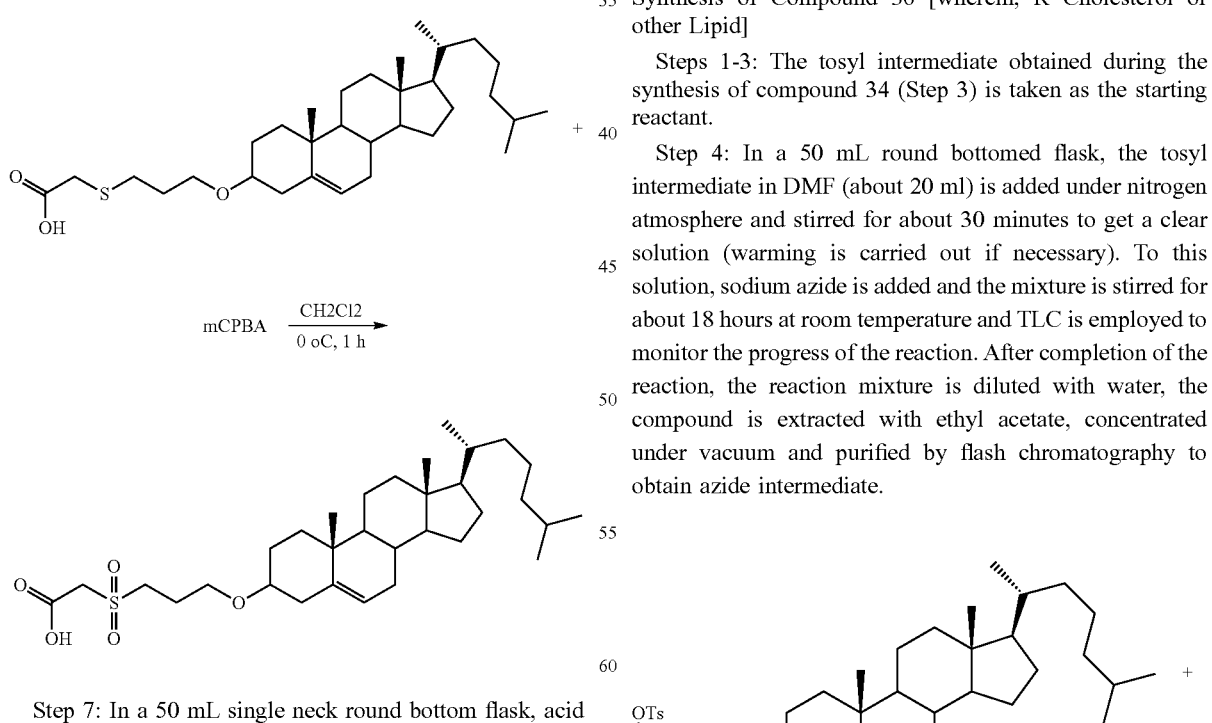

Synthesis of Compound 36 [wherein, R=Cholesterol or other Lipid]

Steps 1-3: The tosyl intermediate obtained during the synthesis of compound 34 (Step 3) is taken as the starting reactant.

Step 4: In a 50 mL round bottomed flask, the tosyl intermediate in DMF (about 20 ml) is added under nitrogen atmosphere and stirred for about 30 minutes to get a clear solution (warming is carried out if necessary). To this solution, sodium azide is added and the mixture is stirred for about 18 hours at room temperature and TLC is employed to monitor the progress of the reaction. After completion of the reaction, the reaction mixture is diluted with water, the compound is extracted with ethyl acetate, concentrated under vacuum and purified by flash chromatography to obtain azide intermediate.

-continued

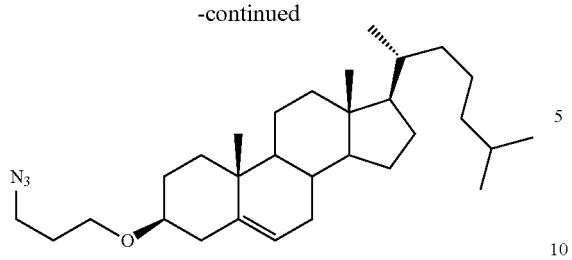

Step 5: To a solution of azide in dry DMF, triphenyl phosphene (TPP) is added under nitrogen atmosphere. The reaction mixture is stirred for about 6 hours at room temperature and water is added to it. The reaction mixture is again stirred at the same temperature for an additional 6 hours and TLC is employed to monitor the progress of the reaction. After completion of the reaction, organic solvent is removed under vacuum and the residue is purified by silica gel chromatography using methanol/chloroform as eluent to obtain amine intermediate.

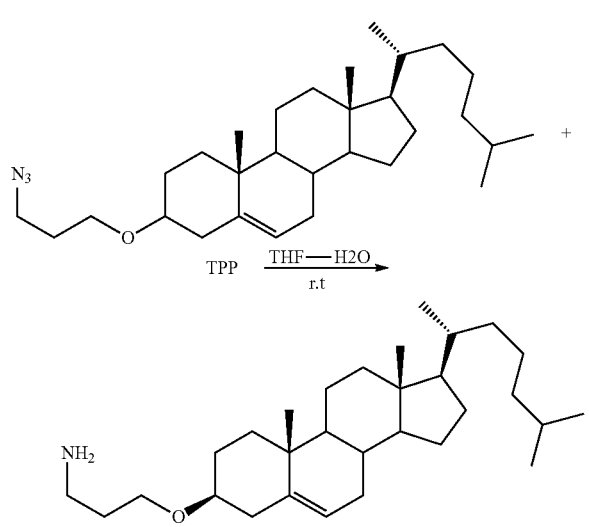

Step 6: To an ice cool solution of amine in THF, NaH is added over a period of about 10 minutes under nitrogen atmosphere. The resulting solution is stirred for about 20 minutes and thereafter ethyl bromo acetate is added. The reaction mixture is stir for another 6 hours at room temperature and TLC is employed to monitor the progress of the reaction. After completion of the reaction, the reaction mixture is cooled to about 0° C. and quenched with water followed by extraction with ethyl acetate. The organic layer is dried over anhydrous $Na_2SO_4$, concentrated and purified by silica gel chromatography to obtain ester intermediate.

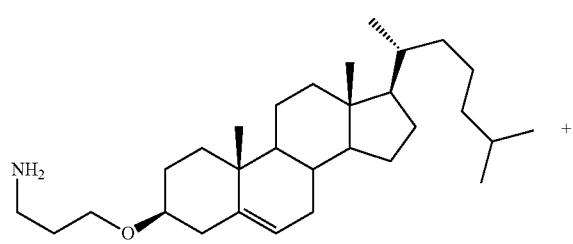

-continued

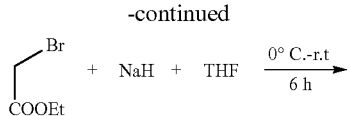

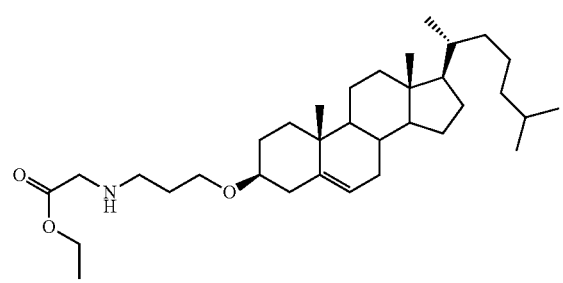

Step 7: To a 50 mL single neck round bottom flask, ester compound in THF/water is taken and cooled to about 0° C. To this solution, LiOH is added and the reaction mixture is stirred at room temperature for a time-period of about 3 hours. After completion of the reaction, the reaction mixture is concentrated under reduced pressure to remove THF and extracted with ethyl acetate. The organic layer is dried over anhydrous $Na_2SO_4$, concentrated and finally purified by silica gel chromatography to obtain acid intermediate.

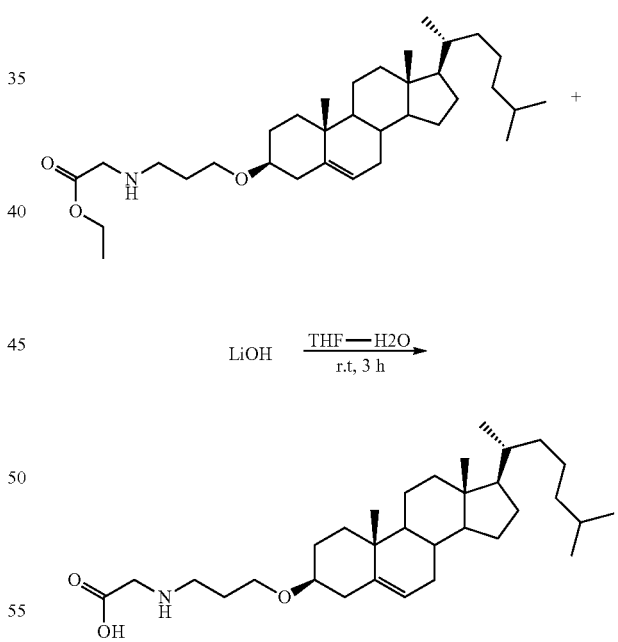

Step 8: In a 50 mL single neck round bottom flask, acid in $CH_2Cl_2$ is taken and cooled to about 0° C. To this solution, mCPBA (about 0.8 equivalents) is added and the mixture is stirred at same temperature for about 1 hour and the reaction progress is monitored by TLC. After completion of the reaction, the reaction mixture is quenched with water and extracted with $CH_2Cl_2$. The organic layer is dried over anhydrous $Na_2SO_4$, concentrated and purified by silica gel chromatography to obtain N-oxide intermediate.

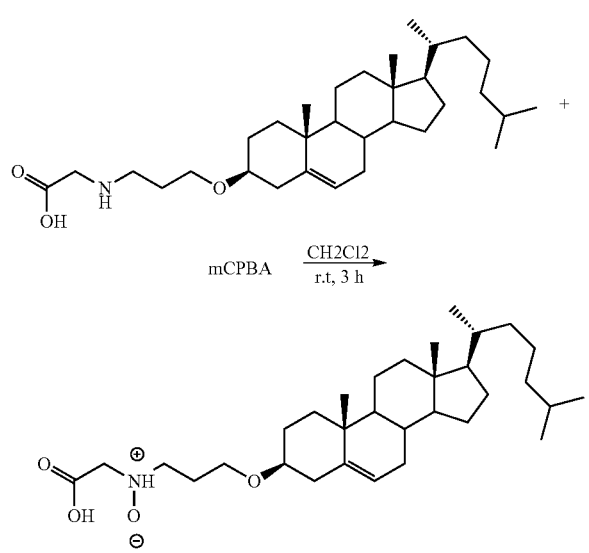

Step 9: In a 50 mL single neck round bottom flask, N-oxide intermediate is taken in DMF and the mixture is stirred at room temperature for about 15 minutes. To this solution, DACHPt(H₂O)₂ is added and the reaction mixture is stirred for a time-period of about 24 hours. The solution is lyophilized to afford Compound 36 in good yield.

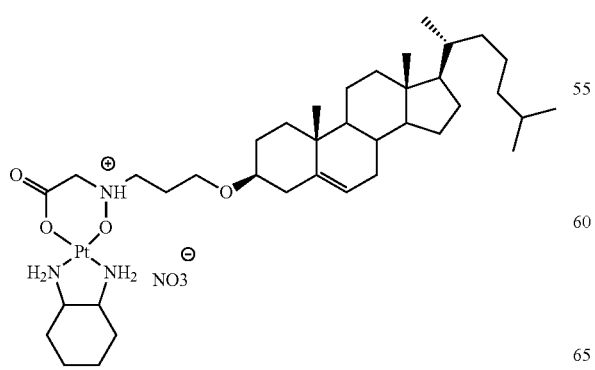

Example 5

Synthesis of Compound 30

Step 1: In a 50 mL single neck round bottom flask, cholesterol 1.01 (about 1.0 g, 2.59 mmol) in 5 mL anhydrous THF is taken under nitrogen atmosphere and cooled to about 0° C. To this solution, NaH (about 414 mg, 10.344 mmol) is added and the mixture is stirred for about 30 minutes at the same temperature (i.e. 0° C.). To this solution, ethyl bromo acetate (about 0.45 mL, 3.885 mmol) in THF (about 2 mL) is added and again the reaction mixture is allowed to stir for about 2 hours at room temperature. After completion, the reaction mixture is cooled to about 0° C. and quenched with water followed by extraction with ethyl acetate (about 2×15 mL). The organic layer obtained is dried over anhydrous $Na_2SO_4$, concentrated and purified by silica gel chromatography to obtain ester intermediate 1.29.

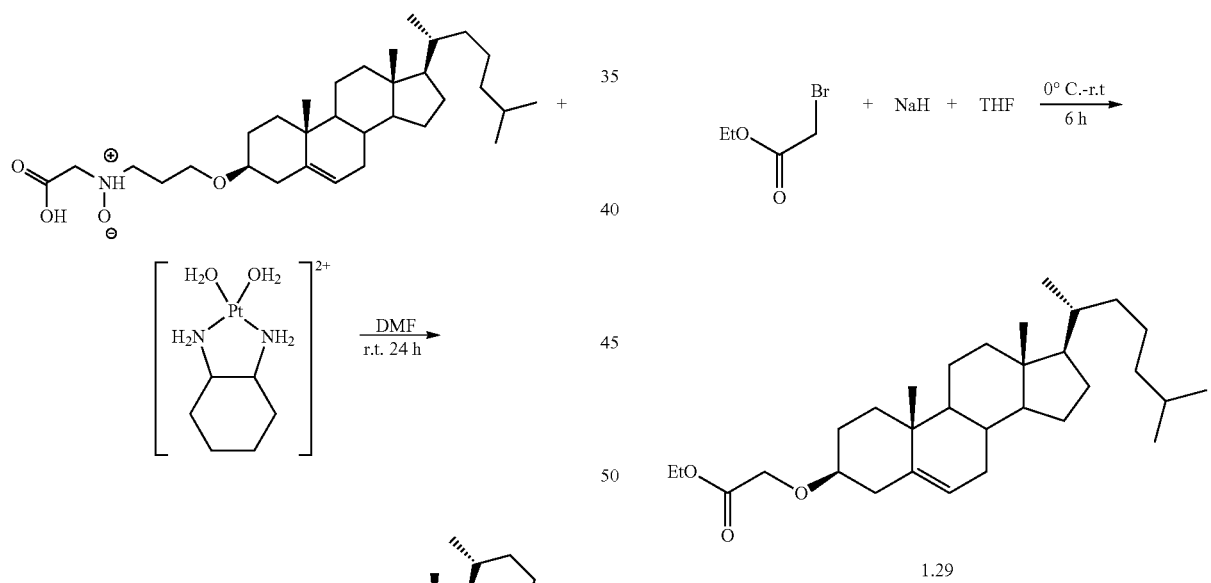

Step 2: In a 50 mL single neck round bottom flask, ester 1.29 (about 220 mg, 0.465 mmol) in THF/water (about 3:1) (about 4 mL) is taken at about 0° C. Solid LiOH (about 33 mg, 1.39 mmol) is added to the reaction mixture and stirred for about 6 hours at room temperature. After completion of the reaction, the reaction mixture is acidified with saturated $NaHSO_4$ up to pH 3 followed by extraction with $CHCl_3$ (about 3×10 mL). The organic layer is dried over anhydrous $Na_2SO_4$, concentrated under rotary evaporator and purified by silica gel chromatography to obtain pure acid intermediate 1.30.

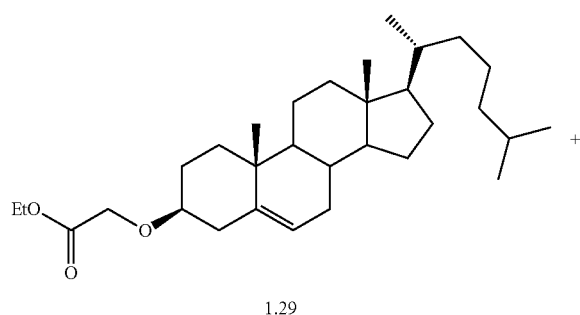

1.29

Step 4: In a 50 mL single neck round bottomed flask, acid 1.30 in DMF (about 1 mL) is taken and stirred at room temperature for about 30 minutes. Mono chloro DACH platinum 1.31 is added to the reaction mixture at room temperature and stirred for about 24 hours. The solid residue is washed with water (about 5 mL) and lyophilized to obtain the final platinum adduct product Compound 30.

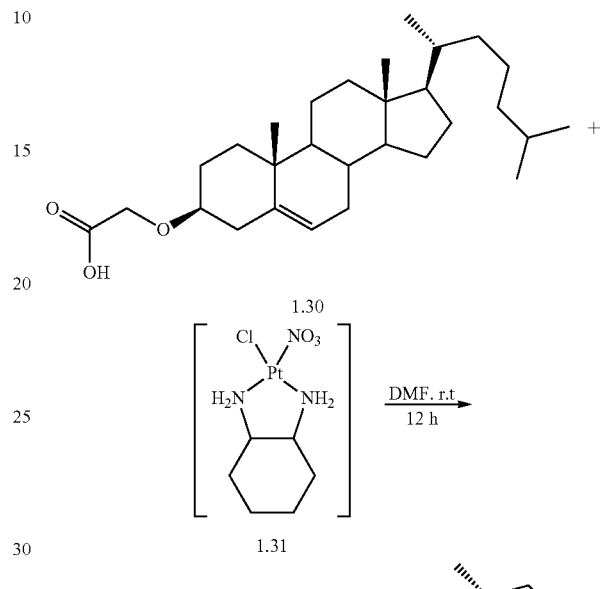

Step 3: In a 50 mL single neck round bottomed flask, DACH(Cl)$_2$Pt (about 50 mg, 0.131 mmol) in DMF (about 5 mL) is taken and stirred for about 10 minutes. AgNO$_3$ (about 22 mg, 0.131 mmol) is added to the reaction mixture at room temperature and stirred for about 24 hours. After completion, the solid AgCl precipitate is removed by centrifugation followed by filtration through 0.2 micron syringe filter to obtain mono chloro compound 1.31.

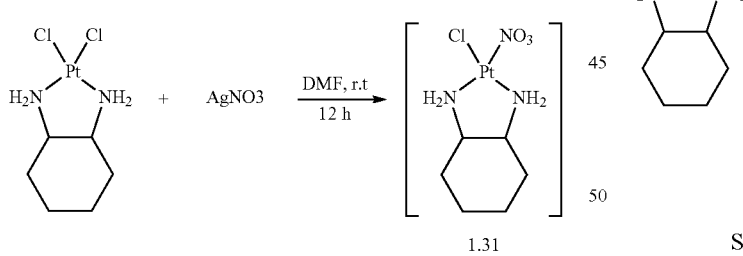

1.31

Example 6

Synthesis of Exemplary Compounds

Synthesis of Compound 63

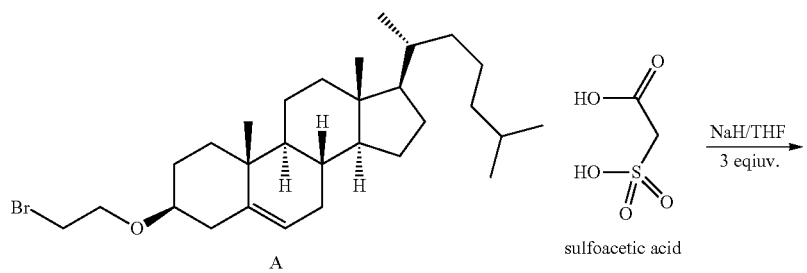

sulfoacetic acid

-continued
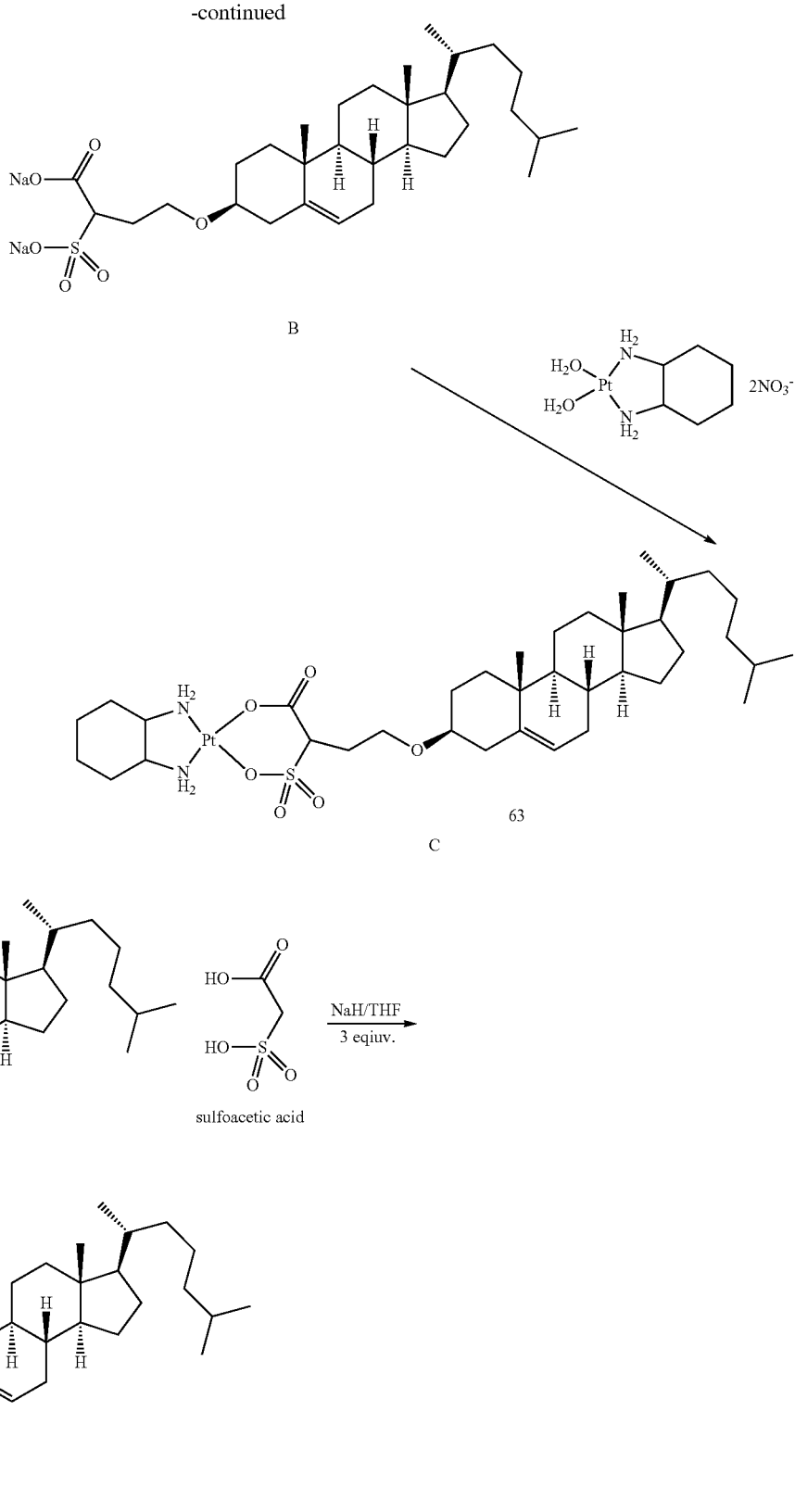
sulfoacetic acid
Experimental Procedure: Compound A (1.0 mmol) is taken in 10 mL THF. To this, sulfoacetic acid (3.0 mmol) is added and the resulting solution is stirred for 24 hr at RT. The TLC is checked and after completion water is added to the reaction mixture and the unreacted A is extracted using ethyl acetate. Water layer used for next step.

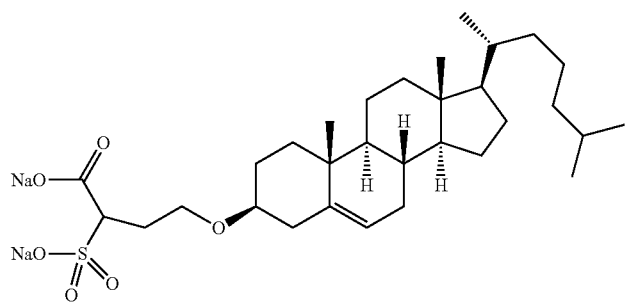
B
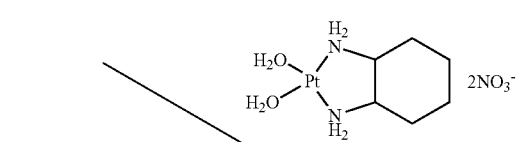
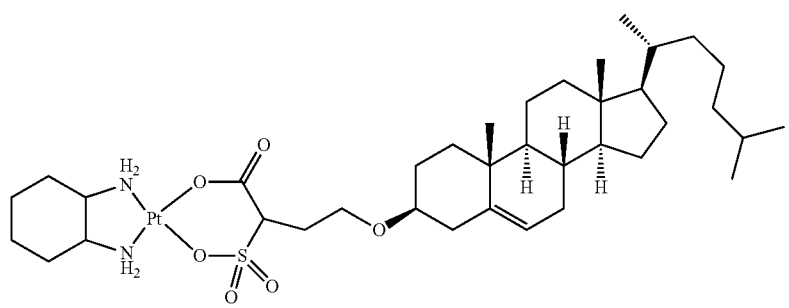
C
Experimental Procedure: To a 50 mL single neck RBF aquated DACH platinum (0.1 mmol, 3 mL, 10 mg/mL solution) is taken. Compound B (0.09 mmol), taken in 10 mL water, is added dropwise and the resulting solution is stirred at room temperature for 24 hrs. White precipitate appeared. Precipitate is washed with water and dried over vacuum to obtain compound C.
Synthesis of Compound 64
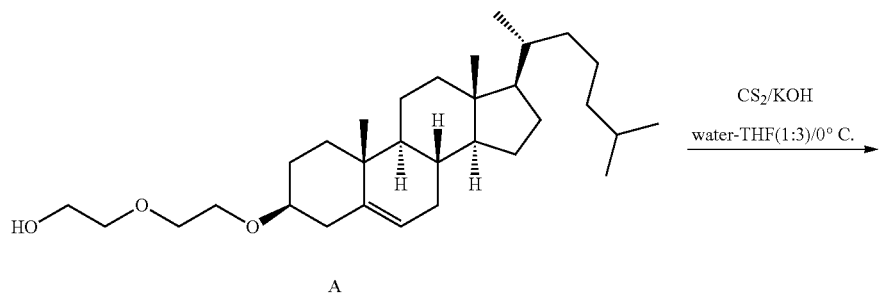
A

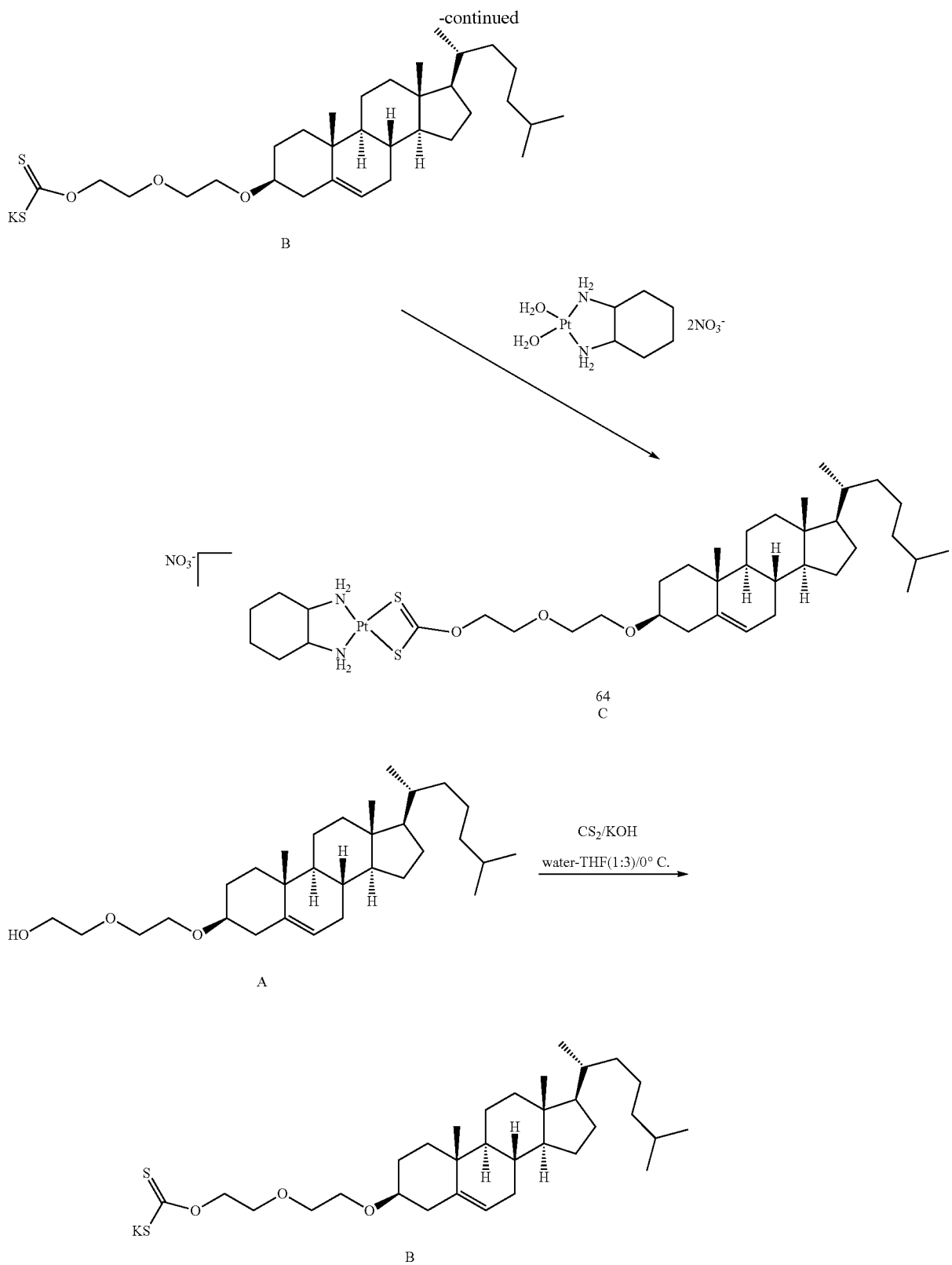

Experimental Procedure: To a 25 mL single neck RBF compound B (1.0 mmol) (synthesized according to the procedure mentioned in compound 64a) is taken in 10 mL THF. To this, selenium (1.0 mmol) is added and the resulting solution is stirred for 24 hr at RT. The TLC is checked and after completion water is added to the reaction mixture and the unreacted A is extracted using ethyl acetate. Water layer is used for next step.

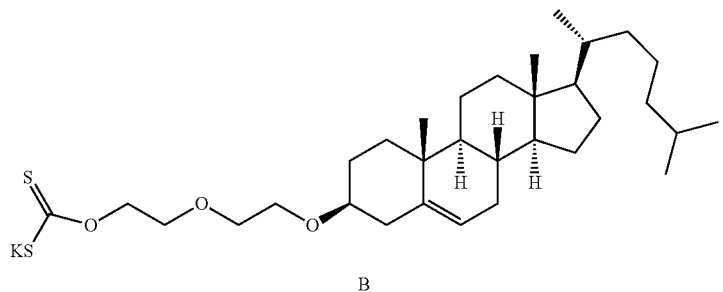

B

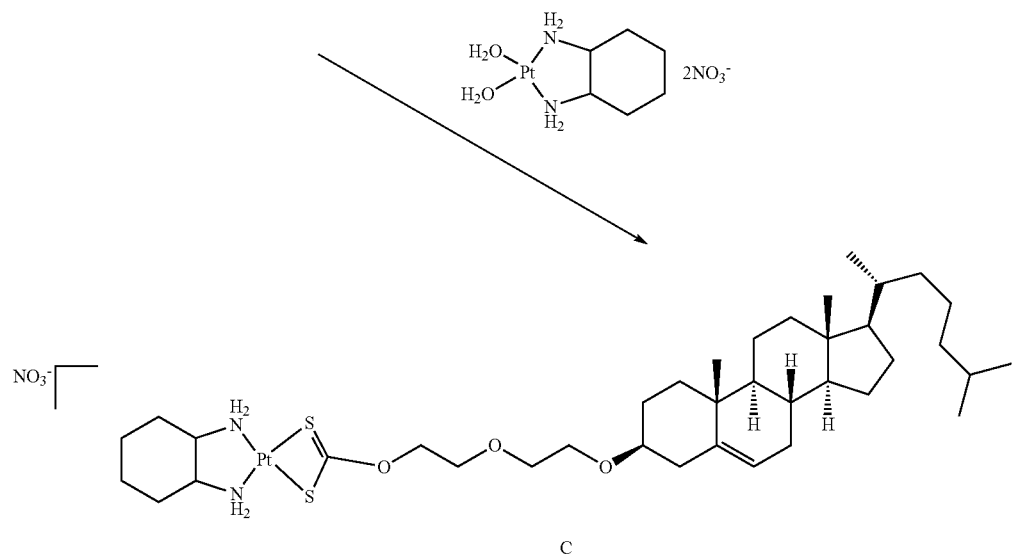

C

Experimental Procedure: To a 50 mL single neck RBF aquated DACH platinum (0.1 mmol, 3 mL, 10 mg/mL solution) is taken. Compound B (0.09 mmol), taken in 10 mL THF, is added dropwise and the resulting solution was stirred at room temperature for 24 hrs. TLC is checked. THF evaporated to get a light yellow precipitate. Precipitate is washed with water and dried over vacuum to obtain compound C.

Synthesis of Compound 65

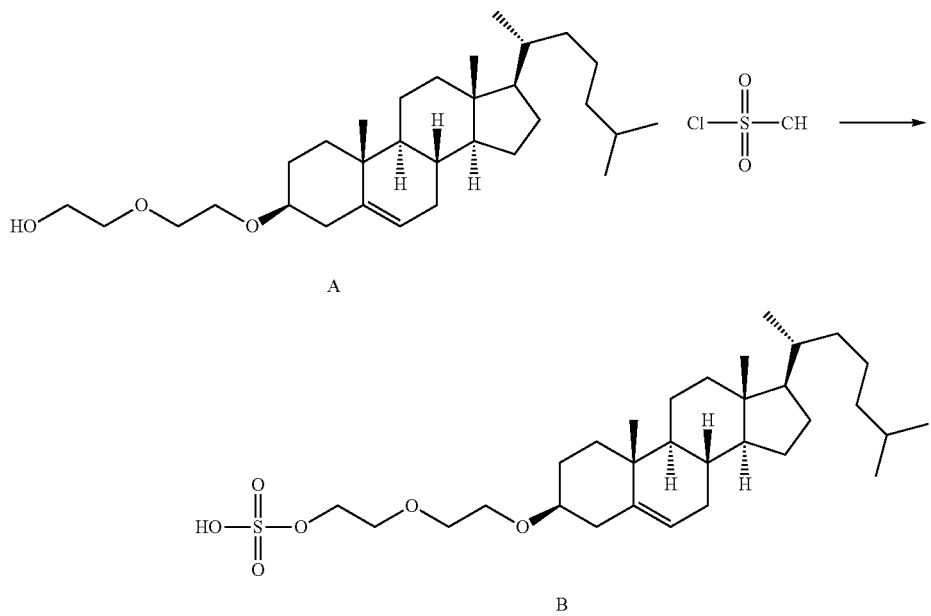

A

B

-continued

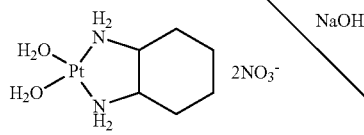

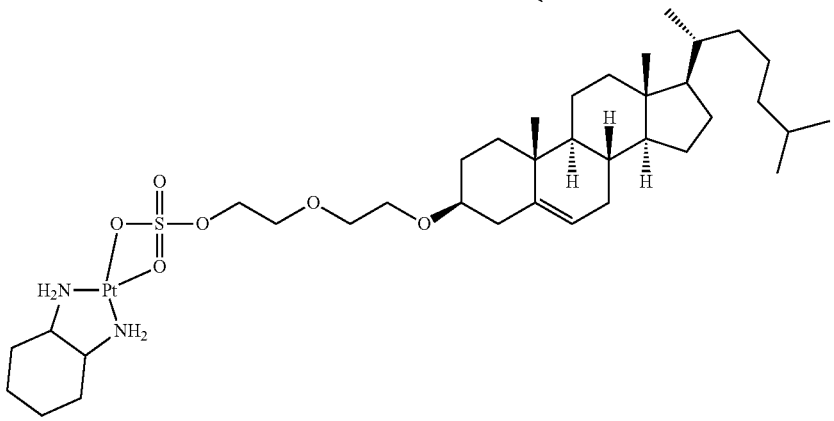

65
C

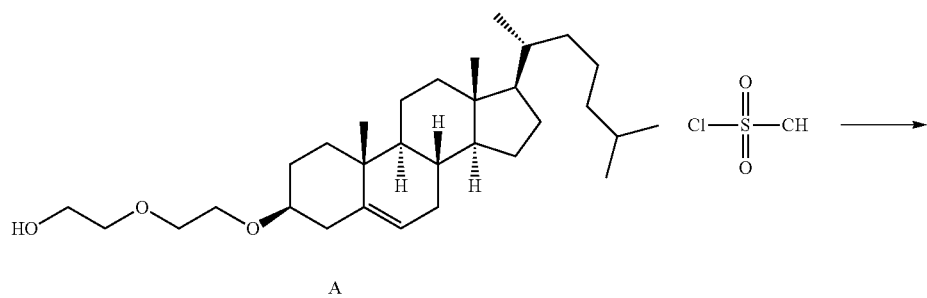

A

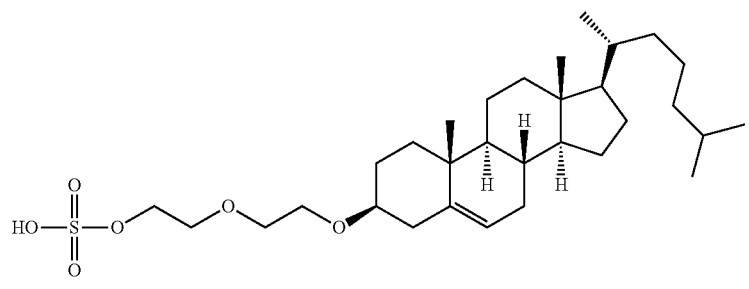

B

Experimental Procedure: To a 25 mL single neck RBF compound B (1.0 mmol) (synthesized according to the procedure mentioned in compound 64a) is taken in 10 mL $CCl_4$. To this, chlorosulfonic acid (1.0 mmol) is added dropwise at 0° C. and the resulting solution is stirred for 24 hr at RT. TLC is checked and after completion $CCl_4$ is evaporated in vac. 50 mL water is added and the crude product is extracted in chloroform to obtain B as white powder.

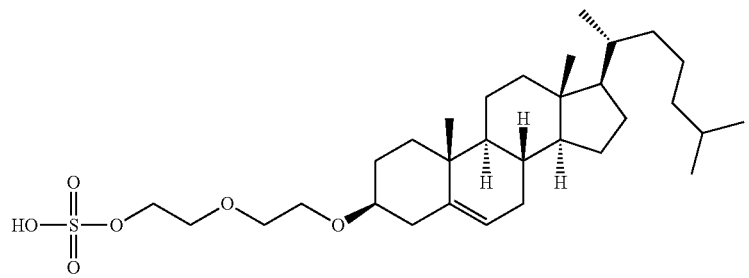

B

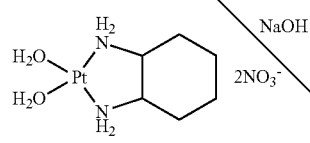

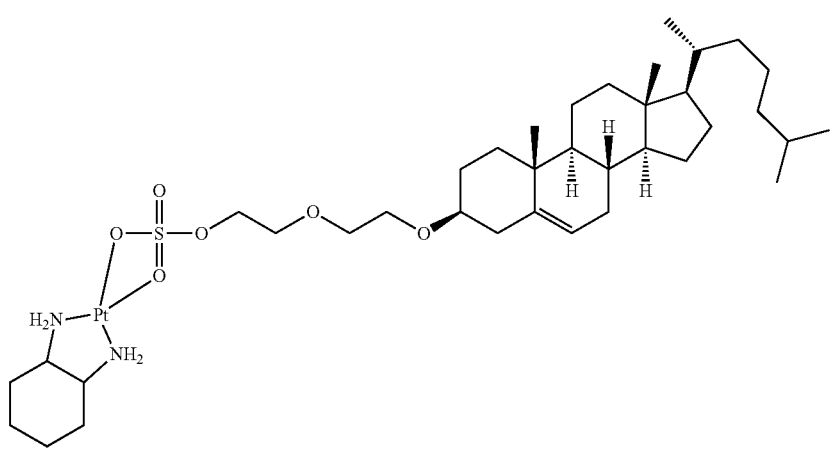

65
C

Experimental Procedure: In a RBF B (0.13 m mol) in 5 mL (1:3 water: THF) is treated with 0.13 mmol of sodium hydroxide at) 0° C. and the resulting solution is stirred for 15 min. THF evaporated and water layer is added dropwise to the solution of aquated platinum diaminocyclohexane (0.13 m mol in 15 ml water). White precipitate formed during the reaction. Reaction mixture centrifuged and precipitate was given water wash to get C as white powder.

Synthesis of Compound 37

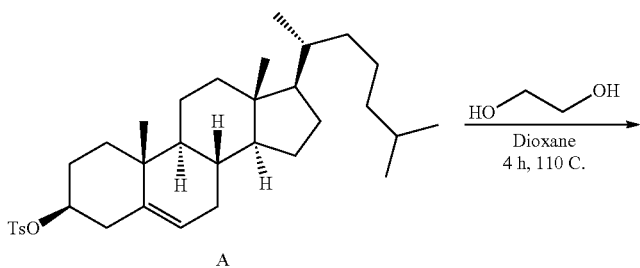

-continued
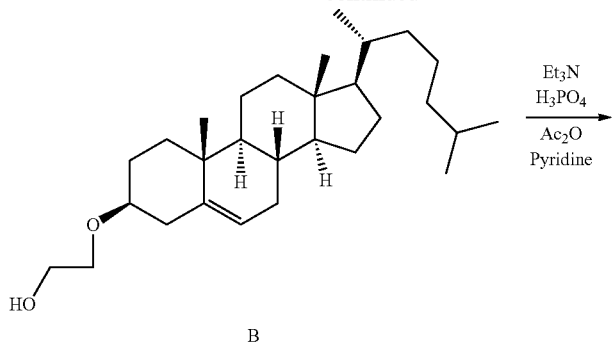
B
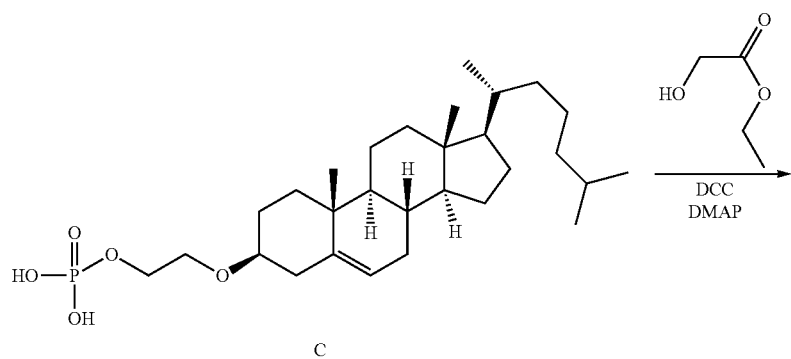
C
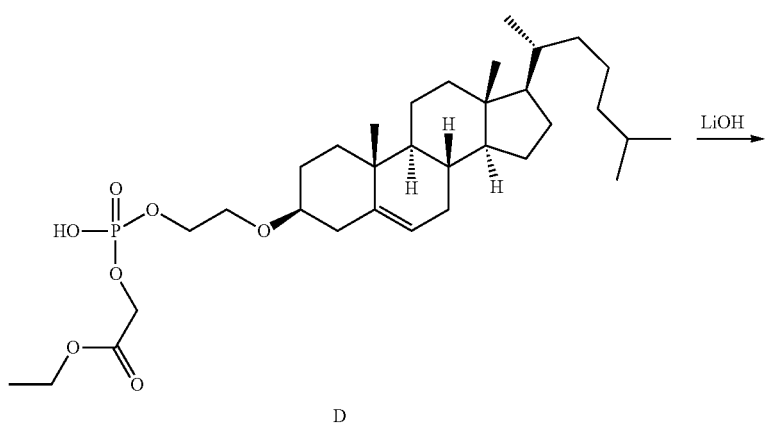
D
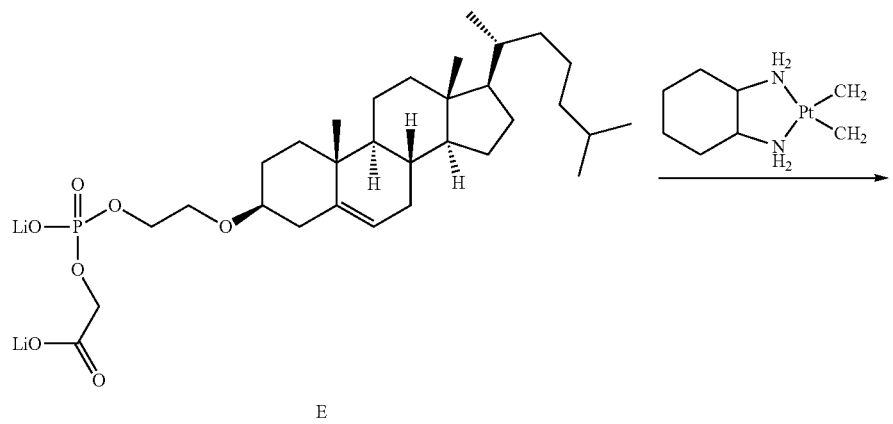
E

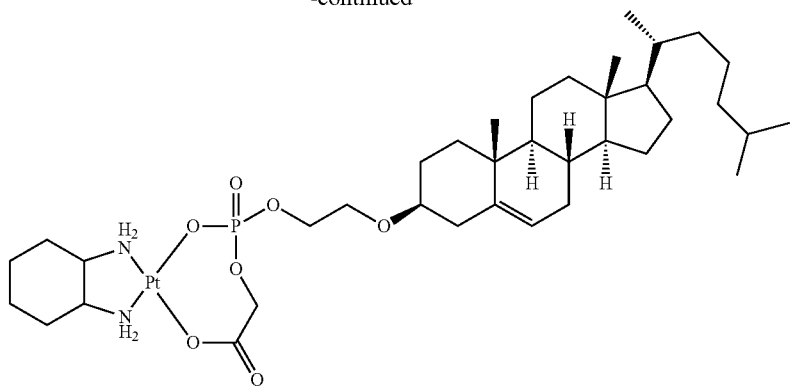

F

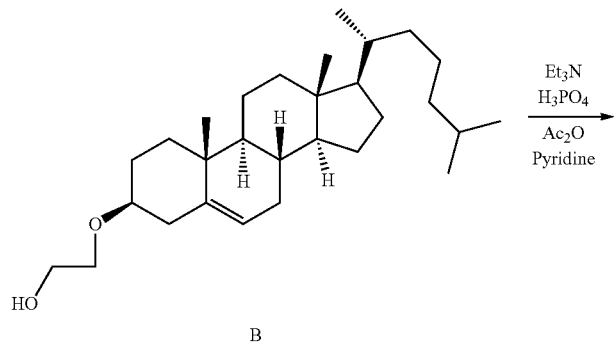

B

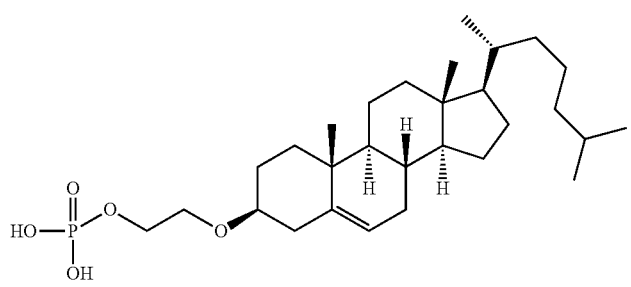

C

Experimental Procedure: To a 25 mL single neck RBF compound B (1.0 mmol) (synthesized according to the procedure mentioned in compound 69) is stirred with phosphoric acid (H$_3$PO$_3$) (1.0 m mol), pyridine (5 m mol) and triethylamine (Et$_3$N) (2 mmol) until clear solution is obtained. Acetic anhydride (2 mmol) is added and the reaction mixture is stirred for 4 hrs at 80° C. After all B is consumed, as indicated by TLC, 5 mL water is added to the reaction mixture. Compound C is extracted by chloroform wash (25 mL×3). Solvent concentrated in vacuum to obtain C.

All successive steps to reach F are carried out according to the procedure described for the preparation of IO-180_01

Synthesis of Compound 55

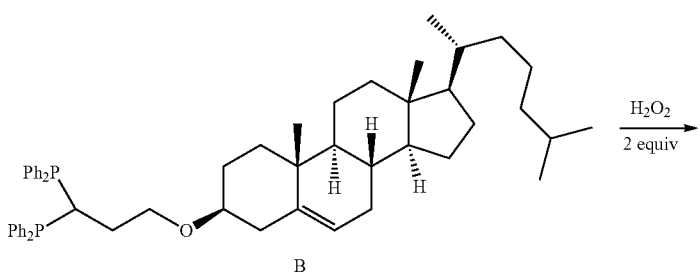

B

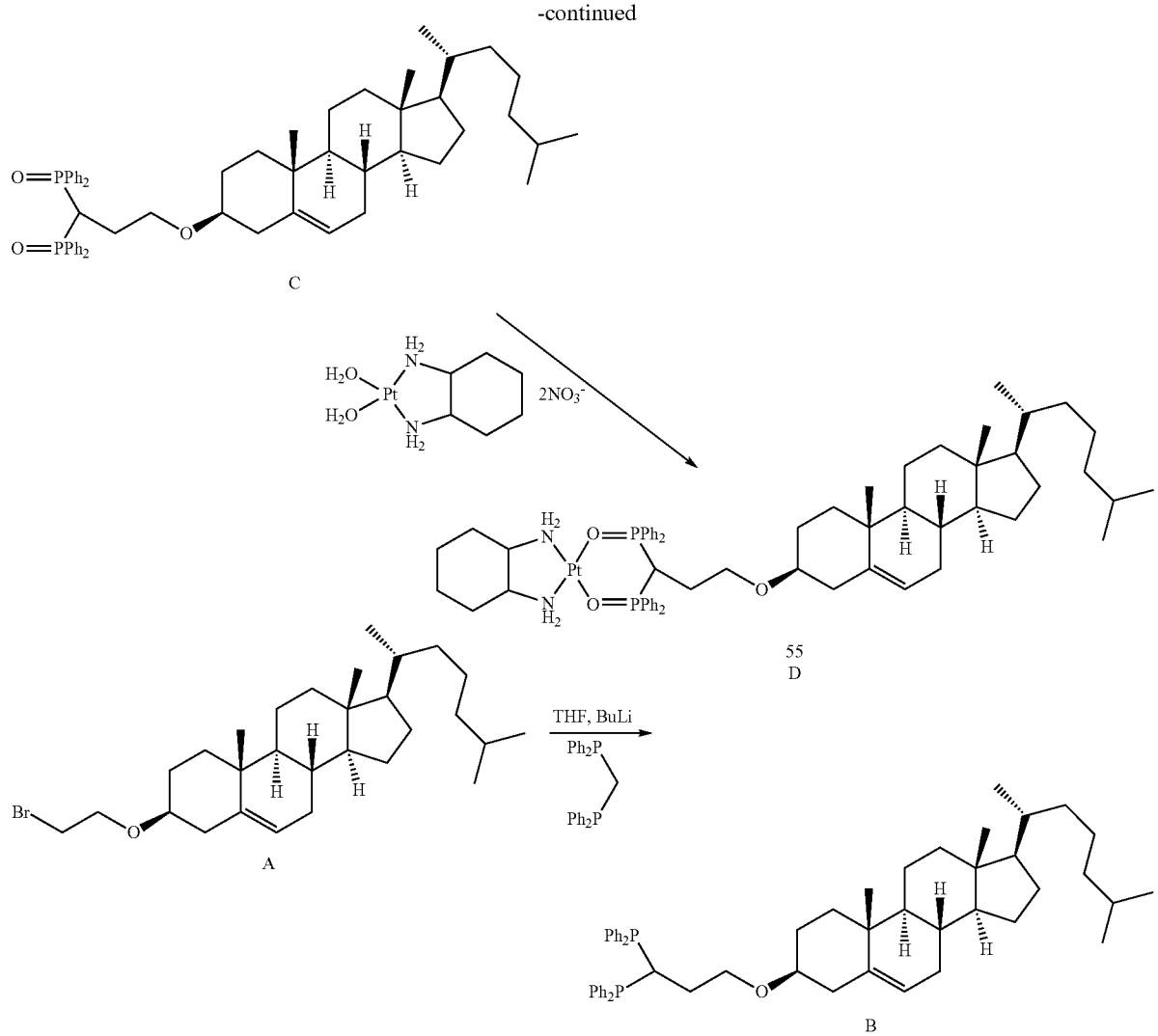

Experimental Procedure: A (compound A is synthesized according to the procedure mentioned in the synthesis of compound 69). To a 25 mL single neck RBF diphenylphosphinomethane (DPPM) (5.0 mmol) is taken in 30 mL THF. To this n-butyl-lithium (5.2 mmol) is added and the resulting solution is stirred for 15 min at 0° C. To the above solution chlolesteryl bromide (A)(4.0 mmol) is added and the reaction is stirred for 16 hrs. The TLC was checked and after completion water is added to the reaction mixture and the compound is extracted using ethyl acetate. The combined organic layer was concentrated under vacuum. Purified by column chromatography.

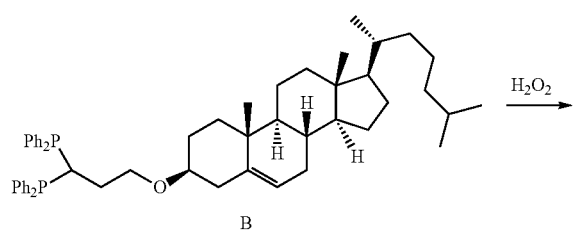

Experimental Procedure: To a 25 mL single neck RBF compound B (1.0 mmol) is taken in 30 mL THF. To this, hydrogenperoxide (2.2 mmol, 35% solution) is added and the resulting solution is stirred for 24 hr at RT. The TLC was checked and after completion water is added to the reaction mixture and the compound is extracted using ethyl acetate. The combined organic layer was concentrated under vacuum. Purified by column chromatography.

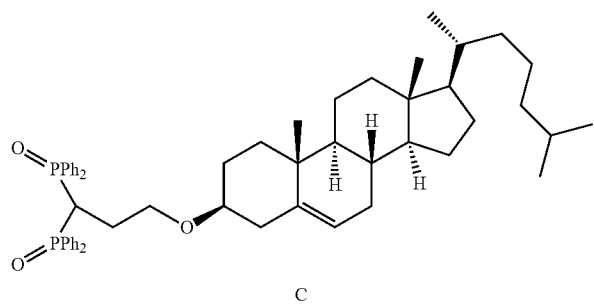

C

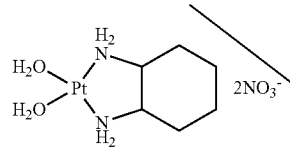

2NO$_3^-$

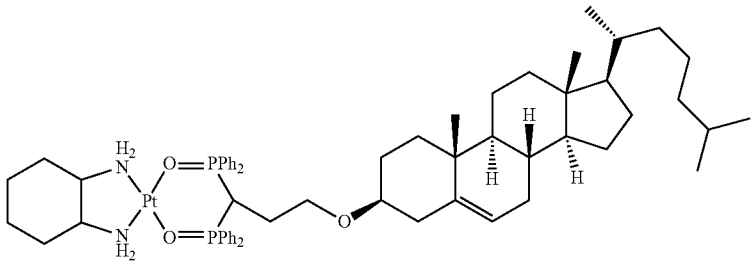

E
55

Experimental Procedure: To a 50 mL single neck RBF aquated DACH platinum (0.1 mmol, 3 mL, 10 mg/mL solution) is taken. Compound C (0.09 mmol), taken in 10 mL THF, is added dropwise and the resulting solution was stirred at room temperature for 24 hrs. TLC is checked. THF evaporated to get a light yellow precipitate. Precipitate is washed with water and dried over vacuum to obtain compound E.

Synthesis of Compound 52

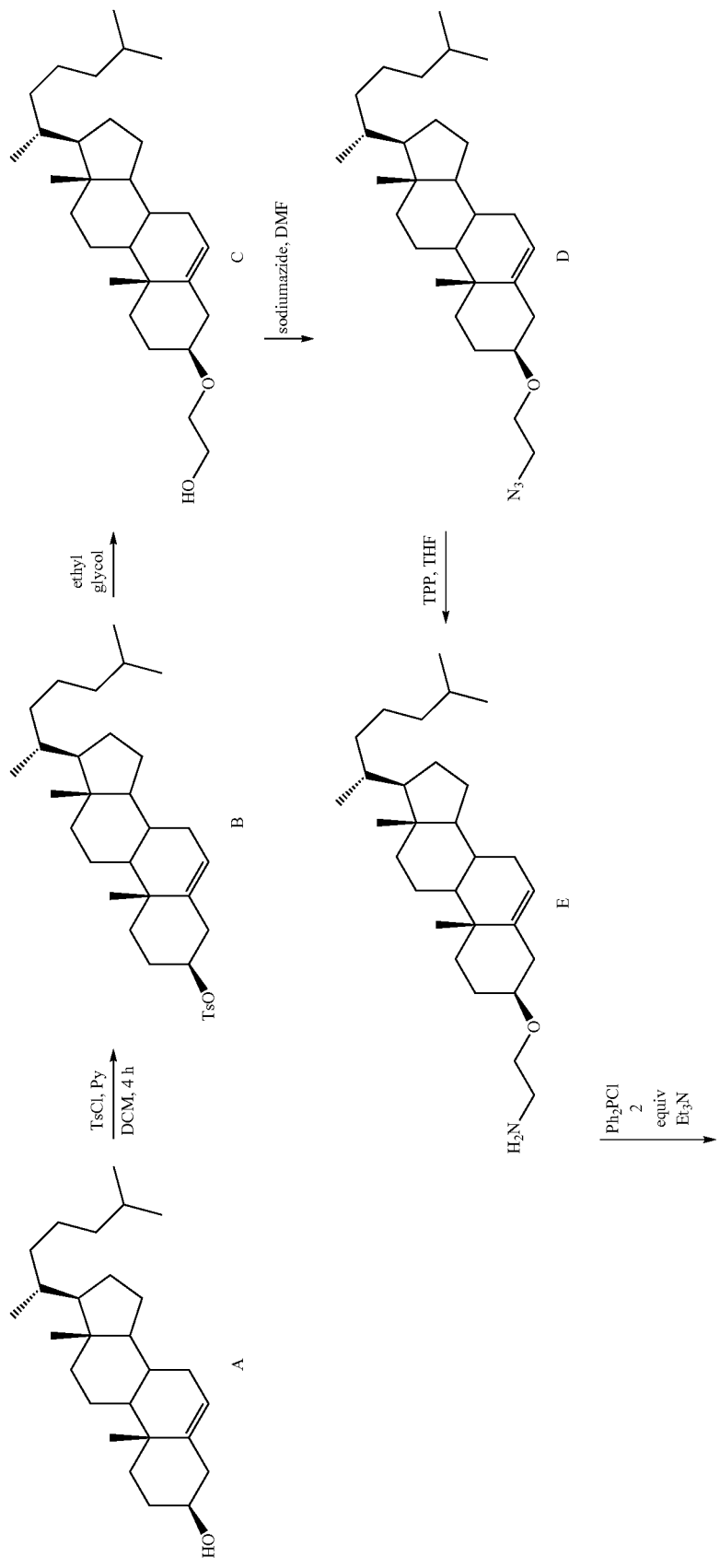

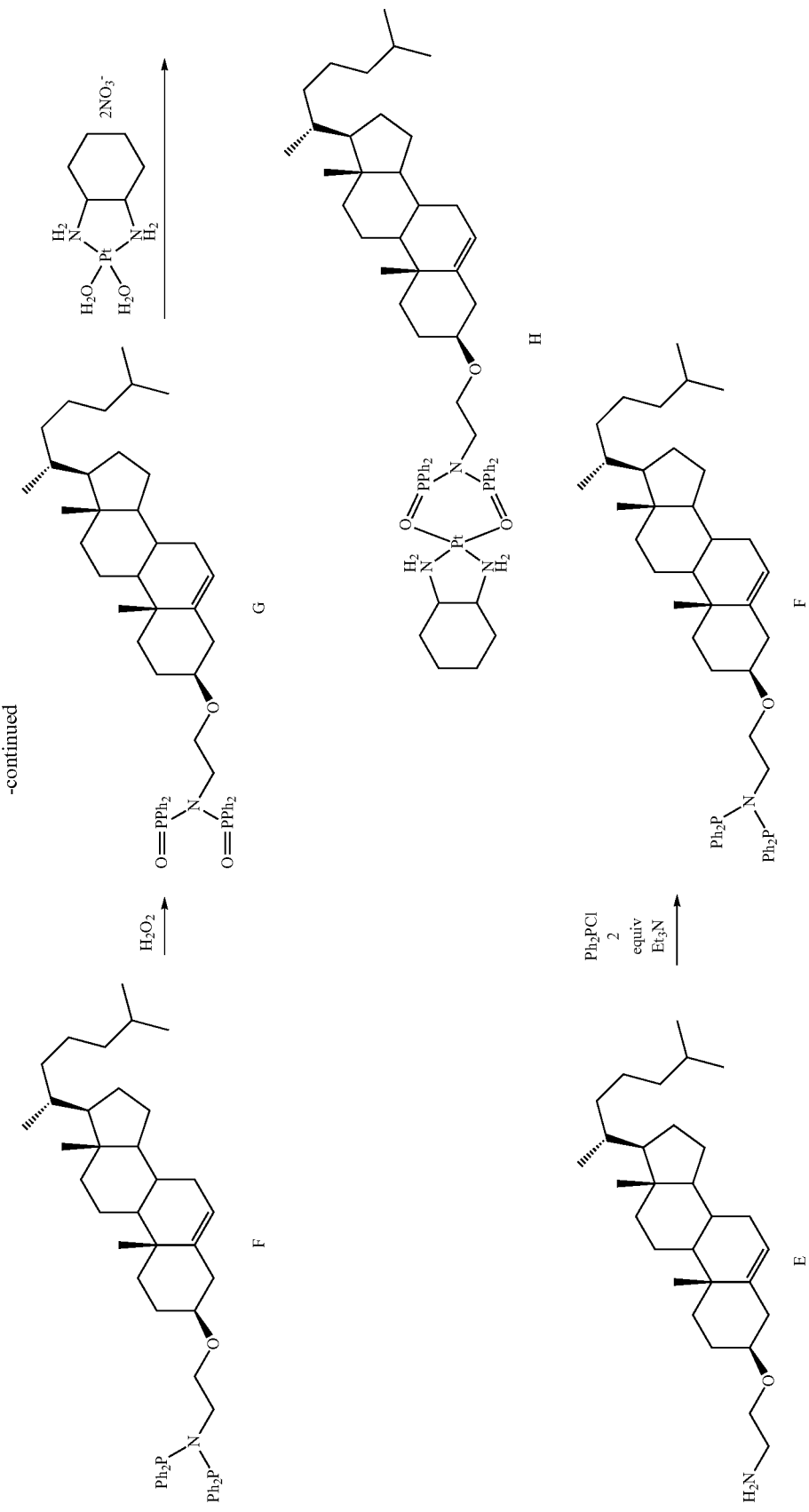

Experimental Procedure: To a 50 mL single neck RBF A (synthesis of A described in the ligand preparation of compound 25) (1 mmol) was taken in 10 mL dry THF. $Ph_2PCl$ (2 mmol) and triethylamine (2 mmol) are added. The reaction mixture is stirred under nitrogen for 12 hrs at RT. Solvent evaporated and column chromatography is performed to obtain F.

Syntheses of F to H are similar as described in the synthesis of compound 55.

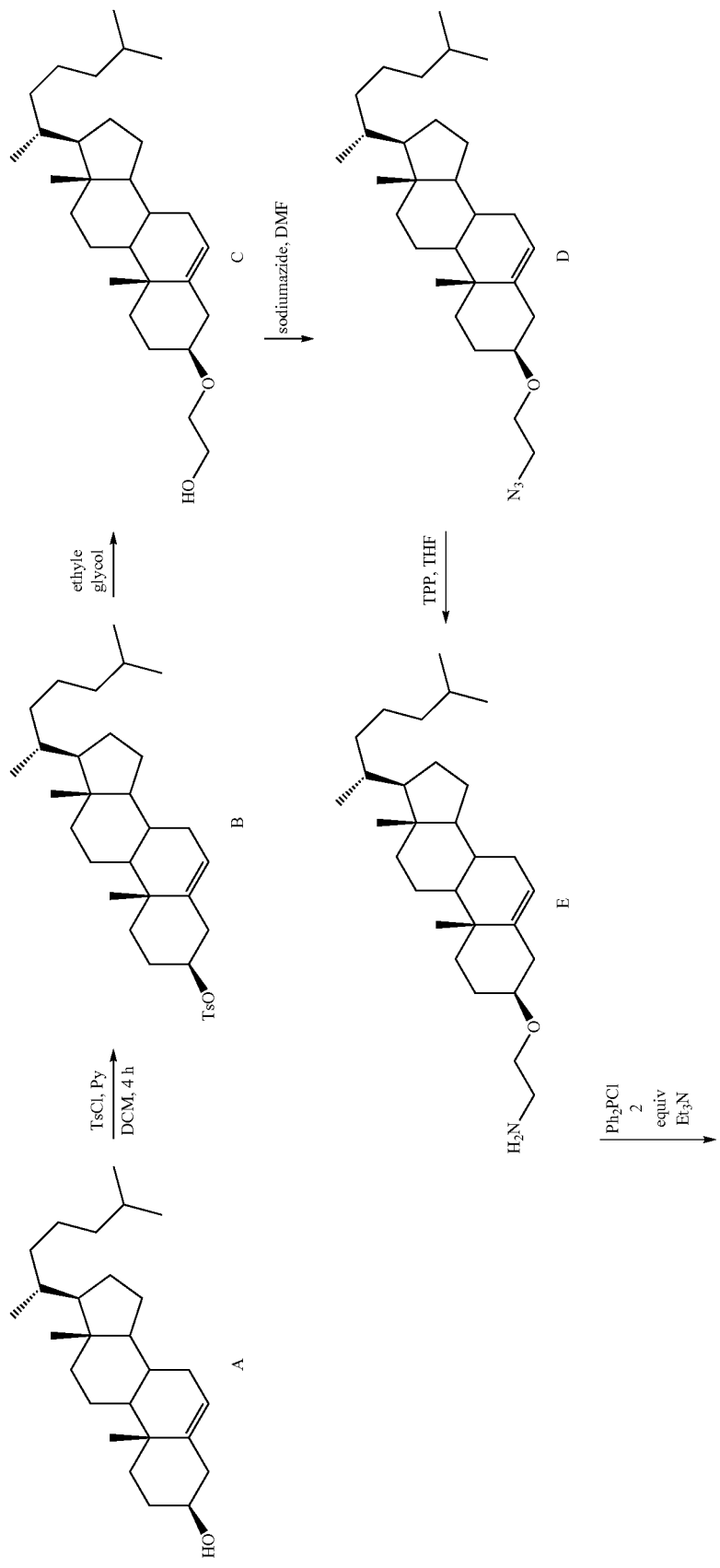

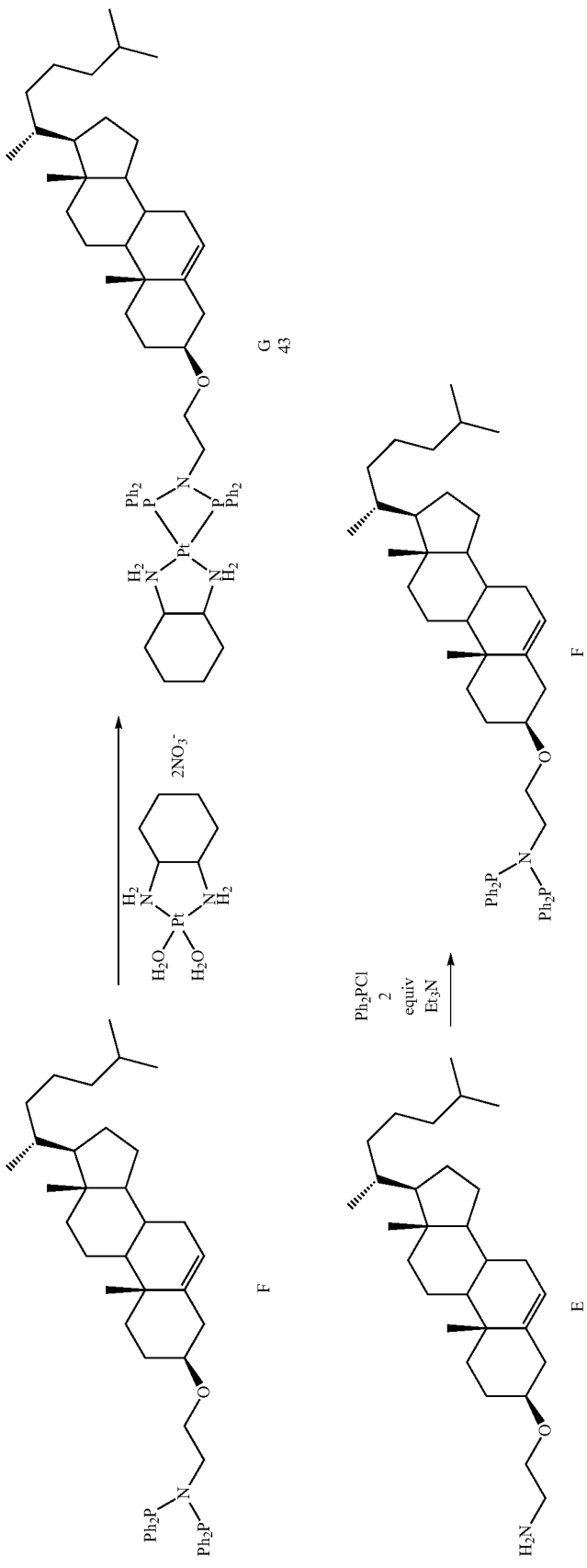

Experimental Procedure: To a 50 mL single neck RBF A (synthesis described in the ligand preparation of compound 25) (1 mmol) was taken in 10 mL dry THF. Ph$_2$PCl (2 mmol) and triethylamine (2 mmol) are added. The reaction mixture is stirred under nitrogen for 12 hrs at RT. Solvent evaporated and column chromatography is performed to obtain F.

Compound (G, 43) synthesis is similar as the synthesis of compound 44.

Synthesis of Compound 46, 47 and 48

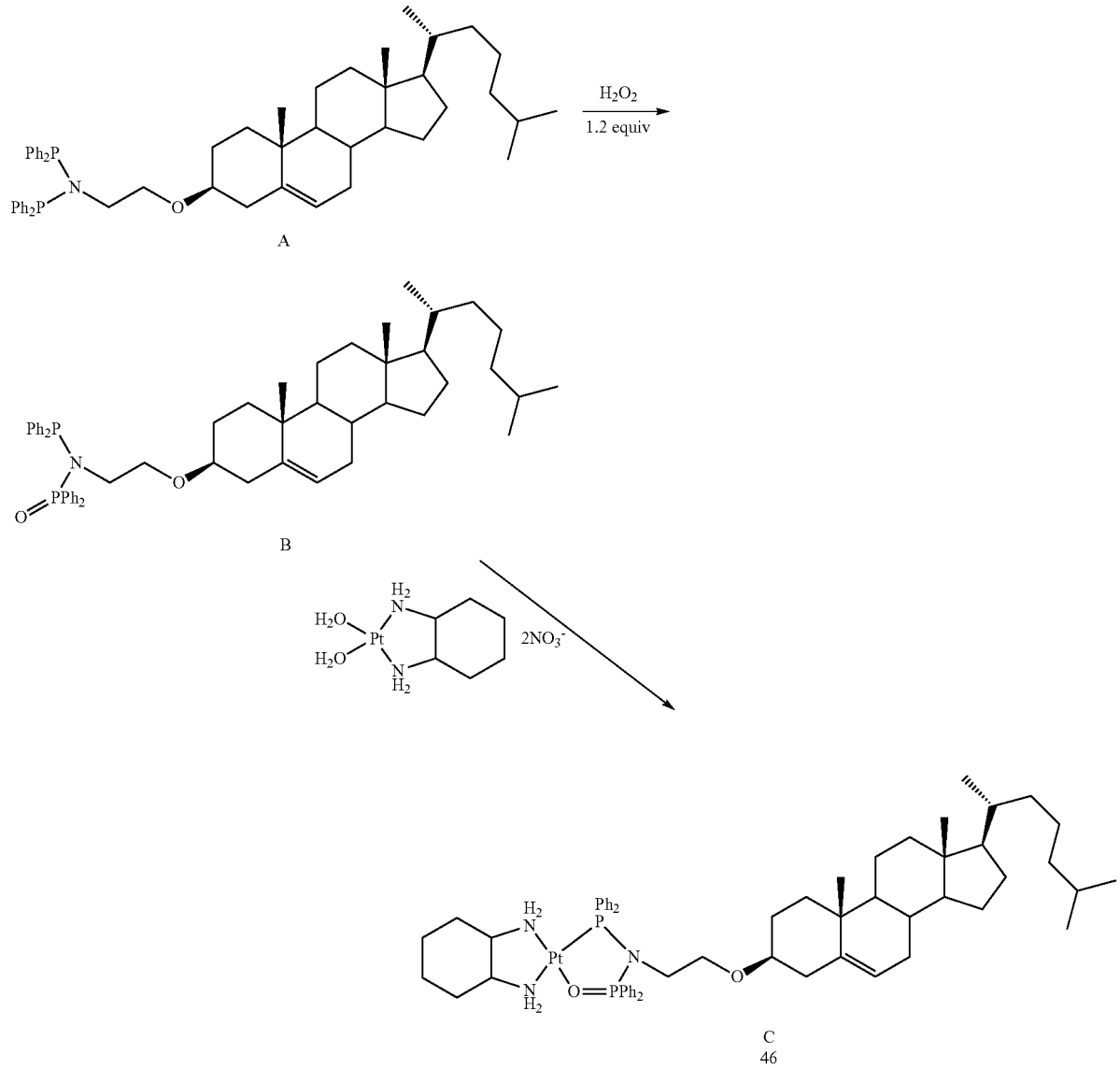

Experimental Procedure: Compound (C, 46) synthesis is similar as the synthesis of compound 49.

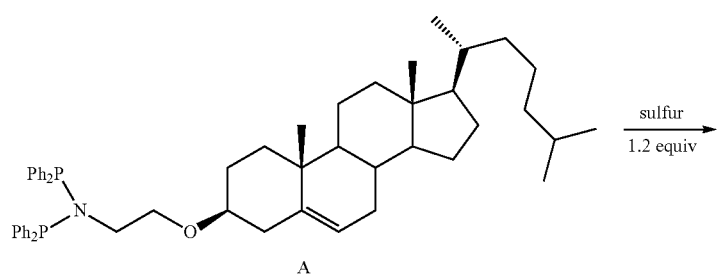

-continued
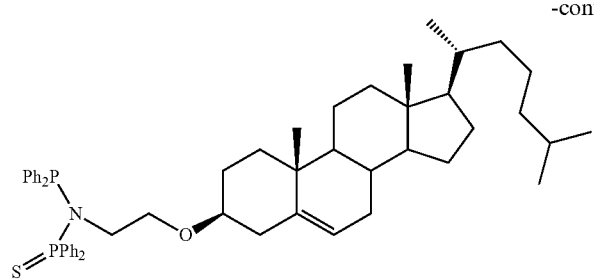
B
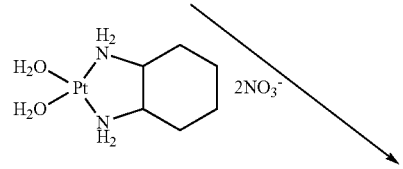
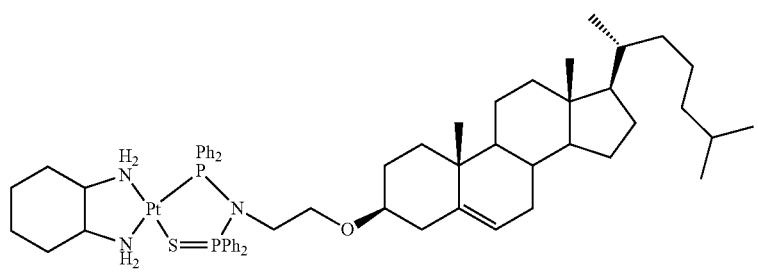
C
47
Experimental Procedure: Compound (C, 47) synthesis is similar as the synthesis of compound 50.
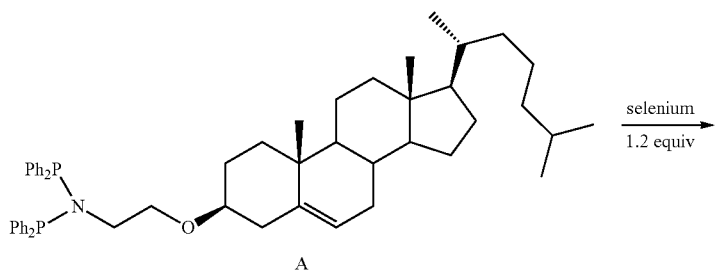
A
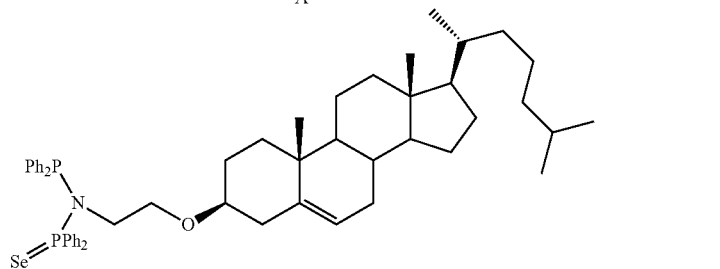
B
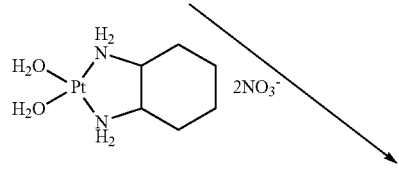

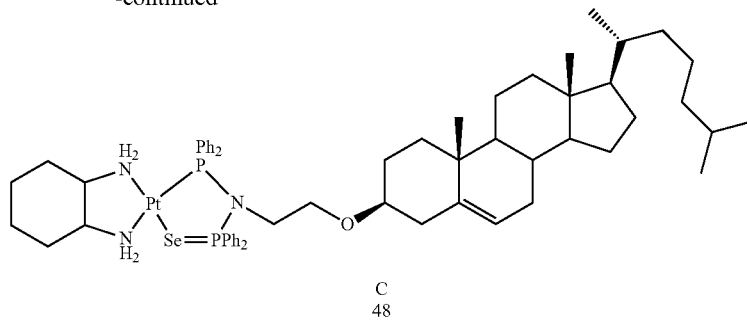

C
48

Experimental Procedure: Compound (C, 48) synthesis is similar as the synthesis of compound 50.

Synthesis of Compound 44 and 49

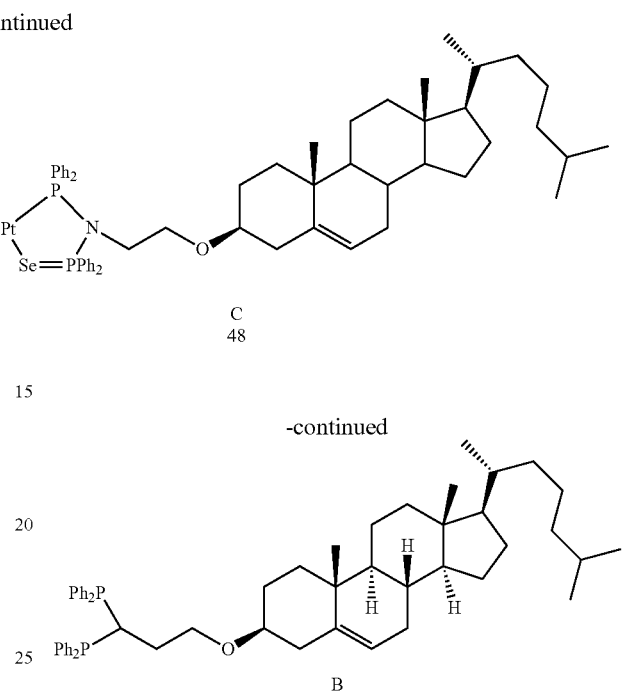

B

Experimental Procedure: A (compound A is synthesized according to the procedure mentioned in the synthesis of compound 69). To a 25 mL single neck RBF diphenylphosphinomethane (DPPM) (5.0 mmol) is taken in 30 mL THF. To this n-butyl-lithium (5.2 mmol) is added and the resulting solution is stirred for 15 min at 0° C. To the above solution chlolesteryl bromide (A)(4.0 mmol) is added and the reaction is stirred for 16 hrs. The TLC was checked and after completion water is added to the reaction mixture and the compound is extracted using ethyl acetate. The combined organic layer was concentrated under vacuum. Purified by column chromatography.

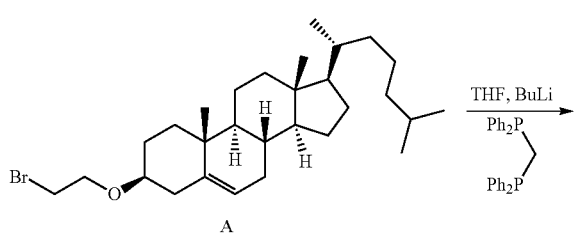

A

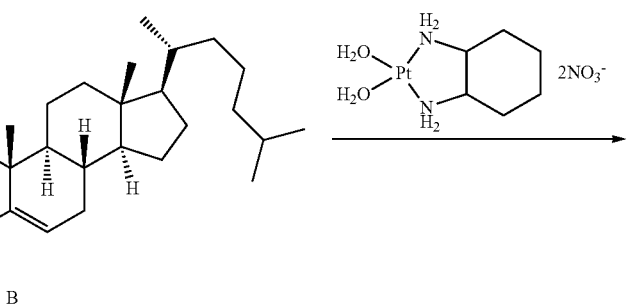

B

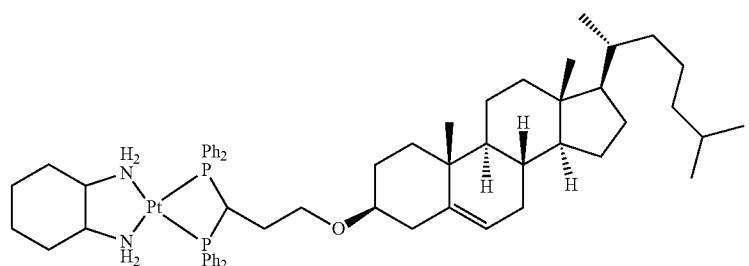

44

Synthesis of Compound 44: To a 25 mL single neck RBF compound B (1.0 mmol) is taken in 30 mL THF. To this, aquated Pt(DACH) (1 mmol in 10 ml water) is added and the resulting solution is stirred for 24 hr at RT. THF is concentrated to obtain compound 44 as precipitate.

mixture and the compound is extracted using ethyl acetate. The combined organic layer was concentrated under vacuum. Purified by column chromatography.

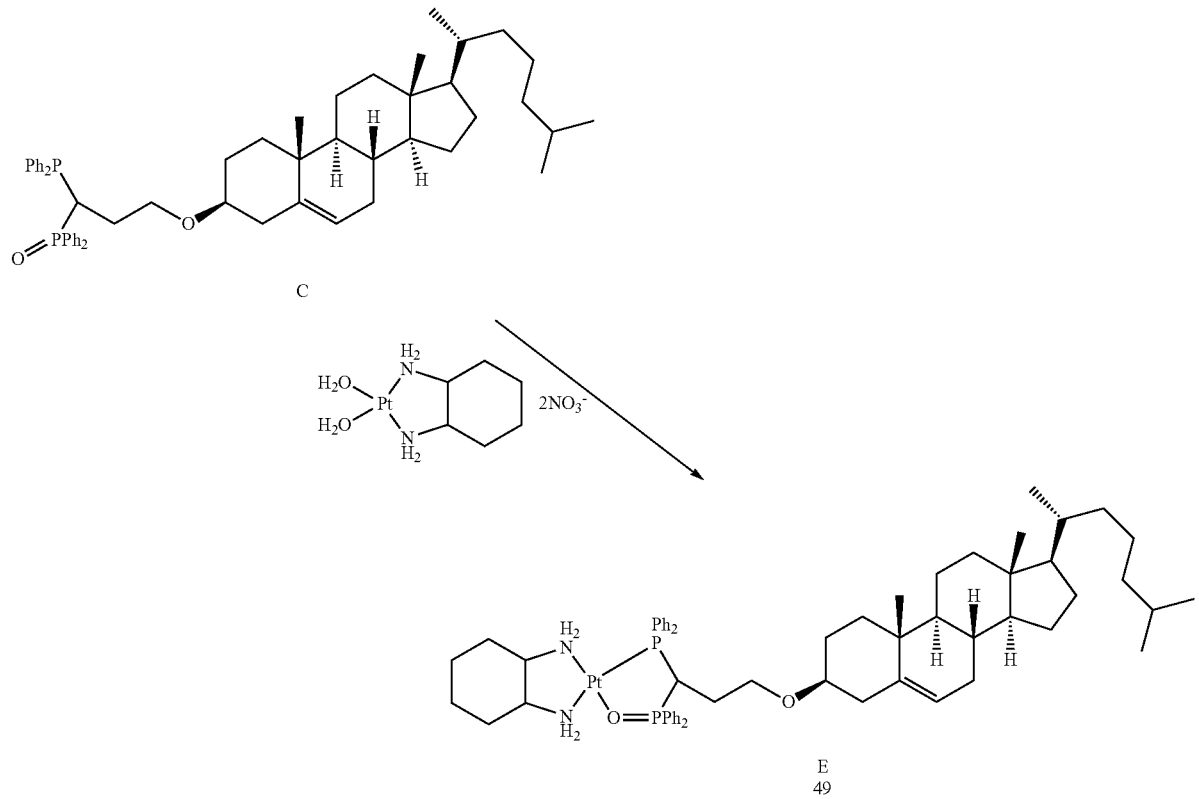

Experimental Procedure: To a 50 mL single neck RBF aquated DACH platinum (0.1 mmol, 3 mL, 10 mg/mL solution) is taken. Compound C (0.09 mmol), taken in 10 mL THF, is added dropwise and the resulting solution was stirred at room temperature for 24 hrs. TLC is checked. THF evaporated to get a light yellow precipitate. Precipitate is washed with water and dried over vacuum to obtain compound E.

Synthesis of Compound 50

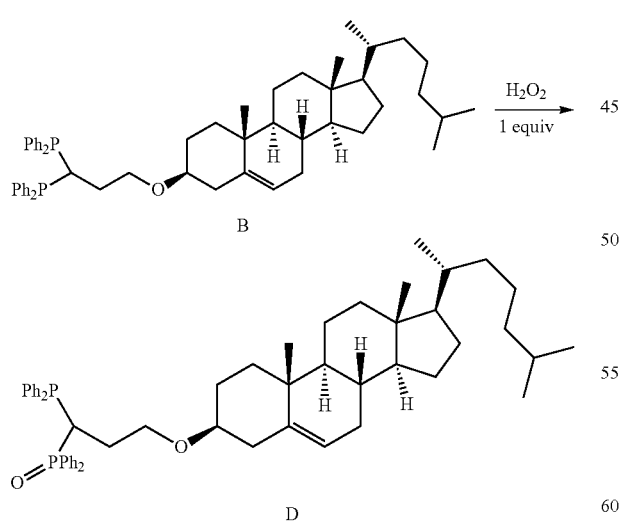

Experimental Procedure: To a 25 mL single neck RBF compound B (1.0 mmol) is taken in 30 mL THF. To this, hydrogenperoxide (1.2 mmol, 35% solution) is added and the resulting solution is stirred for 24 hr at RT. The TLC was checked and after completion water is added to the reaction

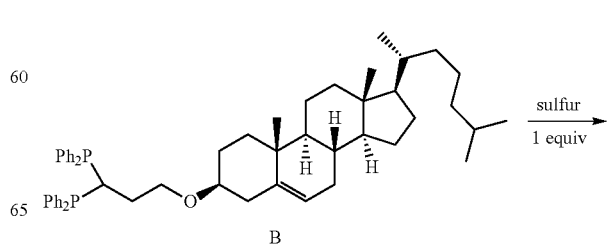

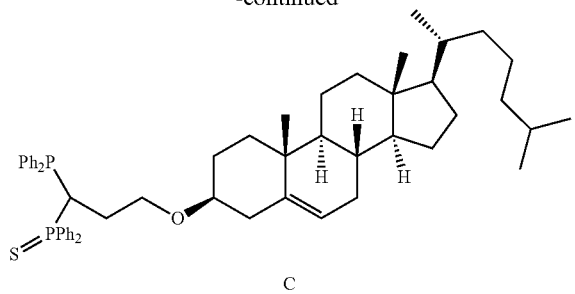

C

Experimental Procedure: To a 25 mL single neck RBF compound B (1.0 mmol) is taken in 30 mL THF. To this, sulfur (1.0 mmol) is added and the resulting solution is stirred for 24 hr at RT. The TLC is checked and after completion water is added to the reaction mixture and the compound is extracted using ethyl acetate. The combined organic layer is concentrated under vacuum. Compound D purified by column chromatography.

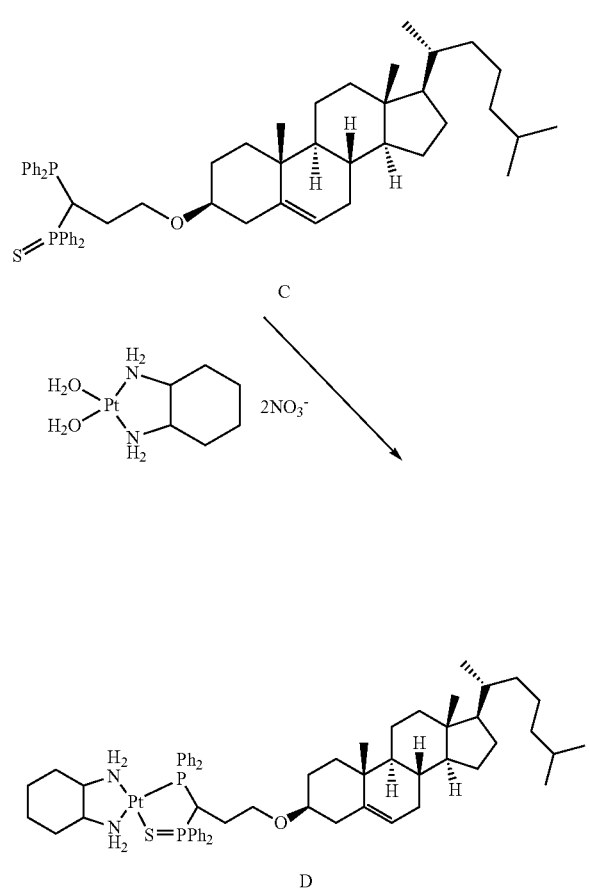

D

Experimental Procedure: To a 50 mL single neck RBF aquated DACH platinum (0.1 mmol, 3 mL, 10 mg/mL solution) is taken. Compound C (0.09 mmol), taken in 10 mL THF, is added dropwise and the resulting solution was stirred at room temperature for 24 hrs. TLC is checked. THF evaporated to get a light yellow precipitate. Precipitate is washed with water and dried over vacuum to obtain compound D.

Synthesis of Compound 51

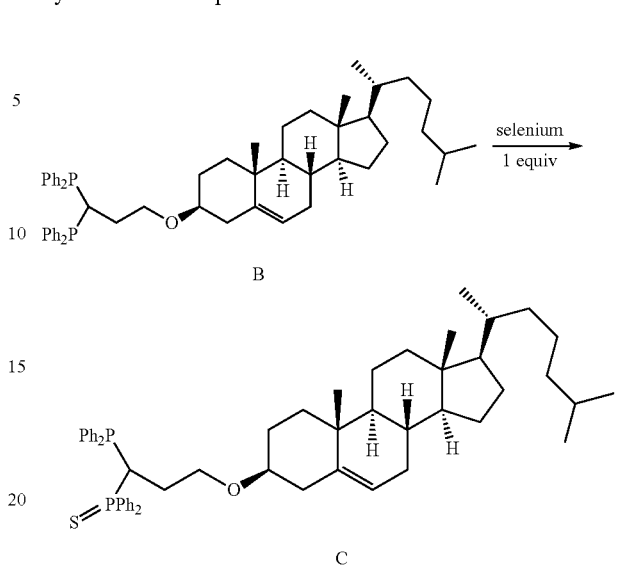

Experimental Procedure: To a 25 mL single neck RBF compound B (1.0 mmol) is taken in 30 mL THF. To this, selenium (1.0 mmol) is added and the resulting solution is stirred for 24 hr at RT. The TLC is checked and after completion water is added to the reaction mixture and the compound is extracted using ethyl acetate. The combined organic layer is concentrated under vacuum. Compound D purified by column chromatography.

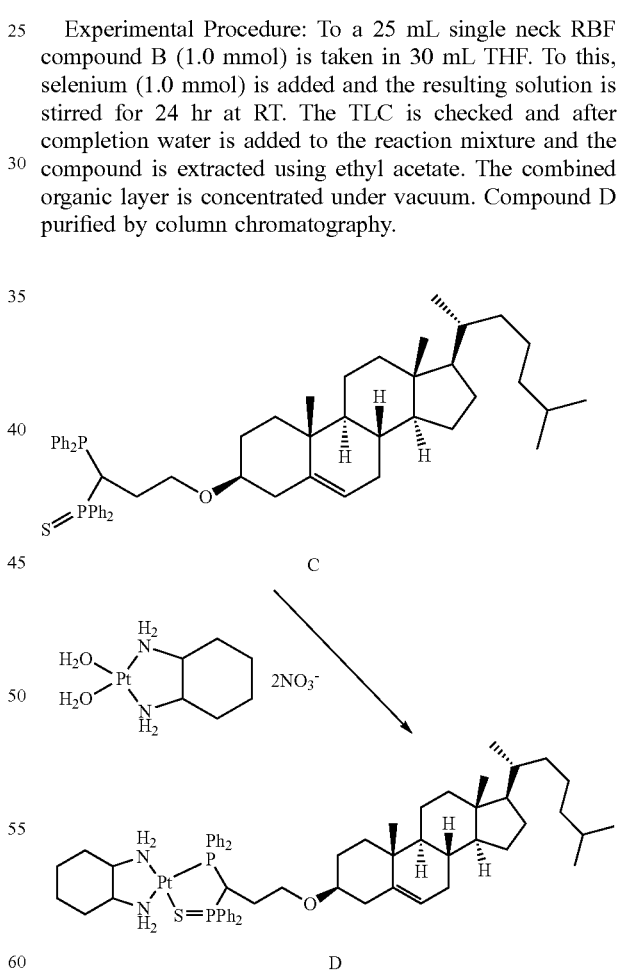

D

Experimental Procedure: To a 50 mL single neck RBF aquated DACH platinum (0.1 mmol, 3 mL, 10 mg/mL solution) is taken. Compound C (0.09 mmol), taken in 10 mL THF, is added dropwise and the resulting solution was stirred at room temperature for 24 hrs. TLC is checked. THF evaporated to get a light yellow precipitate. Precipitate is washed with water and dried over vacuum to obtain compound D.
Synthesis of Compound 54
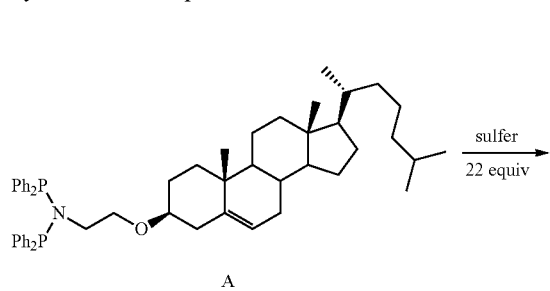
A
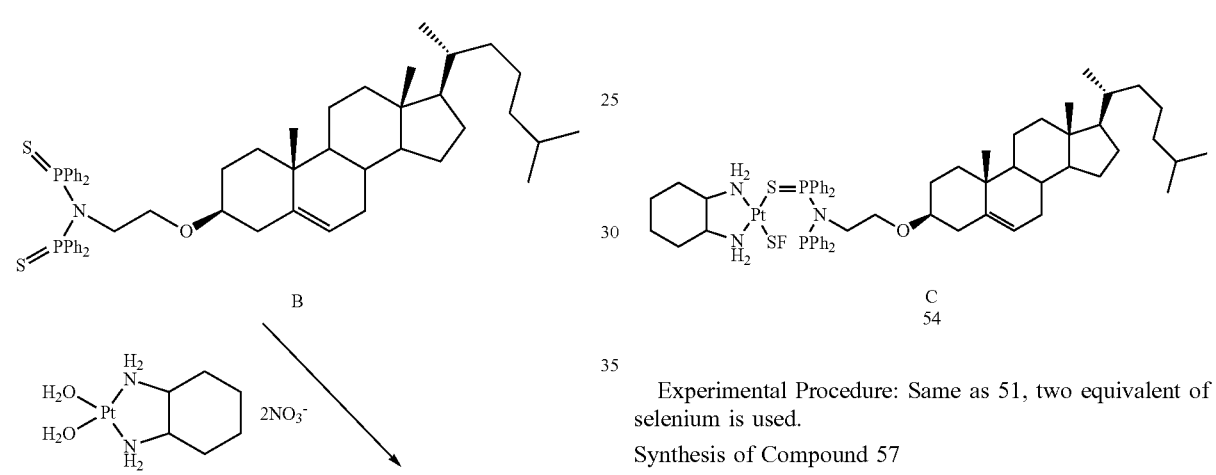
Experimental Procedure: Same as 50, two equivalent of sulfur is used.
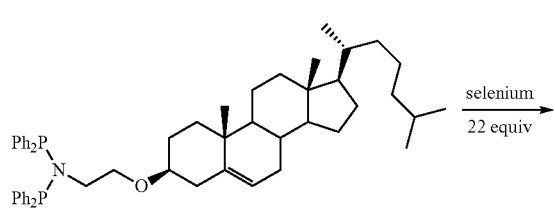
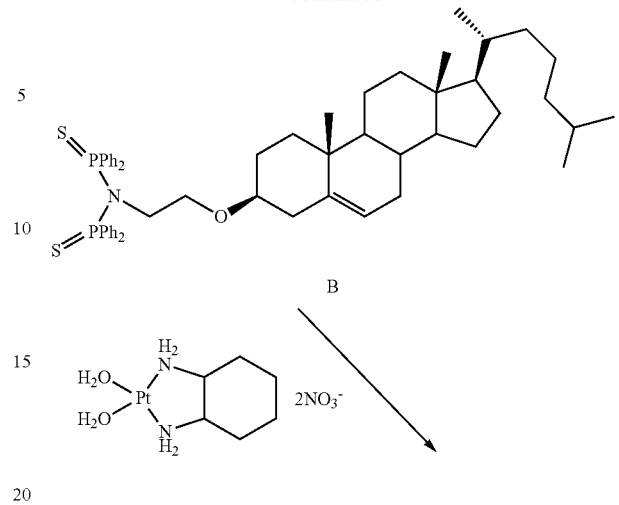
B
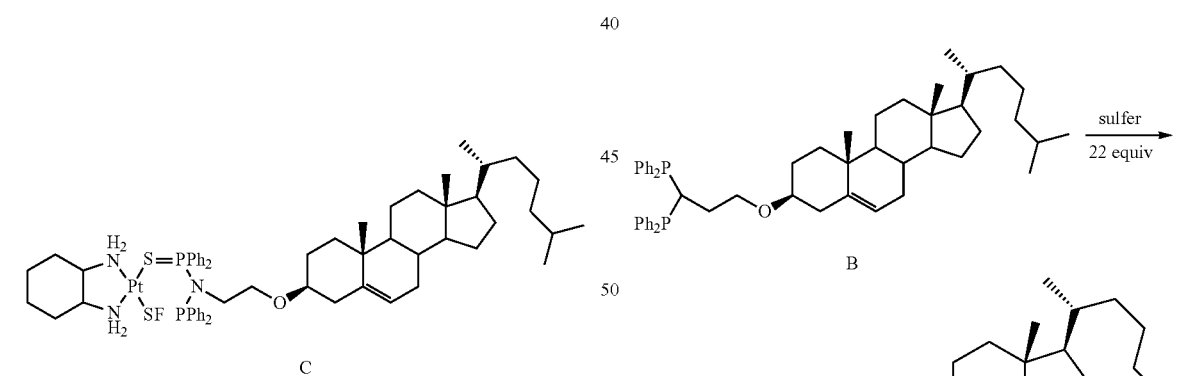
C
54
Experimental Procedure: Same as 51, two equivalent of selenium is used.
Synthesis of Compound 57
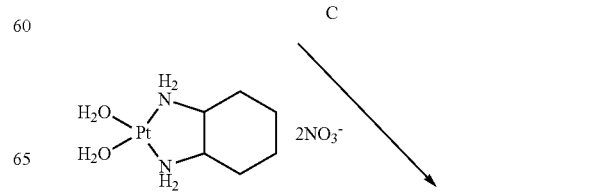

171
-continued

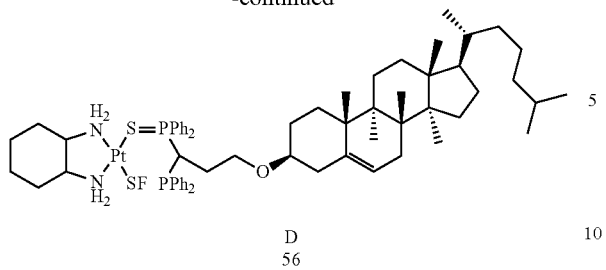

D
56

Experimental Procedure: Same as 50, two equivalent of sulfur is used.

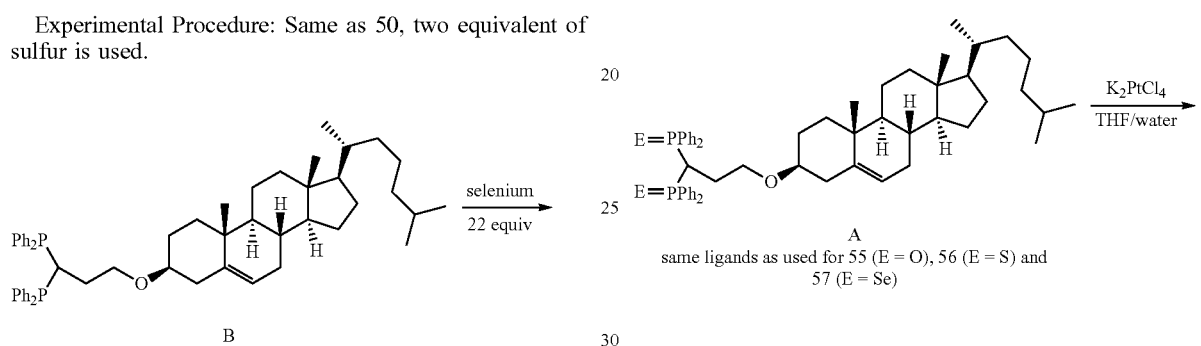

172
-continued

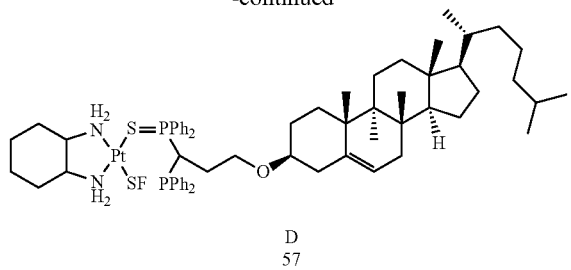

D
57

Experimental Procedure: Same as 51, two equivalent of selenium is used.

Synthesis of Compound 58, 59, 60

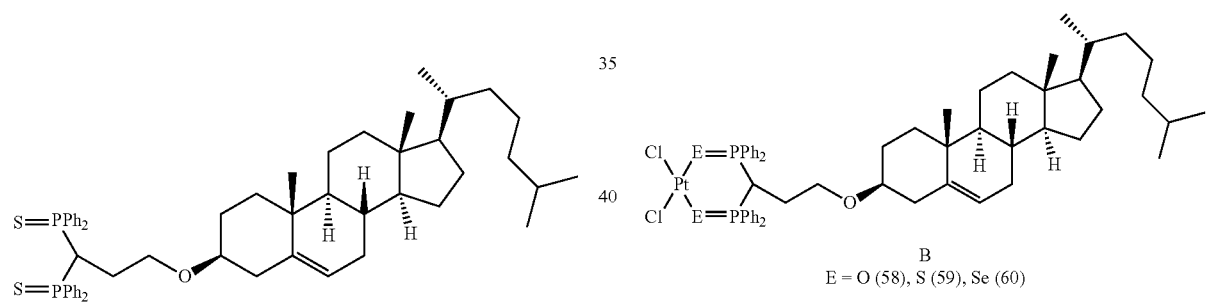

Experimental Procedure: To a 50 mL single neck RBF, K₂PtCl₄ (0.1 mmol, 3 mL, 10 mg/mL solution) is taken. Compound A (0.1 mmol), taken in 10 mL THF, is added dropwise and the resulting solution is stirred at room temperature for 24 hrs. TLC is checked. THF evaporated to get a light yellow precipitate. Precipitate is washed with water and dried over vacuum to obtain compound D.

Synthesis of Compound 61 and 62

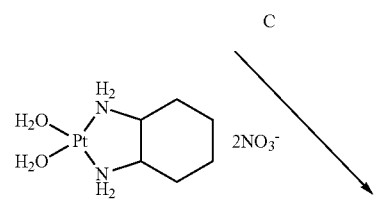

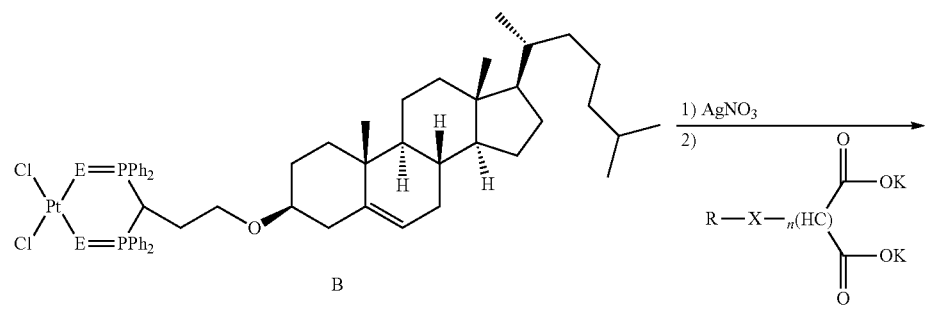

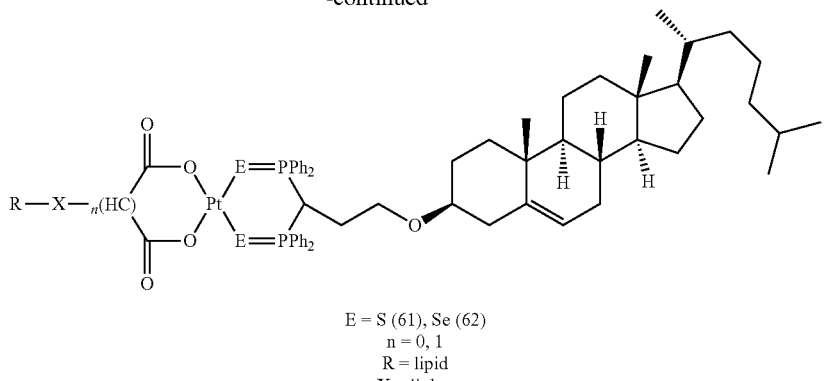

E = S (61), Se (62)
n = 0, 1
R = lipid
X = linker

Experimental Procedure: To a 50 mL single neck RBF, compound B (1 mmol, in 10 ml DMF) is taken. Silver nitrate (2 mmol) is added and stirred for 24 hrs. White precipitate is separated by filtration. Compound C (1 mmol), taken in 10 mL water, is added dropwise to the filtrate and the resulting solution is stirred at room temperature for 24 hrs. TLC is checked. DMF evaporated to get a light yellow precipitate. Precipitate is washed with water and dried over vacuum to obtain compound 61/62.

Synthesis of Compound 78

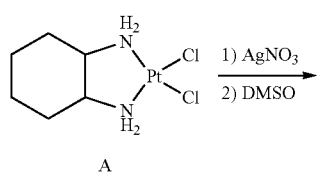

A

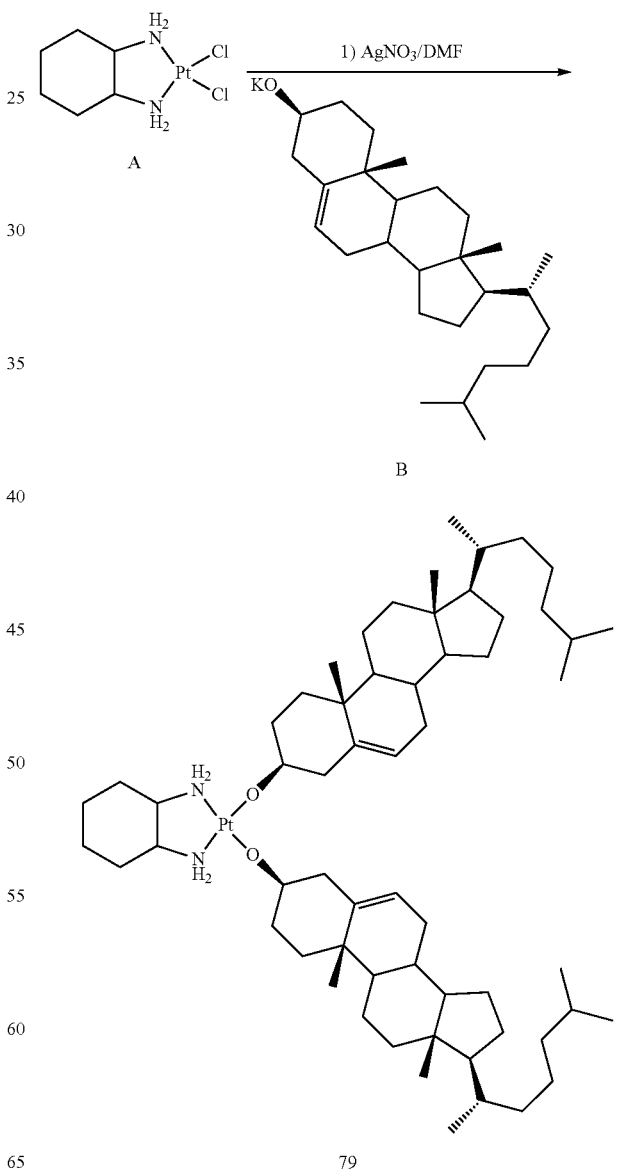

Synthetic Scheme to Obtain Compound 79

Compound A (0.5 mmol) is taken in 20 ml water and silver nitrate (1 mmol) is added. Reaction mixture is stirred for 24 hrs, filtered and DMSO (0.5 mmol) is added. Reaction mixture is stirred at room temperature for 2 hrs to obtain a yellow precipitate as compound 78.

Synthetic Scheme to Obtain Compound 80
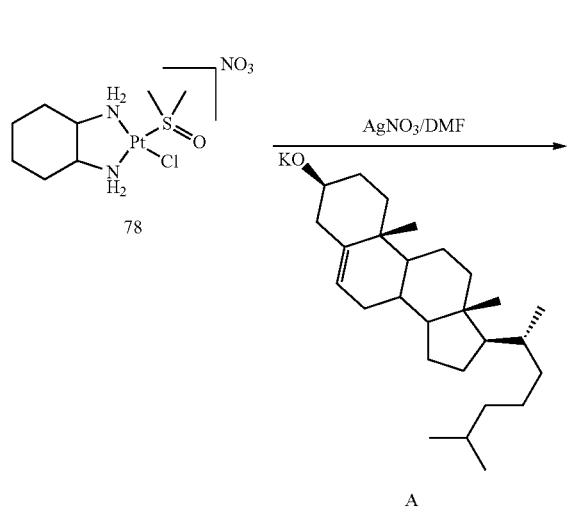
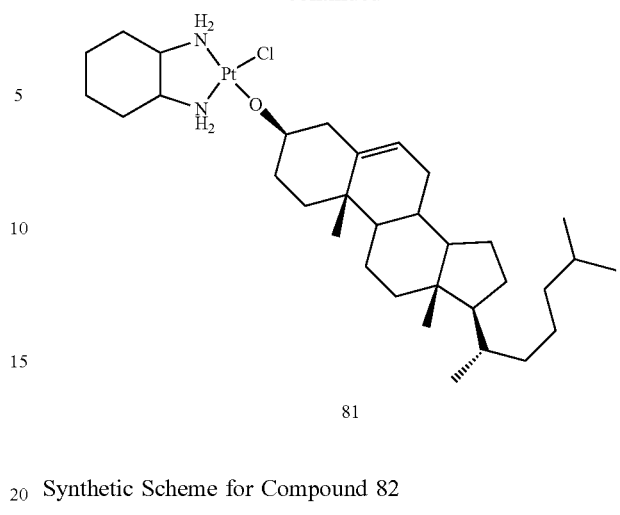
Synthetic Scheme for Compound 82
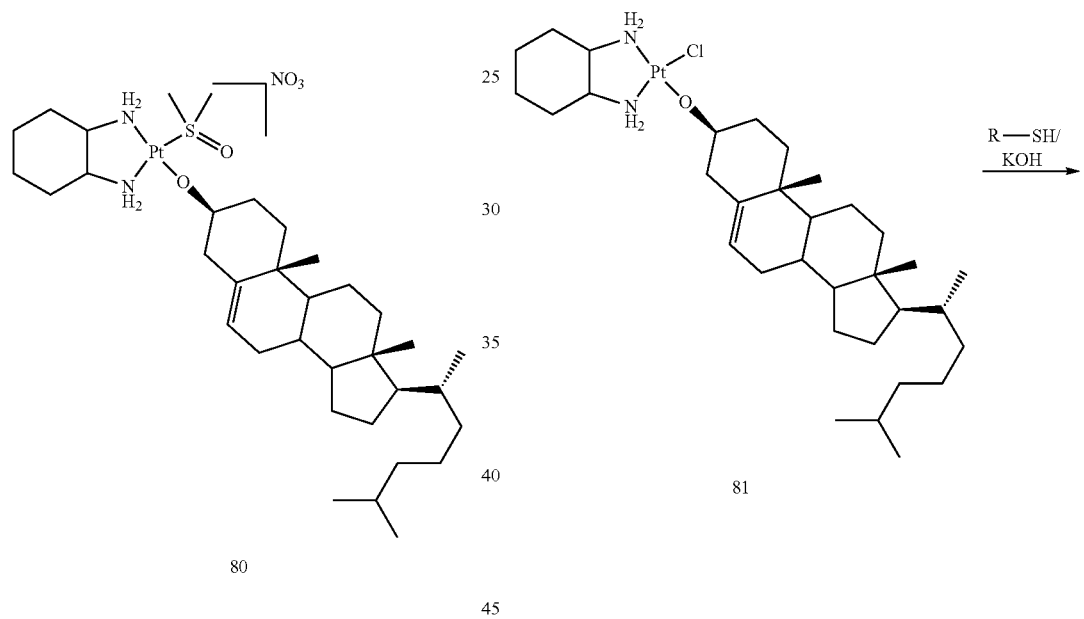
Synthetic Scheme for Compound 81

177
Synthetic Scheme for Compound 83
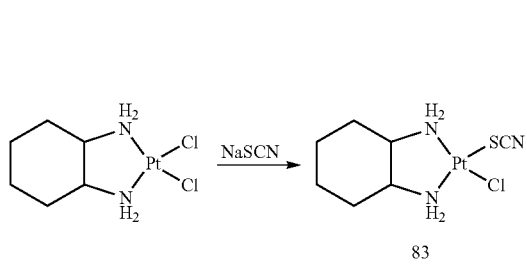
Synthetic Scheme for Compound 84
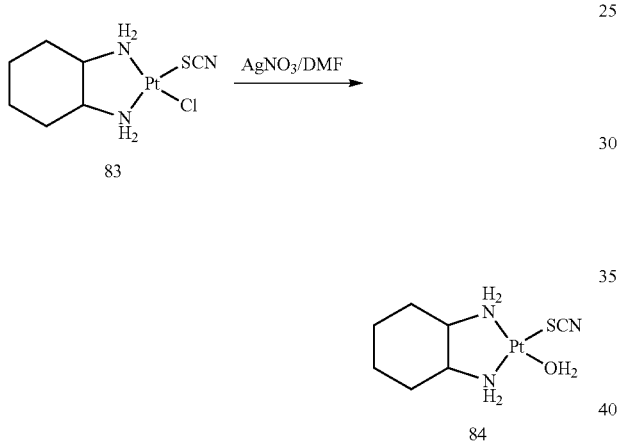
178
Synthetic Scheme for Compound 85
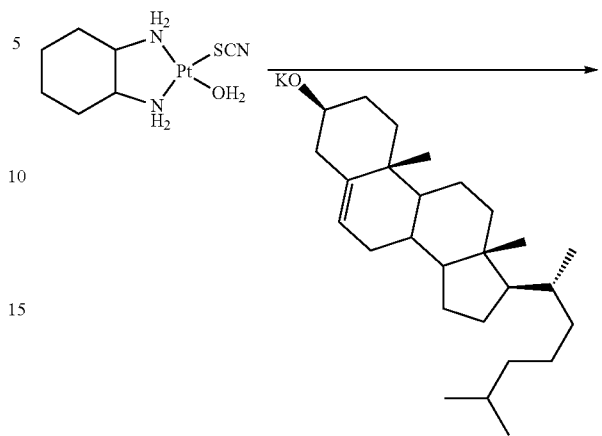
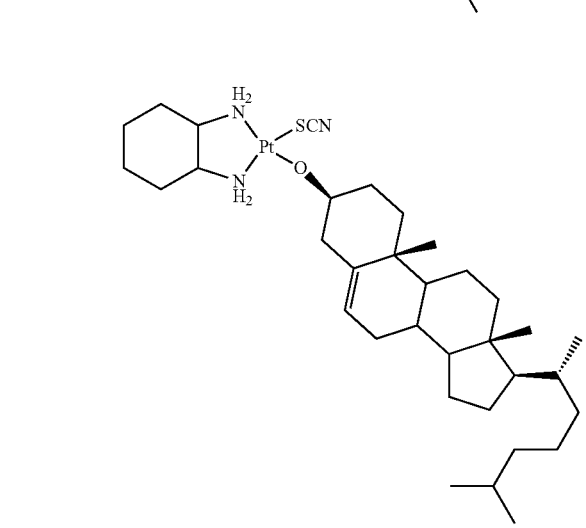
Synthesis of Compound 95
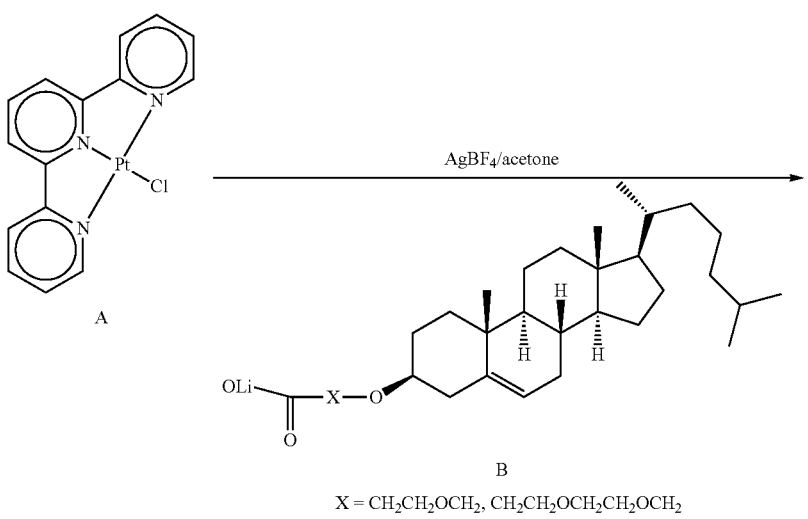
X = CH₂CH₂OCH₂, CH₂CH₂OCH₂CH₂OCH₂

-continued

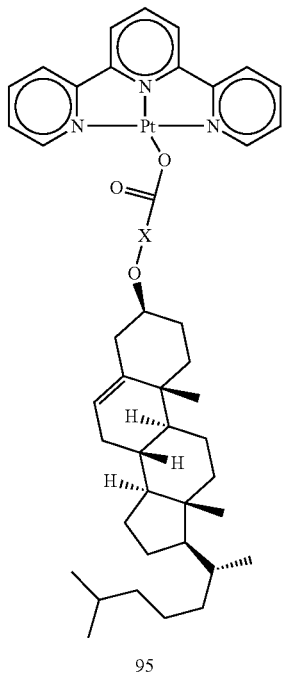

95

Compound A (1 mmol) is taken in a 50 ml rb with 10 ml THF. AgBF$_4$ (1 mmol) is added and stirred at room temperature for 24 hrs. Precipitate is filtered and compound B (1 mmol in 10 ml water) is added to the filtrate dropwise. After 24 hrs RT stirring, THF evaporated and the precipitate obtained is filtered and washed with water to get compound 95.

Example 7

Synthesis of Additional Exemplary Compounds

Synthesis of IO-131

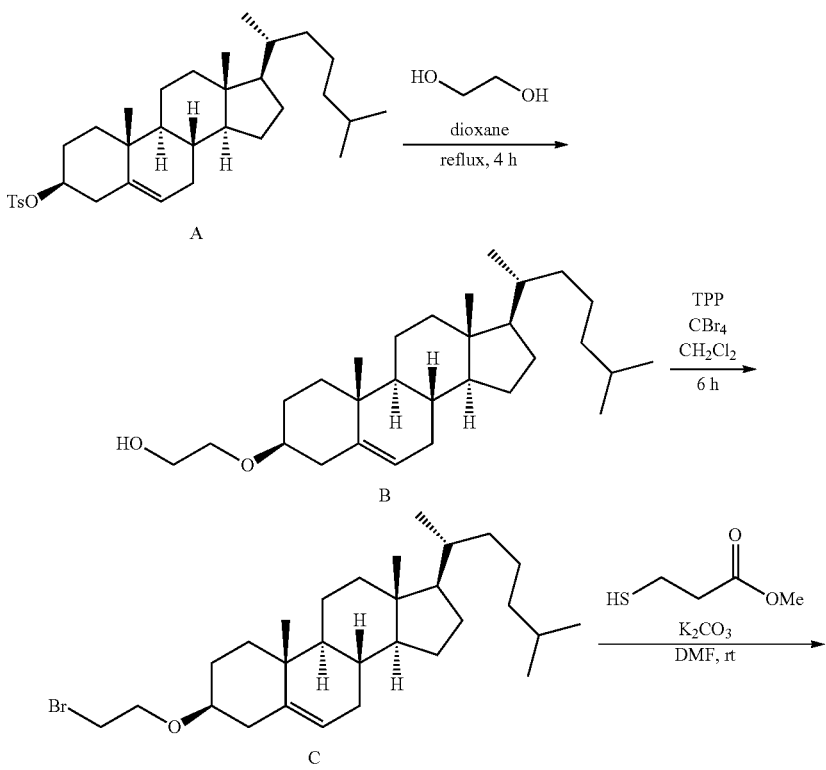

-continued
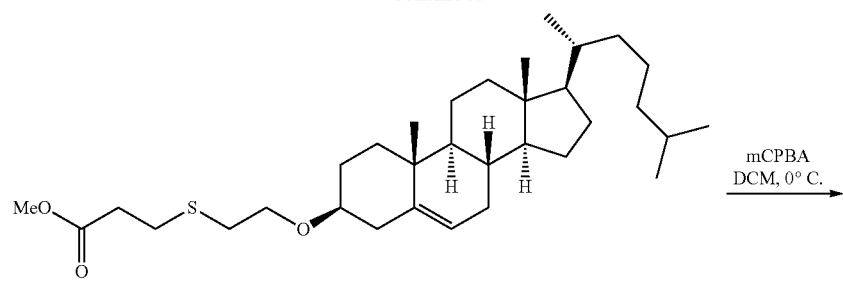
D
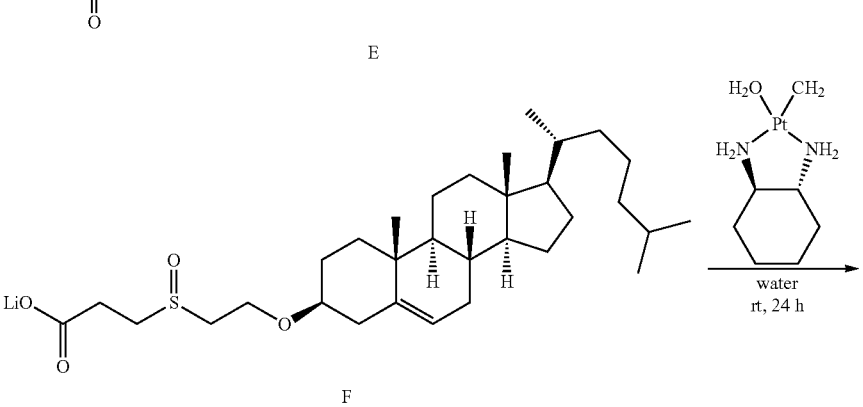
E
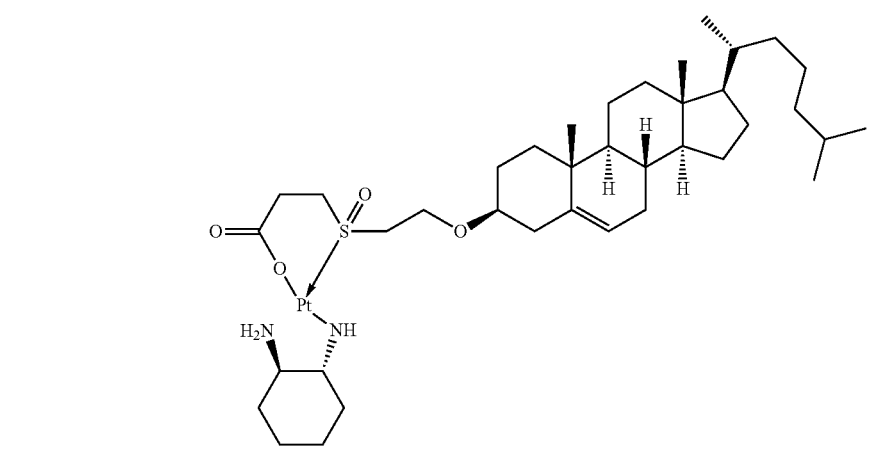
F
G
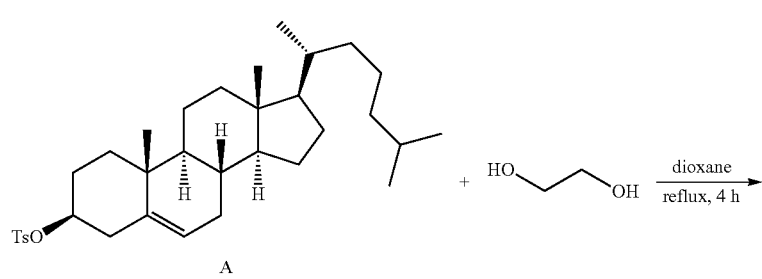
A

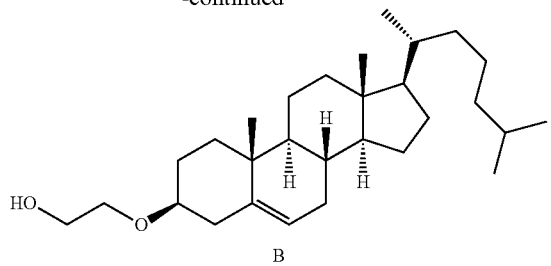

B

Experimental Procedure: To the solution of tosylated cholesterol A (7.4 mmol) in dioxane (50 mL) was added ethylene glycol (35 mL) and refluxed for 4 h. The TLC was checked. After completion the reaction mixture was concentrated under vacuum to remove dioxane and then it was extracted with ethyl acetate and washed with water (3×50 mL) and brine (20 mL) successively. The organic layer was dried over anhydrous Na₂SO₄ and concentrated under vacuum and column was performed.

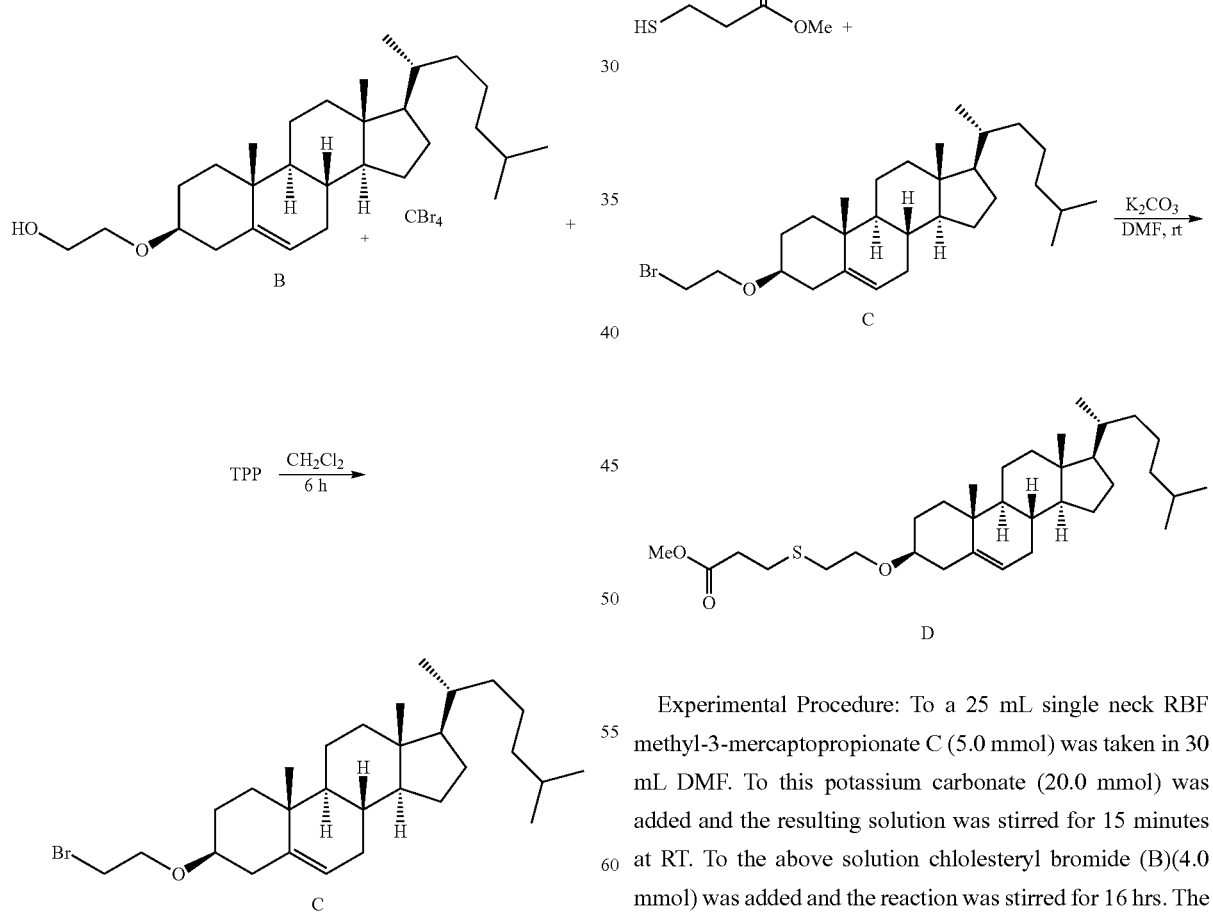

Experimental Procedure: To the solution of cholesteryl ethylene glycol B (4.5 mmol) in DCM 5 ml was added triphenyl phosphine (TPP) (9 mmol) and carbon tetra bromide (9 mmol). The reaction mixture was stirred for 6 h at rt and TLC was checked. After completion the reaction mixture was diluted with CHCl₃ (20 mL) and washed with water (3 ×50 mL) and brine (20 mL) successively. The organic layer was dried over anhydrous Na₂SO₄ and concentrated under vacuum and put for flash column to get the pure compound(C).

Experimental Procedure: To a 25 mL single neck RBF methyl-3-mercaptopropionate C (5.0 mmol) was taken in 30 mL DMF. To this potassium carbonate (20.0 mmol) was added and the resulting solution was stirred for 15 minutes at RT. To the above solution chlolesteryl bromide (B)(4.0 mmol) was added and the reaction was stirred for 16 hrs. The TLC was checked and after completion water was added to the reaction mixture and the compound was extracted using ethyl acetate. The combined organic layer was concentrated under vacuum. Purified by column chromatography.

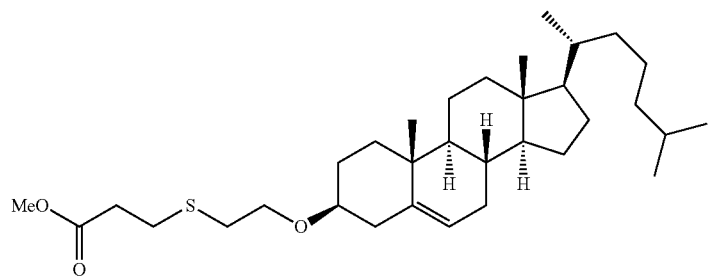

D
+ MCPBA $\xrightarrow{\text{DCM, 0° C.}}$

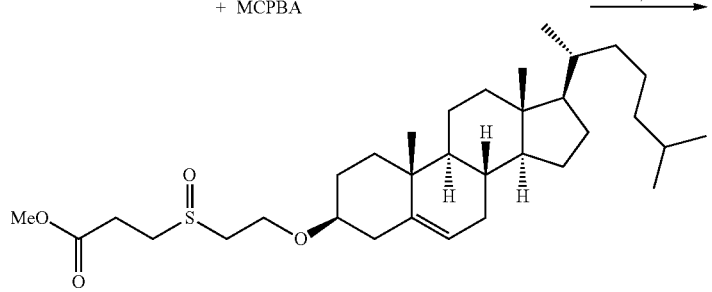

E

Experimental Procedure: To a 50 mL single neck RBF compound D (1.87 mmol) was taken in 60 mL DCM. To this mCPBA (1.31 mmol) was added and the resulting solution was stirred for 3 hrs at 0° C. The TLC was checked and after completion water was added to the reaction mixture and the compound was extracted using chloroform. The combined organic layer was concentrated under vacuum and put for column chromatography. 1H NMR(CDCl$_3$): 0.66(s), 0.84 to 0.47(m), 1.82-1.97(m), 2.21(m), 2.35(m),2.84(m), 2.98(m), 3.16(t),3.21(m), 3.89(br, s), 5.33(br, s). 13C NMR(CDCl$_3$): 11.81, 18.68, 19.32, 21.03, 22.52, 22.78, 23.78, 24.25, 26.96, 27.97, 28.18, 31.84, 35.74, 36.15, 36.79, 37.05, 38.78, 38.91, 39.47, 39.72, 42.27, 47.18, 50.10, 52.14, 53.25, 53.29, 56.11, 56.71, 79.71, 121.90, 140.40, 171.74. Mass-ESI: 571.4 (M+Na) IR(KBr)(v, cm$^{-1}$): 418(w), 668 (m), 750(m), 1020(m), 1104(w), 1134(w), 1178(w), 1259 (m), 1275(m), 1455(m), 1732(m), 2933(s), 3612(m), 3723 (m), 3852(m)

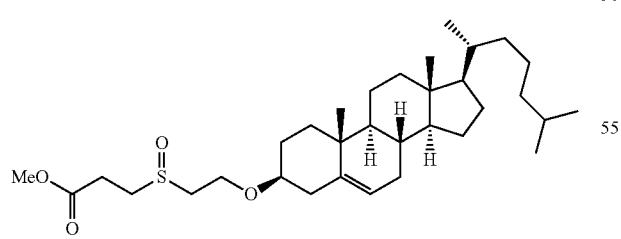

E
+
KOH $\xrightarrow{\text{THF/H}_2\text{O}}_{3\text{ h}}$

-continued

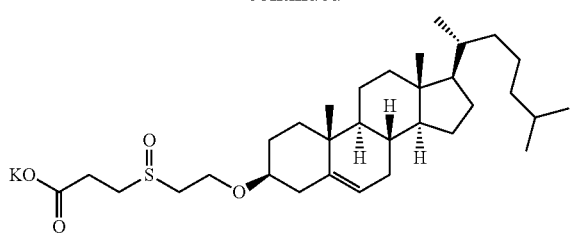

F

Experimental Procedure: To a 50 mL single neck RBF ester E (0.17 mmol) was taken in 3 mL of THF/H$_2$O (3:1) and cooled to 0° C. under ice bath. To this ice cooled solution KOH (0.19 mmol in 2 mL) was added and was stirred at RT for 12 h, the TLC was checked. After completion, THF was evaporated and remaining was extracted using chloroform. Water layer was used for next step.

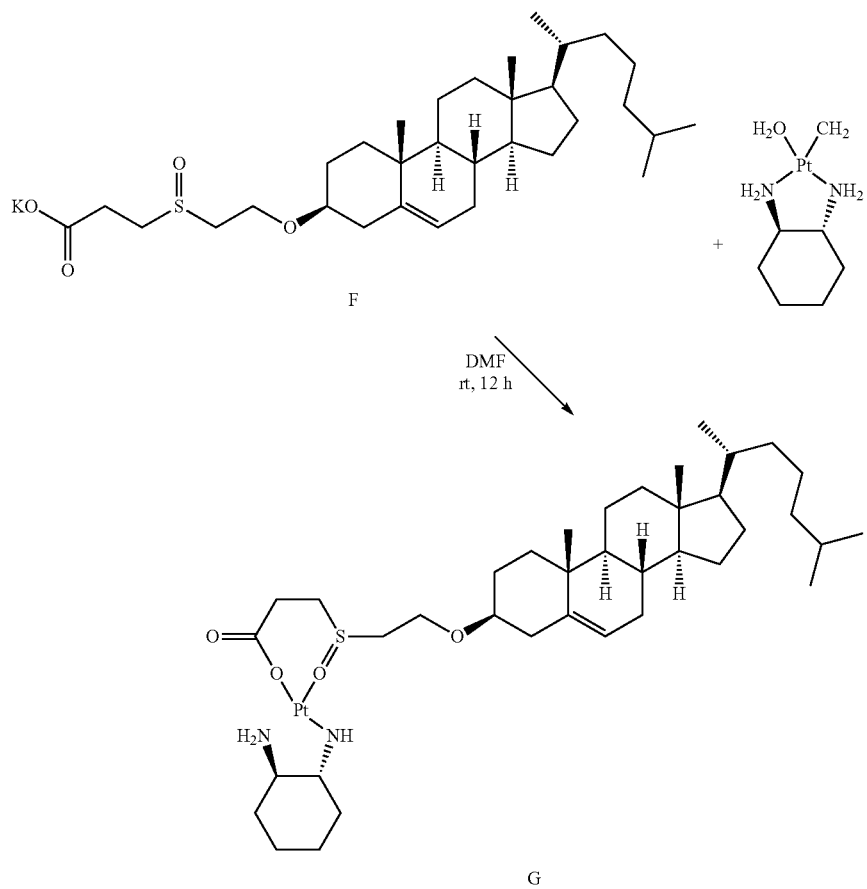

Experimental Procedure: To a 50 mL single neck RBF aquated DACH platinum (3 mL, 10 mg/mL solution) was taken. Salt A (0.09 mmol), taken in 10 mL water was added dropwise and the resulting solution was stirred at room temperature for 24 hrs. White precipitate separated and washed with 30 ml of water to get the pure compound (G). IR(KBr)(v, cm$^{-1}$): 415(w, br), 797(w), 1024(m), 1107(m), 1259(w), 1377(m), 1466(w, br), 1588(m, br), 2933(s), 3176 (w, br), 3440(w, br). $^{195}$Pt NMR(CDCl$_3$): −2893

Synthesis of IO-148_01

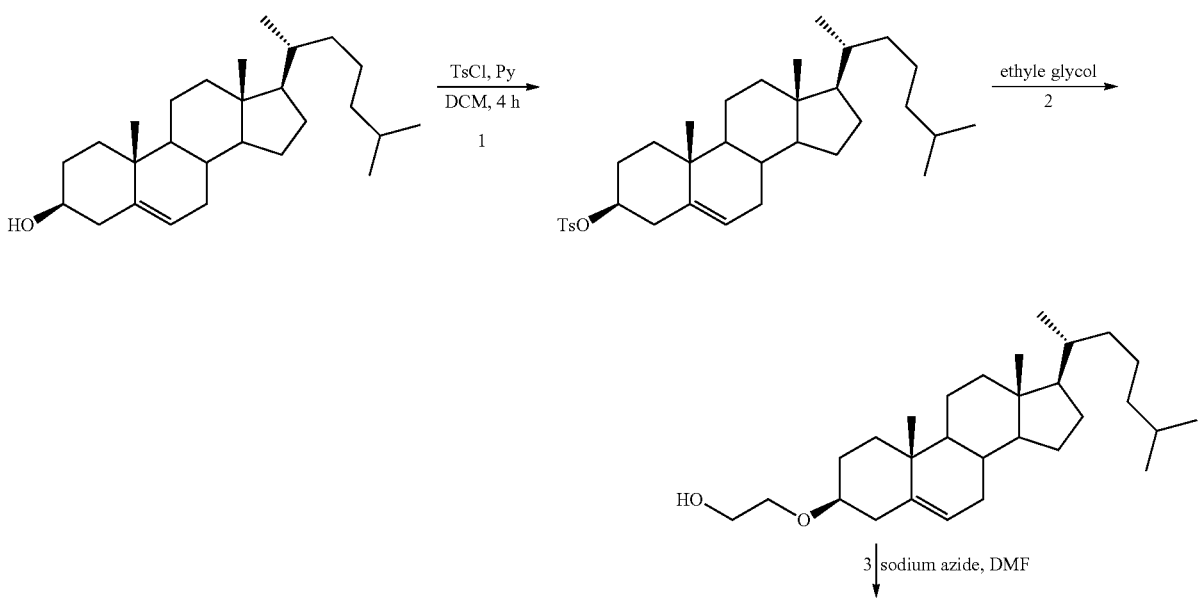

189 190
-continued
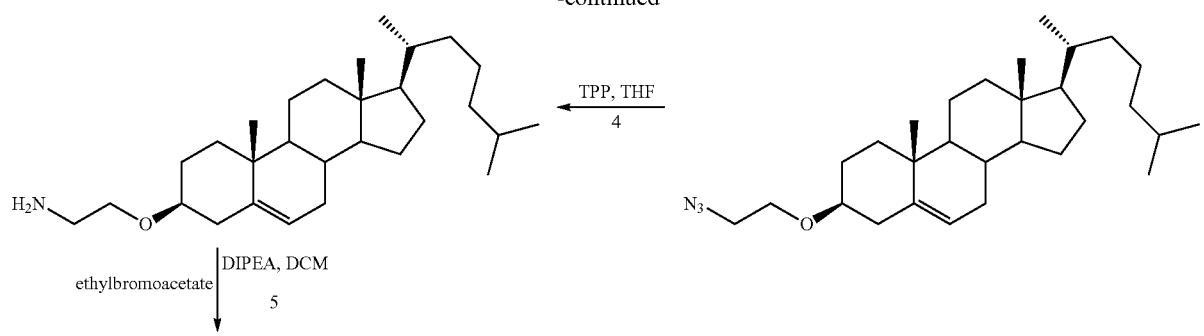
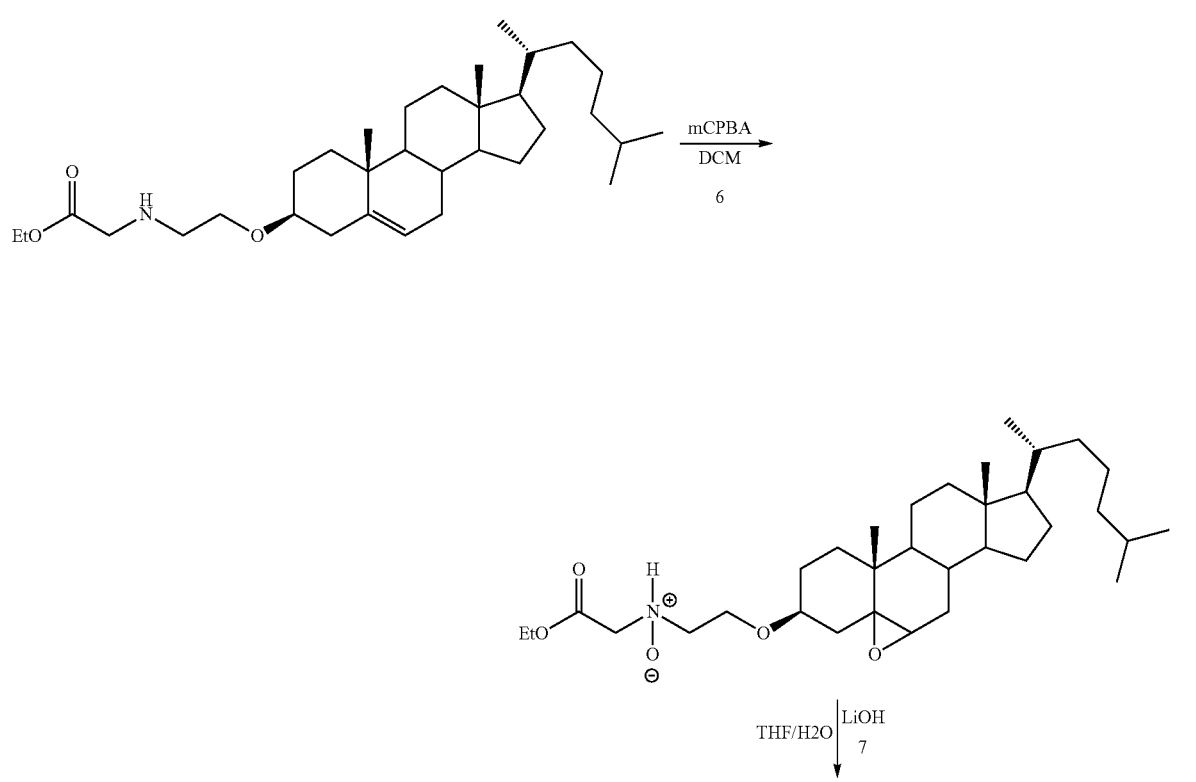
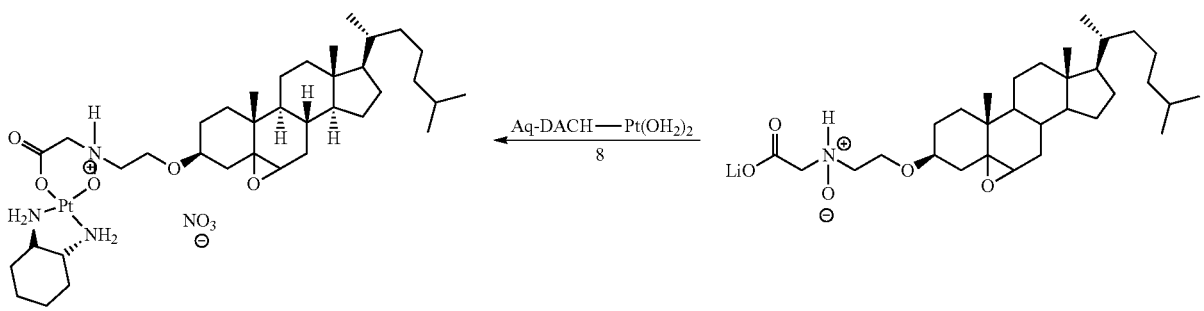
IO-148

Synthesis of Tossyl Intermediate of IO-148_01

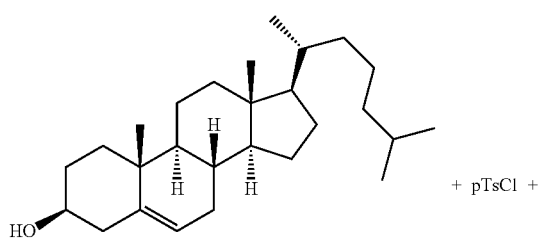

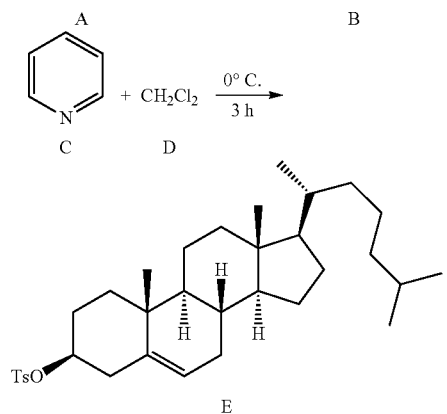

Experimental Procedure: To an ice cooled solution of cholesterol A (10 g, 25.883 mmol) in CH$_2$Cl$_2$ (150 mL) pyridine (10.5 mL, 129.415 mmol) was added dropwise and stirred for 15 minutes. To the above solution p-toluene sulphonyl chloride B (14.75 g, 77.649 mmol) was added and stirred for 2 h under dark conditions. The TLC was checked and after completion of the reaction the organic phase was washed with 0.1 N HCl solution (5×50 mL) and water (2×50 mL); the organic layer was dried over anhydrous Na$_2$SO$_4$ and concentrated under vacuum.

Synthesis of Glycol Intermediate of IO-148_01

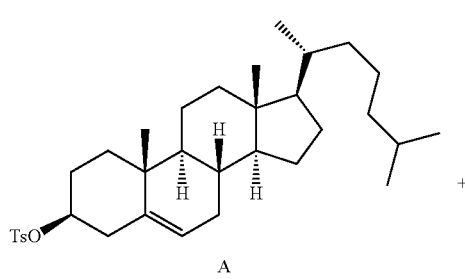

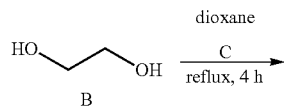

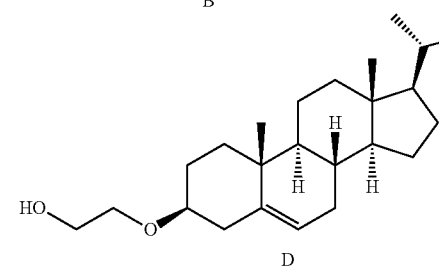

Experimental Procedure: To the solution of tosylated cholesterol A (10 g, 18.48 mmol) in dioxane (50 mL) was added ethylene glycol (35 mL) and refluxed for 4 h. The TLC was checked. After completion the reaction mixture was concentrated under vacuum to remove dioxane and then it was extracted with ethyl acetate and washed with water (3×50 mL) and brine (20 mL) successively. The organic layer was dried over anhydrous Na$_2$SO$_4$ and concentrated under vacuum and column was performed.

Synthesis of Glycol Tosyl Intermediate of IO-148_01

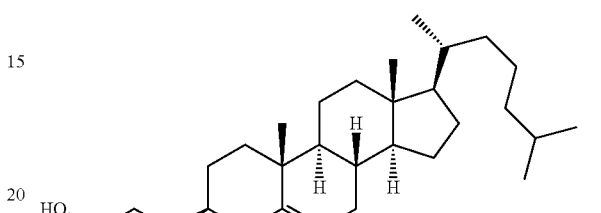

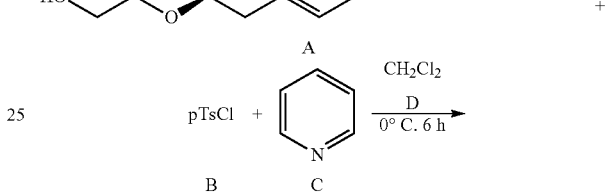

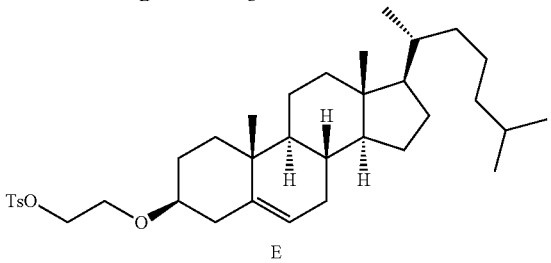

Experimental Procedure: To an ice cooled solution of cholesteryl ethylene glycol A (6 g, 13.93 mmol) in DCM 30 ml under nitrogen atmosphere was added p-toluene sulphonyl chloride B (3.25 g, 16.71 mmol) and stirred for 15 minutes. To this solution pyridine (12 mL) was added and stirred for 6 h at 0° C. and TLC was checked. After completion the reaction mixture was diluted with CHCl$_3$ (20 mL) and washed with saturated CuSO$_4$ (3×50 mL) and brine (20 mL) successively. The organic layer was dried over anhydrous Na$_2$SO$_4$ and concentrated under vacuum.

Synthesis of Azide Intermediate of IO-148_01

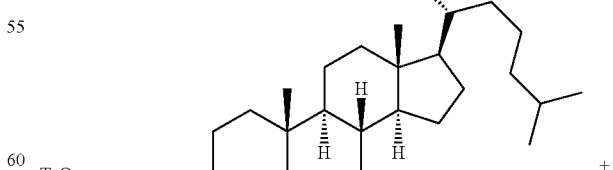

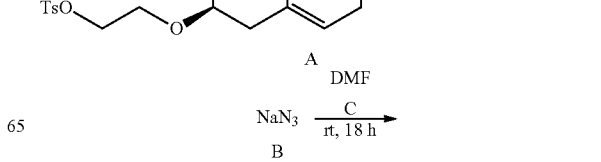

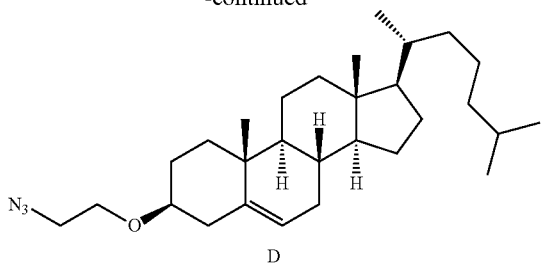

D

Experimental Procedure: To the compound A (7 g, 11.97 mmol) DMF 20 ml was added under nitrogen atmosphere was stirred for 30 minutes to get a clear solution warm if necessary. To this solution sodium azide B 1.5 g, 23.95 mmol) was added at once and stirred for 18 h at rt and TLC was checked. After completion the reaction mixture was quenched with water and extracted with ethyl acetate. The organic layer was given water wash and the combined organic layer was concentrated under vacuum.

Synthesis of Amine Intermediate of IO-148_01

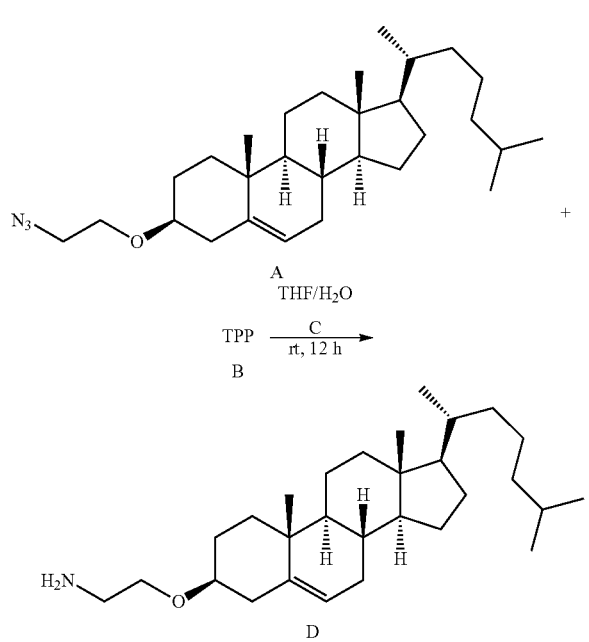

Experimental Procedure: To the Azide A (5 g, 10.97 mmol) dry THF (20 ml) was added under nitrogen atmosphere and TPP (5.74 g, 21.94 mmol) was added. The reaction was stirred for 6 hr. After that 2 mL of water was added to the reaction mixture and reaction was kept at same temperature overnight. The TLC was checked and the after completion of reaction, the reaction mixture was concentrated under vacuum and directly loaded to column.

Synthesis of N-Monoalkyl Intermediate of IO-148_01

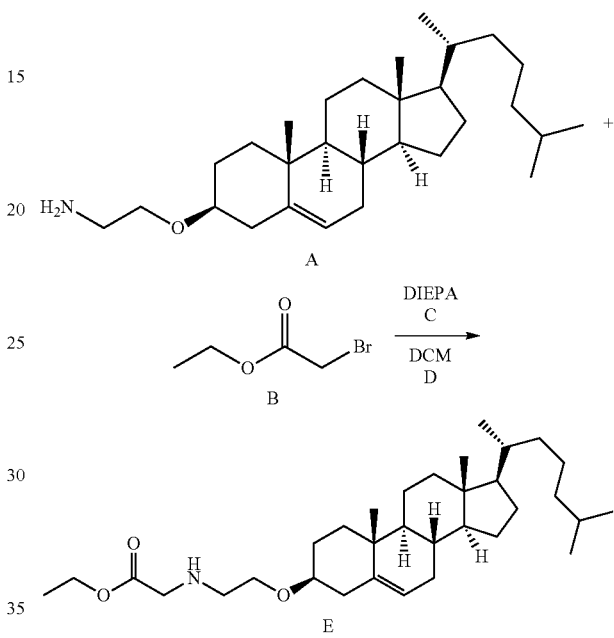

Experimental Procedure: To a 50 mL single neck R.B flask amine A (200 mg, 0.465 mmol) was taken in anhydrous DCM (40 mL) under nitrogen atmosphere at 0° C. To this cooled solution DIEPA (0.06 mL, 0.372 mmol) was added dropwise and stirred at same temperature for 20 minutes. To the above mixture ethylbromoaceate (0.03 mL, 0.279 mmol, in 10 mL DCM) was added dropwise over a period of 1 hrs. Reaction was monitored using TLC. After completion the reaction mixture was directly concentrated under vacuum and put for Column chromatography.

Synthesis of N-Oxide Intermediate of IO-148_01

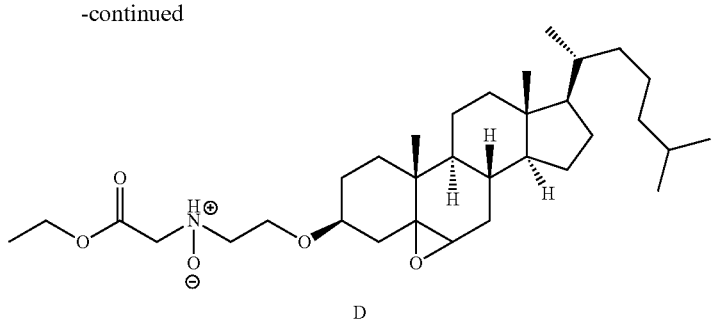

D

Experimental Procedure: To a 50 mL single neck R.B flask ester A (100 mg, 0.193 mmol) was taken in anhydrous CH$_2$Cl$_2$ (10 mL) under nitrogen atmosphere at 0° C. To this cooled solution mCPBA (16.72 mg, 0.135 mmol) was added dropwise as a solution in DCM (2 mL) and stirred at same temperature for 2 h. Reaction was monitored using TLC. After completion the reaction mixture was quenched with NaHCO3, extracted with CHCl3, dried over anhydrous sodium sulphate, concentrated and directly put for column chromatography.

Synthesis of Final Ligand of IO-148_01

Experimental Procedure: To a 50 mL single neck R.B flask N-oxide intermediate A (100 mg, 0.188 mmol) was taken in anhydrous THF/H$_2$O (4 mL) at 0° C. To this cooled solution LiOH.H$_2$O (8 mg, 0.188 mmol) was added and stirred at same temperature for 1 h. Reaction was monitored using TLC. After completion the reaction mixture was concentrated under vacuum to remove THF. The residue was diluted with water 10 mL and washed with DCM and ethyl acetate.

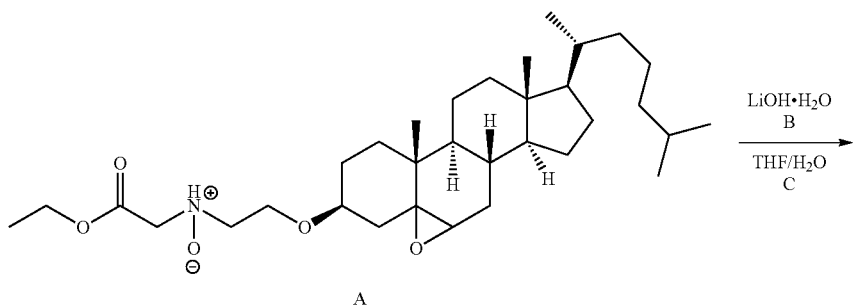

A

LiOH·H$_2$O
B
─────→
THF/H$_2$O
C

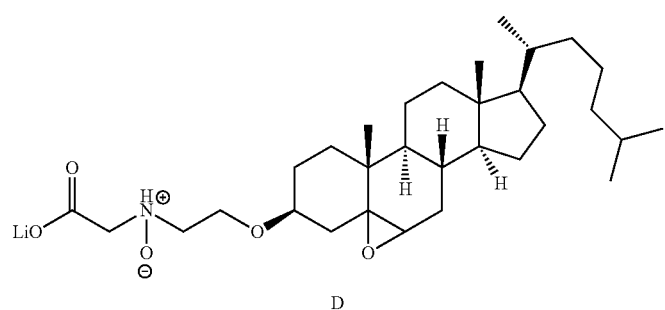

D

Synthesis of IO-148_01

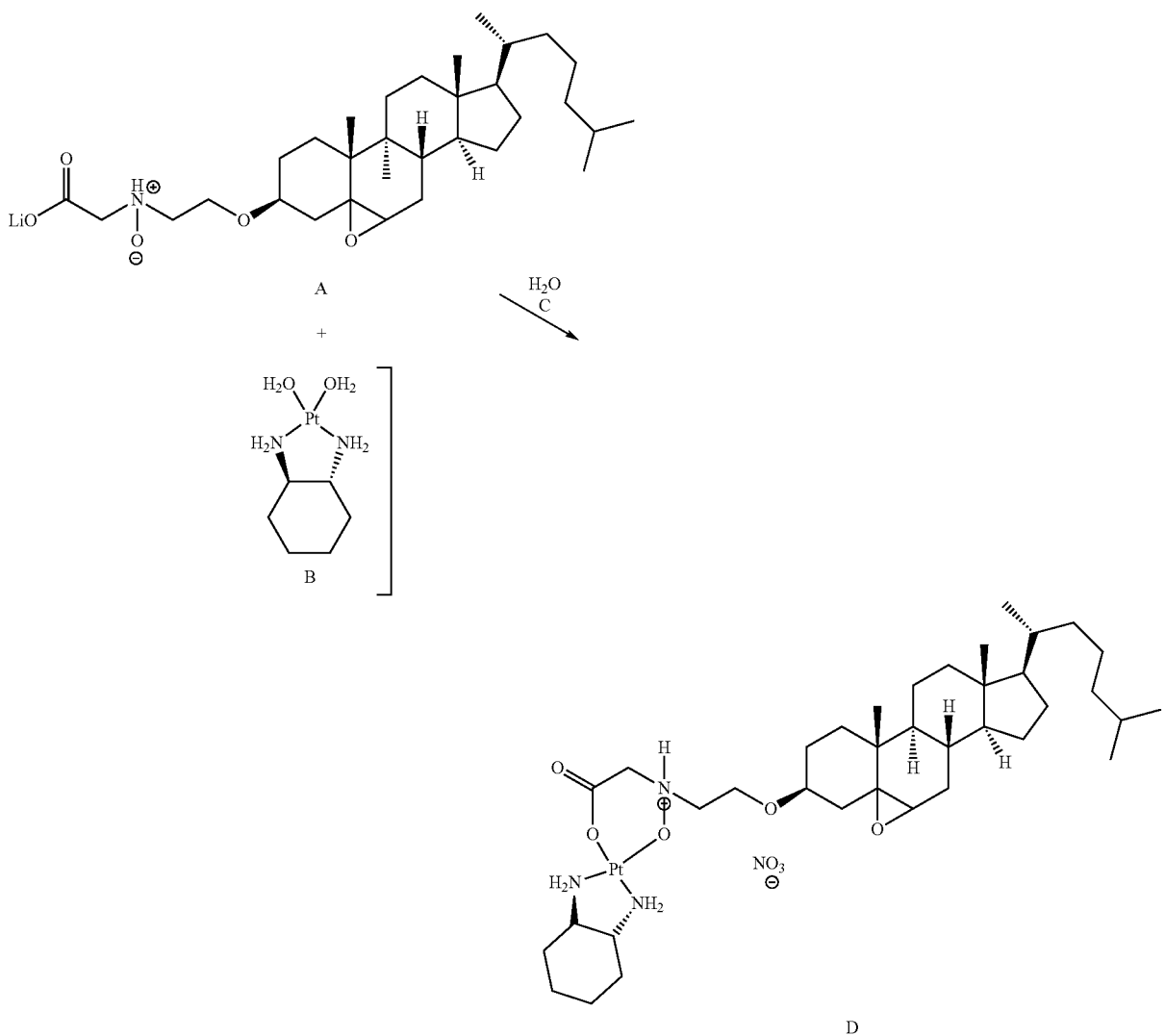

Experimental Procedure: To a 50 mL single neck RBF aquated DACH Platinum (70 mg, 0.188 mmol, 10 mg/mL solution) was taken. To the above solution ligand A (100 mg, 0.188 mmol) in 10 mL water was added dropwise. The resulting solution was stirred for 3 h at room temperature. After completion the reaction mixture was centrifuged to separate the precipitate. The precipitates were washed with water twice (10 mL) and lyophilized to get IO-148_01. ESIMS m/z=827.4

Synthesis of IO-148_02

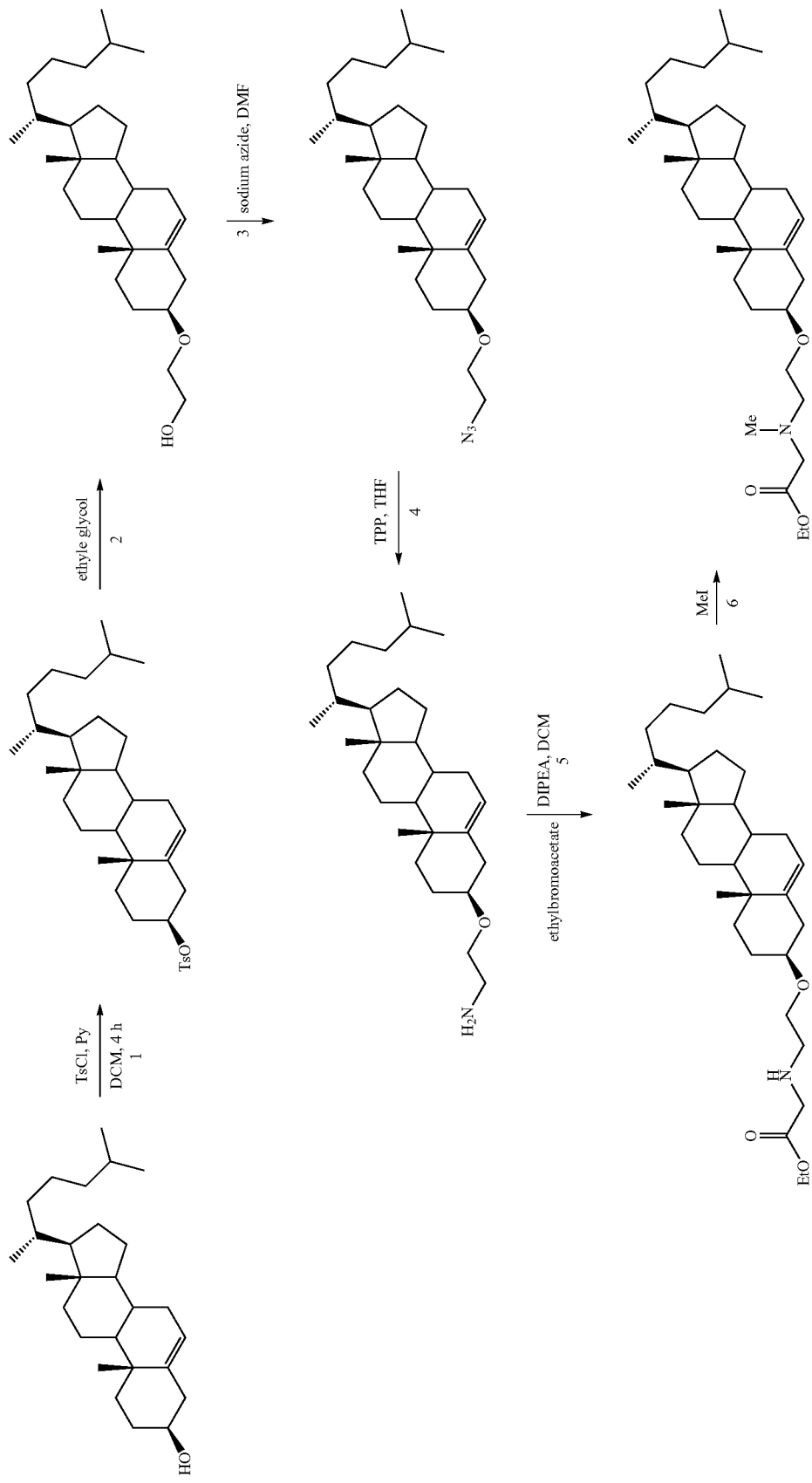

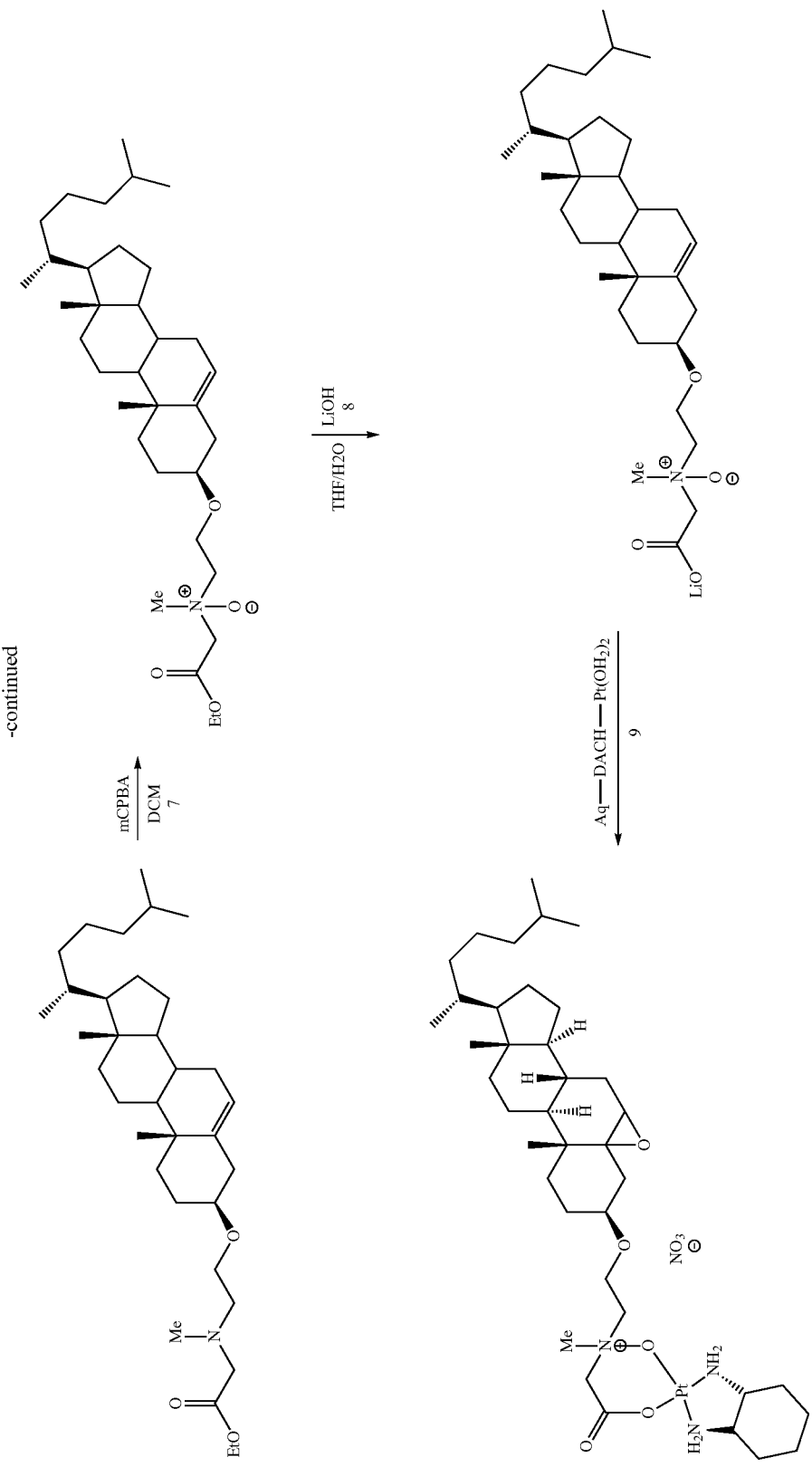

Step 1-5 are similar as IO-148_01:
Step 6: Synthesis of N-Methyl Intermediate of IO-148_02

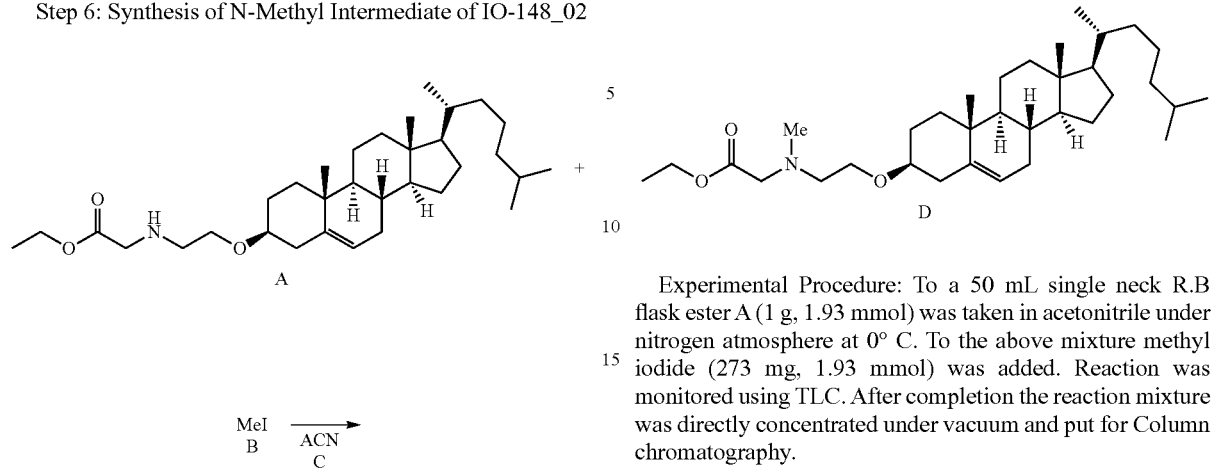

Experimental Procedure: To a 50 mL single neck R.B flask ester A (1 g, 1.93 mmol) was taken in acetonitrile under nitrogen atmosphere at 0° C. To the above mixture methyl iodide (273 mg, 1.93 mmol) was added. Reaction was monitored using TLC. After completion the reaction mixture was directly concentrated under vacuum and put for Column chromatography.

Step 7: Synthesis of N-Oxide Intermediate of IO-148_02

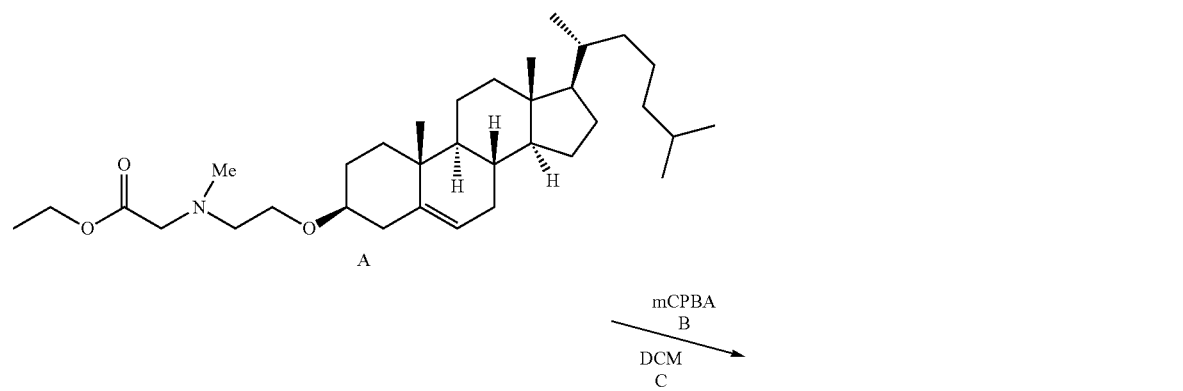

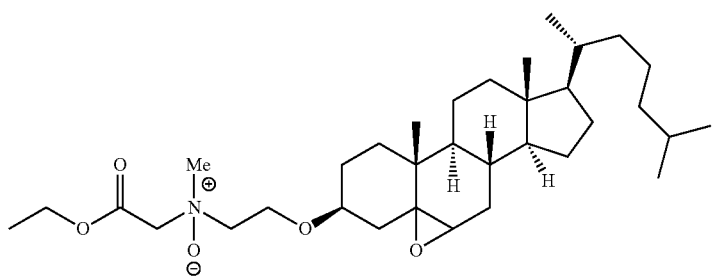

Experimental Procedure: To a 50 mL single neck R.B flask ester A (100 mg, 0.193 mmol) was taken in anhydrous $CH_2Cl_2$ (10 mL) under nitrogen atmosphere at 0° C. To this cooled solution mCPBA (16.72 mg, 0.135 mmol) was added dropwise as a solution in DCM (2 mL) and stirred at same temperature for 2 h. Reaction was monitored using TLC. After completion the reaction mixture was quenched with NaHCO3, extracted with CHCl3, dried over anhydrous sodium sulphate, concentrated and directly put for column chromatography.

Step 8: Synthesis of final ligand of IO-148_02

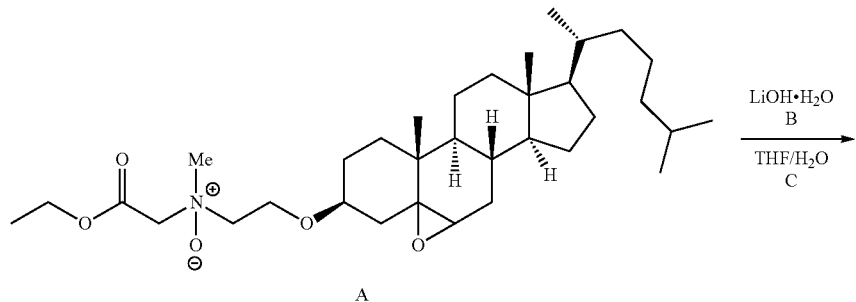

Experimental Procedure: To a 50 mL single neck R.B flask N-oxide intermediate A (100 mg, 0.188 mmol) was taken in anhydrous THF/H₂O (4 mL) at 0° C. To this cooled solution LiOH.H₂O (8 mg, 0.188 mmol) was added and stirred at same temperature for 1 h. Reaction was monitored using TLC. After completion the reaction mixture was concentrated under vacuum to remove THF. The residue was diluted with water 10 mL and washed with DCM and ethyl acetate.

Step 9: Synthesis of IO-148_02

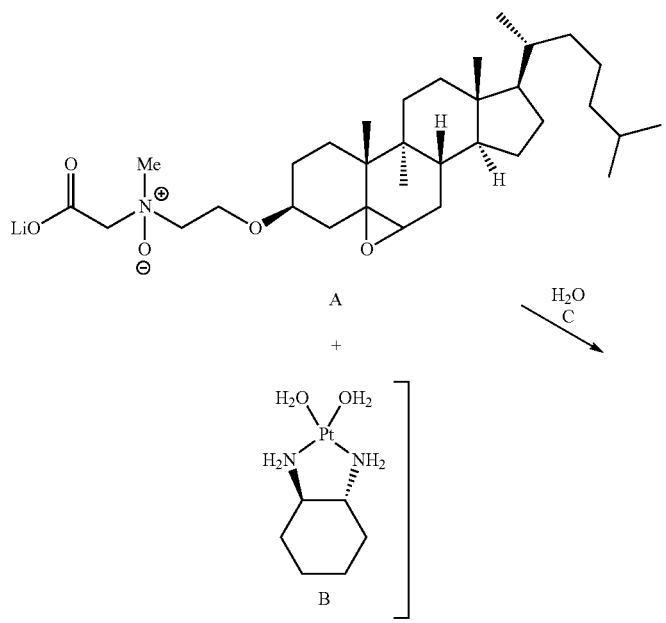

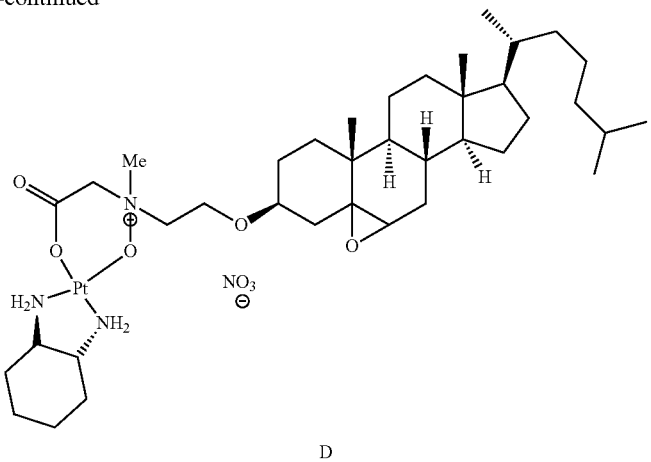

D

Experimental Procedure: To a 50 mL single neck RBF aquated DACH Platinum (70 mg, 0.188 mmol, 10 mg/mL solution) was taken. To the above solution ligand A (100 mg, 0.188 mmol) in 10 mL water was added dropwise. The resulting solution was stirred for 3 h at room temperature. After completion the reaction mixture was centrifuged to separate the precipitate. The precipitates were washed with water twice (10 mL) and lyophilized to get IO-148_01.

Synthesis of IO-183_01

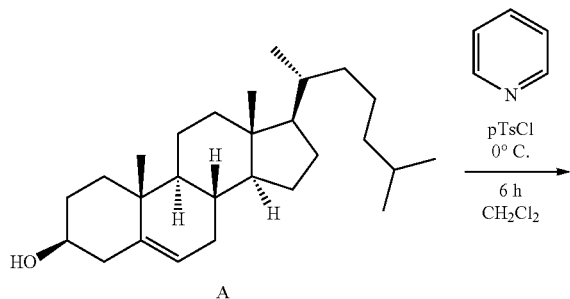

A

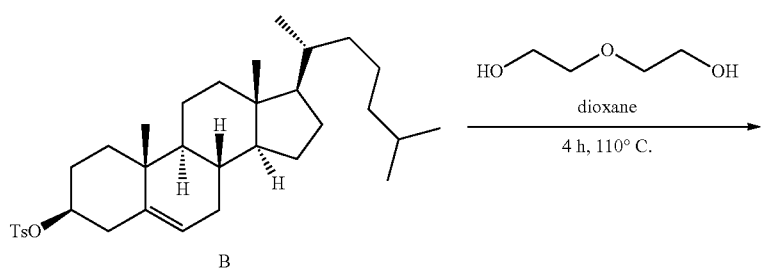

B

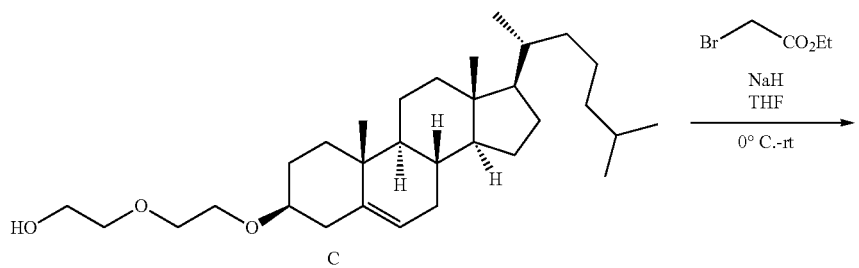

C

-continued
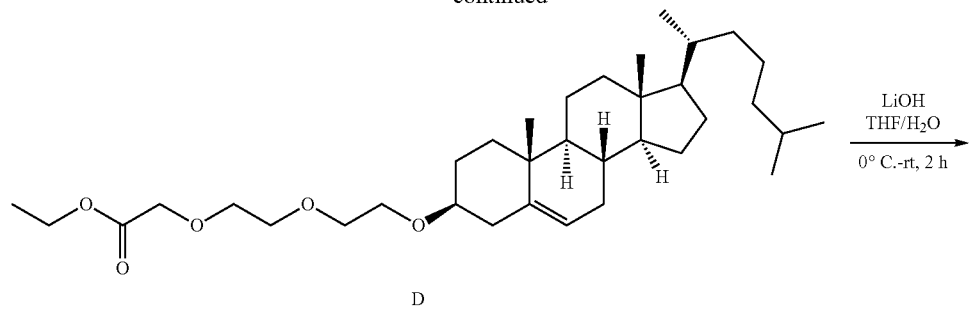
D
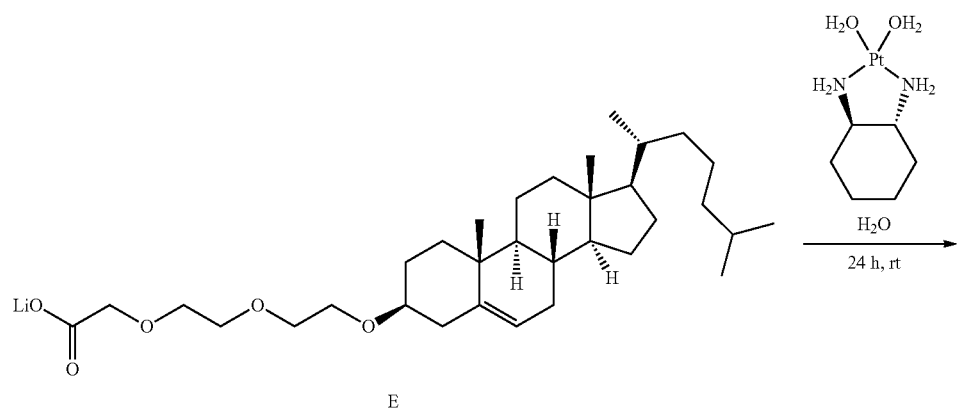
E
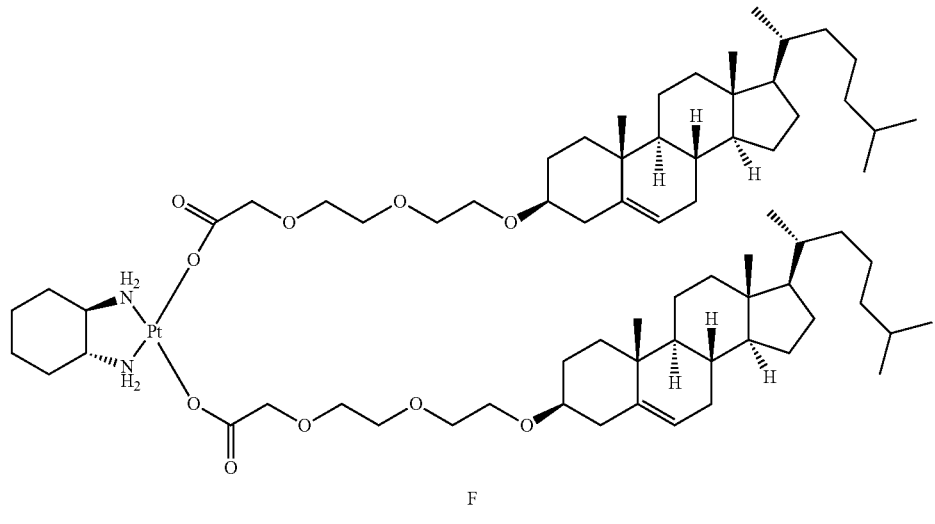
F

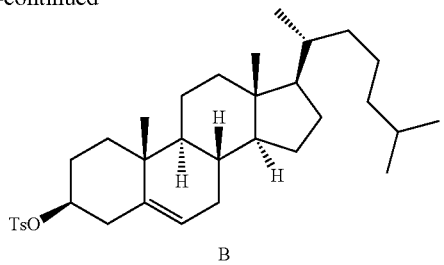

B

Experimental Procedure: To an ice cooled solution of cholesterol A (5 g, 12.93 mmol) in CH$_2$Cl$_2$ (35 mL) was added pyridine (5.22 mL) and stirred for 15 minutes. To this solution p-toluene sulphonyl chloride B (6.15 g, 32.31 mmol) was added and stirred for 6 h at 0° C. and TLC was checked. After completion the reaction mixture was diluted with CHCl$_3$ (20 mL) and washed with 1N HCl (3×50 mL) and brine (20 mL) successively. The organic layer was dried over anhydrous Na$_2$SO$_4$ and concentrated under vacuum. Without purification, the whole compound is used for the next reaction.

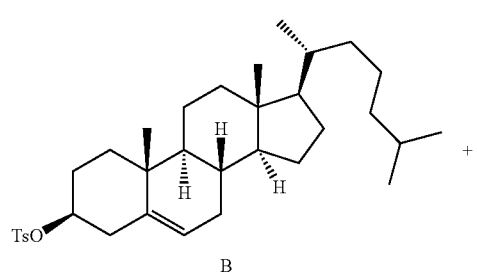

B

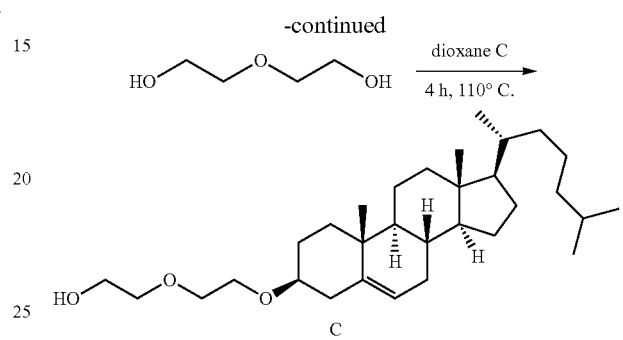

C

Experimental Procedure: To the solution of tosylated cholesterol A (10 g, 18.49 mmol) in dioxane (30 mL) was added diethylene glycol (10 mL) and refluxed for 4 h. The TLC was checked. After completion the reaction mixture was extracted with ethyl acetate and washed with water (3×50 mL) and brine (20 mL) successively. The organic layer was dried over anhydrous Na$_2$SO$_4$ and concentrated under vacuum and column was performed. (Yield 38%)

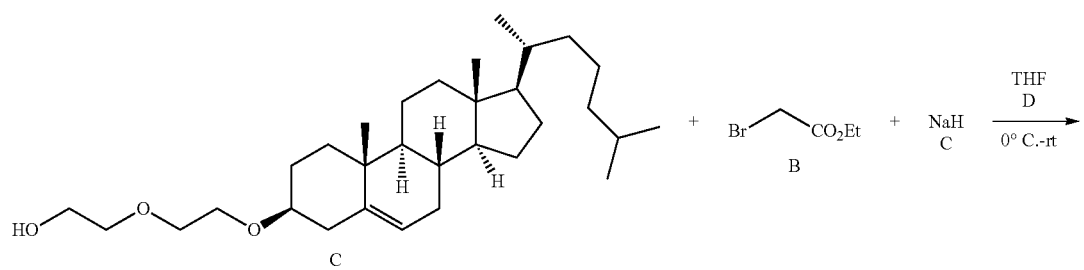

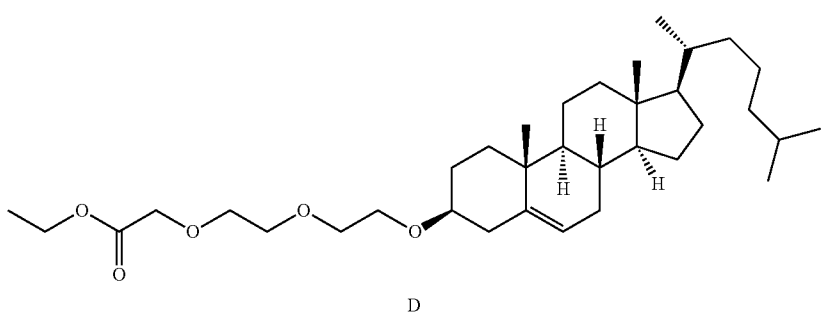

D

Experimental Procedure: To a 100 mL single neck RBF NaH (594 mg) was taken in THF (10 mL) under nitrogen atmosphere. The reaction was cooled to 0° C. under ice bath and to it solution of C (2.35 g, 4.95 mmol) in THF (15 mL) was added slowly. The resulting solution was stirred for 1 h and ethyl bromo acetate was added slowly and stirred for 6 h at room temperature and TLC was checked. After completion the reaction mixture was cooled to 0° C. and quenched with water, extracted with ethyl acetate. The organic layer was washed with water and dried over Na$_2$SO$_4$ and concentrated and the compound was purified by column chromatography. (Yield 46%) $^1$H NMR(CDCl$_3$): 0.66(s), 0.81-2.41 (m), 3.2(br, s), 3.6-3.8(m), 4.36(s), 5.33(s) $^{13}$C NMR (CDCl$_3$): 11.83, 18.68, 19.34, 21.03, 22.53, 22.39, 23.79, 24.26, 27.58, 28.21, 29.67, 31.84, 31.91, 35.35, 36.15, 36.82, 37.15, 38.89, 39.68, 39.75, 42.28, 50.12, 56.11, 56.73, 67.01, 68.76, 70.11, 70.95, 71.41, 79.64, 121.67, 140.74, 172.69 solution LiOH (12 mg, 0.28 mmol) was added and was stirred at rt for 2 h, the TLC was checked. After completion the reaction mixture, THF was removed by rotavapour. Chloroform was added to the reaction mixture. Compound was extracted with water. Then whole reaction mixture was used for the next reaction after rotavapor treatment.

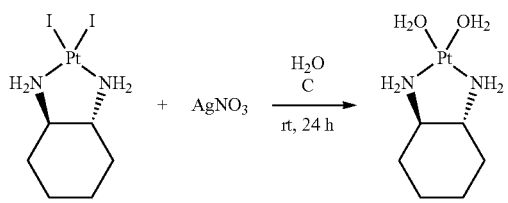

Experimental Procedure: To a 50 mL single neck RBF DACH platinum (78 mg, 0.139 mmol) was taken in 5 mL HPLC Water. To the above solution silver nitrate (47 mg,

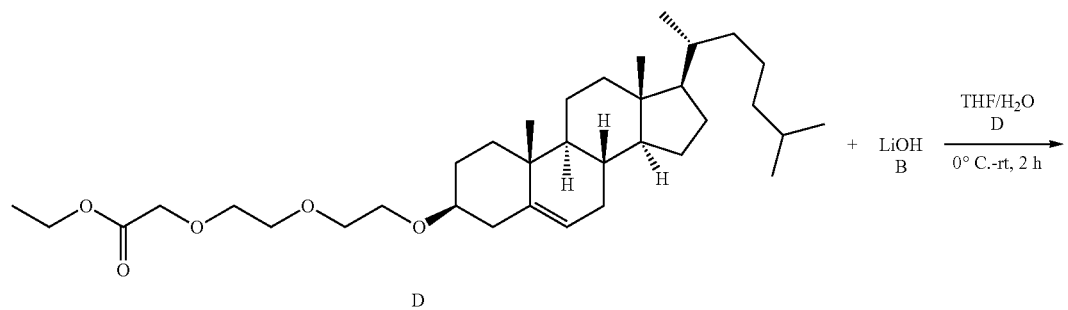

D

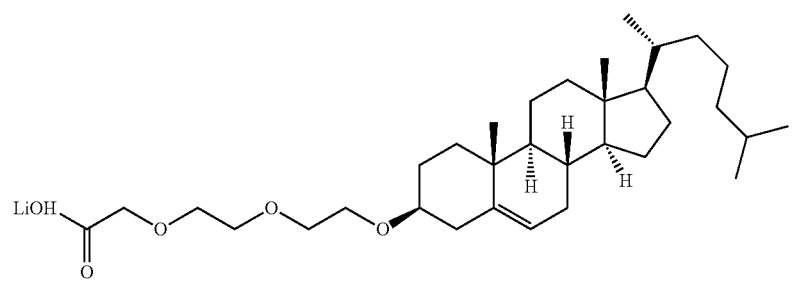

E

Experimental Procedure: To a 100 mL single neck RBF ester D (0.15 g, 0.28 mmol) was taken in 2 mL of THF/H$_2$O (3:1) and cooled to 0° C. under ice bath. To this ice cooled 0.278 mmol) was added. The resulting solution was stirred under protection from light at rt. After 24 h, AgI precipitate was filtered. Filtrate was used for the next step.

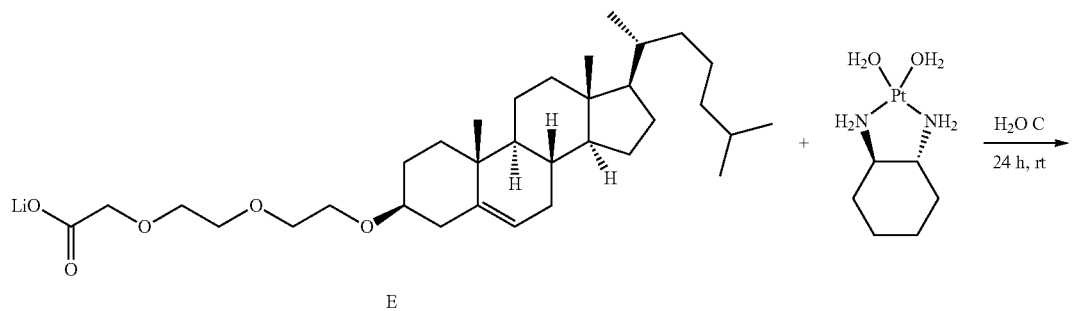

E

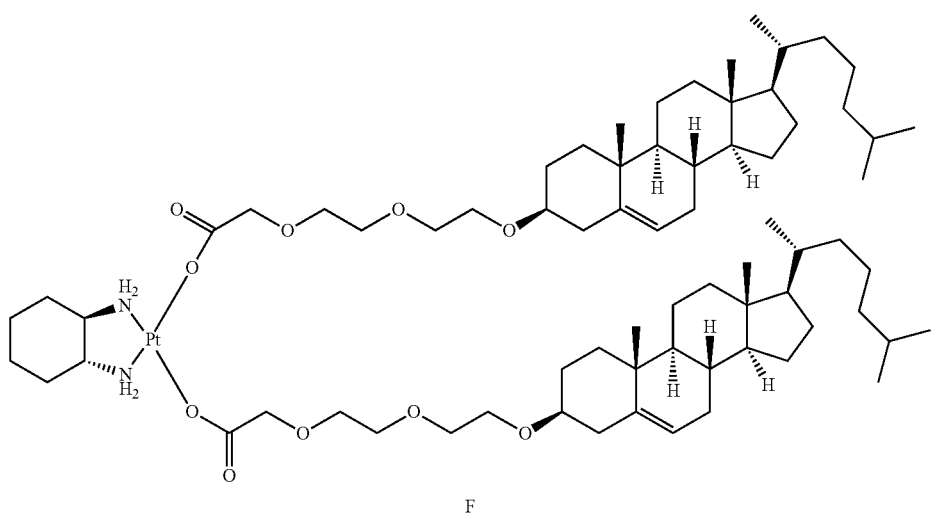

F

Experimental Procedure: To a 100 mL single neck RBF salt E (150 mg, 0.263 mmol) was taken in 40 mL HPLC water and the resulting solution was stirred for 5 min at room temperature and to this solution DACH (OH$_2$)$_2$ platinum B was added and it was stirred under protection from light at rt for 24 h. The precipitate was filtered through filter paper and simultaneously washed with HPLC water, HPLC Methanol and HPLC acetone and dried. (Yield 45%) ESIMS m/z=1395.7 [M+Na]$^+$ for C$_{72}$H$_{124}$N$_2$O$_{10}$P $^1$H NMR: (500 MHz, CDCl3): 5.96(bs), 5.32(s), 4.96(bs), 3.92(q), 3.61(s), 3.15(m), 2.57(m), 2.37(m), 2.21(t), 1.91(m), 1.48(m), 1.32 (m), 1.24(m), 1.11(m), 0.98(s), 0.90(d), 0.85(dd), 0.66(s) ppm. $^{13}$C NMR(500 MHz, CDCl3): 177.22, 140.86, 121.56, 79.58, 70.70, 70.37, 70.31, 70.07, 67.26, 62.24, 56.75, 56.17, 50.15, 42.30, 39.77, 39.50, 39.08, 37.23, 36.85, 36.18, 35.79, 32.04, 31.94, 31.88, 28.36, 28.22, 27.98, 24.62, 24.28, 23.85, 22.79, 22.54, 21.06, 19.38, 18.71, 11.85 ppm. IR: 418(w), 668(br, s), 749(m), 1110(s), 1260(s), 1640(s), 2064(w), 2933(m), 3446(br, s)

Synthesis of IO-183_02

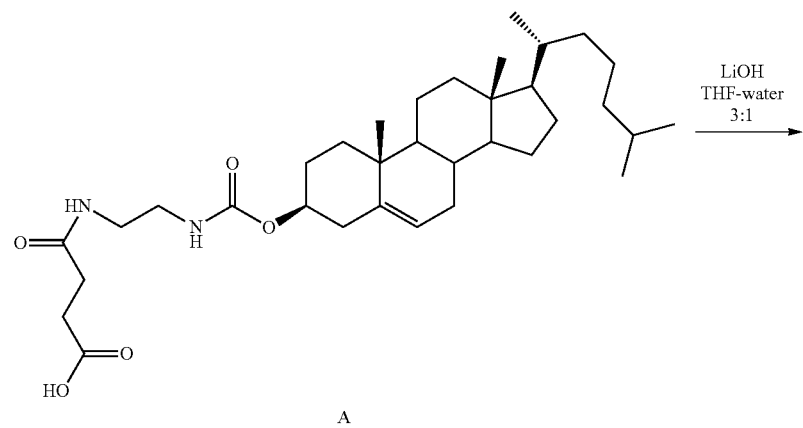

A

217 218
-continued
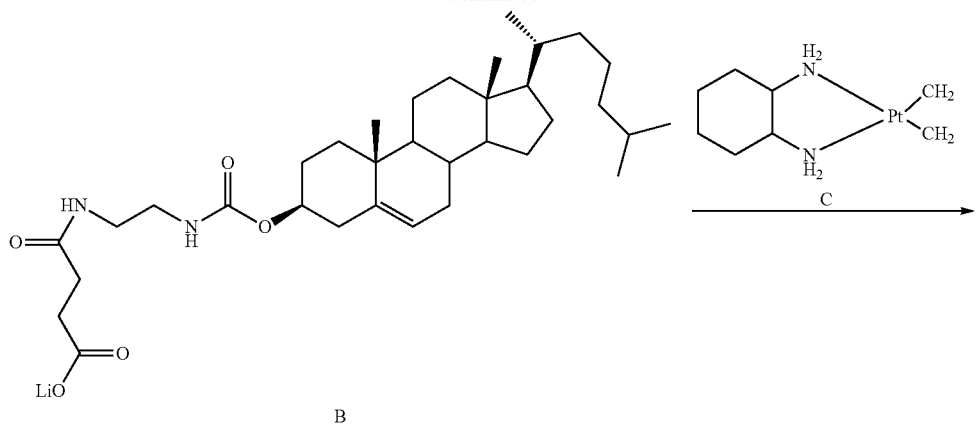
B
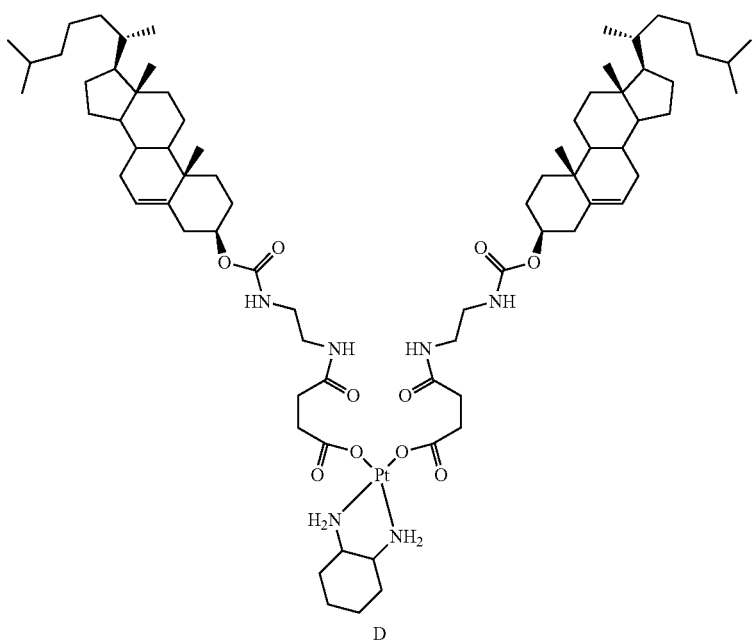
D
Step 1:
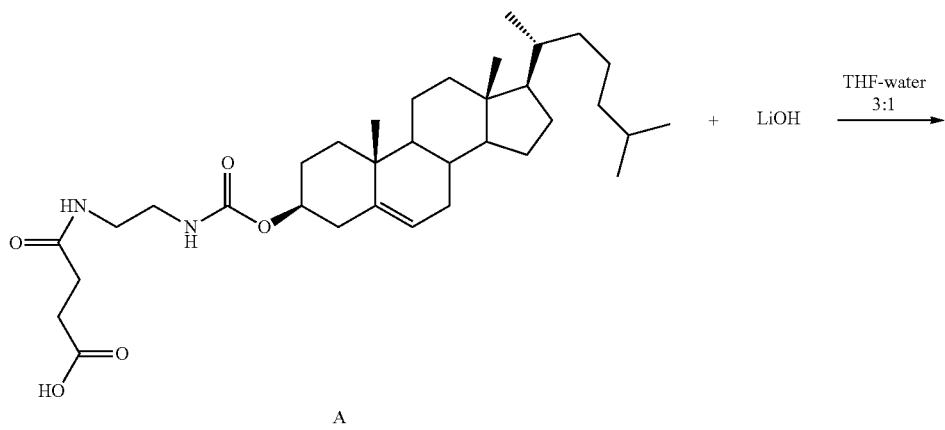
A

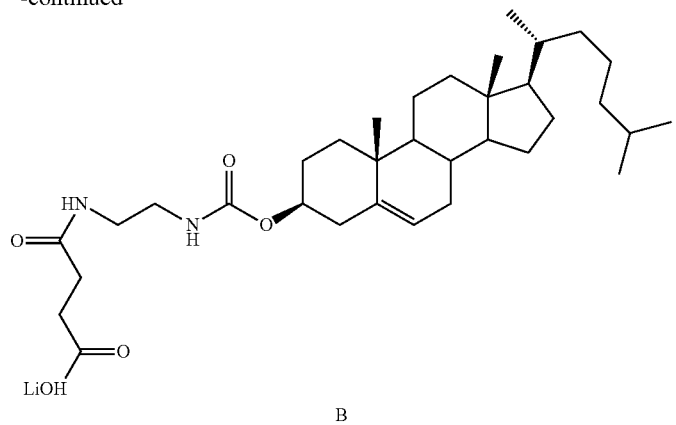

B

Experimental Procedure: A (same procedure followed from ref. PNAS; 109, 2012; 11294) (200 mg, 0.349 mmol) was dissolved in 2.5 mL of THF and 0.8 mL water. To it 16 mg of LiOH was added and stirred for 24 h at RT. White suspension appeared. THF was evaporated under vac and 40 mL of water is added to dissolve the white residue. Water solution was washed with chloroform. Water layer used for next step.

Step 2

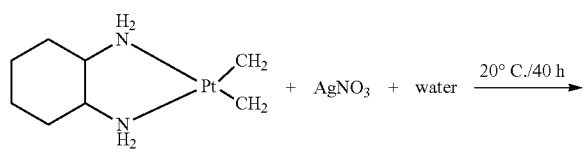

-continued

C

Experimental Procedure: 0.17 mmol cyclohexyldiammin-eplatinum-dichloride, 0.34 silver nitrate and 7 mL water were added in a 25 mL RB and stirred for 48 h at room temp. Solution was centrifuged (4,000 rpm; 10 min) and white precipitate was filtered through syringe filter (25 mm/0.20 μm). Washed with 2 mL of water. Filtrate used for next reaction.

Step 3

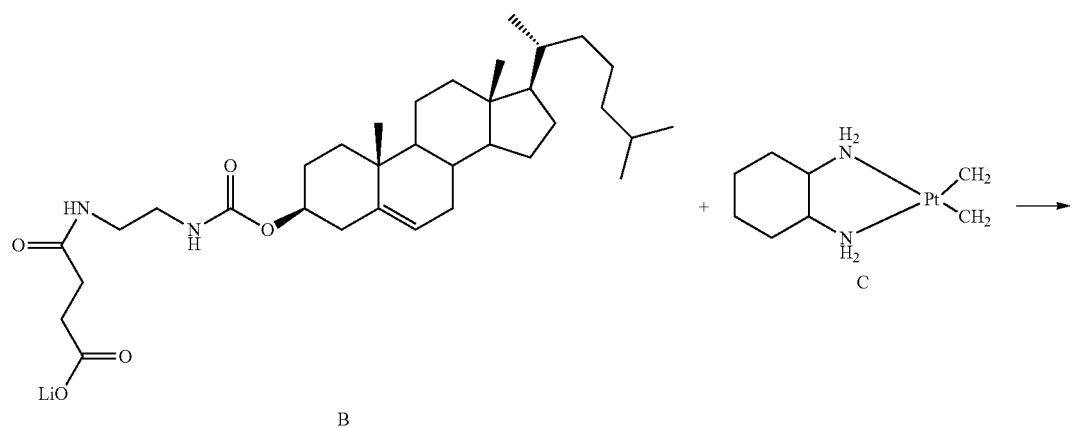

B  C 221 222
-continued
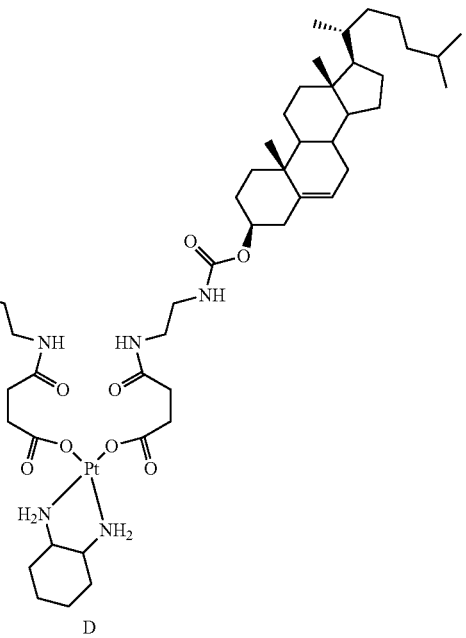
D
Experimental Procedure: Compound B (0.26 mmol) in 20 ml water was added drop-wise to C(0.13 m mol) in water (10 ml). Reaction continued at room temperature for 20 h. White precipitate was separated by filtration. Residue washed with water (10 ml) to get D as white powder. $^1$H NMR(CDCl$_3$+ CD$_3$OD): 0.66(s), 0.84-2.5(br, m), 3.32(br, d), 4.45(br, s), 5.34(br, s) $^{13}$C(CDCl$_3$+CD$_3$OD) NMR: 11.68, 18.53, 19.15, 20.89, 22.36, 22.62, 23.7, 24.12, 24.32, 27.84, 28.02, 29.53, 35.65, 36.03, 36.41, 38.36, 38.42, 39.27, 39.36, 39.58, 40.27, 42.16, 49.56, 49.88, 56.02, 56.55, 62.44, 74.46, 122.42, 139.63, 156.91, 174.20, 180.89 ESIMS: 1475.4 (M+Na) IR: 418(m), 584(m), 799(s), 1027(m), 1260(s), 1454(m), 1535(s), 1643(s), 1700(br, s), 2928(s), 3418(br, s)
Synthesis of IO-147_02
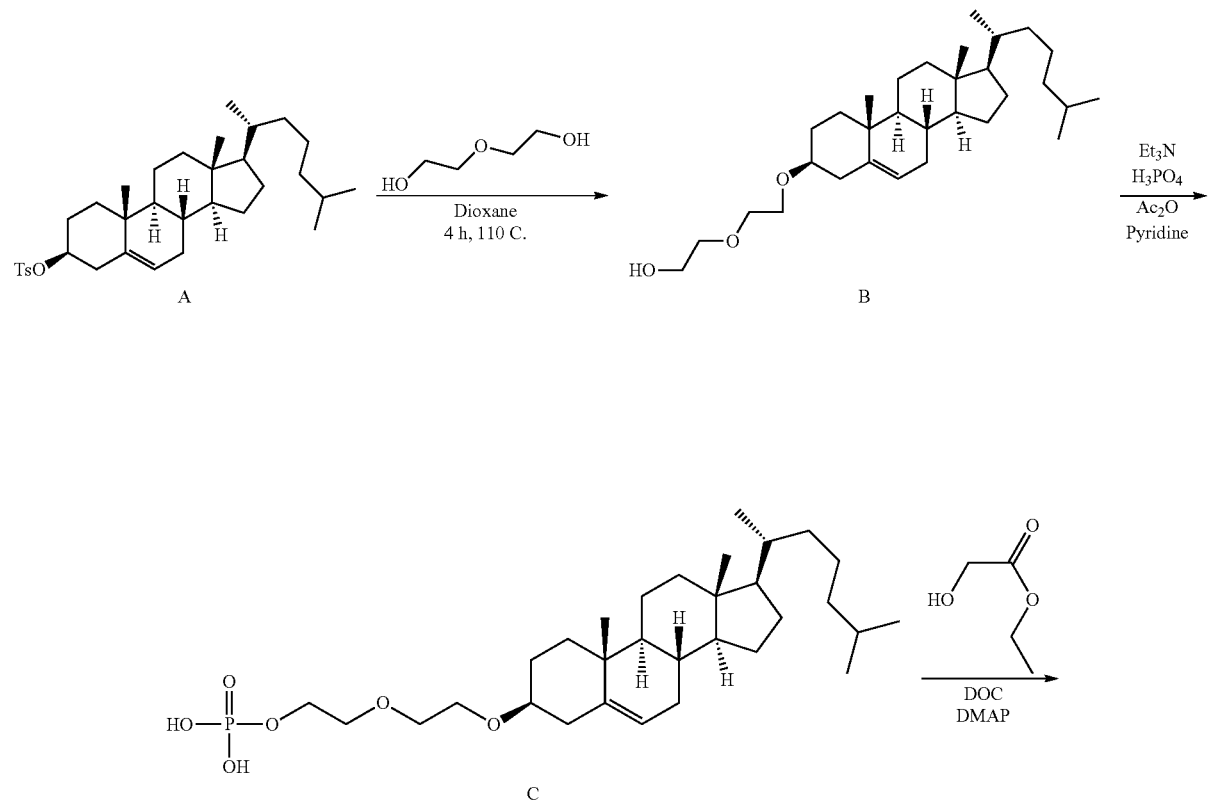

Synthesis of IO-147_02:
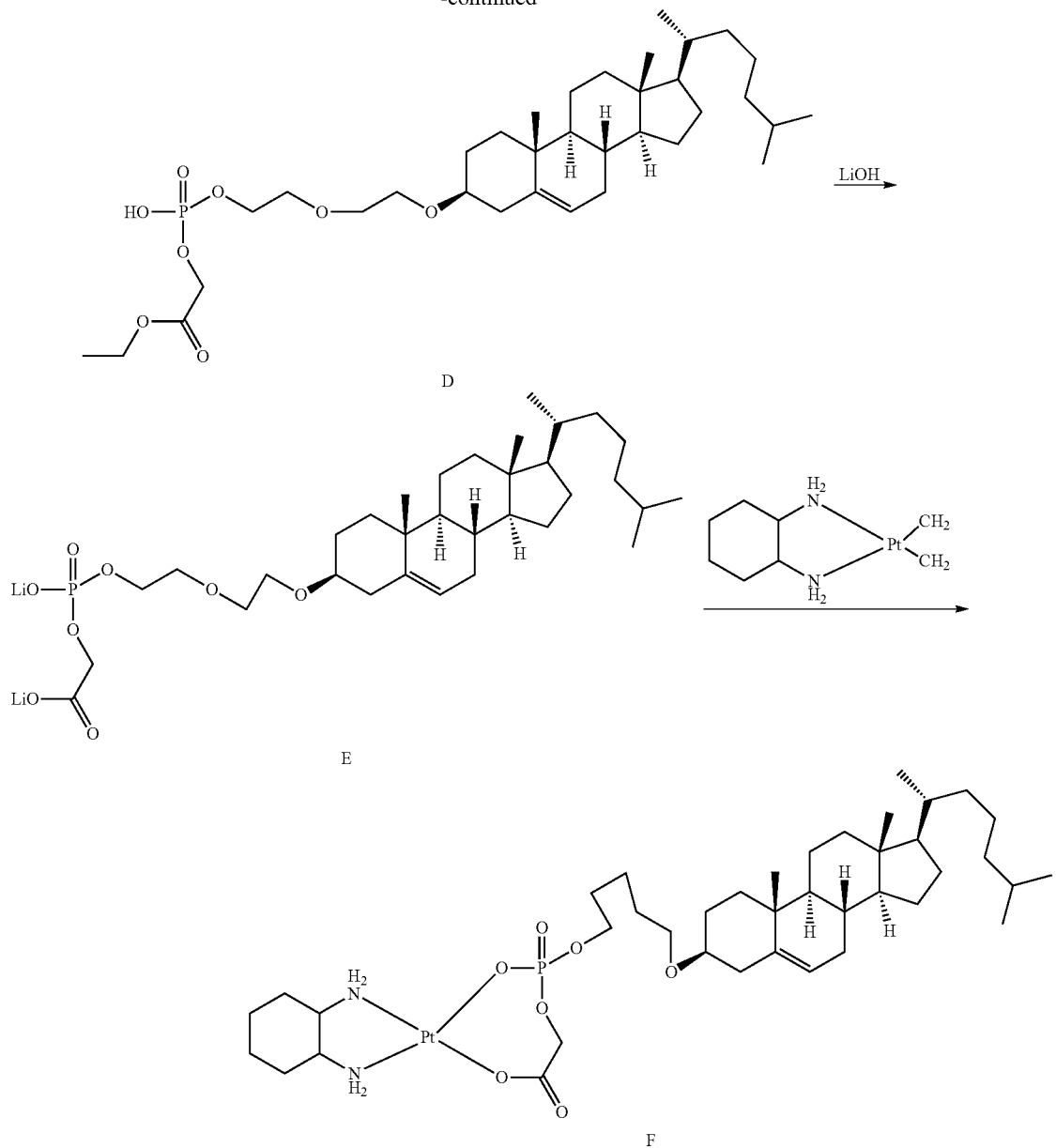
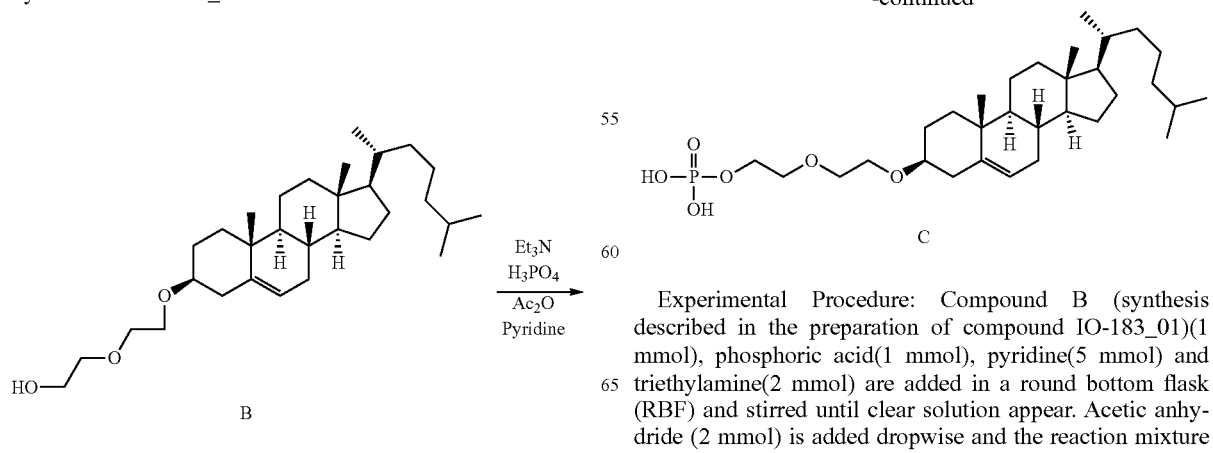
Experimental Procedure: Compound B (synthesis described in the preparation of compound IO-183_01)(1 mmol), phosphoric acid(1 mmol), pyridine(5 mmol) and triethylamine(2 mmol) are added in a round bottom flask (RBF) and stirred until clear solution appear. Acetic anhydride (2 mmol) is added dropwise and the reaction mixture is stirred for 3 hrs at 80° C. Cooled to room temperature and water is added. Compound is extracted by diethylether and concentrated under vacuum to obtain compound C. Rest of the reactions to obtain F is similar as described for the synthesis of IO-180_01.
Synthesis of IO-173_01
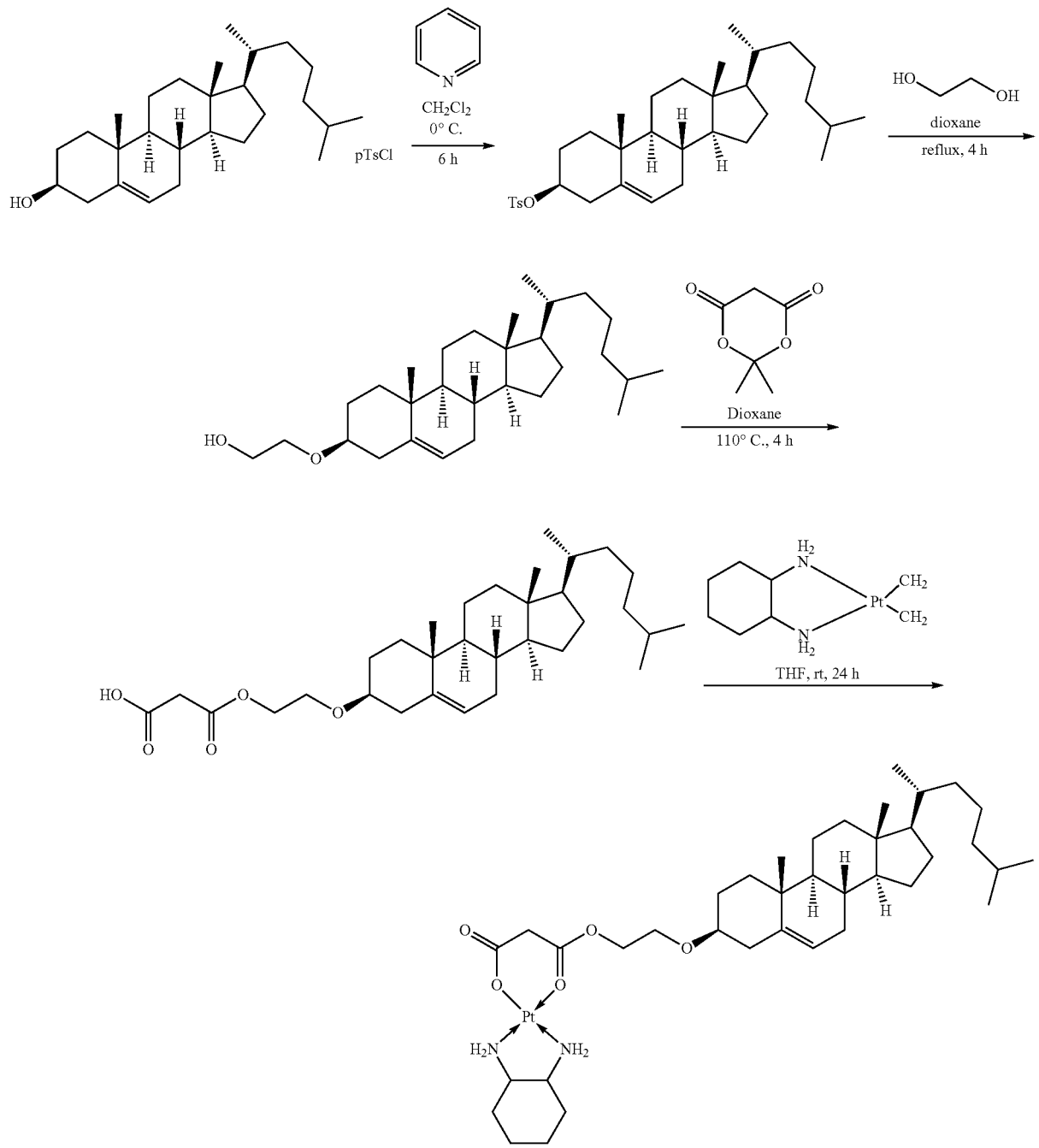
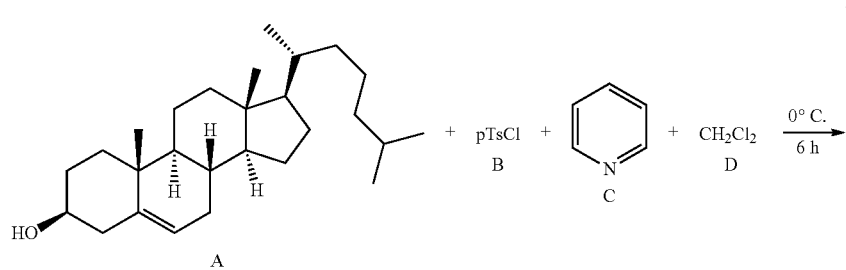

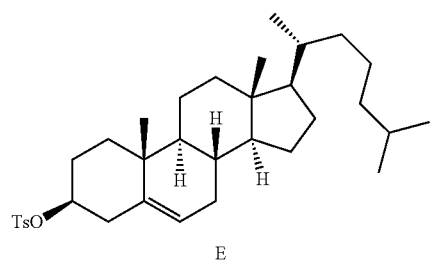

Experimental Procedure: To an ice cooled solution of cholesterol A (5 g, 12.93 mmol) in CH₂Cl₂ (35 mL) was added pyridine (5.22 mL) and stirred for 15 minutes. To this solution p-toluene sulphonyl chloride B (6.15 g, 32.31 mmol) was added and stirred for 6 h at 0° C. and TLC was checked. After completion the reaction mixture was diluted with CHCl₃ (20 mL) and washed with 1N HCl (3×50 mL) and brine (20 mL) successively. The organic layer was dried over anhydrous Na₂SO₄ and concentrated under vacuum. Without purification, the whole compound is used for the next reaction.

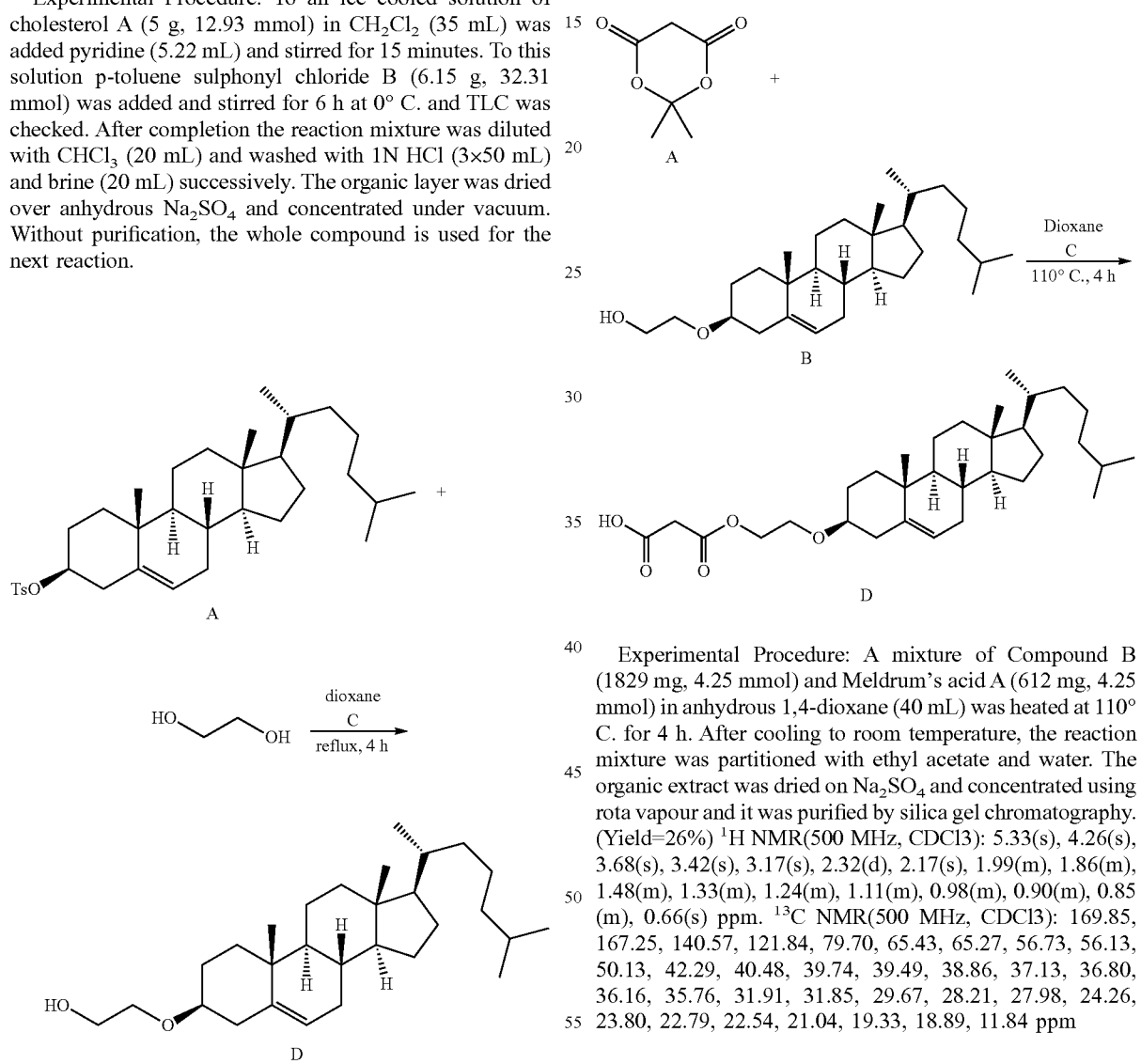

Experimental Procedure: To the solution of tosylated cholesterol A (10 g, 0.018 mol) in dioxane (25 mL) was added ethylene glycol (15 mL) and refluxed for 4 h. The TLC was checked. After completion the reaction mixture was extracted with ethyl acetate and washed with water (3×50 mL) and brine (20 mL) successively. The organic layer was dried over anhydrous Na₂SO₄ and concentrated under vacuum and it was purified by silica gel chromatography. (Yield=37%)

Experimental Procedure: A mixture of Compound B (1829 mg, 4.25 mmol) and Meldrum's acid A (612 mg, 4.25 mmol) in anhydrous 1,4-dioxane (40 mL) was heated at 110° C. for 4 h. After cooling to room temperature, the reaction mixture was partitioned with ethyl acetate and water. The organic extract was dried on Na₂SO₄ and concentrated using rota vapour and it was purified by silica gel chromatography. (Yield=26%) ¹H NMR(500 MHz, CDCl3): 5.33(s), 4.26(s), 3.68(s), 3.42(s), 3.17(s), 2.32(d), 2.17(s), 1.99(m), 1.86(m), 1.48(m), 1.33(m), 1.24(m), 1.11(m), 0.98(m), 0.90(m), 0.85 (m), 0.66(s) ppm. ¹³C NMR(500 MHz, CDCl3): 169.85, 167.25, 140.57, 121.84, 79.70, 65.43, 65.27, 56.73, 56.13, 50.13, 42.29, 40.48, 39.74, 39.49, 38.86, 37.13, 36.80, 36.16, 35.76, 31.91, 31.85, 29.67, 28.21, 27.98, 24.26, 23.80, 22.79, 22.54, 21.04, 19.33, 18.89, 11.84 ppm

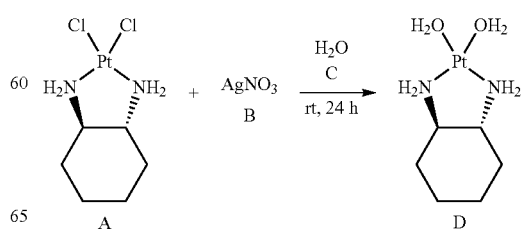

Experimental Procedure: To a 50 mL single neck RBF DACH platinum A (100 mg, 0.263 mmol) was taken in 10 mL HPLC Water. To the above solution silver nitrate (89 mg, 0.526 mmol) was added. The resulting solution was stirred under protection from light at rt. After 24 h, AgCl precipitate was filtered. Filtrate was used for the next step.

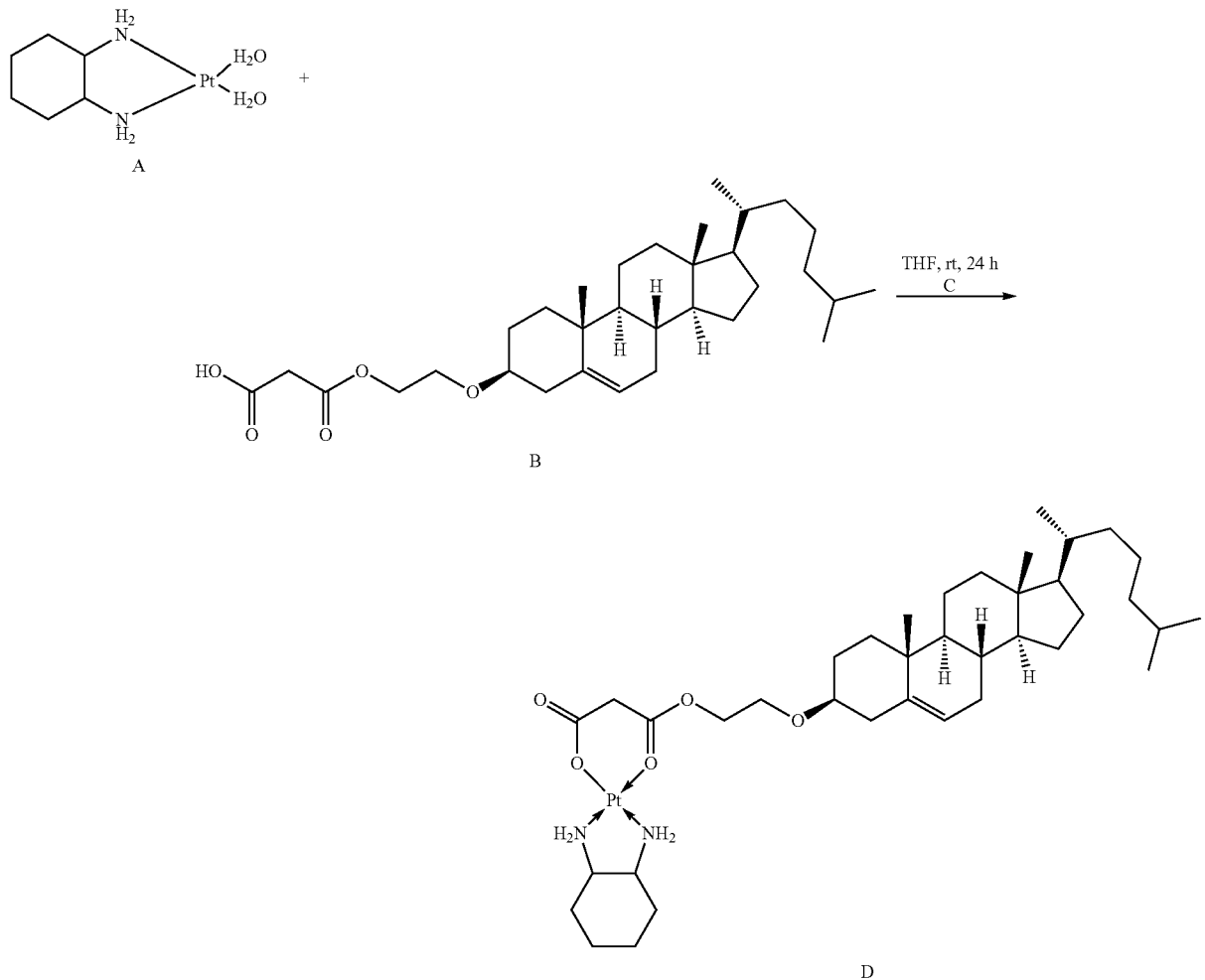

Experimental Procedure: To a 50 mL single neck RBF Acid B (136 mg, 0.263 mmol) was taken in 15 mL Dry THF. To the above solution, DACH $(OH_2)_2$ platinum A (95 mg, 0.263 mmol) was added dropwise under protection from light and stirred for 24 h. Then the whole THF was evaporated. Precipitate was filtered and the water part was lyophilized. ESIMS (M 824)

Synthesis of IO-173_03

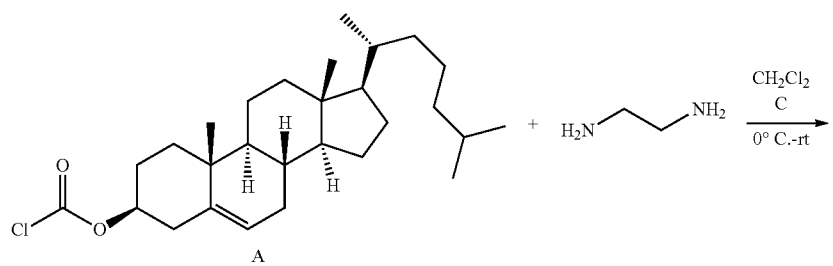

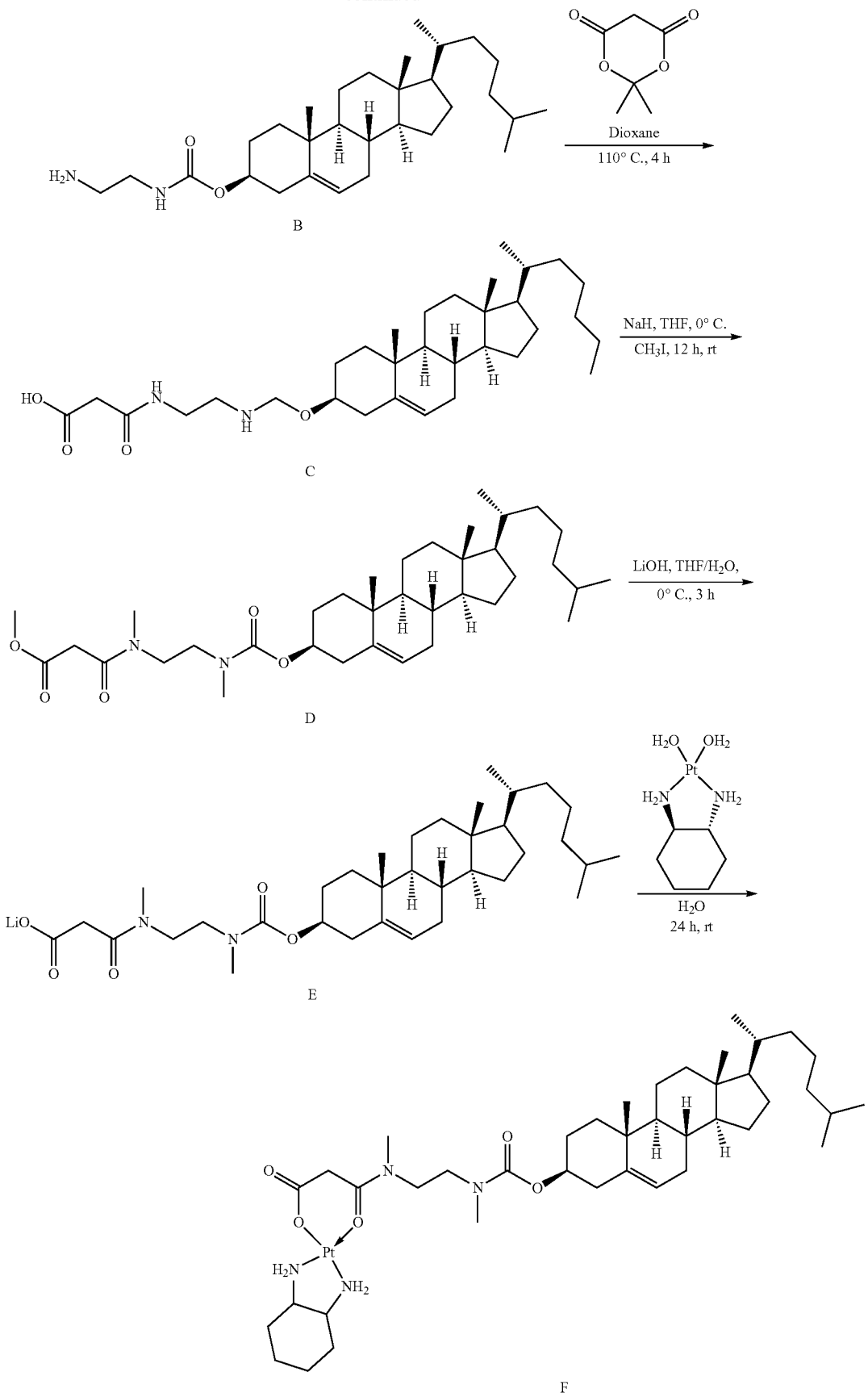

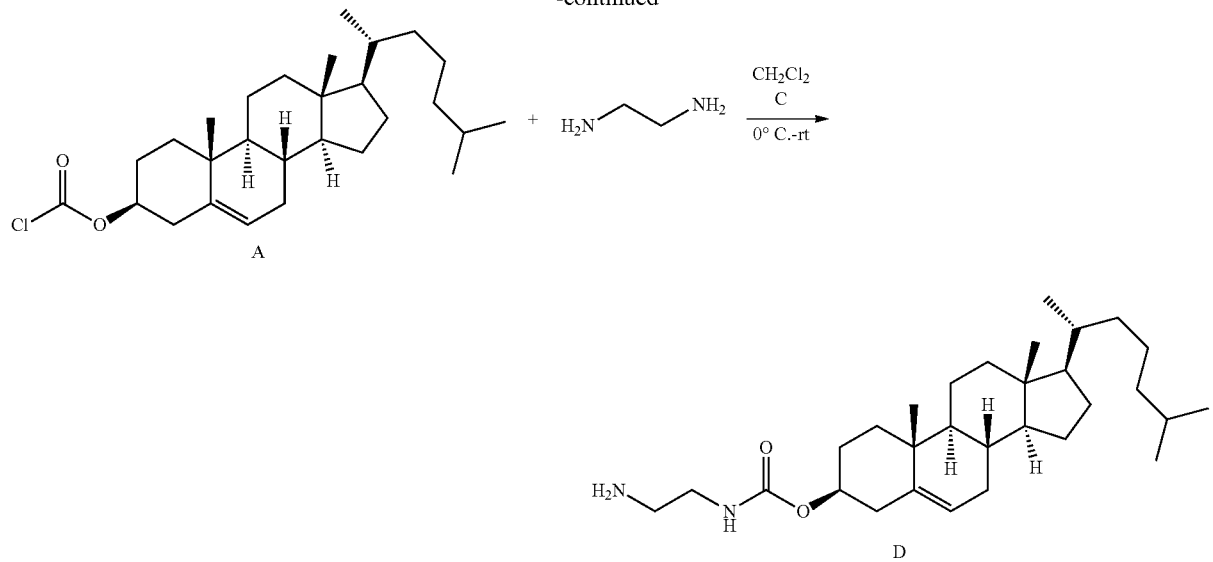

Experimental Procedure: To an ice cooled solution of ethylene diamine B (22.2 mL) in 40 mL. DCM was added solution of compound A (5 g) in DCM (50 mL) dropwise over a period of 45 min and stirred at the same temperature for 1 h. and left at rt for additional 20 h. The TLC was checked and after completion of the reaction was quenched with water (4×100 mL) and the organic layer was extracted with DCM (2×50 mL) and was dried over anhydrous Na$_2$SO$_4$ and concentrated under vacuum and purified by silica gel column chromatography. Yield 90%.

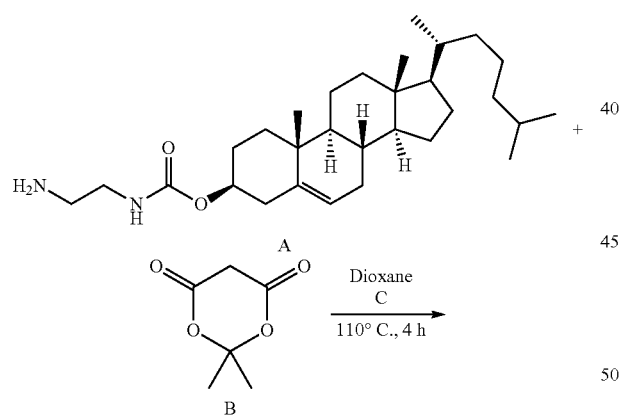

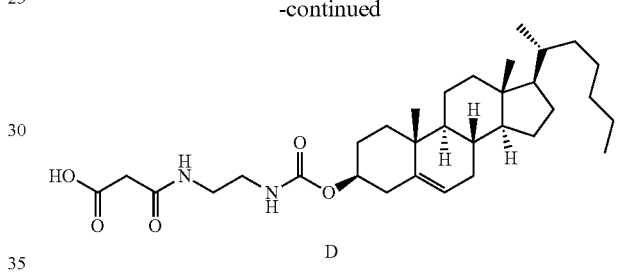

Experimental Procedure: A mixture of Compound A (2.74 g, 5.8 mmol) and Meldrum's acid A (661 mg, 5.8 mmol) in anhydrous 1,4-dioxane (20 mL) was heated at 110° C. for 4 h. After cooling to room temperature, the reaction mixture was partitioned with ethyl acetate and Water. The organic extract was dried on Na$_2$SO$_4$ and concentrated using rota vapour. It was purified by silica gel column chromatography. Yield 50%.

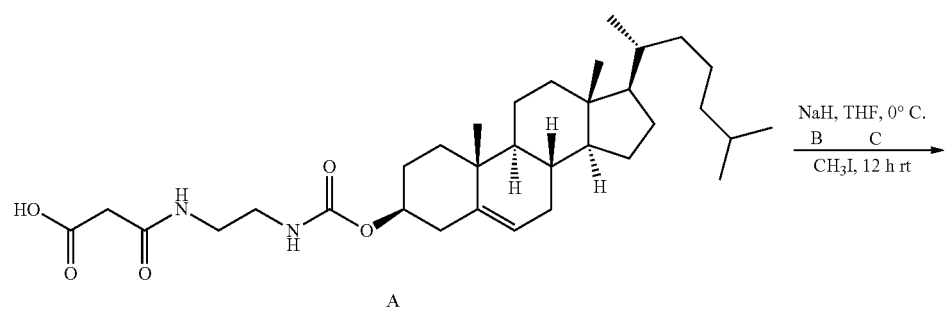

-continued

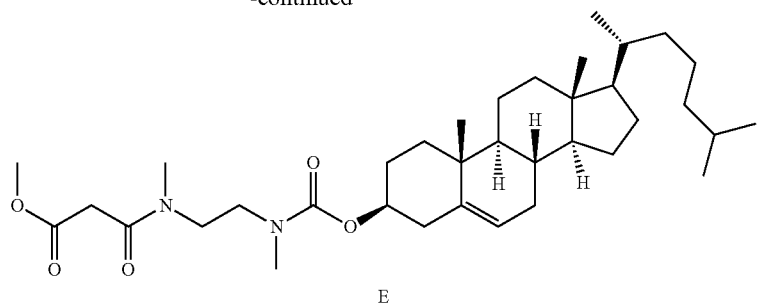

E

Experimental Procedure: To a 50 mL single neck R.B sodium hydride (620 mg, 15.516 mmol) was taken in THF (5 mL) under nitrogen atmosphere. The reaction mixture was cooled to 0° C. under ice bath and cholesterol A (2.82 g, 5.172 mmol) in THF (10 mL) was added dropwise to the reaction mixture over a period of 10 minutes and it was left for 30 min stirring. To this solution Methyl Iodide (2.42 g, 15.516 mmol) was added slowly and stirred for 6 h at room temperature and TLC was checked. After completion the reaction mixture was cooled to 0° C. and quenched with water and extracted with ethyl acetate, dried over anhydrous Na2SO4, concentrated and purified by silica gel chromatography to obtain ester E in 40% yield.

rotavapour. Chloroform was added to the reaction mixture. Compound was extracted with water. Then whole reaction mixture was used for the next reaction after rotavapour treatment.

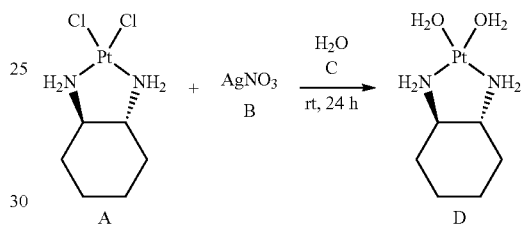

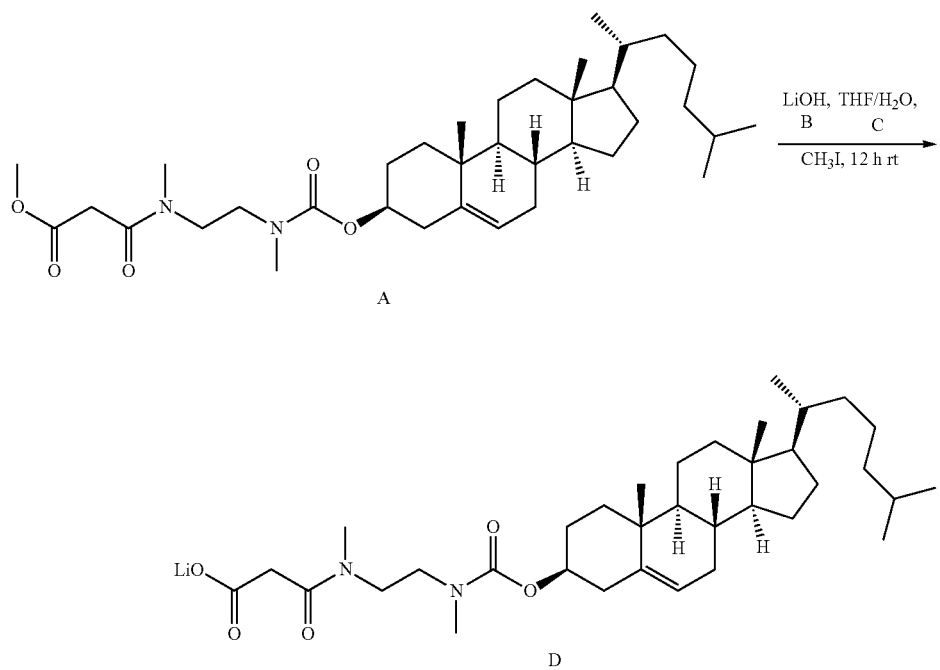

Experimental Procedure: To a 50 mL single neck RBF ester A (0.154 g, 0.263 mmol) was taken in 2 mL of THF/H$_2$O (3:1) and cooled to 0° C. under ice bath. To this ice cooled solution LiOH B (11 mg, 0.263 mmol) was added and was stirred at rt for 3 h, the TLC was checked. After completion the reaction mixture, THF was removed by Experimental Procedure: To a 50 mL single neck RBF DACH platinum A (100 mg, 0.263 mmol) was taken in 10 mL HPLC Water. To the above solution silver nitrate (88 mg, 0.526 mmol) was added. The resulting solution was stirred under protection from light at rt. After 24 h, AgCl precipitate was filtered. Filtrate was used for the next step.

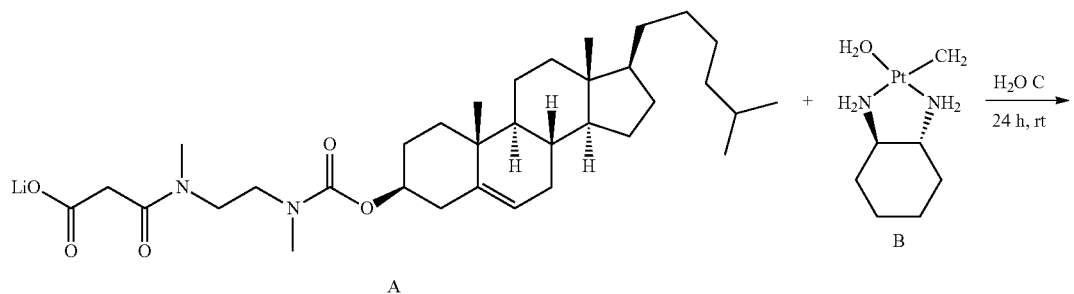

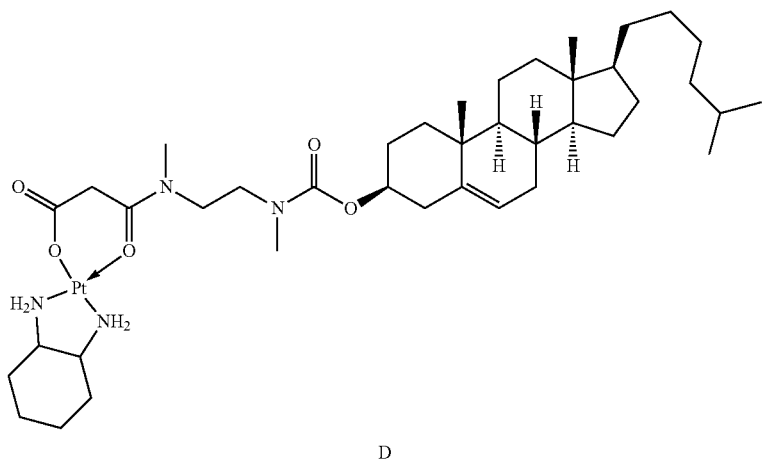

Experimental Procedure: To a 100 mL single neck RBF Acid A (154 mg, 0.263 mmol) was taken in 20 mL HPLC water and the resulting solution was stirred for 5 min at room temperature and to this solution DACH (OH$_2$)$_2$ platinum B was added and it was stirred under protection from light at rt for 24 h. The precipitate was filtered through filter paper and simultaneously washed with HPLC water, HPLC Methanol and HPLC acetone and dried. (Yield 47%)
Synthesis of IO-176_01

Experimental Procedure: To a 50 mL single neck RBF DACH platinum A (100 mg, 0.263 mmol) was taken in 20 mL HPLC Water. To the above solution silver nitrate (44 mg, 0.263 mmol) was added. The resulting solution was stirred under protection from light at rt. After 24 h, AgCl precipitate was filtered. Filtrate was used for the next step.

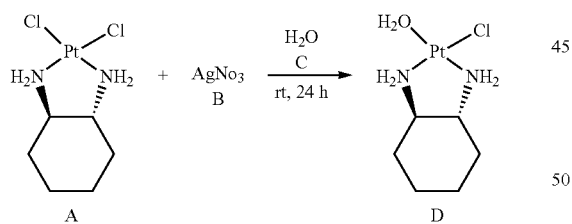

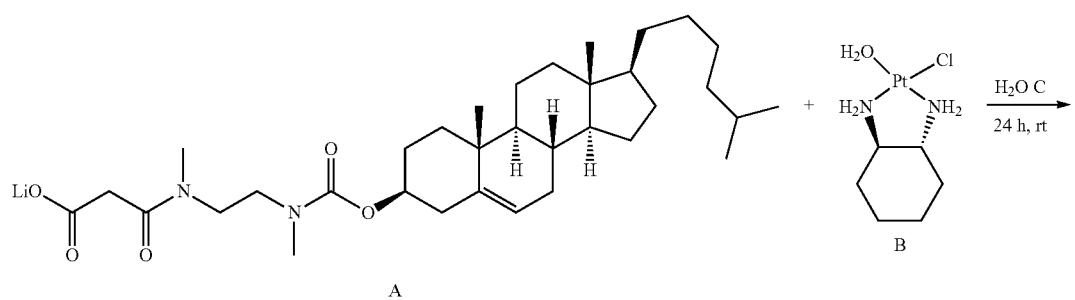

-continued

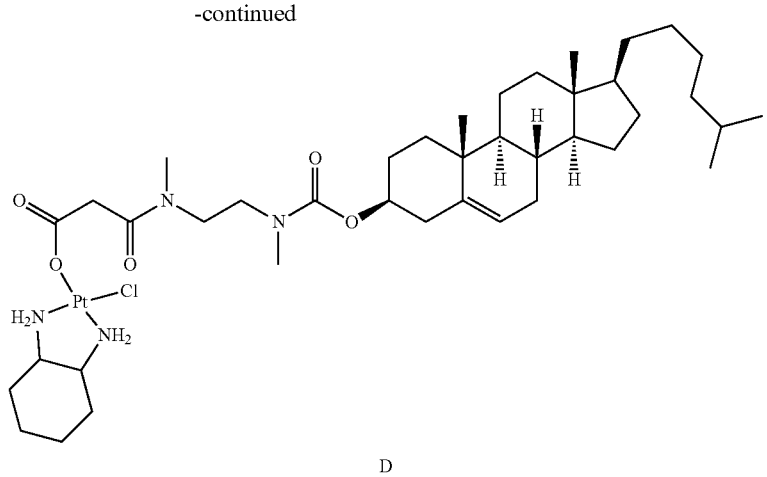

D

Experimental Procedure: To a 100 mL single neck RBF Acid A (same ligand as LB 55c) (154 mg, 0.263 mmol) was taken in 20 mL HPLC water and the resulting solution was stirred for 5 min at room temperature and to this solution DACH $(OH_2)_2$ platinum B (0.263 mmol) was added and it was stirred under protection from light at rt for 24 h. The precipitate was filtered through filter paper and simultaneously washed with HPLC water, HPLC Methanol and HPLC acetone and dried. (Yield 40%)

Synthesis of IO-179_01

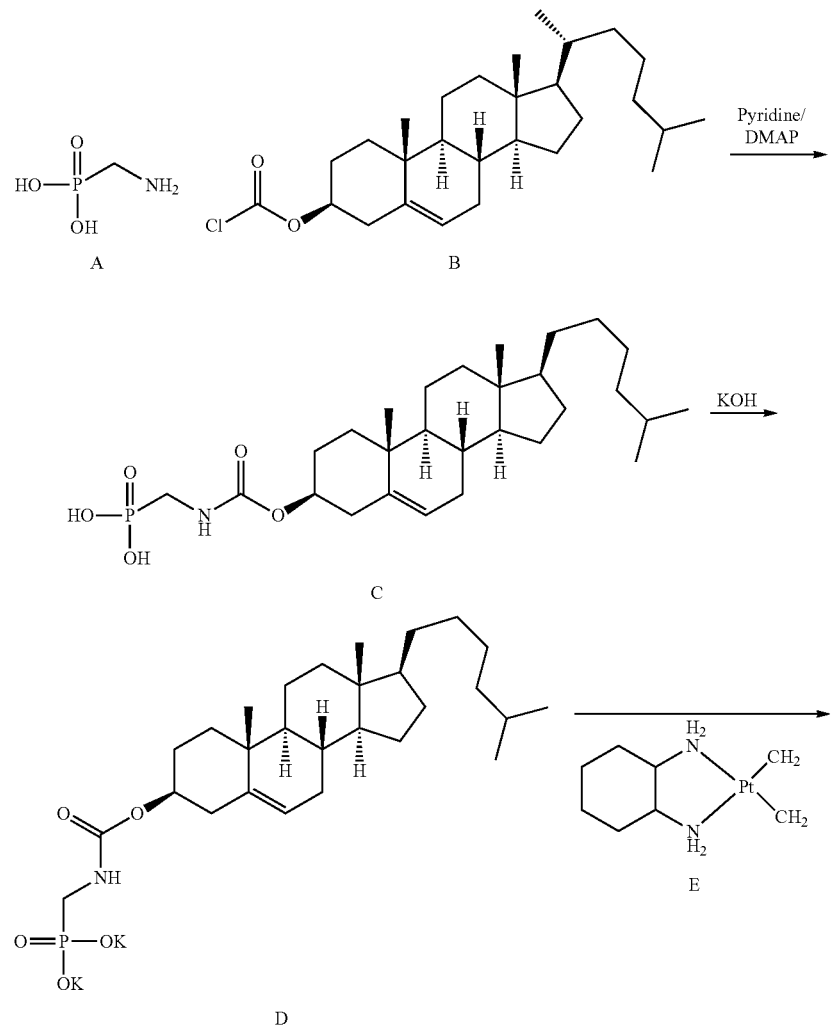

D

-continued

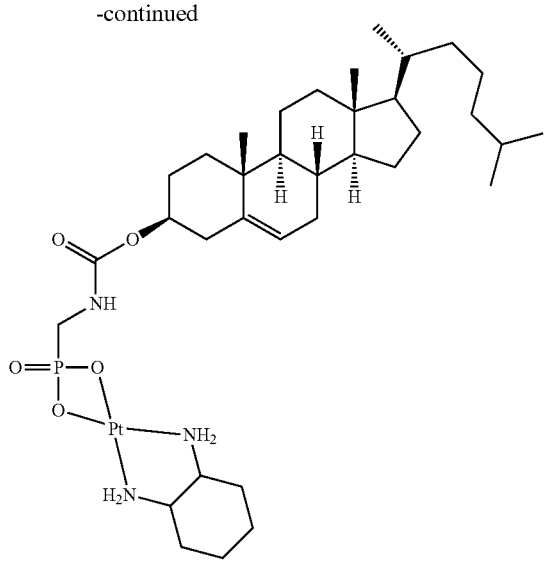

F

Step-1

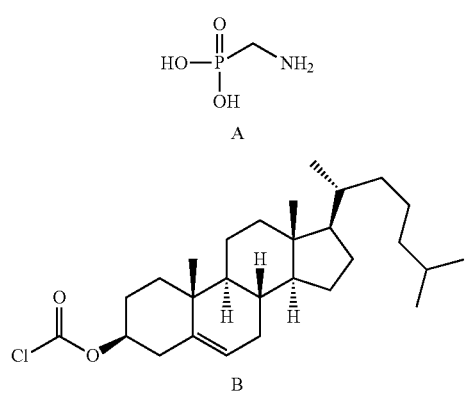

Experimental Procedure: To a 50 mL single neck RBF aminomethylphosphonic acid A (0.77 mmol) is mixed with 2 mL dry pyridine. Cholesterol (0.77 mmol) and DMAP (0.77 mmol) are added to the mixture and the resulting solution is stirred for 16 h at RT. Resulting solution is acidified by dilute sulfuric acid and compound C is extracted by chloroform washing.

Step-2

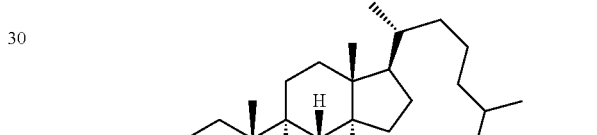

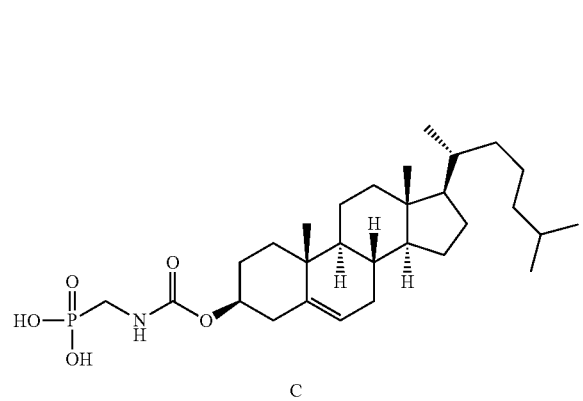

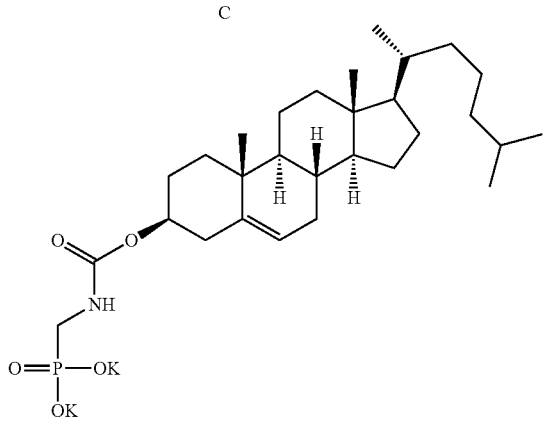

Experimental Procedure: To a 25 mL single neck RBF C (0.13 mmol) is taken in 1 mL THF. To this solution KOH (0.26 mmol) in 1 ml water is added at 0° C. Immediate ppt appeared. 2 ml water is added to dissolve the ppt and the resulting solution is stirred for 2 h at RT. Reaction mixture is given chloroform wash and the water layer is used for next step.

Step 3

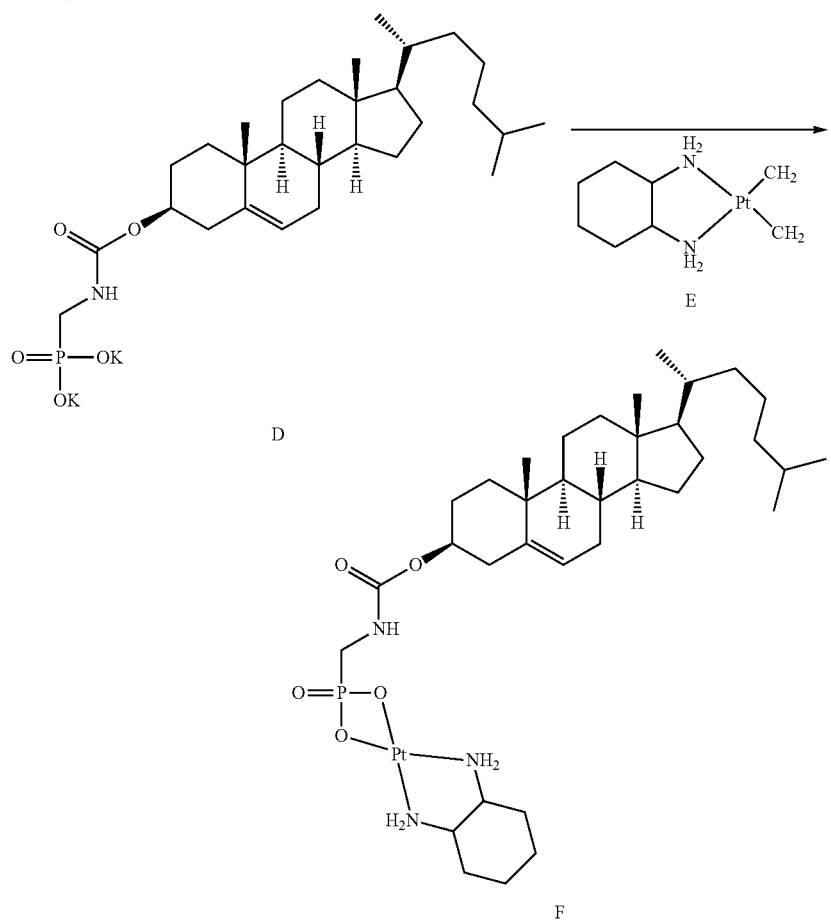

Experimental Procedure: To a 50 mL single neck RBF (0.13 m mol) E is taken in 5 mL water. D (0.13 m mol) in 15 ml water is added at RT and the resulting solution is stirred for 24 h at RT. White precipitate formed during the reaction. Reaction mixture centrifuged and precipitate is given water wash and then lyophilized to get F as white powder.

Synthesis of IO-179_02

Step-1

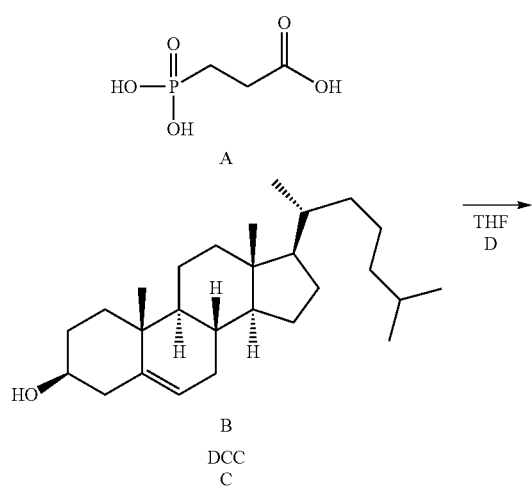

-continued

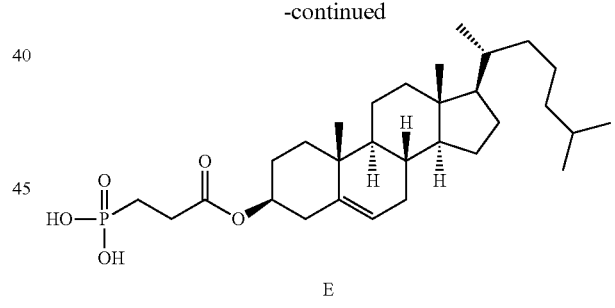

Experimental Procedure: To a 50 mL single neck RBF phosphopropionic acid A (0.77 mmol, 119 mg) was taken in 5 mL dry THF. Cholesterol (200 mg, 0.52 mmol) and DCC (160 mg, 0.77 mmol) were added at 0° C. and the resulting solution was stirred for 16 h at RT. White precipitate formed during the reaction. White ppt separated by filtration; washed with 5 ml THF. Solvent evaporated and washed with hexane to get the product as 150 mg of white powder. $^1$H NMR(CDCl$_3$): 0.67-2.66 (m), 4.22(s), 5.36(s), 8.18(br, s). $^{13}$C NMR(CDCl$_3$): 11.83, 18.74, 19.23, 21.04, 22.55, 22.81, 23.97, 24.28, 24.71, 27.43, 28.00, 28.24, 29.84, 31.82, 31.94, 33.32, 35.85, 36.21, 36.39, 36.96, 39.49, 39.73, 40.13, 42.31, 49.96, 56.23, 56.67, 122.88, 139.48, 176.78(d) ESIMS(-ve mode): 521.3(M–H)

Step-2
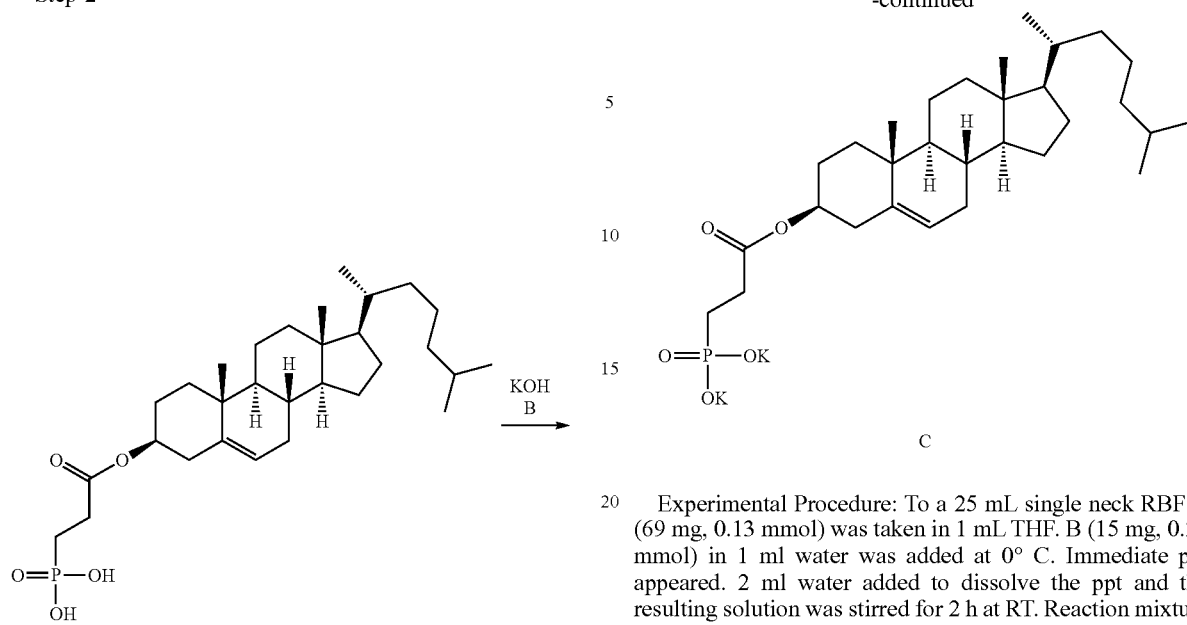
Experimental Procedure: To a 25 mL single neck RBF A (69 mg, 0.13 mmol) was taken in 1 mL THF. B (15 mg, 0.26 mmol) in 1 ml water was added at 0° C. Immediate ppt appeared. 2 ml water added to dissolve the ppt and the resulting solution was stirred for 2 h at RT. Reaction mixture was given chloroform wash and the water layer was used for next step.
Step 3
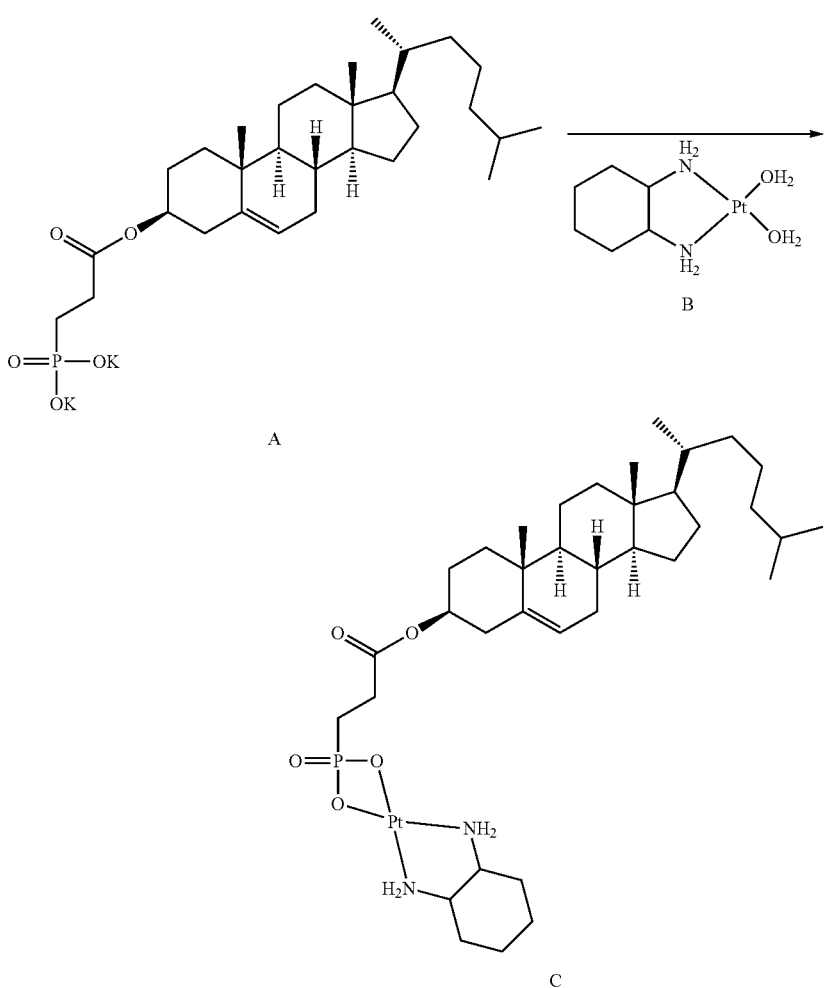

Experimental Procedure: To a 100 mL single neck RBF B (0.13 m mol) was taken in 5 mL water. A (0.13 m mol) in 15 ml water was added at RT and the resulting solution was stirred for 2 h at RT. White precipitate formed during the reaction. Reaction mixture centrifuged and precipitate was given water wash and then lyophilized to get 50 mg of white powder.
Synthesis of IO-179_03
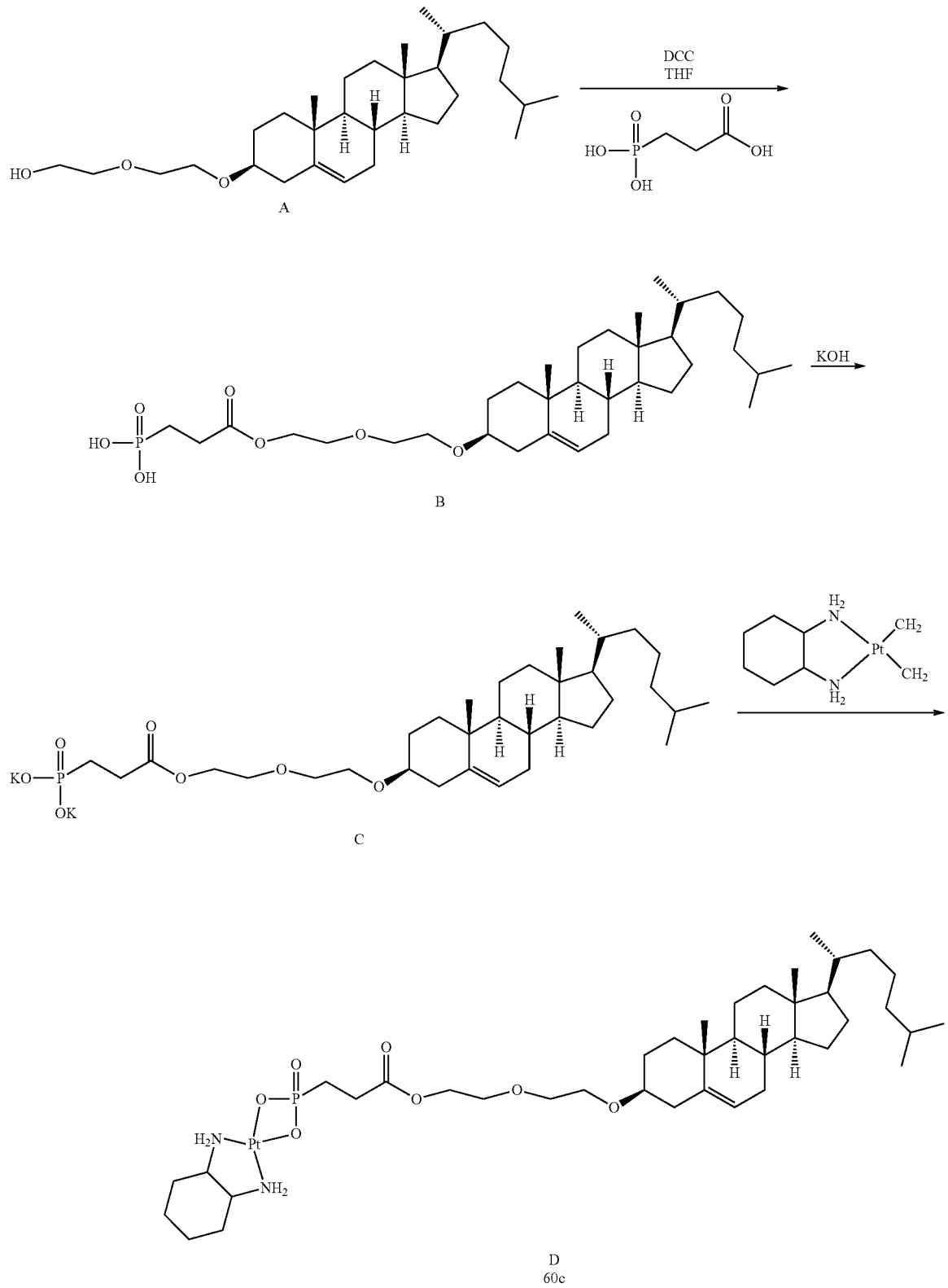

Experimental Procedure: Compound A is prepared according to the procedure described in the preparation of IO-183_01. All the successive steps have carried out according to the preparation of IO-179_02.
Synthesis of IO-180_01
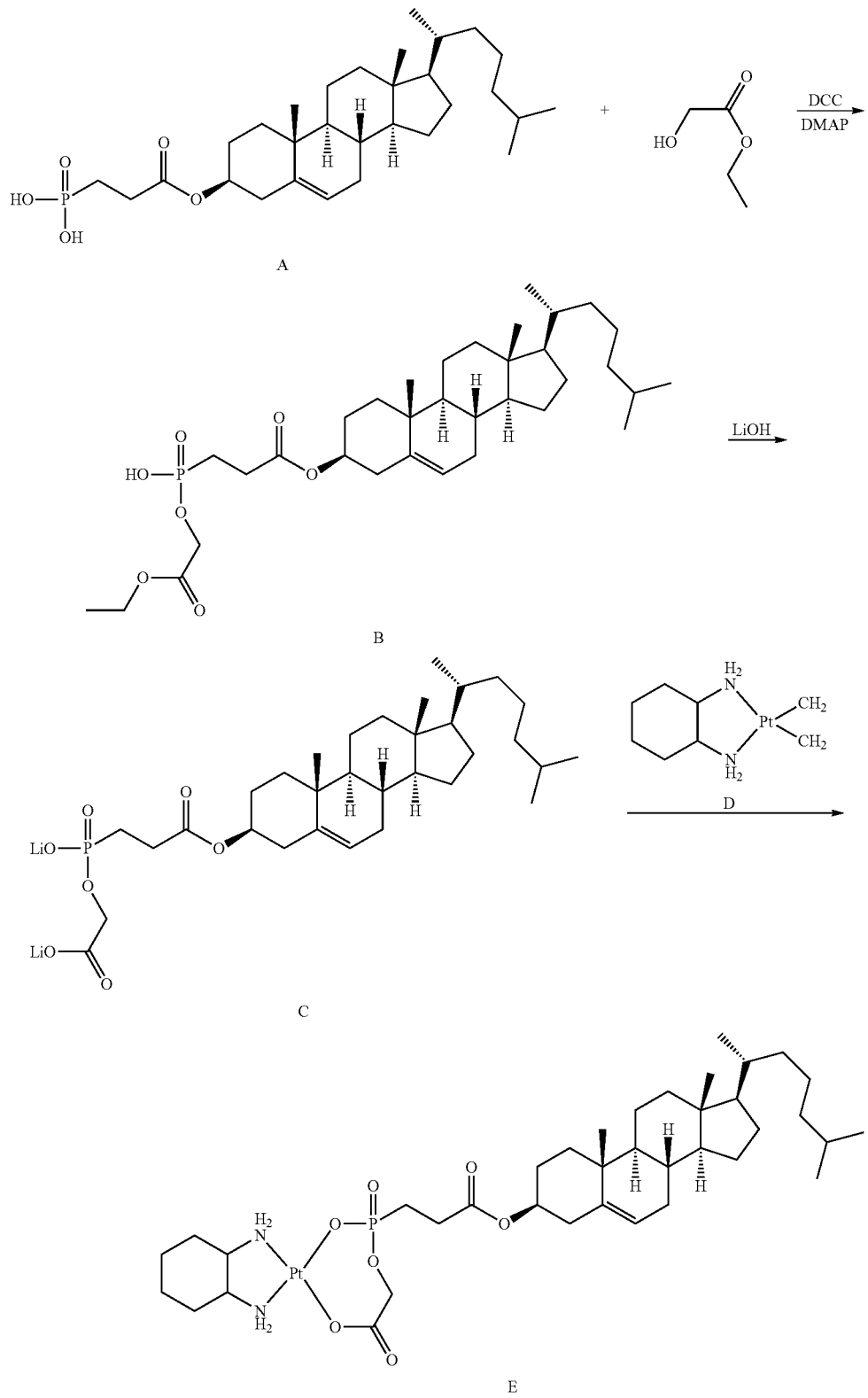

-continued
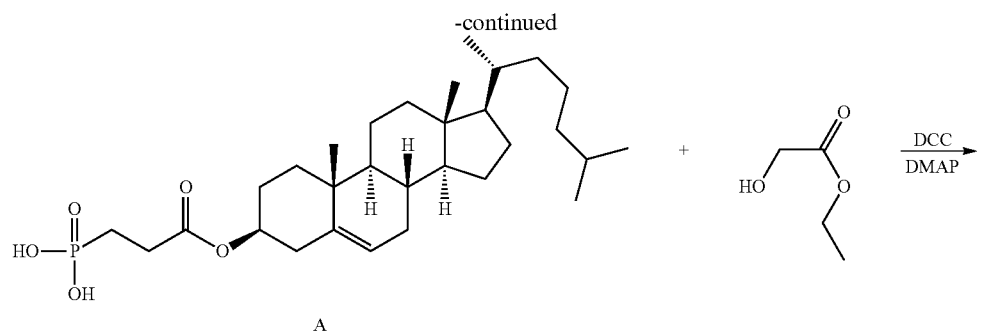
A
B
Experimental Procedure: To a 50 mL single neck RBF A (same compound as 60b step 1 product) (1 mmol) was taken in 25 mL dry THF. Ethyl Glycolate (1 mmol) and DCC (1 mmol) and DMAP (0.1 mmol) were added at 0° C. and the resulting solution was stirred for 16 h at RT. Compound separated as pasty solid by silica gel column chromatography.
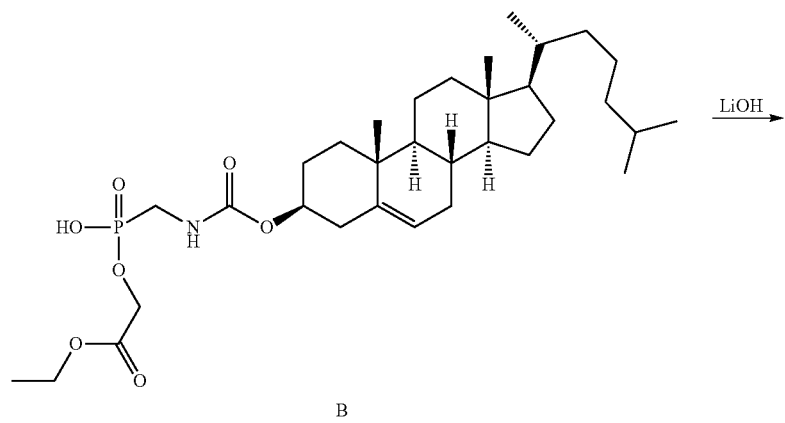
B

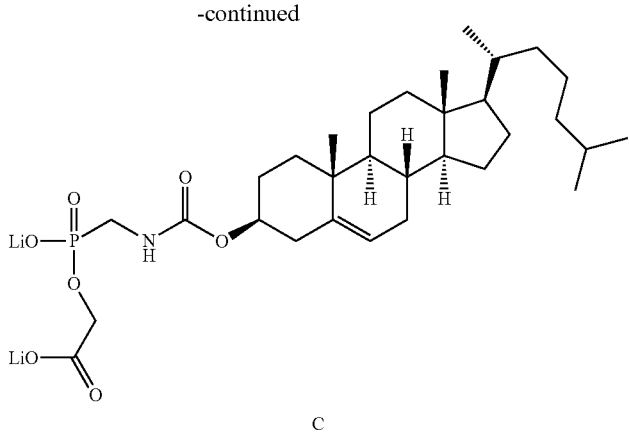

C

Experimental Procedure: To a 25 mL single neck RBF B (0.13 mmol) was taken in 3 mL THF. LiOH (0.26 mmol) in 1 ml water was added at 0° C. Reaction mixture was stirred for 4 h at RT. Reaction mixture was given chloroform wash and the water layer was used for next step.

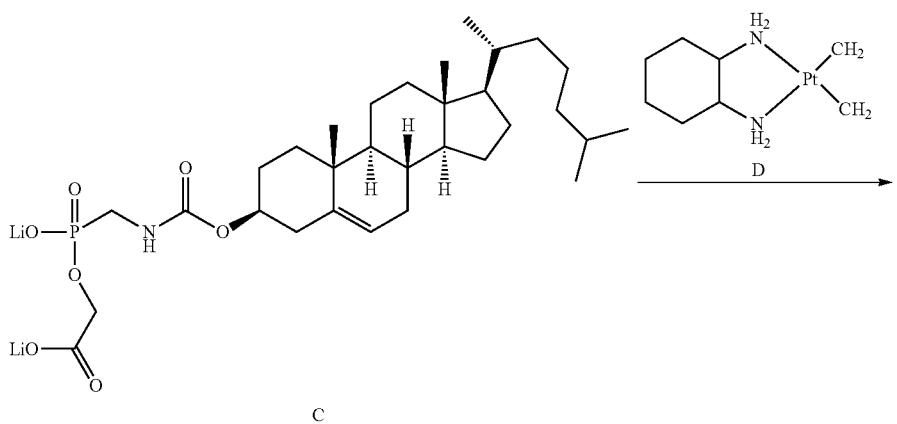

C

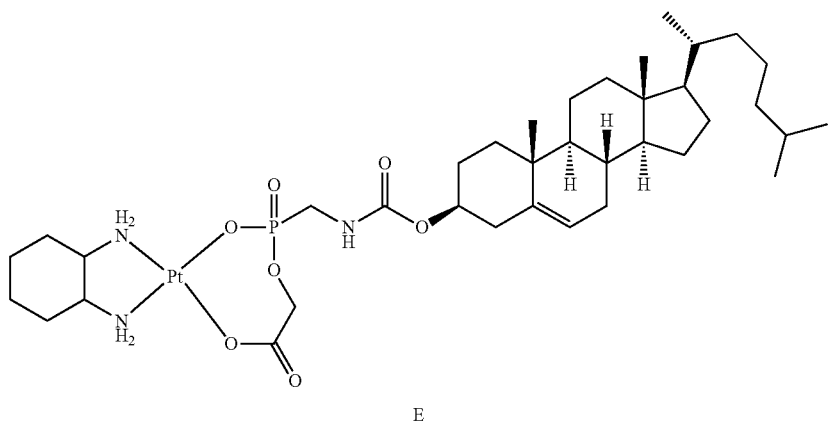

E

Experimental Procedure: To a 100 mL single neck RBF D (0.13 m mol) was taken in 5 mL water. C (0.13 m mol) in 15 ml water was added dropwise at RT and the resulting solution was stirred for 20 h at RT. White precipitate formed during the reaction. Reaction mixture centrifuged and precipitate was given water wash and then lyophilized to get E as white powder.

Synthesis of IO-180_02
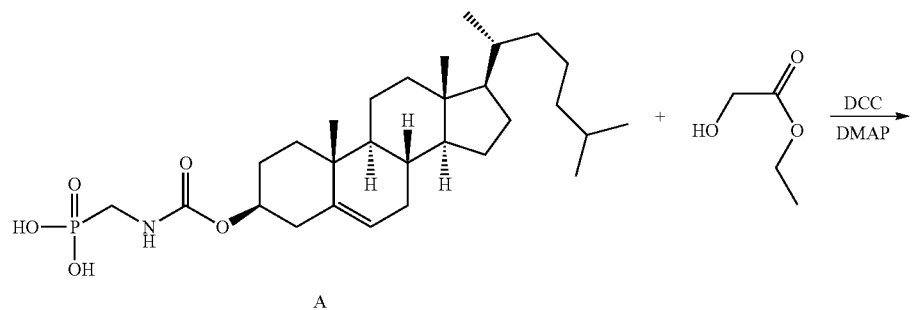
A
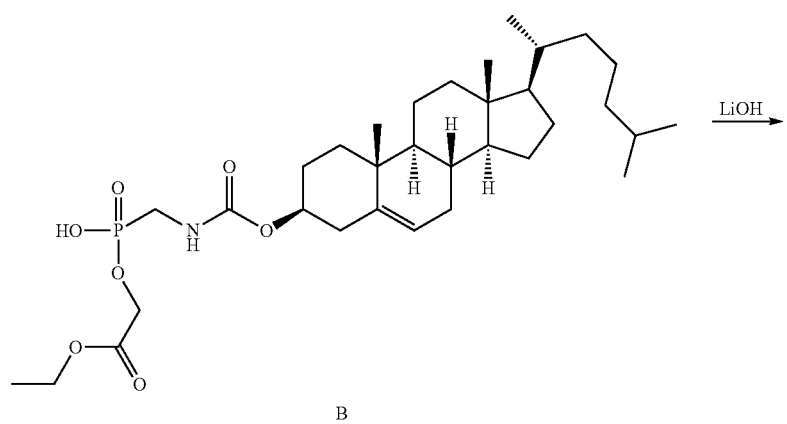
B
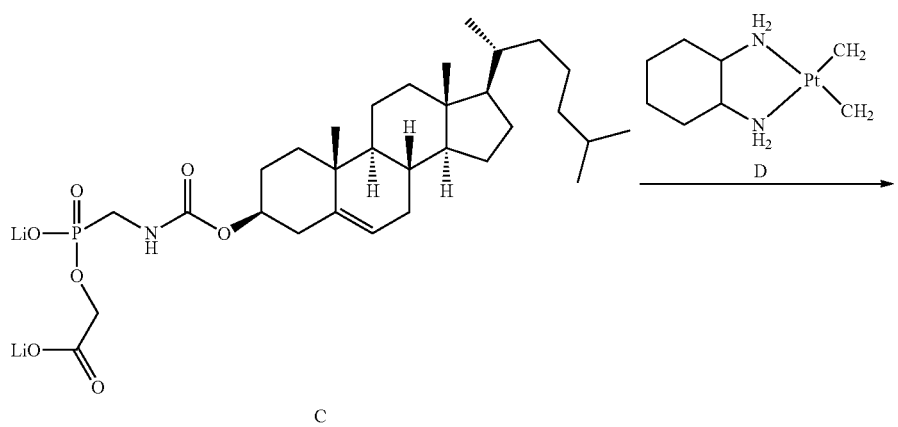
C
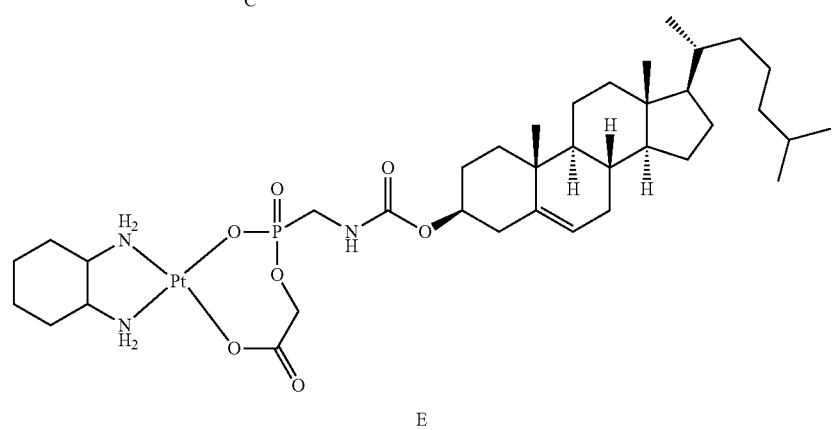
E

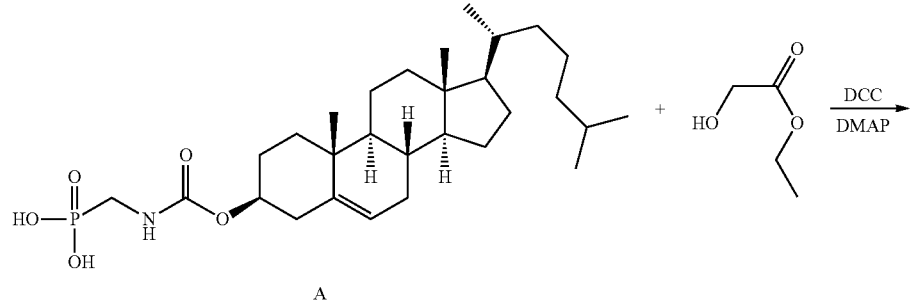
A
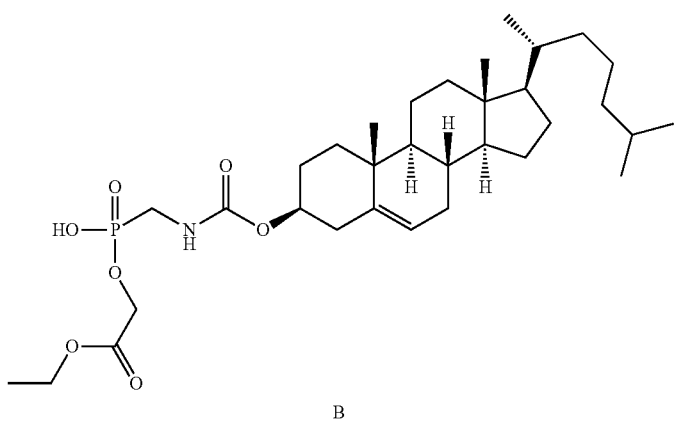
B
Experimental Procedure: To a 50 mL single neck RBF A (same compound as 60a step 1 product) (1 mmol) is taken in 25 mL dry THF. Ethyl Glycolate (1 mmol) and DCC (1 mmol) and DMAP (0.1 mmol) are added at 0° C. and the resulting solution is stirred for 16 h at RT. Compound is separated as pasty solid by silica gel column chromatography.
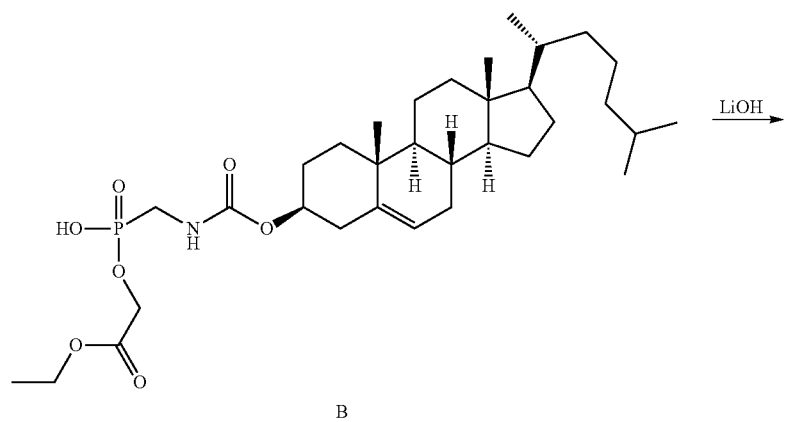
B

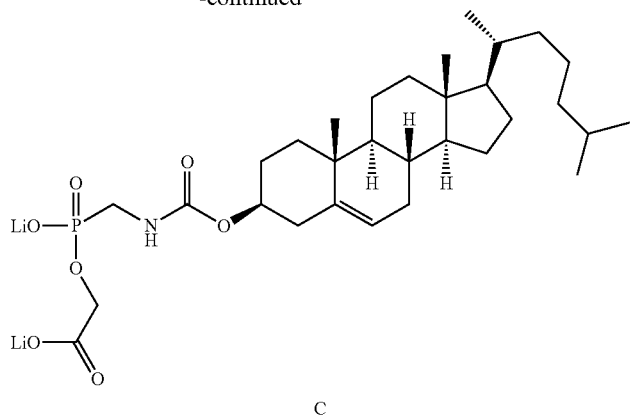
C
Experimental Procedure: To a 25 mL single neck RBF B (0.13 mmol) is taken in 3 mL THF. LiOH (0.26 mmol) in 1 ml water is added at 0° C. Reaction mixture is stirred for 4 h at RT. Reaction mixture is given chloroform wash and the water layer is used for next step.
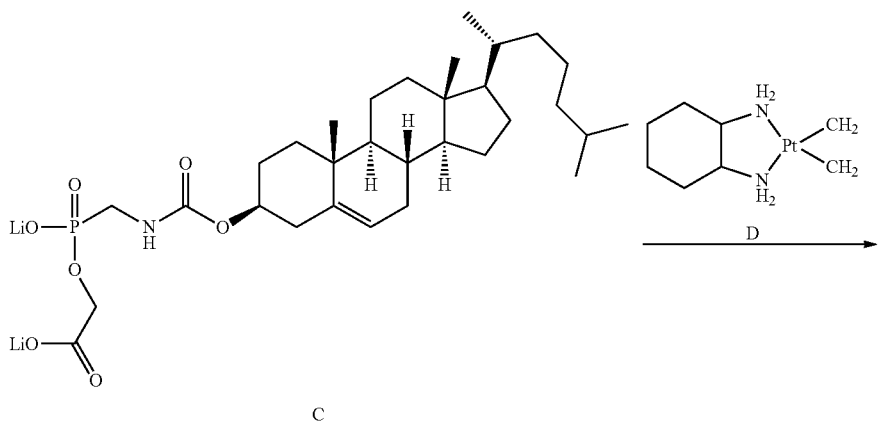
C
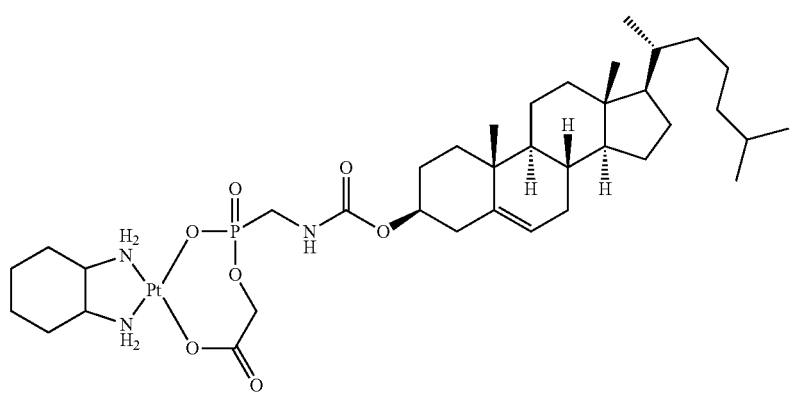
E Experimental Procedure: To a 100 mL single neck RBF D (0.13 m mol) is taken in 5 mL water. C (0.13 m mol) in 15 ml water is added at RT and the resulting solution is stirred for 20 h at RT. White precipitate formed during the reaction. Reaction mixture centrifuged and precipitate is given water wash and then lyophilized to get E as white powder.
Synthesis of IO-180_03
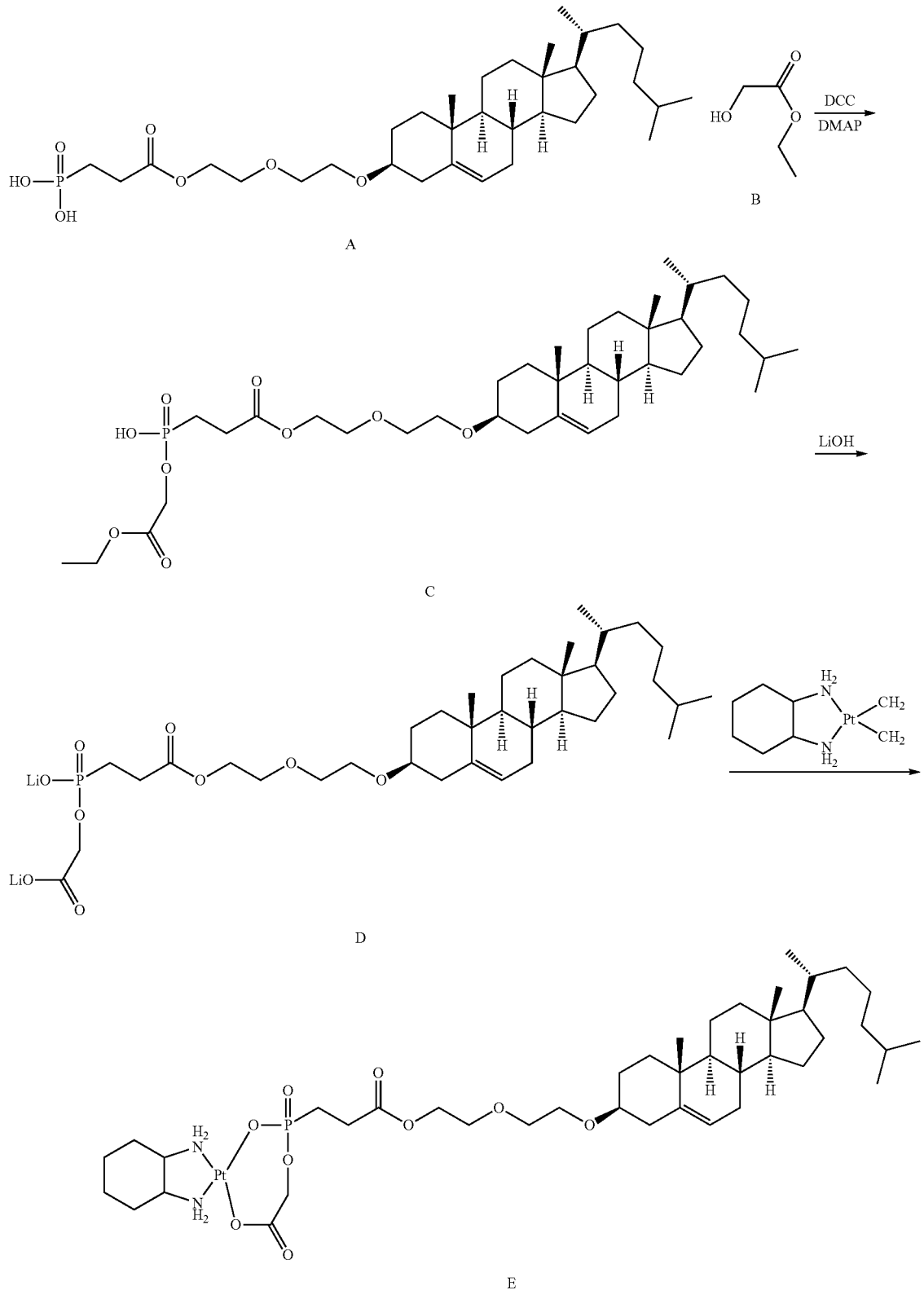

Experimental Procedure: Compound E is prepared following the similar procedure described for the preparation of IO-180_01.
Synthesis of IO-184_01
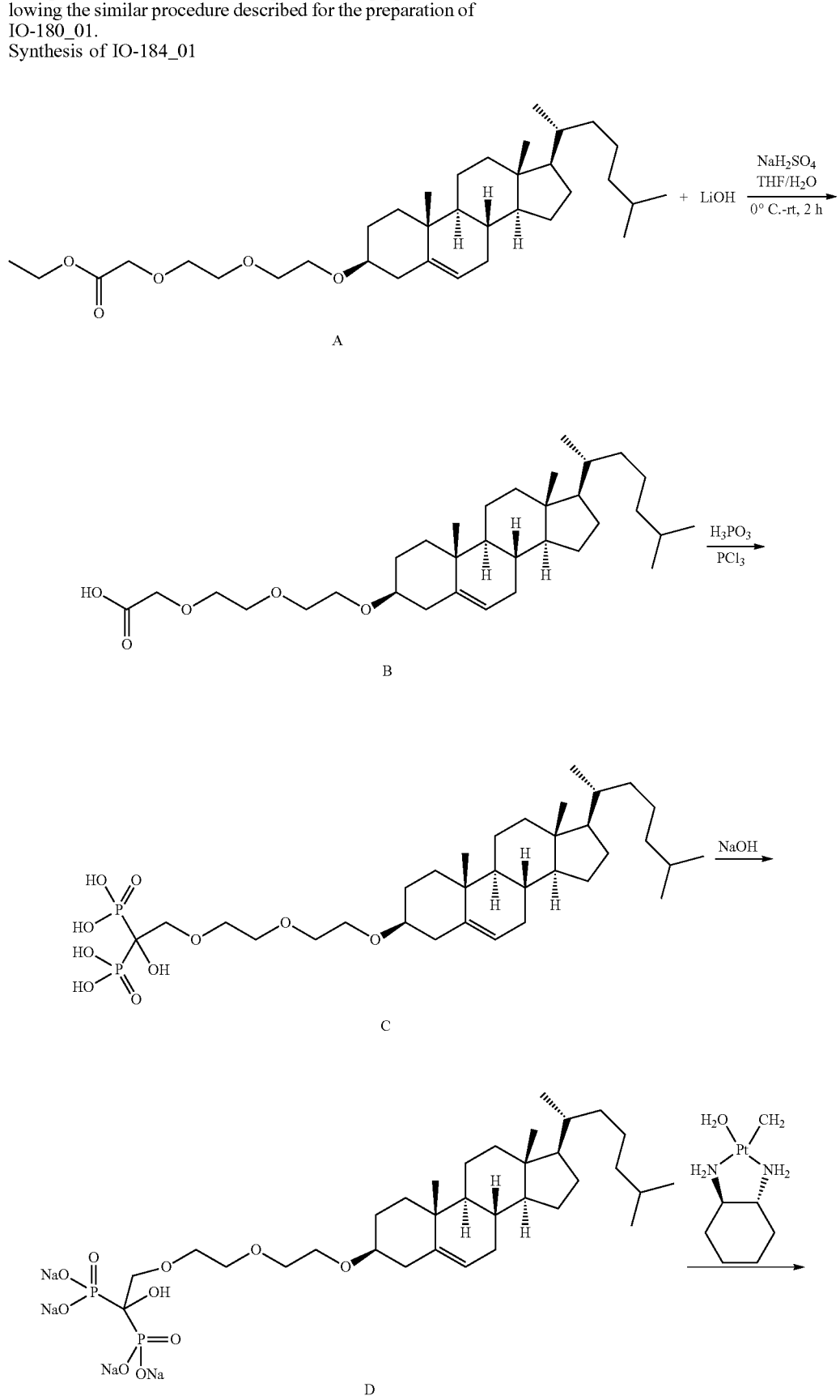

-continued

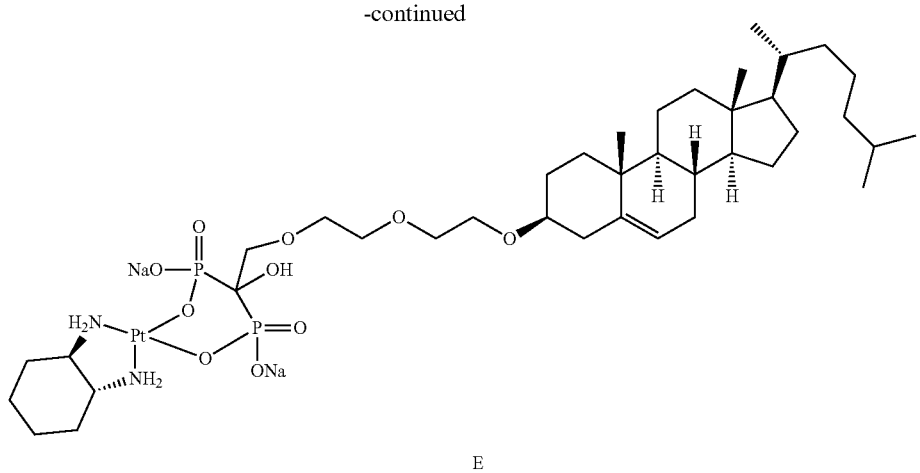

E

Step 1:

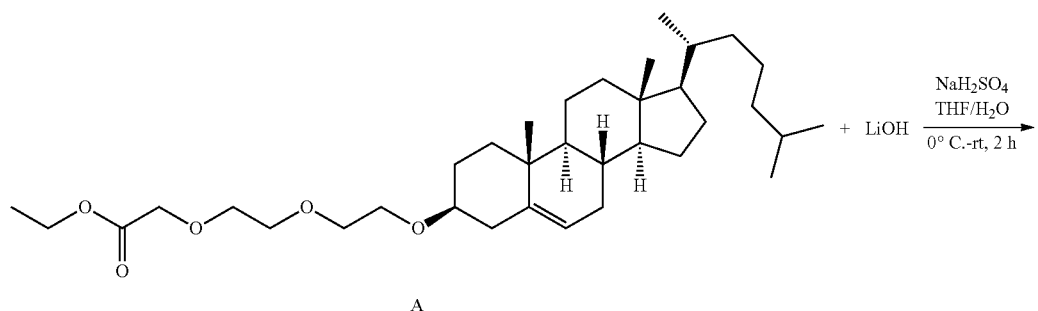

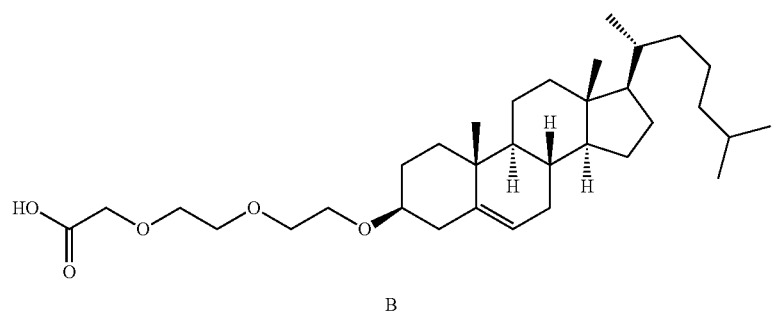

B

Experimental Procedure: To a 100 mL single neck RBF ester A (1.272 g, 2.27 mmol) was taken in 20 mL of THF/H$_2$O (3:1) and cooled to 0° C. under ice bath. To this ice cooled solution LiOH (136 mg, 5.67 mmol) was added and was stirred at rt for overnight, the TLC was checked. After completion the reaction mixture was extracted with ethyl acetate and washed with sodium dihydrogen sulphate solution (40 mL) and brine (20 mL) successively. The organic layer was dried over anhydrous Na$_2$SO$_4$ and concentrated under vacuum and column was performed to yield 1 gm of pure B as white powder.

Step 2:

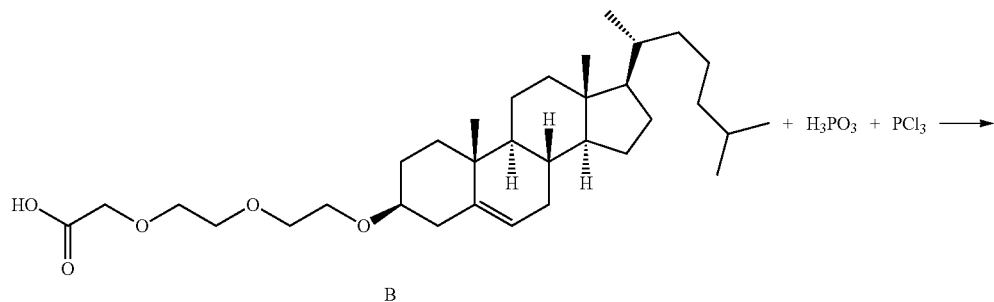

B

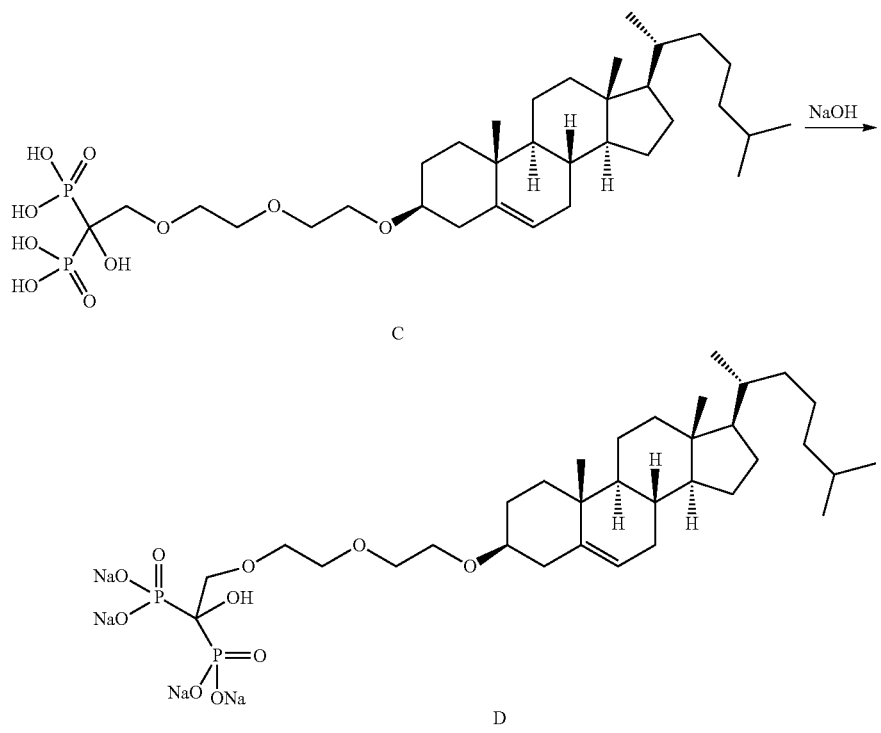

Experimental Procedure: A mixture of B (532 mg, 1 mmol) and $H_3PO_3$ (2 mmol) is heated to 60° C. under $N_2$, until a homogeneous mixture is achieved. $PCl_3$ (1 mmol) is added dropwise and stirred at 60° C. for 2 h. The resulting mixture is cooled to room temperature and extracted by water. Water solution is lyophilized to get compound. C.

Experimental Procedure: To a 25 mL single neck RBF C (0.13 mmol) is taken in 1 mL THF. Sodium hydroxide (0.54 mmol) in 2 ml water is added at 0° C. Resulting solution is stirred for 2 h at RT. Reaction mixture has given chloroform wash and the water layer is used for next step.

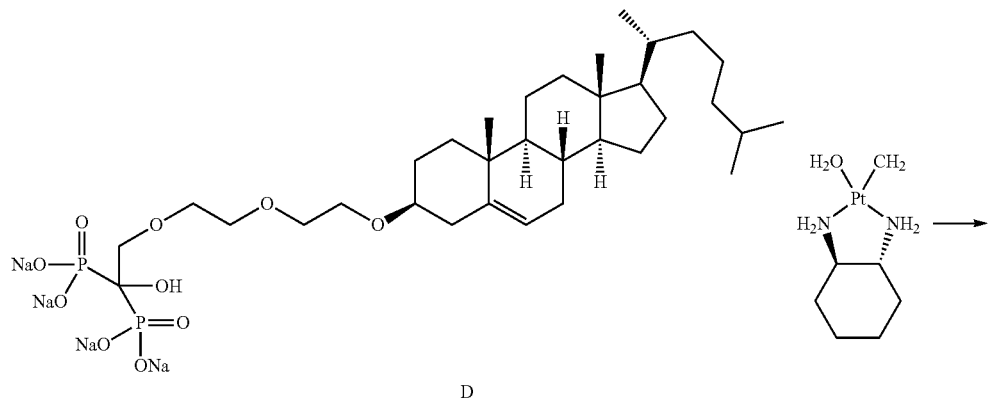

D

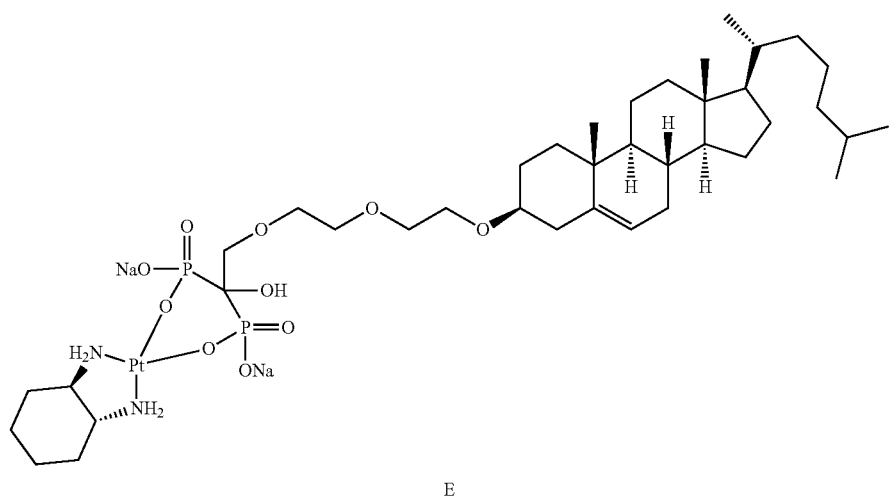

E

Experimental Procedure: To a 100 mL single neck RBF Aquated platinum diaminocyclohexane (0.13 m mol) in 15 ml water is taken. D (0.13 m mol) in 5 mL water is added at RT and the resulting solution is stirred for 2 h at RT. White precipitate formed during the reaction. Reaction mixture centrifuged and precipitate was given water wash to get E as white powder.

Synthesis of IO-190_01

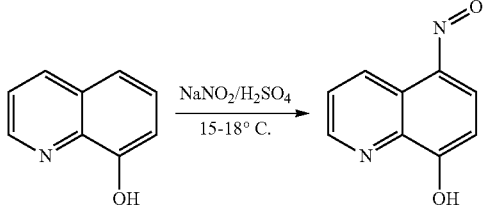 [SMILES: Oc1cccc2cccnc12 ; O=Nc1ccc(O)c2ncccc12]

8-Hydroxyquinoline (7.34 g, 0.05 mol) was dissolved in a continuously stirred solution of 66.7 mL of distilled water and 3 mL of concentrated sulfuric acid at 15-18_C. Sodium nitrite (3.67 g) in distilled water (6.78 mL), was added drop wise to the reaction mixture over a period of 30-40 min at 15-18_C, mixture was maintained at this temperature for 3 h. The reaction mixture was neutralized with 40% sodium hydroxide solution. It was then acidified with glacial acetic acid to pH 3.0-4.0. Yellow precipitate obtained was filtered, washed with distilled water, and dried. Yield: 6.7 g (89.5%).

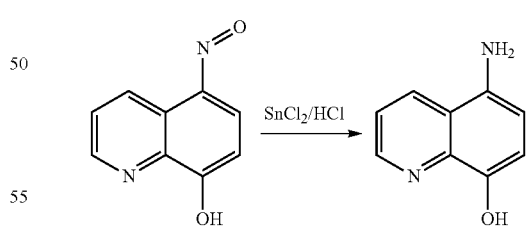

0.174 g (0.01 mol) of 5-nitroso-8-hydroxyquinoline in 25 mL of concentrated hydrochloric acid was allowed to warm. To this was added slowly, in small portions tin (Sn) metal (0.236 g, 0.02 mol). The reaction mixture was heated at reflux for 6 h in boiling water bath. The reaction mixture was allowed to cool to room temperature. To the reaction mixture was slowly added 20% solution of sodium hydroxide to get the precipitate. 5-Amino-8-hydroxyquinoline was extracted with ether. Yield: 0.154 g (79.87%).

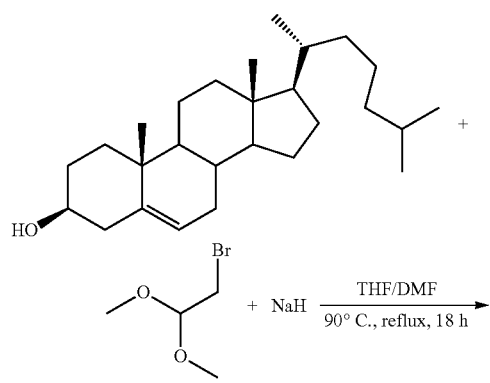

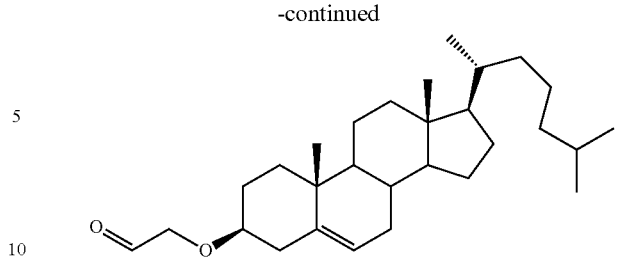

Trifluoroacetic acid/water (1:1) (2.5 mL, 16.2 mmol) was added to a solution of cholesterol acetal (0.5 g, 1 mmol) in 10 mL of CH$_2$Cl$_2$, and the mixture was stirred at room temperature for 6 h. The mixture was neutralized with 1N NaOH, extracted twice with CH$_2$Cl$_2$, dried over Na$_2$SO$_4$, filtered and concentrated, to obtain the product as white solid.

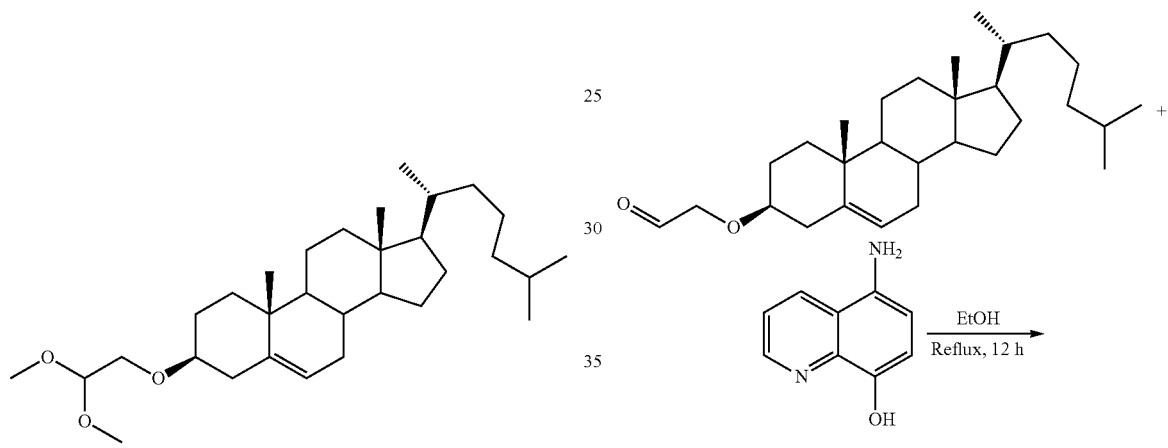

Cholesterol (1 g, 2.6 mmol) was dissolved in 40 mL of THF/DMF (1:1) and 60% sodium hydride (w/w) in mineral oil (0.6 g, 15.5 mmol) was added, followed by stirring for 10 min. 2-bromo-1,1-dimethoxy ethane (1.21 mL, 7.8 mmol) was added dropwise, and the mixture was stirred at 90° C. under reflux for 18 h. The mixture was cooled and CH$_2$Cl$_2$/MeOH (1:1) was added to eliminate excess NaH. After elimination of solvent was eliminated under vacuo, the residue was taken up in EtOAc, washed several times with water, dried over Na$_2$SO$_4$, filtered and concentrated. The crude was purified by flash column chromatography on silica gel using 2-10% P.E. in EtOAc, to obtain the product as a white solid, yield 1.23 g, 94%.

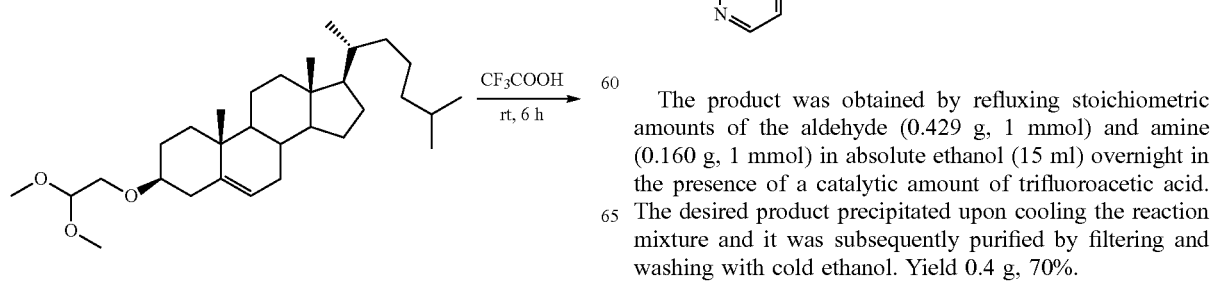

The product was obtained by refluxing stoichiometric amounts of the aldehyde (0.429 g, 1 mmol) and amine (0.160 g, 1 mmol) in absolute ethanol (15 ml) overnight in the presence of a catalytic amount of trifluoroacetic acid. The desired product precipitated upon cooling the reaction mixture and it was subsequently purified by filtering and washing with cold ethanol. Yield 0.4 g, 70%.

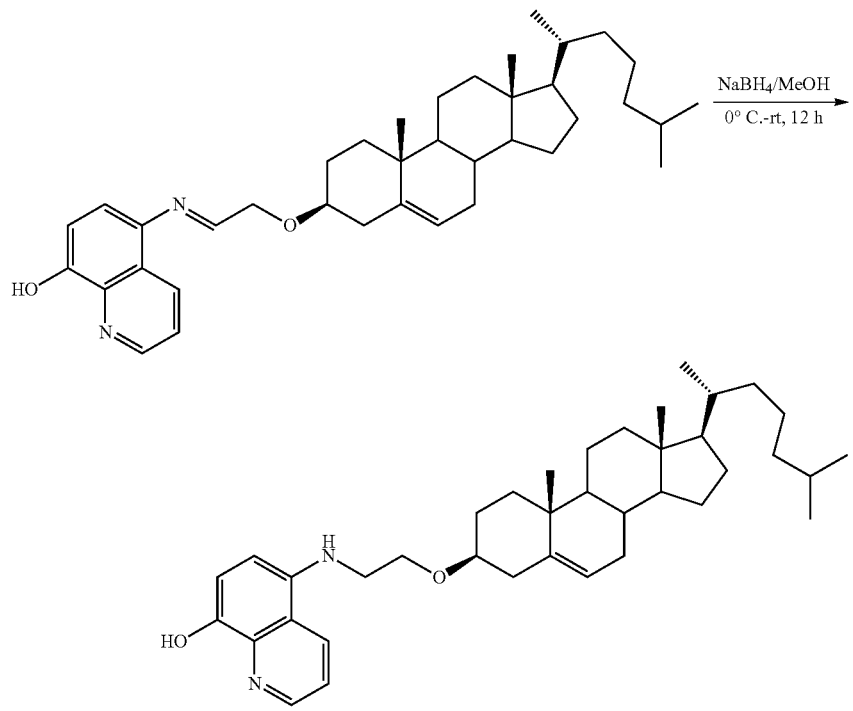

Sodium borohydride (0.875 g, 23.12 mmol) was added portion-wise to cholesterol quinoline (0.617 g, 1.08 mmol) in C₂H₅OH:THF mixture (1:1) at room temperature under inert atmosphere. After 6 hour stirring at room temperature, the solvent was evaporated and the residue washed with saturated brine solution and was extracted with DCM to get light yellowish crystalline solid. Yield: 384 mg (62%).

To a 100 mL single neck RBF, cholesterol quinoline (0.151 g, 0.263 mmol) was taken in 3 mL of THF and cooled to 0° C. under ice bath. To this ice cooled solution LiOH (11 mg, 0.263 mmol) in 1 mL H₂O was added and was stirred at rt for 2 h, the TLC was checked. After completion the reaction mixture, THF was removed by rotavapour. Chloroform was added to the reaction mixture. Compound was extracted with water. Then whole reaction mixture was used for the next reaction after rotavapour treatment.

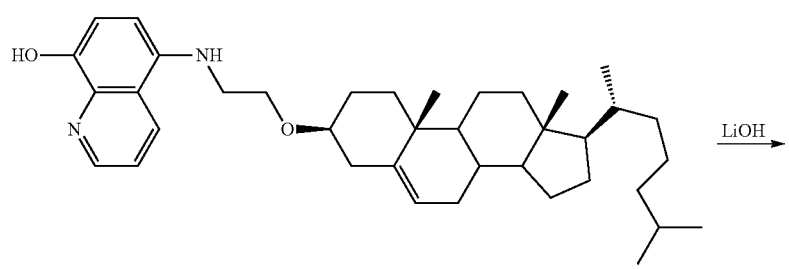

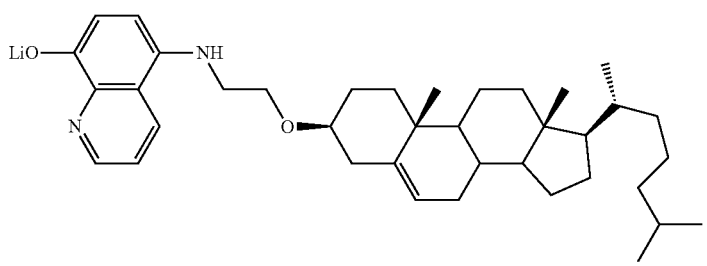

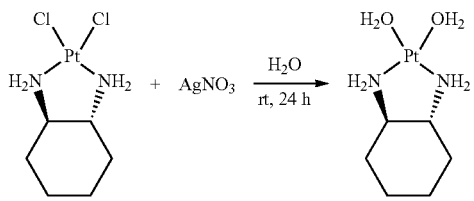

To a 50 mL single neck RBF, DACH platinum (100 mg, 0.263 mmol) was taken in 10 mL HPLC Water. To the above solution silver nitrate (89 mg, 0.526 mmol) was added. The resulting solution was stirred under protection from light at rt. After 24 h, AgCl precipitate was filtered. Filtrate was used for the next step.

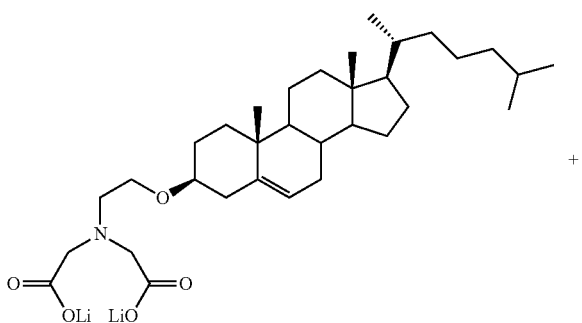

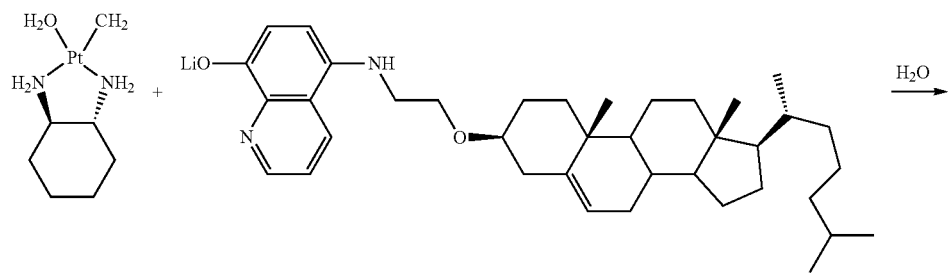

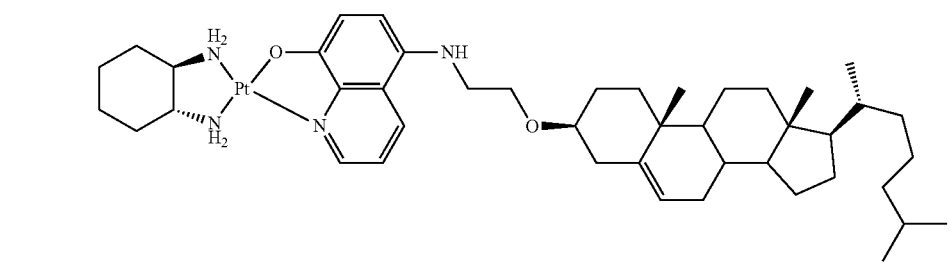

To a 100 mL single neck RBF, Lithium salt of cholesterol quinoline (161 mg, 0.263 mmol) was taken in 20 mL HPLC water and the resulting solution was stirred for 5 min at room temperature and to this solution DACH (OH$_2$)$_2$ platinum was added and it was stirred under protection from light at rt for 24 h. The precipitate was filtered through filter paper and simultaneously washed with HPLC water, HPLC Methanol and HPLC acetone and dried. (Yield 60%).

Synthesis of compound IO-185_01, IO-186_01, IO-187_01, IO-188_01, IO-189_01, IO-183_03, IO-183_04, IO-180_04

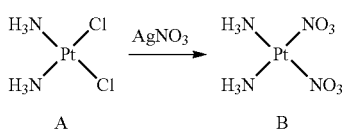

A        B

Synthesis of Aquated Cisplatin(B): 0.17 mmol diamminplatinum-dichloride(A), 0.34 mmol silver nitrate and 7 mL water were added in a 25 mL RB and stirred for 48 h at room temp. Solution was centrifuged (4,000 rpm; 10 min) and white precipitate was filtered through syringe filter (25 mm/0.20 μm). Washed with 2 mL of water. Filtrate used for next reaction.

-continued

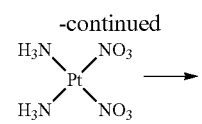

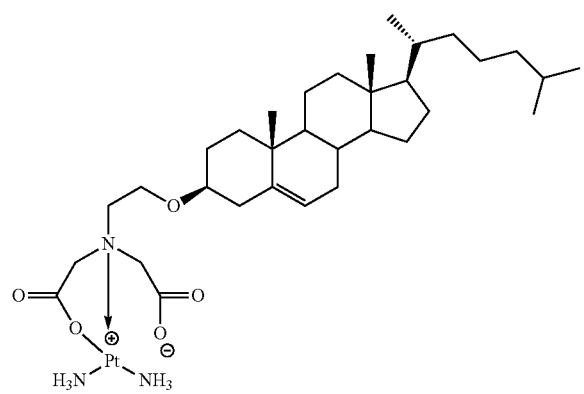

Synthesis of IO-185: Procedure is similar as described for compound 25.

277
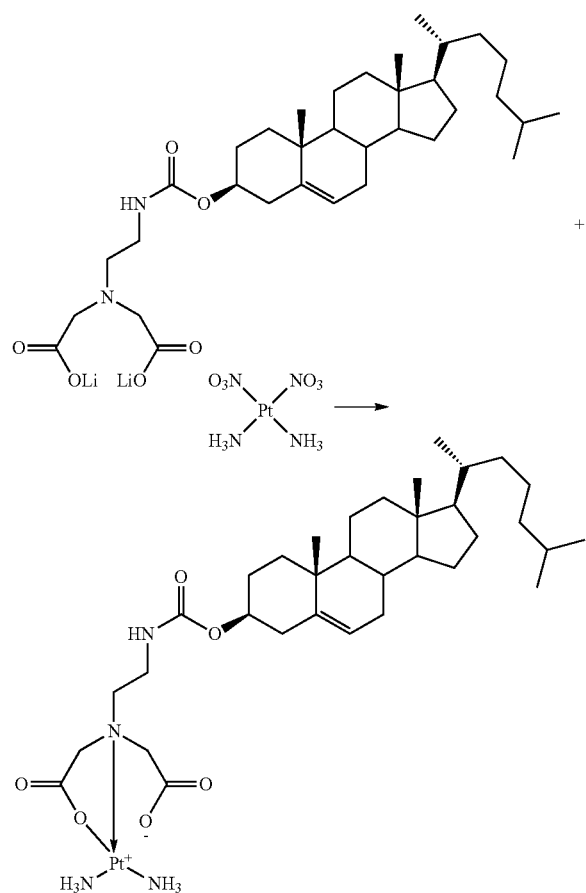
Synthesis of IO-186: Procedure is similar as described for compound 26.
Synthesis of IO-187: Procedure is similar as described for compound 27.
278
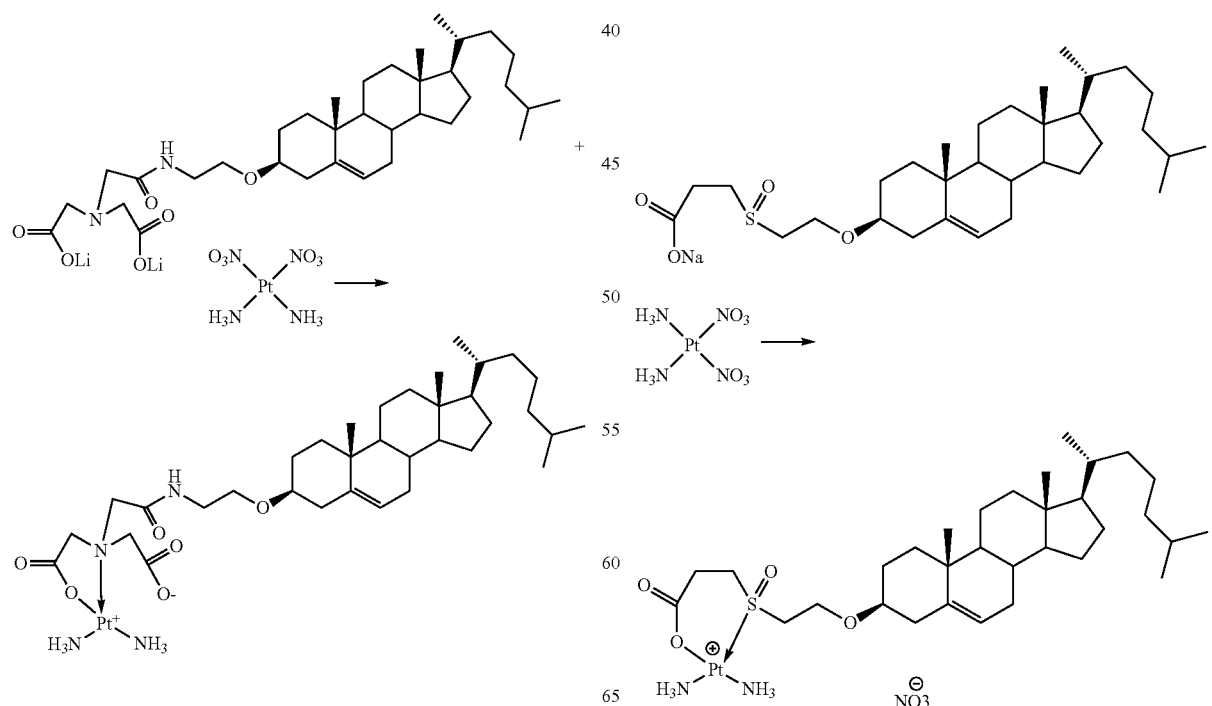
Synthesis of IO-188: Procedure is similar as described for compound 28.

Synthesis of IO-189: Procedure is similar as described for compound IO-131.
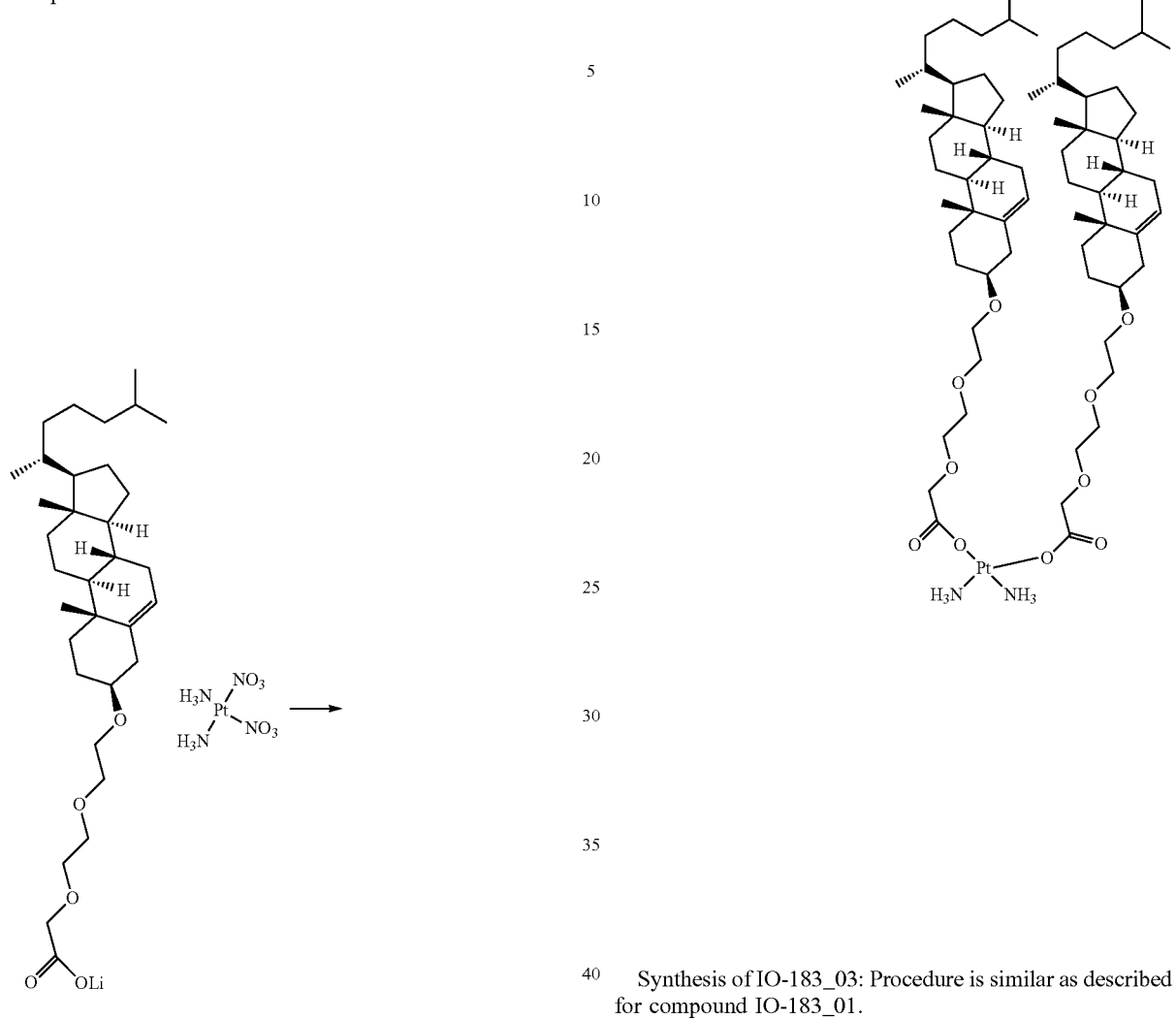
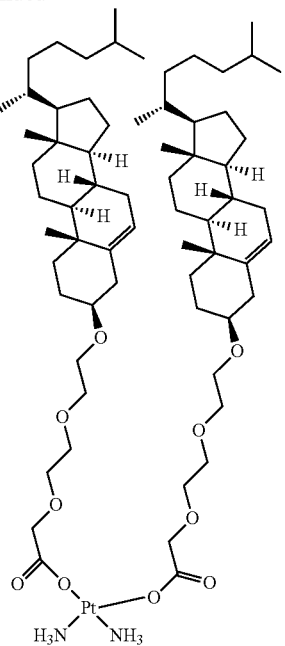
Synthesis of IO-183_03: Procedure is similar as described for compound IO-183_01.
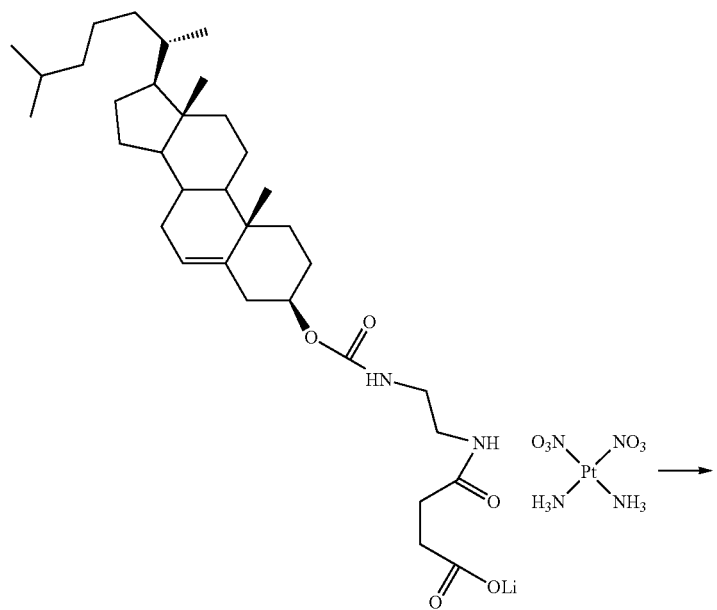

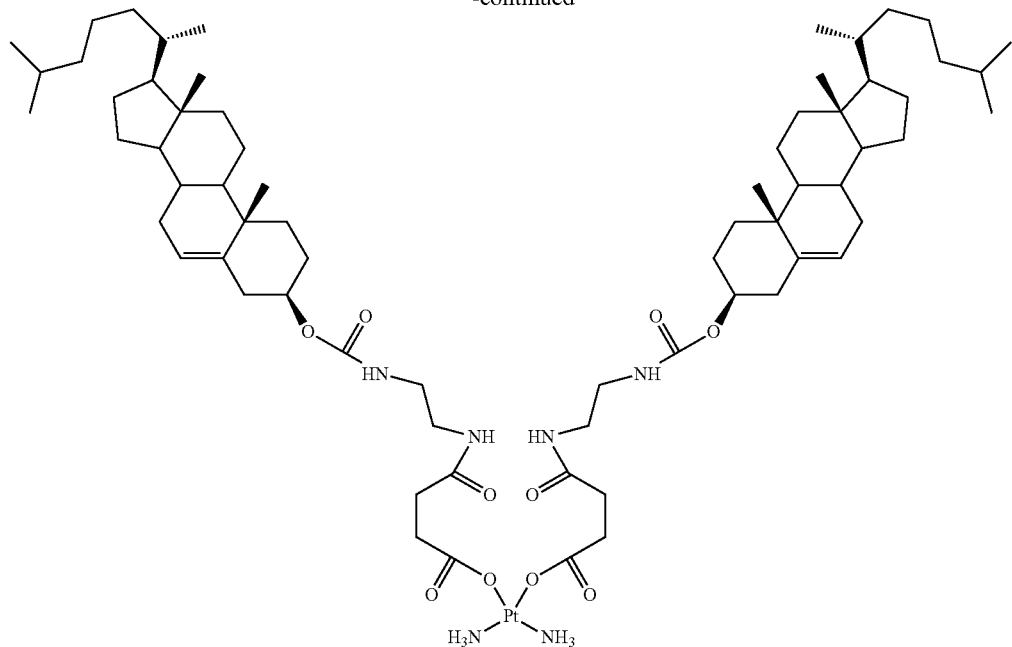

Synthesis of IO-183_04: Procedure is similar as described for compound IO-183_02.

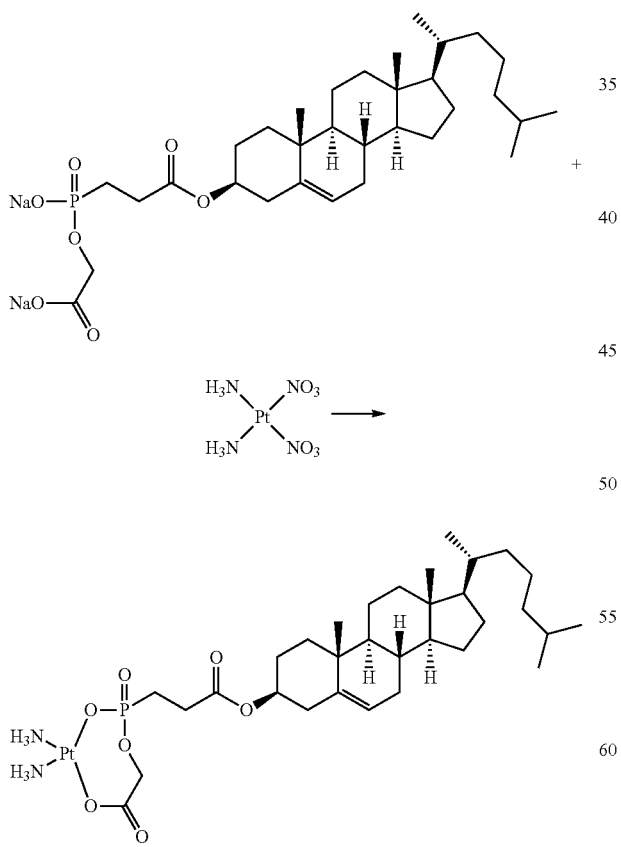

Synthesis of IO-180_04: Procedure is similar as described for compound IO-180_01.

Example 8

Preparation of Lipid-Based Nanoparticles

Soy-phosphatidyl choline (fully hydrogenated, HSPC), 1,2-Distearoyl-sn-Glycero-3-Phosphoethalonamine-N-[Methoxy(Polyethylene glycol)-2000] (Ammonium Salt) (DSPE-PEG-OMe) and cholesterol are selected as co-lipids. Liposomal nanoparticles are prepared by dissolving cholesterol-oxaliplatin lipid based platinum compounds of the present disclosure (as obtained in Examples 1 and 2) and colipids (HSPC, DSPE-PEG-OMe and cholesterol) in a 1:2:0.05:0.5 mol ratios respectively, in a mixture of dichloromethane and methanol in a glass vial. The organic solvent is removed with a gentle flow of moisture-free nitrogen and the remaining dried film of lipid is then kept under high vacuum for about 8 hours. 300 mOsm buffer (sucrose and disodium hydrogen phosphate) is added to the vacuum-dried lipid film and the mixture is allowed to hydrate at 60° C. for 1 h. The vial is vortexed for about 2-3 minutes at room temperature, and occasionally shaken in a 45° C. water bath to produce multilamellar vesicles (MLV). Small unilamellar vesicles (SUV) are prepared by passing of the MLV through extruder sequentially through 400 μm, 200 μm and 100 μm membrane. The particle size of the nanoparticles obtained is measured by DLS instrument (Malvern).

Example 9

In-vitro Cell Culture and Cell Viability Assays

The breast cancer cell line (4T1), cervical cancer cell line (HeLa) and Lewis lung cancer cell line (LLC) are employed to study the cell viability assays. The 4T1 cells are cultured in RPMI1640 medium supplemented with 10% FBS, 50 unit $ml^{-1}$ penicillin and 50 unit $ml^{-1}$ streptomycin-penicillin. HeLa and LLC cells are cultured in DMEM medium supplemented with 10% FBS, 50 unit $ml^{-1}$ penicillin and 50 unit $ml^{-1}$ streptomycin-penicillin. The trypsinized cultured cancer cells are seeded into 96 well flat bottomed plates at a density of 3000 cells per well one day prior to drug treatment. The following day, the plated cells are treated with various concentrations of nanoparticle formulations (as prepared by Example 3) with oxaliplatin as control. The plates are then incubated for about 48 h in a 5% CO2 atmosphere at about 37° C. About 10 µl MTT reagent (10 mg/ml) is added and incubated for 2 hours. The media is removed and the precipitate is solubilized in about 100 µl of 1:1 DMSO-Methanol. The absorbance of the solubilized precipitate sample is measured in BioRad Elisa reader at 550 nm. The relative cell viability is thereafter calculated from the recorded absorption data.

Figure 6A:
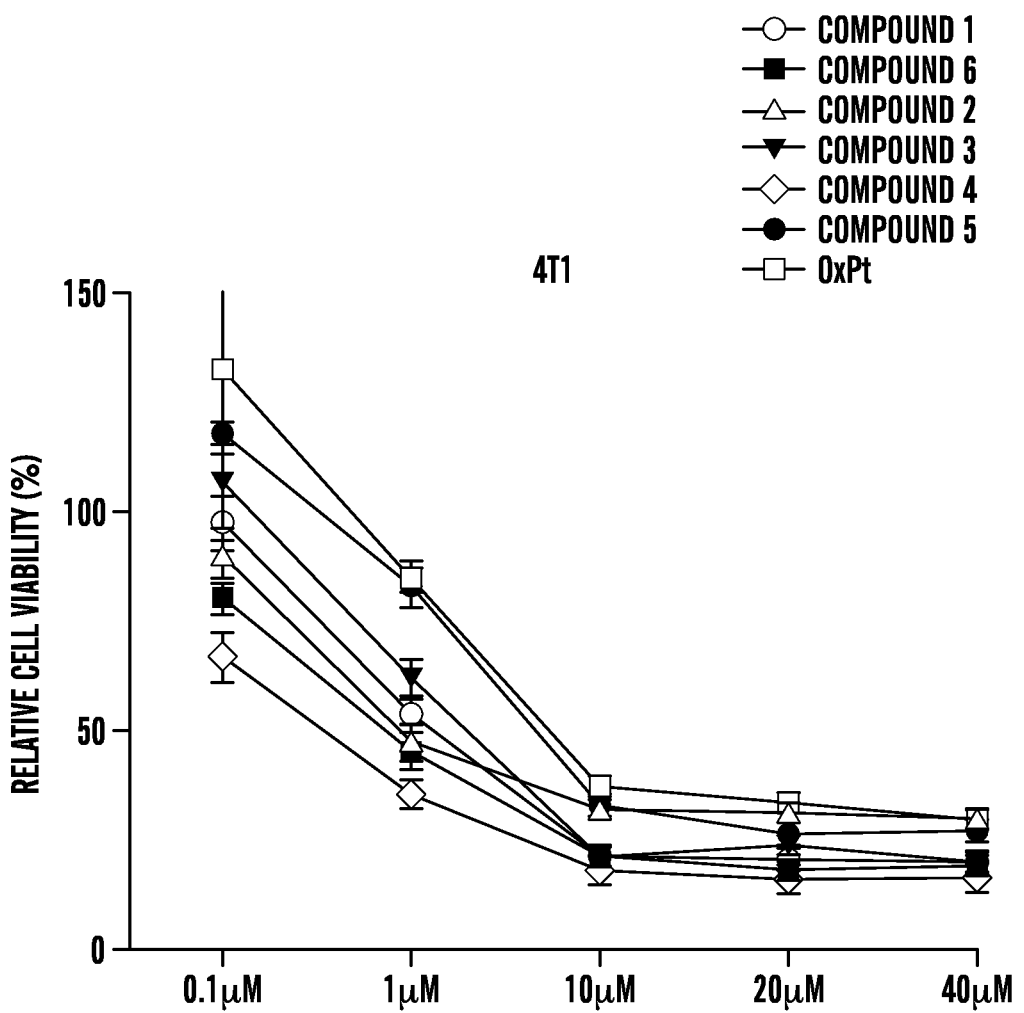
FIGS. 6A-6C depict the in-vitro characterization of synthesized cholesterol-oxaliplatin nanoparticle compositions. The graphs show the concentration-effect of different cholesterol-oxaliplatin nanoparticle compositions and Oxaliplatin (control) on cellular viability of 4T1 (breast cancer cell line) (FIG. 6A), HeLa (cervical cancer cell line) (FIG. 6B) and LLC (lung cancer cell line) (FIG. 6C) cancer cells as measured using MTT assay. The x-axis depicts the equivalent concentrations of platinum.
Figure 6B:
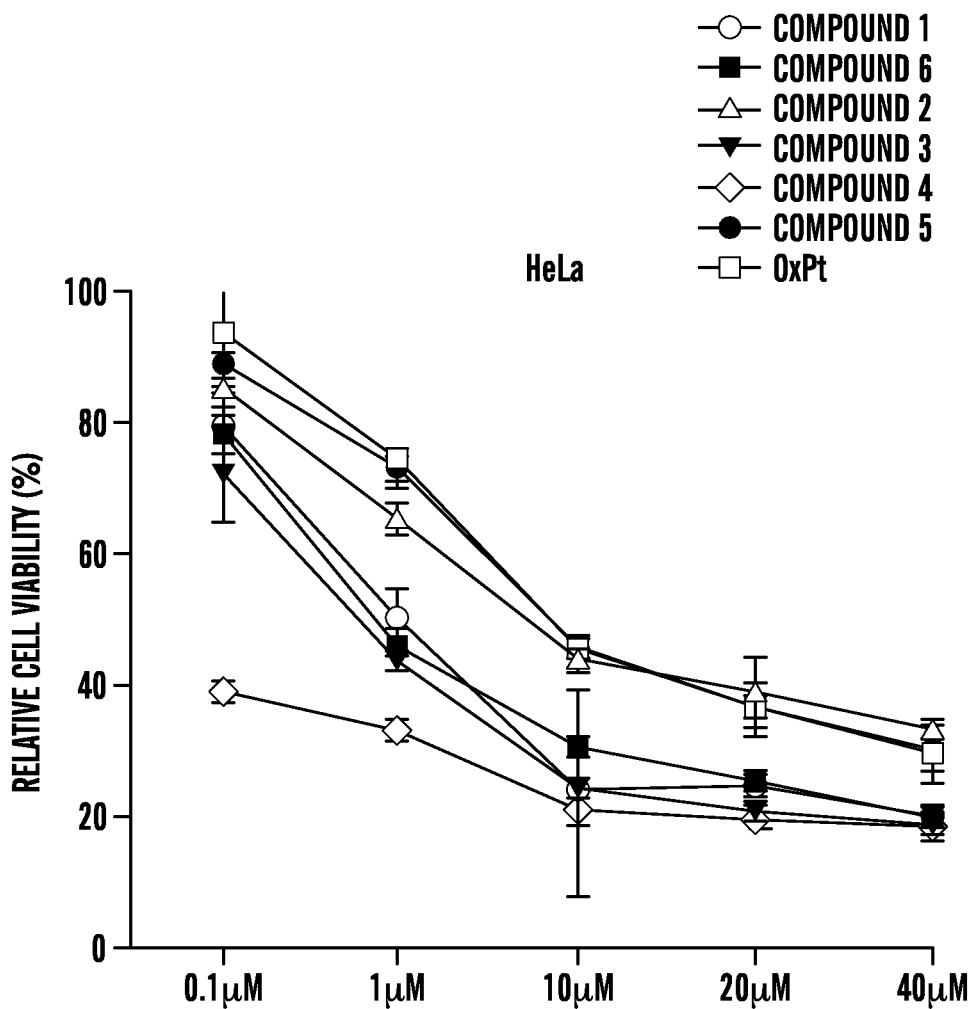
Figure 6C:
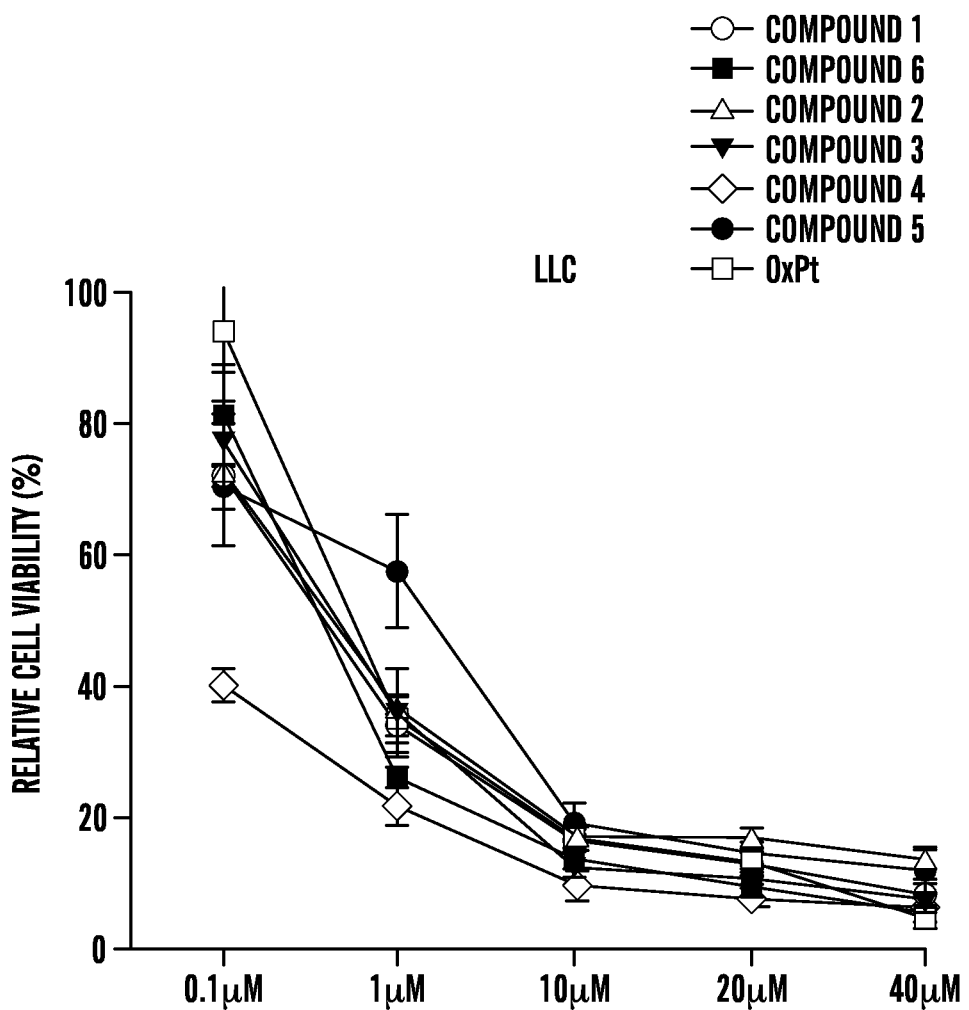
Figure 7A:
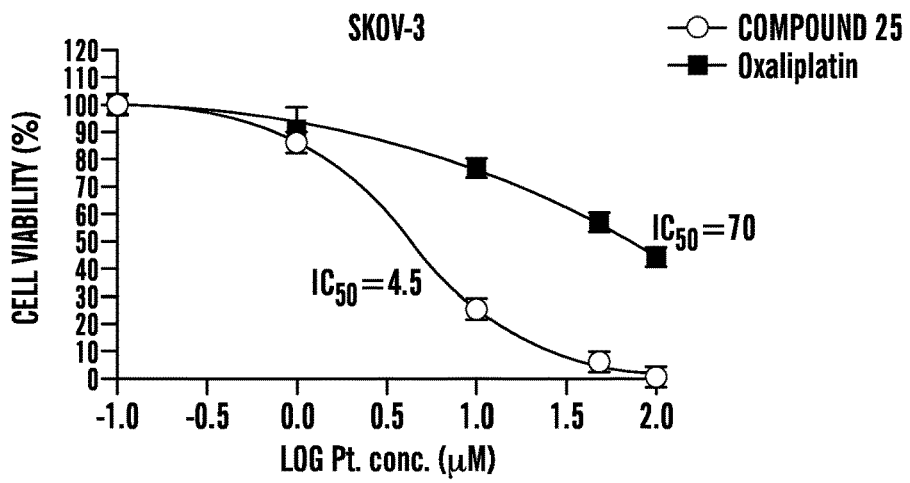
FIGS. 7A-7F show MTT assay results for some exemplary compounds disclosed herein. Graphical representation of MTT assay for the activity of exemplary compounds examined on various human cancer cell lines. The MTT assay showed a reduction in cell viability for the various exemplary compounds tested. The IC$_{50}$ values of compound/oxaliplatin tested in cell-lines are mentioned alongside, in corresponding colors as the cell viability curve.
Figure 7B:
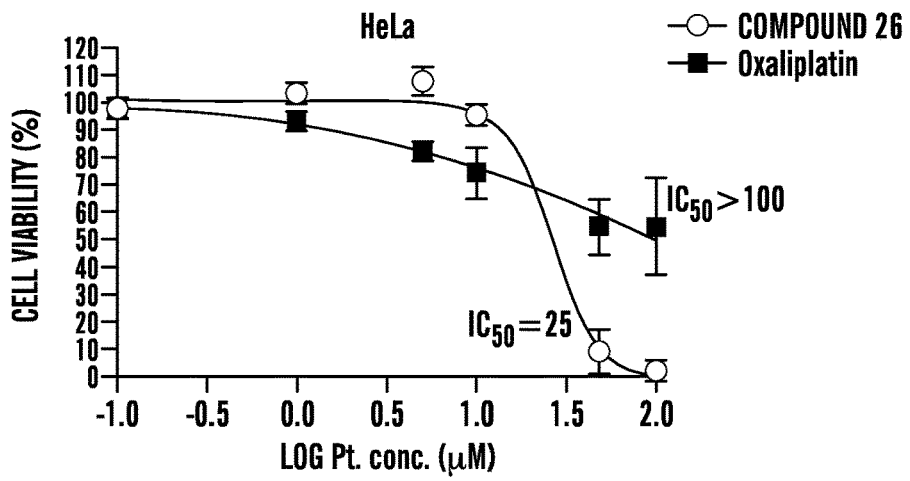
Figure 7C:
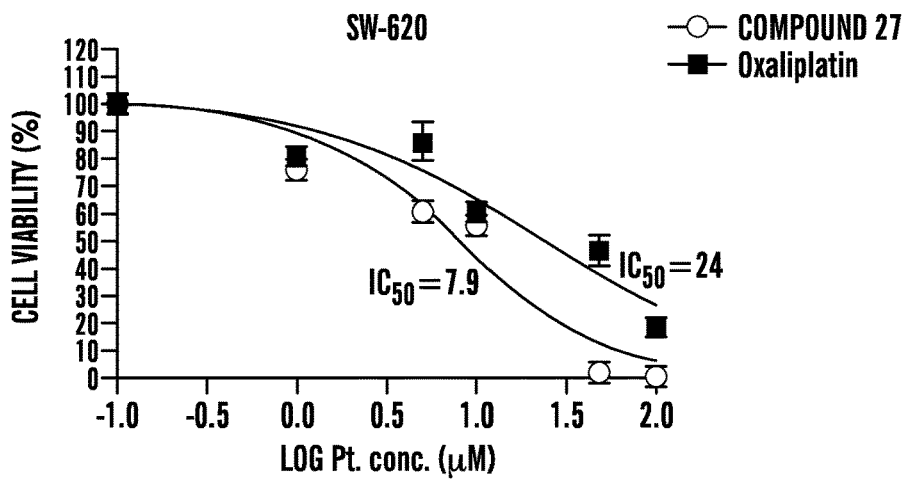
Figure 7D:
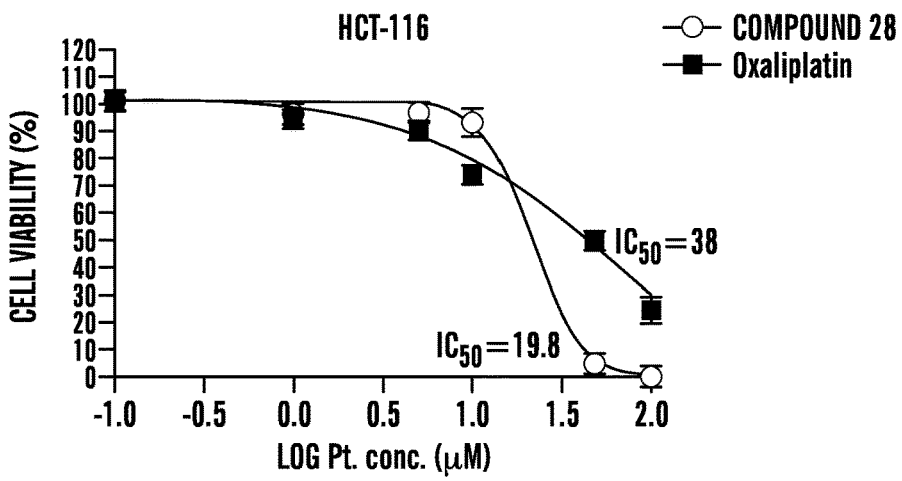
Figure 7E:
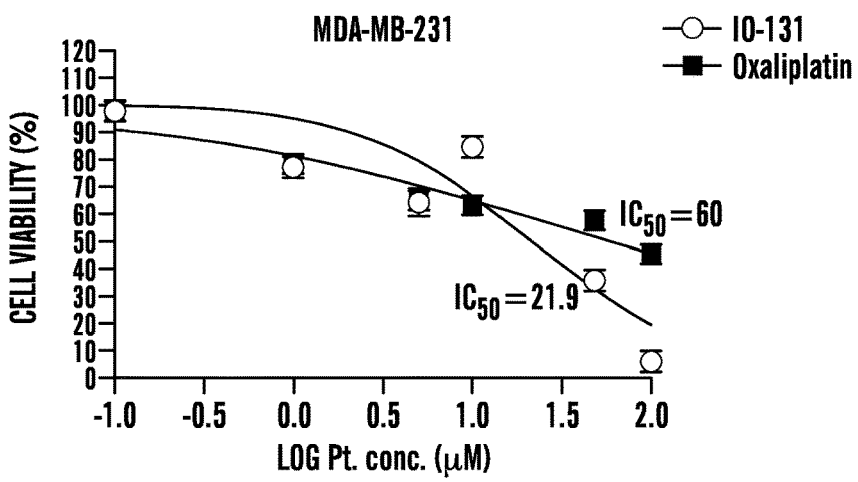
Figure 7F:
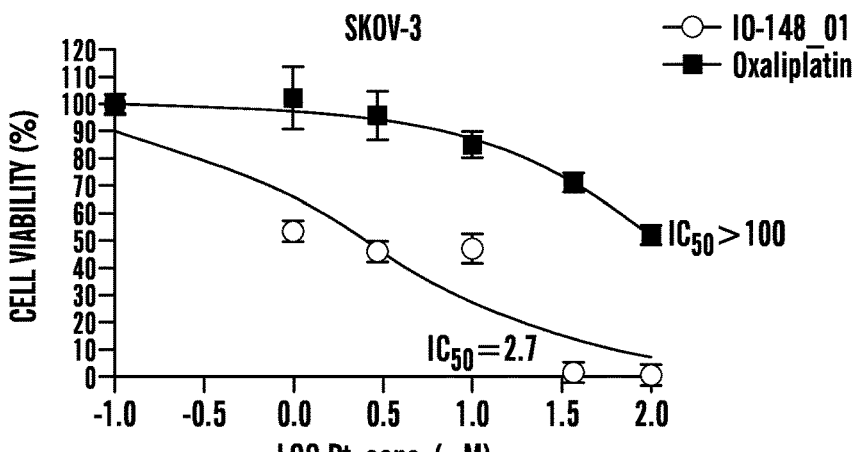

The nanoparticle compositions of the present disclosure show significant cancer cell killing efficacy (FIG. 6). The said nanoparticles are tested in different cancer cell lines as described above and it is observed that the compounds of the which have six-member co-ordination with platinum (Compound 2, Compound 5) have a similar cell killing efficacy when compared with oxaliplatin (control). Other compounds (Compound 1, Compound 6, Compound 3 and Compound 4) with five or seven member platinum co-ordination have better cell killing efficacy than oxaliplatin. Most importantly, among these four compounds, Compound 4 show significantly better cancer cell killing activity than oxaliplatin control.

In conclusion, the present disclosure aims at arriving at various platinum based amphiphiles as disclosed above. The said compounds have a general backbone of platinum-linker-lipid. Further, the disclosure also relates to carbenes, and more particularly, platinum containing carbenes, wherein said platinum based carbenes are also employed as the platinum moiety in platinum based amphiphiles. The various platinum based amphiphiles of the present disclosure showcase significantly improved efficacy in cancer treatment and therefore, can be employed as successful alternatives in cancer treatment.

Example 10

Bioassays

Cell culture: Mammalian cells were grown in specific culture media, supplemented with 10% fetal bovine serum (FBS) and antibiotics in a humidified environment containing 5% $CO_2$ at 37° C.

Cell viability assay: The effects of supramolecular platinum conjugates on the viability of cancer cells were measured using MTT assay. Cells in 100 µl culture-media were plated in 96-well plates (3000-5000 cells/well) and allowed to adhere overnight in a humidified environment containing 5% $CO_2$ at 37° C. Fresh media (100 µL) containing different concentrations of compounds were added to cells and incubated for 72 hours. Following incubation, cell viability was determined using the MTT assay. The MTT assay measures cell viability through assessment of active mitochondrial dehydrogenase, which converts MTT into water-insoluble purple formazan crystals. Cell viability was plotted as dose-response curves using curve fitting.

The effects of exemplary compounds (compound 25, 26, 27, 28, 31, 48) were evaluated in vitro in comparison with oxaliplatin in breast cancer (MDA-MB-231), ovarian cancer (SKOV-3), cervical cancer (HeLa) and colorectal cancer (SW-620 and HCT-116) cell lines. The results showed a significant inhibition of cell viability in 0-25 µM concentration range for all exemplary compounds tested, showing a dose-response relationship (FIGS. 7A-7F). The $IC_{50}$ values for the individual exemplary compounds were lower than oxaliplatin, revealing better efficacy for these compounds on human cancer cells.

Cellular uptake of platinum compounds: MDA-MB-231 cells ($1 \times 10^6$) were seeded in 2 ml media per well of a 6-well plate and grown for 24 hrs. Required volume of compounds was added to achieve a final concentration of 50 µM platinum equivalent per well. Cells were incubated for 5 hrs after adding the compounds, then washed twice with PBS, harvested by trypsinization, resuspended in PBS and counted. Cells were centrifuged and pellets stored at −80° C. until further processing. The cell pellets were digested with 100 µl nitric acid at 70° C. for 4 hours. Following digestion, the samples were diluted in 2% HCl and the quantity of accumulated platinum was determined using Atomic absorption spectroscopy (AAS). The assay was validated using a linear standard curve, generated from serial dilutions of certified stock platinum standard and cellular uptake of platinum was expressed as ng of platinum per $1 \times 10^5$ cells.

The results indicate that the uptake of cisplatin and oxaliplatin are similar in MDA-MB-231 cells, while all exemplary compounds tested show higher uptake (~7-20 fold) (FIG. 8). These results demonstrate that when administered at platinum equivalent concentrations, the uptake of exemplary compounds is significantly higher in comparison to cisplatin or oxaliplatin in cancer cells.

Measurement of platinum in mouse tumors: 4T1 breast cancer cells were implanted subcutaneously in Balb/c mice on day 0. Tumor-bearing mice were treated with oxaliplatin and compound 27 at a dose equivalent to 8 mg/kg of platinum (n=3) on day 9 post tumor implantation. Approximately 40 mg of tumor was weighed, ground to fine powder in mortar and pestle with liquid nitrogen and digested overnight in nitric acid at 110° C. in ace high pressure tubes to achieve homogeneity. After acidification, each sample was diluted with 2% HCl and analyzed by atomic absorption spectrophotometry (AAS) to measure absorbance associated with platinum content. The assay was validated using a linear standard curve, generated from serial dilutions of certified stock platinum standard. The averaged platinum concentration was reported as ng of platinum per milligram of tissue.

Figure 9:
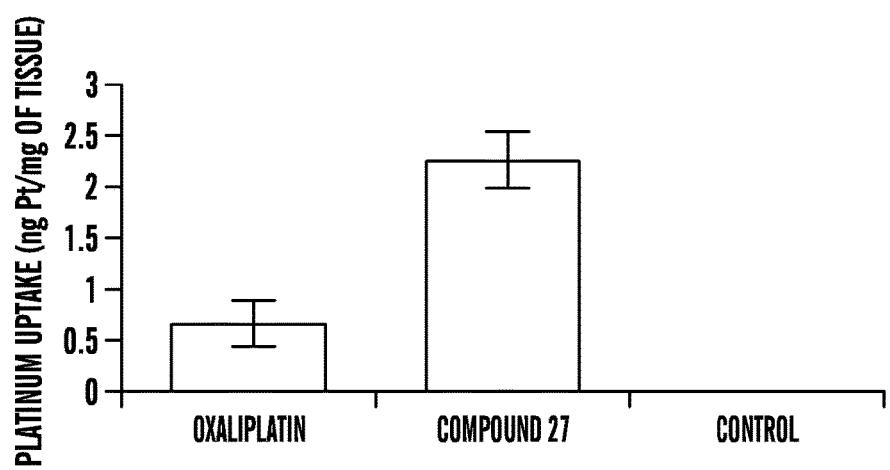
FIG. 9 shows platinum distribution in tumors. The total platinum content in tumors was measured by AAS and expressed as ng of platinum accumulated per mg of tumor.

As shown in FIG. 9, there was a significantly higher accumulation of platinum (as quantified per gram of tissue using atomic absorption spectrophometry) in tumors for compound 27 treated mice as compared to tumors harvested from mice dosed with an equivalent amount of oxaliplatin. Our findings suggest that enhanced uptake of platinum associated with exemplary compounds could account for increased cellular killing in tumors.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A compound of Formula (VIII):

Q-linker-lipid  (VIII)

wherein:

the linker is:
(a) —X—CH$_2$—X$_2$—X$_1$—, wherein X is NH; X$_1$ is C(O)O, C(O)NH, O(CH$_2$)—O, NH, or O; X$_2$ is (CH$_2$)$_n$ or C(O); and n is 0, 1, 2, 3, 4, or 5;
(b) —(CH$_2$)$_n$O—, —(CH$_2$)$_n$NHC(O)O—, —(CH$_2$)$_n$OC(O)NH—, —(CH$_2$)$_n$C(O)NH(CH$_2$)$_m$O—, —(CH$_2$)$_n$O(CH$_2$)$_m$O—, —(CH$_2$)$_n$O(O)—, —(CH$_2$)$_n$NHC(O)(CH$_2$)$_m$O—, or —(CH$_2$)$_n$C(O)O—; wherein n and m are, independently, 0, 1, 2, 3, 4, or 5;
(c) —X$_3$—X$_4$X$_5$—X$_6$—, wherein X$_3$ is CH, CH$_2$, or O; and X$_4$, X$_5$ and X$_6$ are, independently,—CH$_2$O— or O; or
(d) a combination of (a)-(c);

the lipid is a fat, wax, sterol, steroid, bile acid, fat-soluble vitamin, monoglyceride, diglyceride, phospholipid, glycolipid, sulpholipid, aminolipid, chromolipid, glycerophospholipid, sphingolipid, prenol lipid, saccharolipid, polyketide, fatty acid, or a combination thereof;

Q is

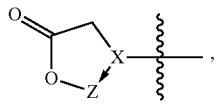  (i)

wherein X is NH or N(CH$_2$COO$^-$); and Z is a platinum containing compound, wherein the platinum forms a part of the ring;

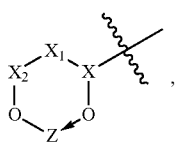  (ii)

wherein X is S$^+$, C, S$^+$═O, N$^+$H, or P═O; X$_1$ is —CH, —CH$_2$ or CH$_2$O; X$_2$ is C═O; and Z is a platinum containing compound, wherein the platinum forms a part of the ring;

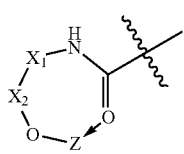  (iii)

wherein X$_1$ is (CH$_2$)$_n$; X$_2$ is C═O; Z is a platinum containing compound, wherein the platinum forms a part of the ring; and n is 0, 1, or 2;

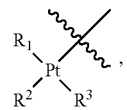  (iv)

wherein R$_1$, R$_2$ and R$_3$ are, independently, halogen, alkyl, amino, alkylamino, dialkylamino, hydroxyl, alkoxy, thiol, thioalkyl, O-acyl, -linker-lipid, or a combination thereof, or R$_1$ and R$_2$ together with the Pt atom or R$_2$ and R$_3$ together with the Pt atom form an optionally substituted cyclyl or heterocyclyl or R$_1$ and R$_2$ together with the Pt atom and R$_2$ and R$_3$ together with the Pt atom form an optionally substituted cyclyl or heterocyclyl; or

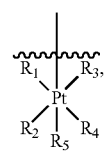  (v)

wherein R$_1$, R$_2$, R$_3$, R$_4$ and R$_5$ are, independently, halogen, alkyl, amino, alkylamino, dialkylamino, hydroxyl, alkoxy, thiol, thioalkyl, O-acyl, -linker-lipid, or a combination thereof, or R$_1$ and R$_2$ together with the Pt atom form an optionally substituted cyclyl or heterocyclyl, or R$_3$ and R$_4$ together with the Pt atom form an optionally substituted cyclyl or heterocyclyl.

2. The compound of claim 1, wherein Z is

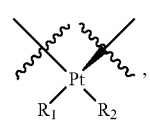

wherein R$_1$ and R$_2$ are, independently, halogen, alkyl, amino, alkylamino, dialkylamino, hydroxyl, alkoxy, thiol, thioalkyl, O-acyl, or a combination thereof, or R$_1$ and R$_2$, together with the Pt atom form an optionally substituted cyclyl or heterocyclyl.

3. The compound of claim 2, wherein Z is

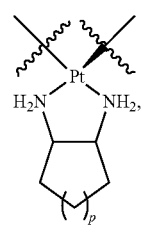

wherein p is 0, 1, 2, or 3.

4. The compound of claim 1, wherein the linker is a bond, ethylene diamine, ethylene glycol, diethylene glycol, 1,3- propanediol, glycine, beta alanine, —O—, —CH₂O—HCH₂CH₂NHC(O)—, —NHCH₂CH₂NHC(O)O—, —NHCH₂CH₂—, —NHCH₂CH₂O—, —NHCH₂C(O)—, —NHCH₂C(O)O—, —NHCH₂C(O)OCH₂CH₂CH₂—, —NHCH₂C(O)OCH₂CH₂CH₂O—, —NHCH₂C(O)NH—, —CH₂CH₂—, —CH₂CH₂O—, —CH₂CH₂NHC(O)—, —CH₂CH₂NHC(O)O—, —CH₂CH₂O—, —CH₂C(O)NHCH₂CH₂—, —CH₂C(O)NHCH₂CH₂O—, —CH₂CH₂OCH₂CH₂—, —CH₂CH₂OCH₂CH₂O—, —CH₂C(O)—, —CH₂C(O)O—, —CH₂CH₂CH₂—, —CH₂CH₂CH₂O—, =CH—CH=CH₂—, =CH—CH=CHCH₂O—, —CH=CHCH₂—, —CH=CHCH₂O—, —OCH₂CH₂O—, —CH₂—, —CH₂O—, —NHC(O)CH₂—, —NHC(O)CH₂O—, —C(O)CH₂—, —C(O)CH₂O—, —OC(O)CH₂—, —OC(O)CH₂O—, —C(O)CH₂CH₂C(O)NHCH₂CH₂—, —OC(O)CH₂CH₂C(O)NHCH₂CH₂—, —C(O)CH₂CH₂C(O)NHCH₂CH₂O—, —OC(O)CH₂CH₂C(O)NHCH₂CH₂O—, —C(O)CH₂CH₂C(O)NHCH₂CH₂NHC(O)—, —C(O)CH₂CH₂C(O)NHCH₂CH₂NHC(O)—, —C(O)CH₂CH₂C(O)NHCH₂CH₂NHC(O)O—, —OC(O)CH₂CH₂C(O)NHCH₂CH₂NHC(O)O—, or a combination thereof.

5. The compound of claim 1, wherein the lipid is cholesterol or alphatocopherol.

6. The compound of claim 1, wherein the compound is of:

(i) Formula I:

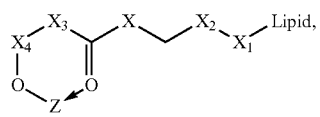

(I)

wherein,

X is NH;

X₁ is COOH, CONH₂, O—(CH₂)ₙ—OH, NH₂ or OH;

X₂ is (CH₂)ₙ or CO;

X₃ is (CH₂)ₙ, CH₂—NH or C₄H₈;

X₄ is CO or —CH—CH₃; and

Z is platinum containing compound, wherein the platinum forms a part of the Formula I ring; and n is 0, 1, or 2;

(ii) Formula II:

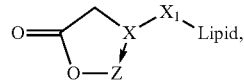

(II)

wherein,

X is NH or N—CH₂COO⁻;

X¹ is —(CH₂)ₙOH, —(CH₂)ₙNHCOOH, —(CH₂)ₙCONH(CH₂)ₙOH, (CH₂)ₙO(CH₂)ₙOH, (CH₂)ₙC=O, —(CH₂)ₙNHCO(CH₂)ₙOH or (CH₂)ₙ—COOH;

Z is platinum containing compound, wherein the platinum forms a part of the Formula II ring; and n is 0, 1, or 2;

(iii) Formula III:

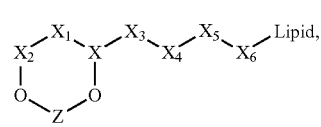

(III)

wherein,

X is S⁺, C, S⁺=O, N⁺H or P=O;

X₁ is —CH, —CH₂ or —CH₂O;

X₂ is C=O;

X₃ is CH, CH₂ or O;

X₄, X₅, X₆ is —CH₂O or O; and

Z is platinum containing compound, wherein the platinum forms a part of the Formula III ring;

(iv) Formula IV:

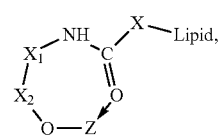

(IV)

wherein,

X is CH₂OH;

X₁ is (CH₂)ₙ;

X₂ is C=O;

Z is platinum containing compound, wherein the platinum forms a part of the Formula IV ring; and n is 0, 1, or 2;

(v) Formula VI:

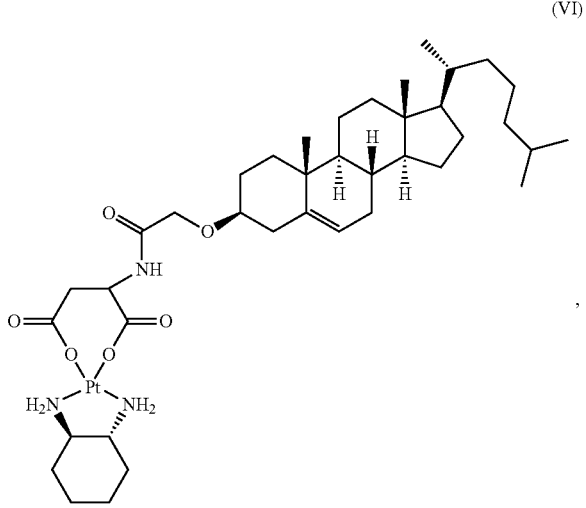

(VI)

or (vi) Formula VII:

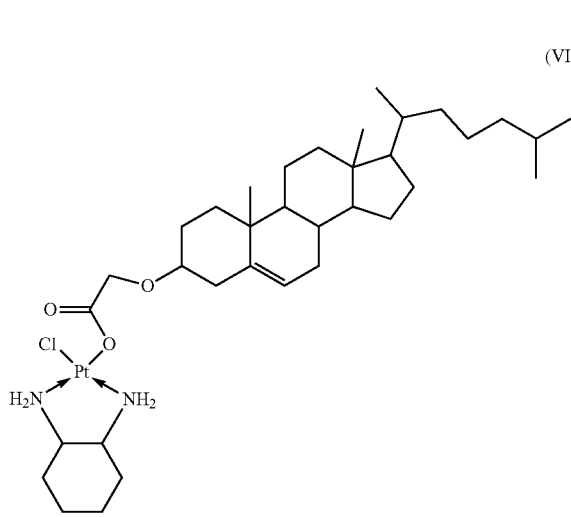

7. A nanoparticle comprising a compound of claim 1.

8. The nanoparticle of claim 7, wherein the nanoparticle further comprises a co-lipid and/or stabilizer.

9. A method of treating or managing cancer in a subject, the method comprising administering a therapeutically effective amount of a compound of claim 1 to a subject in need thereof.

10. The compound of claim 1, which is

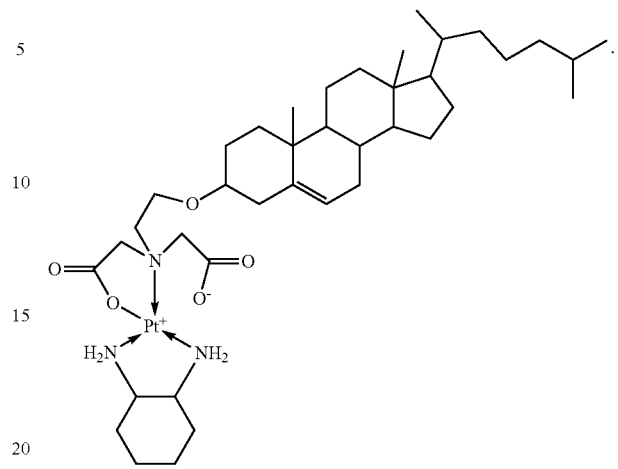

11. The compound of claim 1, wherein the lipid is a sterol that is cholesterol, cholesterol chloroformate or a derivative thereof, or a combination thereof.

12. The method of claim 9, wherein the cancer is breast cancer, ovarian cancer, a glioma, gastrointestinal cancer, prostate cancer, lung carcinoma, hepatocellular carcinoma, testicular cancer, cervical cancer endometrial cancer, bladder cancer, head and neck cancer, or gastro-esophageal cancer.

* * * * *

UNITED STATES PATENT AND TRADEMARK OFFICE
CERTIFICATE OF CORRECTION

PATENT NO. : 10,081,648 B2  
APPLICATION NO. : 14/898355  
DATED : September 25, 2018  
INVENTOR(S) : Sengupta et al.

Page 1 of 1

It is certified that error appears in the above-identified patent and that said Letters Patent is hereby corrected as shown below:

On the Title Page

Item (72) Inventors: delete "Swadhin K. Mandal, Mohanpur (IN)"

Signed and Sealed this
Thirteenth Day of November, 2018

Andrei Iancu
*Director of the United States Patent and Trademark Office*